United States Patent
Fancelli et al.

(10) Patent No.: US 8,669,261 B2
(45) Date of Patent: Mar. 11, 2014

(54) ACRYLOMIDO DERIVATIVES USEFUL AS INHIBITORS OF THE MITOCHONDRIAL PERMEABILITY TRANSITION

(71) Applicants: Daniele Fancelli, Milan (IT); Mario Varasi, Milan (IT); Simon Plyte, Cadorago (IT); Marco Ballarini, Milan (IT); Anna Cappa, Visso (IT); Giacomo Carenzi, Busto Arsizio (IT); Saverio Minucci, Noverasco di Opera (IT); Gilles Pain, Castelforte (IT); Manuela Villa, Lurago d'Erba (IT)

(72) Inventors: Daniele Fancelli, Milan (IT); Mario Varasi, Milan (IT); Simon Plyte, Cadorago (IT); Marco Ballarini, Milan (IT); Anna Cappa, Visso (IT); Giacomo Carenzi, Busto Arsizio (IT); Saverio Minucci, Noverasco di Opera (IT); Gilles Pain, Castelforte (IT); Manuela Villa, Lurago d'Erba (IT)

(73) Assignee: Congenia SLR, Milan (IT)

( * ) Notice: Subject to any disclaimer, the term of this patent is extended or adjusted under 35 U.S.C. 154(b) by 0 days.

(21) Appl. No.: 13/874,081

(22) Filed: Apr. 30, 2013

(65) Prior Publication Data

US 2013/0245019 A1 Sep. 19, 2013

Related U.S. Application Data

(62) Division of application No. 13/123,852, filed as application No. PCT/IB2009/006939 on Sep. 23, 2009, now Pat. No. 8,470,831.

(51) Int. Cl.
| | | |
|---|---|---|
| *A61K 31/4965* | (2006.01) | |
| *A61K 31/445* | (2006.01) | |
| *A61K 31/4178* | (2006.01) | |
| *A61K 31/416* | (2006.01) | |
| *A61K 31/22* | (2006.01) | |
| *A61K 31/19* | (2006.01) | |
| *A61K 31/18* | (2006.01) | |
| *A61K 31/167* | (2006.01) | |

(52) U.S. Cl.
USPC ...... 514/255.01; 514/331; 514/397; 514/403; 514/546; 514/570; 514/603; 514/620

(58) Field of Classification Search
USPC ............ 514/255.01, 331, 397, 403, 546, 570, 514/603, 620
See application file for complete search history.

(56) References Cited

U.S. PATENT DOCUMENTS

2004/0235888 A1   11/2004   Yamamori et al.

FOREIGN PATENT DOCUMENTS

| EP | 1256574 | 11/2002 |
|---|---|---|
| JP | 03300886 | 10/2003 |
| WO | 02079144 | 10/2002 |
| WO | 2006076706 | 7/2006 |

OTHER PUBLICATIONS

Vippagunta et al., Crystalline solids, 2001, Advanced Drug Delivery Reviews, 48, pp. 3 and 18.*
Ciampa, Guiseppe et al., "Syntheses and properties of N, N'-bis (hydroxybenzoyl) and N, N'-bis (hydroxycinnamoyl)-4, 4'-diaminodiphenylmethane" Ricerca Scientifica, 39(4-6), pp. 386-391, 1969.
George, M. V. et al., "condensation of .omicron.-, m-, and p-chloromalonanilic acids with aldehydes. I. With benzaldehyde and .omicron.-, m-, and p-hydroxybenzaldehydes", Agra Univ. J. Research, 4 (Pt. 2), 551-4, 1955.
Ghatak, S. et al., "Condensation of aromatic aldehydes with malonic-1, 3, 4-xylidic acid. II with .omicron.-,m-and p-hydroxybenzaldehydes, .omicron.-, m-, and p-methoxybenzaldehydes, piperonal, vanillin, veratraldehyde, and 5-bromovanillin", Agra Univ. J. Resarch, 3, 489-92, 1954.
Ittyerah, P.I. et al., "Condensation of aromatic aldehydes with malon-o-, m-, p-toluidic acids. I. With benzaldehyde, o-, m-, p-hyroxy- and -methoxybenzaldehydes", Journal of the Indian Chemical Society, 30, 717-19, 1953.
Kroemer Guido: "The Mitochondiral Permeability Transition Pore Complex as a Pharmacological Target An Introduction", Current Medicinal Chemistry, Bentham Science Publishers BV, BE, vol. 10, No. 16, Aug. 1, 2003, pp. 1469-1472.
Morin D. et al., "Effect of the mitochondrial transition pore inhibitor, S-15176, on rat liver mitochondria: ATP synthase modulation and mitochondrial uncoupling induction", Biochemical Pharmacology, Pergamon, Oxford, GB, vol. 72, No. 7, Sep. 28, 2006, pp. 911-918.
International Search Report issued by the International Searching Authority (ISA/O.E.P.M.) on Dec. 17, 2009 in connection with International Application No. PCT/IB2009/006939.

* cited by examiner

*Primary Examiner* — Kristin Vajda
(74) *Attorney, Agent, or Firm* — Gary J. Gershik; Cooper & Dunham LLP

(57) ABSTRACT

Acrylamido derivatives useful as therapeutic agents, particularly for the prevention and/or treatment of diseases and conditions associated with the activity of the mitochondrial permeability transition pore (MPTP), such as the diseases characterized by ischemia/reperfusion, oxidative or degenerative tissue damage, are herein described. These compounds belong to the structural formula (I) wherein R, R', R", W and a are as defined in the specification. The invention also relates to the preparation of these compounds, as well as to pharmaceutical compositions comprising them.

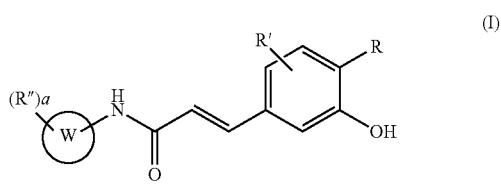

4 Claims, No Drawings

ACRYLOMIDO DERIVATIVES USEFUL AS INHIBITORS OF THE MITOCHONDRIAL PERMEABILITY TRANSITION

This application is a divisional of U.S. Ser. No. 13/123,852, filed Apr. 12, 2011, which is a §371 national stage of PCT International Application No. PCT/IB2009/006939, filed Sep. 23, 2009, designating the United States and claiming priority of European Patent Application EP 08018742.0, filed Oct. 27, 2008, the contents of all of which are hereby incorporated by reference into this application.

FIELD OF THE INVENTION

The present invention relates to acrylamido derivatives and to their use as therapeutic agents, particularly for the prevention and/or treatment of diseases and conditions associated with the activity of the mitochondrial permeability transition pore (MPTP), such as the diseases characterized by ischemia/reperfusion, oxidative or degenerative tissue damage. The invention also relates to the preparation of these compounds, as well as to pharmaceutical compositions comprising them.

BACKGROUND OF THE INVENTION

The mitochondrial permeability transition (MPT) refers to a transition in the permeability of the inner mitochondrial membrane to solutes with molecular mass below approximately 1500 Da. The MPT is thought to be mediated by the reversible opening of a voltage and $Ca^{2+}$-dependent, high conductance, protein channel in the inner mitochondrial membrane, the MPT pore (MPTP). The consequences of MPTP opening are twofold: firstly, there is uncoupling of oxidative phosphorylation and as a consequence the $F_1F_0$-ATPase reverses to try and maintain mitochondrial membrane potential ($\Delta\Psi_m$) which results in a decline in cellular ATP levels and a loss of metabolic homeostasis. Secondly, the MPTP allows solutes to freely enter the mitochondrial matrix which results in swelling and eventual rupture of the outer mitochondrial membrane with subsequent release of stored calcium and proapoptotic factors. The release of stored calcium can cause calcium overload, production of reactive oxygen species (ROS) and MPT in neighbouring mitochondria resulting in a "chain reaction" throughout the cell. Depending on the energy status of the cell, apoptosis or necrosis then occurs leading to irreversible tissue and organ damage (Grimm S., Brdiczka D. The permeability transition pore in cell death Apoptosis, 2007, 12, 841-847).

The precise molecular composition of the MPTP is still not known. Cyclophilin D has been shown both pharmacologically (using an inhibitor, Cyclosporin A) and genetically to be a major regulator of the MPTP. Many studies demonstrating a role for the MPTP in disease have been conducted using cyclophilin D null mice (Ppif−/−) or Cyclosporin A. The MPTP can be regulated by several factors including, high [$Ca^{2+}$], oxidative damage (by ROS), chemical cross-linking agents, stress signalling and the PI3-kinase signalling pathway, conditions which are often present in the cells from diseased tissues (Rasola, A., Bernardi, P., The mitochondrial permeability transition pore and its involvement in cell death and in disease pathogenesis. Apoptosis, 2007, 12, 815-833).

The role of mitochondria-mediated apoptosis and necrosis in the aetiology of many diseases is well established and the increased rate of apoptosis/necrosis typical of pathological stress conditions such as those observed during myocardial infarction, renal ischemia, or neurodegenerative diseases correlates with the MPT and loss of mitochondrial integrity.

Hence the MPTP has been implicated in the aetiology and progression of several diseases including:
  Acute Myocardial Infarction (Lethal Reperfusion Injury);
  Stroke and Neurological Diseases;
  Inherited dystrophies;
  Hepatitis;
  Diabetes and Diabetic retinopathy.

Acute Myocardial Infarction (Lethal Reperfusion Injury)

In ischemic heart disease, sequential ischemia-reperfusion events occur resulting in myocardium cell death by necrosis and/or apoptosis. Lethal reperfusion injury, (cardiomyocyte death as a direct result of tissue reperfusion) is thought to account for up to 50% of the final myocardial infarct size and has been shown to be dependent on the RISK (Reperfusion Injury Salvage Kinase) pathway and MPTP opening (Yellon, D. M., Hausenloy, D. J., Myocardial Reperfusion Injury. N. Engl. J. Med., 2008, 357, 1121-1135.). During ischemia there is depletion of ATP, a drop in cellular pH and intracellular loading of $Ca^{2+}$. At reperfusion the increased intracellular [$Ca^{2+}$] leads to $Ca^{2+}$ overload in the mitochondria which together with a large burst of ROS and a return to physiological pH causes, paradoxically, opening of the MPT and cardiomyocyte cell death via necrosis and/or apoptosis. Thus, inhibition of the MPTP would be expected attenuate cardiomyocyte death and reduce infarct size after ischemia/reperfusion injury. Indeed, Debio-025, a cyclosporin A analogue endowed with MPT inhibitory activity, reduced infarct size and improved functional recovery and mortality in a mouse model of myocardial infarction and reperfusion injury (Gomez, L., Thibault. H., Gharib, A., Dumont, J-M., Vuagniaux, G., Scalfaro, P., Derumeaux, G., Ovize, M. Inhibition of mitochondrial permeability transition improves functional recovery and reduces mortality following acute myocardial infarction in mice. Am. J. Physiol. Heart Circ. Physiol., 2007, 293, 1654-1661).

Stroke and Neurological Diseases.

Cerebral ischemia followed by reperfusion activates several pathways including one that causes the release of large quantities of the excitatory amino acid glutamate into the synapses. Activation of N-methyl-D-aspartate receptors causes an increase in calcium uptake and ROS production leading to opening of the MPTP and mitochondrial dysfunction. Hence MPTP opening has been implicated in the neuronal cell death and clinical symptoms associated with stroke. Further, NIM811, a cyclosporin A analogue MPT inhibitor, afforded 40% protection in a rat model of transient focal cerebral ischemia characterized by a reduction in cytochrome C release and ROS production (Korde, A. S., Pettigrew, L. C., Craddock, S. D., Pocernich, C. B., Waldmeier, P. C., Margolis., W. F. Protective effects of NIM811 in transient focal cerebral ischemia suggests involvement of the mitochondrial permability transition. J. Neurotrauma, 2007, 24 (5), 895-908).

Severe insulin-induced hypoglycaemia causes neuronal damage to selective regions of the brain including the outer layers of the cortex and the dentate gyrus. In a rat model of insulin-induced hypoglycaemic coma Cyclosporin A, an immunosuppressant drug endowed with MPTP inhibitory activity, but not FK506 (an immunosupressant similar to CSA but devoid of MPTP activity) showed a robust reduction in ultra-structural brain damage when administered 30 minutes prior to hypoglycaemic insult (Friberg, H., Ferrand-Drake, M., Bengtsson, F., Halestrap, A. P., Wieloch, T. Cyclosporin A, but not FK 506, protects mitochondria and neurons against hypoglycaemic damage and implicates the mitochondrial permeability transition in cell death. J. Neurosci., 1998, 18, 5151.5159).

Mitochondrial dysfunction, aberrant $Ca^{2+}$ signalling and oxidative stress are characteristic of Amyotrophic Lateral Sclerosis, Alzheimer's, Parkinson's and Huntington's diseases and MPTP opening has been causally linked to all four diseases by the selective use of Cyclosporin A (Norenberg, M. D., Rama Rao, K. V. The mitochondrial permeability transition in neurologic disease. Neurochem. Int., 2007, 50, 983-997).

MPTP and mitochondrial swelling has also been implicated in brain damage resulting from hyperglycaemic insult, experimental trauma and epilepsy (Li, P. A., Uchino, H., Elmer, E., Siesjö, B. K. Amelioration by cyclosporin A of brain damage following 5 or 10 min of ischemia in rats subjected to preischemic hyperglycaemia. Brain Res., 1997, 753, 133-140; Scheff, S. W., Sullivan P. G. Cyclosporin A significantly ameliorates cortical damage following experimental traumatic brain injury in rodents. J. Neurotrauma, 1999, 16, 783-792; Kudin, A. P., Debska-Vielhaber, G., Vielhaber, S., Elger, C. E., Kunz, W. S. The mechanism of neuroprotection by topiramate in an animal model of epilepsy. Epilepsia, 2004, 45, 1478-1487).

Inherited Dystrophies

Many of the pathological features leading to MPTP opening ($Ca^{2+}$ overload and ROS accumulation) are present in muscular dystrophies and mitochondria isolated from skeletal muscle from Scgd$^{-/-}$ mice (model of severe dystrophy) are swollen consistent with opening of the MPTP. Scgd$^{-/-}$ Ppif$^{-/-}$ mice (devoid of cyclophilin D) did not have swollen mitochondria and did not exhibit severe muscle degeneration at 8 weeks of age. Further, treatment of mdx (model of Duchene muscular dystrophy) and Scgd$^{-/-}$ mice with Debio-025 reduced mitochondrial swelling and necrotic disease (Millay, D. P., Sargent, M. A., Osinska, H., Baines, C. P., Barton, E. R., Vuagniaux, G., Sweeney, H. L. Robbins, J., Molkentin, J. D. genetic and pharmacologic inhibition of mitochondrial-dependent necrosis attenuates muscular dystrophy. Nature Medicine, 2008, 14, 442-447).

Ullrich congenital muscular dystrophy and Bethlem myopathy are two inherited dystrophies characterized by mutations in the collagen VI gene. Mice models of the diseases have highlighted a latent mitochondrial dysfunction characterized by increased susceptibility to MPTP opening and myofibre degeneration. Myoblasts from patients with Ullrich congenital muscular dystrophy showed mitochondrial dysfunction and precocious opening of the MPTP leading to increased apoptosis. Patients with Collagen VI myopathies treated with the MPTP inhibitor Cyclosporin A for one month showed amelioration of mitochondrial function and had signs of muscle regeneration (Merlini, L., Angelin, A., Tiepolo, T., Braghetta, P., Sabatelli, P., Zamparelli, A., Ferlini, A., Maraldi, M., Bonaldo, P., Bernardi, P. Cyclosporin A corrects mitochondrial dysfunction and muscle apoptosis in patients with collagen VI myopathies. P.N.A.S., 2008, 105 (13), 5225-5229).

Hepatitis

Liver can be damaged by different agents such as chemical poisons, inflammatory factors or viruses. In all cases, hepatocytes undergo massive apoptosis that is driven by the MPTP. Furthermore, it has been reported that inhibiting MPTP opening by treatment with cyclosporine A strongly reduces liver damage in a rat model of TNF-α-dependent acute inflammatory hepatitis (Soriano, M. E., Nicolosi, L. Desensitization of the permeability transition pore by cyclosporine A prevents activation of the mitochondrial apoptotic pathway and liver damage by tumour necrosis factor-alpha. J. Biol. Chem., 2004, 279, 36803-36808).

Diabetes

Diabetes induces damage and cell death by several mechanisms. Diabetic retinopathy (DR) is one of the peripheral micro-vascular complications strongly enhancing the morbidity of diabetic vascular diseases. DR begins with an early pre-proliferative stage (background retinopathy) characterized by loss of capillary pericytes, progressive capillary closure, micro-aneurysms and retinal oedema. The subsequent retinal ischemia (or hypoxia) due to vessel occlusion, triggers abnormal retinal vessel growth. Neo-vessels extend along the inner surface of the retina and/or into the vitreous cavity and can lead to retinal detachment and hemorrhage. This stage is known as proliferative diabetic retinopathy (PDR). Hyperglycaemic stress is considered a key factor in PDR since it induces increased production of vascular endothelium growth factor (VEGF) by retinal cells leading to neovascularization and causes cellular oxidative damage having repercussions on the mitochondria. ROS, formed in higher amounts during diabetes, could trigger most of the pathologic intracellular pathways involved in PDR and it has been demonstrated that ROS are produced in retina during reperfusion following diabetes-induced ischemia. In addition, oxidative stress was also correlated with incidence and progression of retinopathy of prematurity (ROP). The immature retina contains relatively low levels of antioxidants such as heme-oxygenase-1 and catalase. During hyper-oxygenation ROS are produced and, among other things, favour the generation of biologically active isoprostanes concurring to ischemia and, therefore, to the pathogenesis of ROP. The MPTP is triggered by ROS and its opening can lead to the further production of ROS and so mitochondrial dysfunction could be central to diabetic complications.

To date, inhibition of the MPTP has been mainly restricted to pharmacological modulation of the cyclophilin-D component of the MPTP using the potent immunosuppressant drug cyclosporine-A or its analogues NIM811 and Debio-025 (that are devoid of immunosuppressant activity). These are large, complex molecules based on the peptidic structure of cyclosporine-A. In addition, the inhibitory efficacy of these molecules is restricted by the limits of the regulatory role of cyclophilin D in MPTP function and its level of expression.

Other known compounds, which often show a variety of biological activities and pharmacological profiles, have been reported to have some additional non-specific interactions also with the MPTP. As an example, the agent N-[(3,5-di-tert-butyl-4-hydroxy-1-thiophenyl)]-3-propyl-N'-(2,3,4-tri-methoxybenzyl)piperazine (S-15176) has been shown to interact with several targets on rat liver mitochondrial membranes and displays some anti-ischemic properties when dosed in vitro at low concentration. Conversely, at higher doses it induces depolarization of the mitochondrial membrane and respiration uncoupling, which are typically associated to severe cytotoxicity. (Morin D. et al. Effect of the mitochondrial transition pore inhibitor, S-15176, on rat liver mitochondria: ATP synthase modulation and mitochondrial uncoupling induction. Biochemical Pharmacology, Pergamon, Oxford, GB, 72, 7, 911-91).

Hence there is a need to identify more potent and effective small molecule inhibitors of the MPTP having a different and more efficacious target within the MPTP which are useful in the prevention or therapy of diseases and conditions associated with the activity of the MPTP.

The acrylamido compounds of the present invention are small molecules endowed with potent MPT inhibitory activity, which are useful in the treatment of a variety of diseases such as those resulting from ischemia/reperfusion damage or oxidative damage, age-related diseases, degenerative and neurodegenerative diseases.

Certain acrylamido compounds are known in the art as therapeutic agents.

As an example, aryl and heteroaryl propene amides have been disclosed as antiproliferative, radioprotective and cytoprotective agents in the patent application WO 04/037751. Acrylamido compounds ligand of vanilloid receptor have been disclosed in the patent application WO 03/049702 as analgesics for the treatment of pain of various genesis and etiology. N-heterocyclyl amide compounds serotoninergic antagonists have been disclosed in the patent application WO 01/068585 for the treatment or prevention of central nervous system disorders.

In addition, certain caffeic acid anilides are also known in the art as anti-platelet aggregation and anti-oxidative agents, as reported in Bioorganic & Medicinal Chemistry 2005, 13(5), 1791-7.

SUMMARY OF THE INVENTION

The present invention is directed towards compounds that are endowed with MPT inhibiting activity and are useful in therapy as agents against a host of MPTP related diseases.

We have now discovered that acrylamido compounds of general formula (I), and derivatives thereof, are endowed with MTP inhibiting activity.

The present invention provides a compound of formula (I)

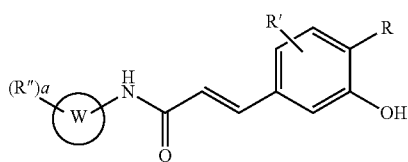

(I)

wherein:
W is aryl or heteroaryl;
a is 0, 1, 2, or 3;
R and R' are the same or different and, independently from each other, are selected from: hydrogen; halogen; (C1-C3) alkoxy; (C1-C2)haloalkoxy; (C1-C2)haloalkyl; NR$_1$R$_2$; CN; SO$_2$NH$_2$; or optionally substituted (C1-C6)alkyl, aryl or heteroaryl;
R" is independently selected from:
halogen; (C1-C3)alkyl; (C1-C3)alkoxy; (C1-C3)alkoxyalkyl; (C1-C2)haloalkoxy; (C1-C2)haloalkyl; NR$_3$R$_4$; or (CH$_2$)$_n$—X—(CH$_2$)$_m$-Q; wherein:
n, m independently, are 0, 1, or 2;
X is a direct bond; O; S; NH; N(C1-C3)alkyl;
Q is an optionally substituted aryl, heteroaryl, heterocycloalkyl or cycloalkyl;
R$_1$, R$_2$, R$_3$, and R$_4$ are the same or different and, independently from each other, are a hydrogen atom; a (C1-C3) alkyl or, taken together with the nitrogen atom to which they are attached, R$_1$—N—R$_2$ and R$_3$—N—R$_4$ may form a heterocyclic ring of formula:

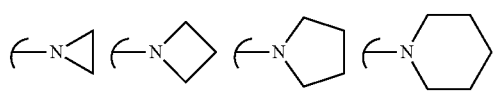

-continued

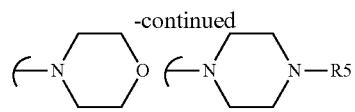

wherein:
R$_5$ is a hydrogen atom or a (C1-C3)alkyl group;
with the proviso that:
when W is phenyl, a is not 0;
when W is phenyl and R is hydrogen, R" is other than chlorine, methyl, isopropyl, CF$_3$ or NH$_2$;
when W is indazol-5-yl or pyrid-2-yl, R is other than hydrogen, (C1-C3)alkoxy;
as well as its isomers, tautomers, racemic forms, enantiomers, diastereomers, epimers, polymorphs, mixtures thereof, prodrugs, and the pharmaceutically acceptable salts thereof.

The present invention also relates to methods of synthesizing the acrylamido compounds of general formula (I), their prodrugs, and pharmaceutically acceptable salts.

The invention provides a process for the preparation of a compound of general formula (I), the process comprising:
(a) reacting a hydroxycinnamic acid of formula (II), wherein R and R' are as defined above, with an hydroxyl protecting agent, to give the corresponding protected compound of formula (III),

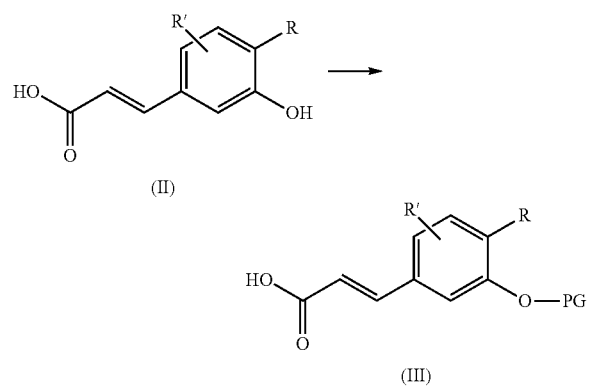

wherein R and R' are as defined above and PG is the said protecting group;
(b) activating the carboxyl moiety of a compound of formula (III), as defined above, towards amidation to give a compound of formula (V),

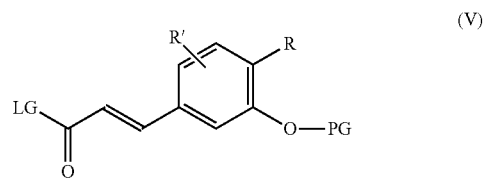

wherein R, R' and PG are as defined above and LG is any suitable activation group of the carboxyl moiety;
(c) acylating an amino compound of formula (IV), wherein W, R" and a are as defined above, with a compound of formula (V), as defined above, to give a compound of formula (VI), wherein R, R', R", W, a and PG are as defined above

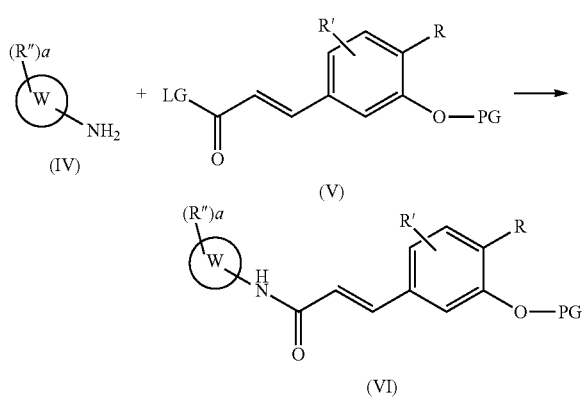

(d) removing the protecting group PG from a compound of formula (VI), as defined above, to obtain a compound of formula (I) and, if desired, converting a compound of formula (I) into another compound of formula (I), or converting a compound of formula (I) into a pharmaceutically acceptable salt or converting the salt thereof into the free compound of formula (I).

In another embodiment, the invention provides a process for the preparation of a compound of general formula (I), the process comprising:

(a) activating the carboxyl moiety of a compound formula (II), as defined above, towards amidation, to give a compound of formula (Va),

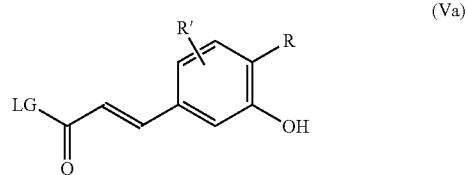

wherein R, R' and LG are as defined above;

(b) acylating an amino compound of formula (IV), as defined above, with a compound of formula (Va), as defined above, to give a compound of formula (I), wherein R, R', R", W and a are as defined above,

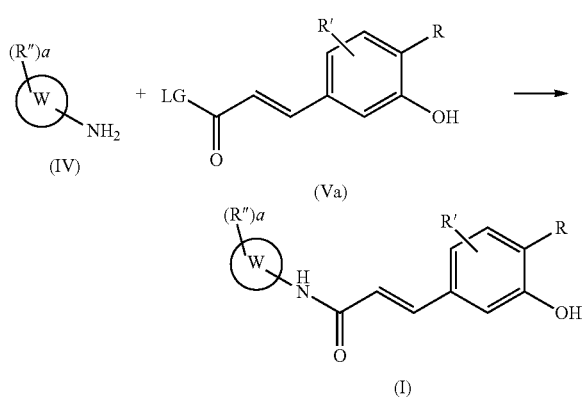

and, if desired, converting a compound of formula (I) into another compound of formula (I), or converting a compound of formula (I) into a pharmaceutically acceptable salt or converting the salt thereof into the free compound of formula (I).

In another embodiment, the invention provides a process for the preparation of a compound of general formula (I), the process comprising:

(a) acylating an amino compound of formula (VII), wherein W, R" are as defined above, a is 0, 1 or 2 and X is O or S, with a compound of formula (V), as defined above, to give a compound of formula (VIII), wherein R, R', R", W, a, X and PG are as defined above

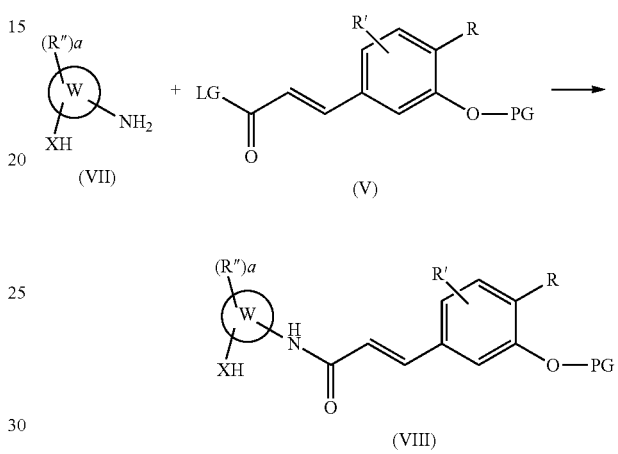

(b) alkylating a compound of formula (VIII), as defined above, with a compound of formula (IX), wherein Y is any suitable leaving group or a hydroxy group, m and Q are as defined above, to give a compound of formula (X), wherein R, R', R", W, a, m, X, Q and PG are as defined above

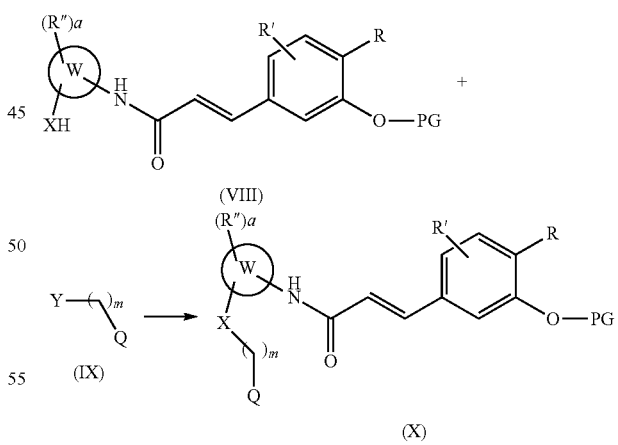

(c) removing the protecting group from a compound of formula (X), as defined above, to give a compound of formula (Ia), wherein R, R', R", W, a, m, X and Q are as defined above, and, if desired, converting a compound of formula (Ia) into another compound of formula (Ia), or converting a compound of formula (Ia) into a pharmaceutically acceptable salt or converting the salt thereof into the free compound of formula (Ia).

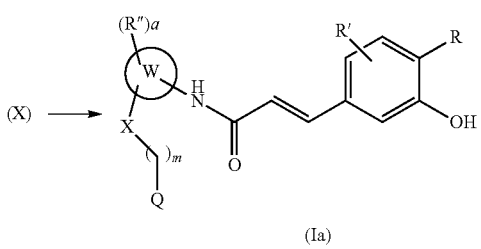

(Ia)

In another embodiment, the invention provides compounds of general formula (I), as defined above, as well as their isomers, racemic forms, tautomers, enantiomers, diastereomers, epimers, polymorphs, mixtures thereof, prodrugs and the pharmaceutically acceptable salts thereof, for use in therapy.

The present invention also relates to the use of the compounds of general formula (I) as defined above, as well as their isomers, racemic forms, tautomers, enantiomers, diastereomers, epimers, polymorphs, mixtures thereof, prodrugs and the pharmaceutically acceptable salts thereof, for the preparation of a medicament for the prevention and/or treatment of diseases and conditions associated with the activity of the MPTP.

The present invention also relates to the pharmaceutical compositions containing one or more compounds of general formula (I), as defined above, and/or prodrugs, and/or a pharmaceutically acceptable salt thereof, and at least one pharmaceutically acceptable excipient.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "aryl" refers to any aromatic carbocyclic ring system of 1 or 2 ring moieties, either fused or linked to each other through a single bond. Suitable aryl groups include, but are not limited to, phenyl, α- or β-naphthyl, biphenyl, indanyl, indenyl, and the like.

The term "heteroaryl" refers to monocyclic- or polycyclic aromatic rings comprising carbon atoms and one or more heteroatoms, preferably, 1 to 3 heteroatoms, independently selected from nitrogen, oxygen, and sulfur. As is well known to those skilled in the art, heteroaryl rings have less aromatic character than their all-carbon counter parts. Thus, for the purposes of the invention, a heteroaryl group need only have some degree of aromatic character. Illustrative examples of heteroaryl groups include, but are not limited to, furyl, benzofuranyl, benzodioxolyl, thienyl, pyridyl, pyridyl-N-oxide, pyrimidyl, pyrimidinyl, pyridazinyl, pyrazyl, pyrazinyl, pyrazolyl, oxazolyl, thiazolyl, isoxazolyl, quinolyl, (1,2,3,)- and (1,2,4)-triazolyl, tetrazolyl, triazinyl, pyridazinyl, pyrrolyl, imidazolyl, imidazo[1,2-a]pyridin-3-yl, indazolyl, isothiazolyl, indolyl, benzoimidazolyl, benzotriazolyl, benzoxazolyl, oxadiazolyl and the like.

The term "heterocycloalkyl" refers to a non-aromatic monocyclic or polycyclic ring comprising carbon and hydrogen atoms and at least one heteroatom, preferably, 1 to 4 heteroatoms selected from nitrogen, oxygen, and sulfur. A heterocycloalkyl group can have one or more carbon-carbon double bonds or carbon-heteroatoms double bonds in the ring as long as the ring is not rendered aromatic by their presence. Examples of heterocycloalkyl groups include, but are not limited to, aziridinyl, morpholinyl, thiomorpholinyl, piperidinyl, piperazinyl, thiazolidinyl, oxazolidinyl, tetrahydrothienyl, dihydrofuranyl, tetrahydrofuranyl, tetrahydrothiofuranyl, tetrahydropyranyl, pyrazolidinyl, 1,3-dioxolanyl, pyrrolidinyl, pyranyl, dihydropyranyl, isoxazolidinyl, imidazolidinyl and the like. A heterocycloalkyl group can be unsubstituted or substituted with one or two substituents.

The term "cycloalkyl" refers to any non-aromatic carbocyclic ring system of 1 or 2 ring moieties. A cycloalkyl group can have one or more carbon-carbon double bonds in the ring so long as the ring is not rendered aromatic by their presence. Examples of cycloalkyl groups include, but are not limited to, (C3-C7)cycloalkyl groups, such as cyclopropyl, cyclobutyl, cyclopentyl, cyclohexyl and cycloheptyl, and saturated cyclic and bicyclic terpenes and (C3-C7)cycloalkenyl groups, such as cyclopropenyl, cyclobutenyl, cyclopentenyl, cyclohexenyl and cycloheptenyl, and unsaturated cyclic and bicyclic terpenes.

The terms "(C1-C3)alkyl" or "(C1-C3)alkoxy" refer to any group such as methyl, ethyl, n-propyl, isopropyl, methoxy, ethoxy, n-propoxy and isopropoxy.

The term "(C1-C2)haloalkoxy" refers to a (C1-C2)alkoxy group substituted at the carbon atoms with one or more halogen atom. Such groups include, but are not limited to, trifluoromethoxy, difluoromethoxy, 2,2-difluoroethoxy, 2,2,2-trifluoroethoxy, 2-chloroethoxy, 1-fluoro-2,2,-dichloroethoxy, and the like.

The term "(C1-C2)haloalkyl" refers to a C1-C2 haloalkyl group, being in particular $CF_3$.

The term "halogen" refers to fluorine, chlorine, bromine or iodine atom.

The terms "alkyl", "(C1-C6)alkyl" or "alkoxy" refer, unless otherwise provided, to any straight or branched $C_1$-$C_6$ alkyl or alkoxy group, hence comprehensive of the aforementioned "(C1-C3)alkyl" or "(C1-C3)alkoxy" groups and also comprising n-butyl, iso-butyl, sec-butyl, tert-butyl, n-pentyl, n-hexyl, n-butoxy, iso-butoxy, sec-butoxy, tert-butoxy, n-pentyloxy, n-hexyloxy, and the like.

Any of the above (C1-C6)alkyl, aryl, heteroaryl, heterocycloalkyl, or cycloalkyl groups may be optionally further substituted in any of their free positions by one or more groups, for instance 1 to 6 groups, selected from: halogen, carboxy, cyano, alkyl, polyfluorinated alkyl, alkenyl, alkynyl, cycloalkyl, aryl, heteroaryl, alkyl-heteroaryl, heteroarylalkyl, amino-alkyl, amino groups and derivatives thereof, such as, for instance, alkylamino, dialkylamino, arylamino, diarylamino, ureido, alkylureido or arylureido; carbonylamino groups and derivatives thereof, such as, for instance, formylamino, alkylcarbonylamino, alkenylcarbonylamino, arylcarbonylamino, alkoxycarbonylamino; hydroxy groups and derivatives thereof, such as, for instance, alkoxy, polyfluorinated alkoxy, aryloxy, heteroaryloxy, alkylcarbonyloxy, arylcarbonyloxy, or cycloalkyloxy, heterocycloalkyloxi, aryl-alkoxi, heteroaryl-alkoxy; carbonyl groups and derivatives thereof, such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives, such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

The terms "alkenyl" or "alkynyl" refer, unless otherwise provided, any unsaturated straight or branched C2-C6 alkenyl or alkynyl group such as, for instance, vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

The terms "polyfluorinated alkyl" or "polyfluorinated alkoxy" refer to any straight or branched C1-C6 alkyl or alkoxy group as defined above, wherein more than one hydrogen atom is replaced by fluorine atoms such as, for instance, trifluoromethyl, trifluoromethoxy, 2,2,2-trifluoroethyl, 2,2,2-trifluoroethoxy, 1,2-difluoroethyl, 1,1,1,3,3,3-hexafluoropropyl-2-yl, and the like.

From all of the above, it is clear to the skilled man that any group which name has been identified as a composite name such as, for instance, cycloalkylalkyl, arylalkyl, heteroarylalkyl, alkylheteroaryl, (C1-C3)alkoxyalkyl, alkylthio, arylthio, amino-alkyl, alkylamino, dialkylamino, arylamino, diarylamino, alkylureido, arylureido, alkylcarbonylamino, alkenylcarbonylamino, arylcarbonylamino, aryloxy, arylalkyloxy, alkylcarbonyloxy, alkoxycarbonylamino; heteroaryloxy, arylcarbonyloxy, alkylideneaminoxy; alkylcarbonyl, arylcarbonyl, alkoxycarbonyl, aryloxycarbonyl, cycloalkyloxycarbonyl, aminocarbonyl, alkylaminocarbonyl, dialkylaminocarbonyl, alkylsulfonyl, arylsulfonyl, alkylsulfinyl, arylsulfinyl, arylsulfonyloxy, aminosulfonyl, alkylaminosulfonyl or dialkylaminosulfonyl and the like, has to be intended as conventionally construed from the parts to which they derive. So far, as an example, the term cycloalkylalkyl stands for a straight or branched alkyl group substituted by a cycloalkyl group, wherein alkyl and cycloalkyl are as defined above. Likewise, the term alkoxycarbonyl stands for a radical containing an alkoxy radical, as defined above, attached via an oxygen atom to a carbonyl radical.

The term "about" encompasses the range of experimental error that may typically occurs in a measurement.

The term "leaving group" as used herein, has the same meaning to the skilled man (Advanced Organic Chemistry: reactions, mechanisms and structure—Third Edition by Jerry March, John Wiley and Sons Ed.; 1985, page 179) and represents a group which is part of and attached to a substrate molecule; in a reaction where the substrate molecule undergoes a displacement reaction (with for example a nucleophile), the leaving group is then displaced. Preferred leaving groups are halogen, sulfonic esters, such as p-toluenesulfonate, p-bromobenzenesulfonate, p-nitrobenzenesulfonate, methanesulfonate, trifluoromethanesulfonate, . . . .

The term "pharmaceutically acceptable salts" refers to the relatively non-toxic mineral and organic acid-addition salts, and the base-addition salts, of the compounds of the present invention. These salts may be prepared in situ during the final isolation and purification of the compounds.

In particular, the acid-addition salts may be prepared by separately reacting the purified compound in its purified form with an organic or mineral acid and isolating the salt thus formed. The resulting salts are, for example, hydrochlorides, hydrobromides, sulfates, hydrogenosulfates, dihydrogenophosphates, citrates, maleates, fumarates, trifluoroacetates, 2-naphtalenesulfonates, para-toluenesulfonates.

The invention also relates to pharmaceutically acceptable salts with organic or inorganic bases. In particular, the basic-addition salts may be prepared by separately reacting the purified compound in its purified form with an organic or inorganic base and isolating the salt thus formed. The resulting salts are, for example, metal salts, particularly alkali metal salts, alkaline-earth metal salts and transition metal salts (such as sodium, potassium, calcium, magnesium, aluminum), or salts obtained with bases, such as ammonia or secondary or tertiary amines (such as diethylamine, triethylamine, piperidine, piperazine, morpholine), or with basic amino-acids, or with osamines (such as meglumine), or with aminoalcohols (such as 3-aminobutanol and 2-aminoethanol).

The present invention also relates to the all the isomers and their admixtures, tautomeric forms, racemic forms, enantiomers, diastereoisomers, epimers, as well as their crystalline forms, including their polymorphic forms, and mixtures thereof.

In cases when compounds may exist in tautomeric forms, each form is contemplated as being included within this invention whether existing in equilibrium or predominantly in one form.

The present invention is directed not only to racemic mixtures of these compounds, but also to individual stereoisomers and/or diastereoisomers thereof, as well or as mixtures of these in all proportions.

Likewise, the metabolites and the pharmaceutically acceptable bio-precursors (otherwise referred to as prodrugs) of the compounds of formula (I) are included within the scope of, and suitable for use in, the present invention.

So-called "prodrugs" of the compounds of formula (I) are also within the scope of the invention. A "prodrug" is a compound which is metabolically converted to a therapeutically active compound after administration. The term "prodrug" should be interpreted as broadly herein as is generally understood in the art. While not intending to limit the scope of the invention, conversion may occur by in vivo hydrolysis of biologically labile groups. For example, a compound comprising a hydroxy group may be administered as an ester that is converted by hydrolysis in vivo to the hydroxy compound. Thus certain derivatives of compounds of formula (I), which may have little or no pharmacological activity themselves can, when administered into the body, be converted into compounds of formula (I) having the desired activity, for example, by hydrolytic cleavage.

Prodrugs in accordance with the invention can, for example, be produced by replacing appropriate functionalities present in the compounds of formula (I) with certain moieties known to those skilled in the art as pro-moieties as described, for example, in Design of Prodrugs by H. Bundgaard (Elsevier, 1985) or in Prodrugs: design and clinical applications by Jarkko Rautio et al. (Nature reviews drug discovery, volume 7, March 2008, 255-270).

Non limiting examples of prodrugs include:

i) a carboxylic ester of a phenolic moiety of compounds of formula (I);

ii) a phosphate ester of a phenolic moiety of compounds of formula (I);

iii) a phosphonooxymethyl ether of a phenolic moiety of compounds of formula (I);

iv) a carbamate derivative a phenolic moiety of compounds of formula (I).

Preferred prodrugs are a carboxylic or a a phosphate ester of a phenolic moiety of compounds of formula (I). While not intending to be limiting, an ester may be an alkyl ester, an aryl ester, a heteroaryl ester or an inorganic ester.

Acrylamido derivatives according to the invention have the following formula (I):

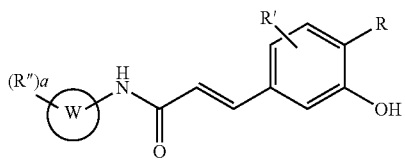

wherein R, R', R", a and W are as defined above.

In a preferred embodiment, the invention provides acrylamido derivatives of formula (I),
wherein:
W is a phenyl ring substituted by 1 or 2 groups R";
R is halogen; (C1-C3)alkoxy; (C1-C3)alkyl;
R' is hydrogen;
R" is independently selected from: halogen; (C1-C3)alkoxyalkyl; (C1-C2)haloalkyl; or $(CH_2)_n$—X—$(CH_2)_m$-Q,
  wherein:
  n is 0 or 1;
  m is 0 or 1;
  X is O; S; NH; N(C1-C3)alkyl;
  Q is aryl or heteroaryl.
Even more preferably,
R is fluorine; methoxy; methyl;
R" is halogen or $(CH_2)_n$—X—$(CH_2)_m$-Q, wherein:
  n and m are chosen in a way that their sum (n+m) is equal to 1;
  X is O;
  and Q is aryl or heteroaryl;
as well as its isomers, tautomers, racemic forms, enantiomers, diastereomers, epimers, polymorphs, mixtures thereof, prodrugs and the pharmaceutically acceptable salts thereof.

In another preferred embodiment, the invention provides acrylamido derivatives of formula (I),
wherein:
W is a bicyclic aryl or a bicyclic heteroaryl ring, optionally substituted by 1 or 2 groups R";
R is halogen; (C1-C3)alkoxy; (C1-C3)alkyl;
R' is hydrogen;
R" are independently selected from:
  halogen; (C1-C2)haloalkyl; 4-(C1-C3)alkylpiperazin-1-yl or $(CH_2)_n$—X—$(CH_2)_m$-Q,
  wherein:
  n is 0 or 1;
  m is 0 or 1;
  X is O; S; NH; N(C1-C3)alkyl;
  Q is aryl or heteroaryl.
Even more preferably,
W is a bicyclic aryl or a bicyclic heteroaryl ring, unsubstituted or substituted by one group $(CH_2)_n$—X—$(CH_2)_m$-Q,
  wherein:
  n and m are chosen in a way that their sum (n+m) is equal to 1;
  X is O;
  Q is aryl or heteroaryl;
  and optionally substituted by a second group R" selected from chlorine; bromine; (C1-C2)haloalkyl; 4-(C1-C3)alkylpiperazin-1-yl;
R is fluorine; methoxy; methyl;
as well as its isomers, tautomers, racemic forms, enantiomers, diastereomers, epimers, polymorphs, mixtures thereof, prodrugs and the pharmaceutically acceptable salts thereof.

For a reference to any specific compound of formula (I) of the invention, optionally in the form of a pharmaceutically acceptable salt, see the following experimental section.

Specific, non limiting examples of compounds of formula (I) are shown in the following list:
(E)-3-(3-Hydroxy-4-methoxy-phenyl)-N-naphthalen-1-yl-acrylamide;
(E)-N-(2-Benzyloxy-phenyl)-3-(3-hydroxy-4-methoxy-phenyl)-acrylamide;
(E)-3-(3-Hydroxy-4-methoxy-phenyl)-N-[3-(4-methyl-piperazin-1-yl)-phenyl]-acrylamide;
(E)-N-(2-Chloro-pyridin-4-yl)-3-(3-hydroxy-4-methoxy-phenyl)-acylamide;
(E)-N-(3-Chloro-2-methoxy-phenyl)-3-(3-hydroxy-4-methoxy-phenyl)-acrylamide;
(E)-N-(3,4-Dichloro-phenyl)-3-(3-hydroxy-4-methoxy-phenyl)-acrylamide;
(E)-N-(3-Chloro-4-methoxy-phenyl)-3-(3-hydroxy-4-methoxy-phenyl)-acrylamide;
(E)-N-(2,3-Dichloro-phenyl)-3-(3-hydroxy-4-methoxy-phenyl)-acrylamide;
(E)-N-(3-Benzylamino-phenyl)-3-(3-hydroxy-4-methoxy-phenyl)-acrylamide;
(E)-N-[3-(Benzyl-methyl-amino)-phenyl]-3-(3-hydroxy-4-methoxy-phenyl)-acrylamide;
(E)-N-[2-Chloro-3-(pyridin-4-ylmethoxy)-phenyl]-3-(3-hydroxy-4-methoxy-phenyl)-acrylamide hydrochloride;
(E)-3-(3-Hydroxy-4-methoxy-phenyl)-N-{3-[(pyridin-4-ylmethyl)-amino]-phenyl}-acrylamide;
(E)-N-(3-Benzyloxy-2-chloro-phenyl)-3-(3-hydroxy-4-methoxy-phenyl)-acrylamide;
(E)-N-(2-Benzyloxy-3-chloro-phenyl)-3-(3-hydroxy-4-methoxy-phenyl)-acrylamide
(E)-N-(1-Benzyl-1H-indol-4-yl)-3-(3-hydroxy-4-methoxy-phenyl)-acrylamide;
(E)-N-[3-Chloro-2-(pyridin-4-ylmethoxy)-phenyl]-3-(3-hydroxy-4-methoxy-phenyl)-acrylamide;
(E)-N-[4-Chloro-3-(pyridin-4-ylmethoxy)-phenyl]-3-(3-hydroxy-4-methoxy-phenyl)-acrylamide;
(E)-3-(3-Hydroxy-4-methoxy-phenyl)-N-(1-methyl-1H-indol-4-yl)-acrylamide;
(E)-N-(1-Benzyl-1H-indol-7-yl)-3-(3-hydroxy-4-methoxy-phenyl)-acrylamide;
(E)-3-(3-Hydroxy-4-methoxy-phenyl)-N-[3-(3-methyl-3H-imidazol-4-ylmethoxy)-phenyl]-acrylamide;
(E)-3-(4-Fluoro-3-hydroxy-phenyl)-N-(2-phenoxymethyl)-acrylamide
(E)-3-(3-Hydroxy-4-methoxy-phenyl)-N-[3-(1H-imidazol-4-ylmethoxy)-phenyl]-acrylamide hydrochloride;
(E)-3-(3-Hydroxy-4-methoxy-phenyl)-N-[3-(pyridin-4-ylmethoxy)-phenyl]-acrylamide hydrochloride;
(E)-3-(3-Hydroxy-4-methoxy-phenyl)-N-(3-oxazol-5-yl-phenyl)-acrylamide;
(E)-3-(3-Hydroxy-4-methoxy-phenyl)-N-indan-yl-acrylamide;
(E)-N-(2-Benzylsulfanyl-phenyl)-3-(3-hydroxy-4-methoxy-phenyl)-acrylamide;
(E)-3-(3-Hydroxy-4-methoxy-phenyl)-N-(1-methyl-1H-benzimidazol-2-yl)-acrylamide hydrochloride;
(E)-3-(3-Hydroxy-4-methoxy-phenyl)-N-(2-phenoxyethyl-phenyl)-acrylamide;
(E)-N-Benzoxazol-4-yl-3-(3-hydroxy-4-methoxy-phenyl)-acrylamide;
(E)-N-(1-Benzyl-1H-benzimidazol-4-yl)-3-(3-hydroxy-4-methoxy-phenyl)-acrylamide;
(E)-3-(3-Hydroxy-4-methoxy-phenyl)-N-(1-methyl-1H-benzimidazol-4-yl)-acrylamide hydrochloride;

(E)-N-(1-Benzyl-1H-indazol-7-yl)-3-(3-hydroxy-4-methoxy-phenyl)-acrylamide;
(E)-3-(3-Hydroxy-4-methoxy-phenyl)-N-(1-methyl-1H-benzotriazol-4-yl)-acrylamide
(E)-N-(1-Benzyl-1H-indazol-4-yl)-3-(3-hydroxy-4-methoxy-phenyl)-acrylamide hydrochloride;
(E)-N-(1-Benzyl-2H-indazol-7-yl)-3-(3-hydroxy-4-methoxy-phenyl)-acrylamide;
(E)-3-(3-Hydroxy-4-methoxy-phenyl)-N-(2-methyl-2H-benzimidazol-7-yl)-acrylamide;
(E)-N-[3-(2,5-Dimethyl-2H-pyrazol-3-ylmethoxy)-phenyl]-3-(3-hydroxy-4-methoxy-phenyl)-acrylamide;
(E)-3-(3-Hydroxy-4-methoxy-phenyl)-N-[3-(1-methyl-1H-imidazol-2-ylmethoxy)-phenyl]-acrylamide;
(E)-3-(3-Hydroxy-4-methoxy-phenyl)-N-[2-(3-methoxy-phenoxymethyl)-phenyl]-acrylamide;
(E)-3-(3-Hydroxy-4-methoxy-phenyl)-N-[2-(3-methoxy-phenoxymethyl)-phenyl]-acrylamide;
(E)-3-(3-Hydroxy-4-methoxy-phenyl)-N-[2-(3-methoxy-phenoxymethyl)-phenyl]-acrylamide;
(E)-N-(2-Cyclobutoxymethyl-phenyl)-3-(3-hydroxy-4-methoxy-phenyl)-acrylamide;
(E)-3-(3)-Hydroxy-4-methoxy-phenyl)-N-[2-(pyridin-4-yloxymethyl)-phenyl]-acrylamide hydrochloride;
(E)-N-[2-(4-Fluoro-phenoxymethyl)-phenyl]-3-(3-hydroxy-4-methoxy-phenyl)-acrylamide;
(E)-3-(3)-Hydroxy-4-methoxy-phenyl)-N-[2-(4-imidazol-1-yl-phenoxymethyl)-phenyl]-acrylamide;
(E)-N-[2-(2-Fluoro-phenoxymethyl)-phenyl]-3-(3-hydroxy-4-methoxy-phenyl)-acrylamide;
(E)-3-(3-Hydroxy-4-methoxy-phenyl)-N-(2-methoxymethyl-phenyl)-acrylamide;
(E)-N-[2-(3-Fluoro-phenoxymethyl)-phenyl]-3-(3-hydroxy-4-methoxy-phenyl)-acrylamide; hydrochloride;
(E)-N-(3-Bromo-phenyl)-3-(4-fluoro-3-hydroxy-phenyl)-acrylamide;
(E)-N-(2-Benzyloxy-phenyl)-3-(4-fluoro-3-hydroxy-phenyl)-acrylamide;
(E)-N-(2,3-Dichloro-phenyl)-3-(4-fluoro-3-hydroxy-phenyl)-acrylamide;
(E)-N-(1-Benzyl-1H-indol-7-yl)-3-(4-fluoro-3-hydroxy-phenyl)-acrylamide;
(E)-N-(3-Fluoro-phenyl)-3-(3-hydroxy-4-methoxy-phenyl)-acrylamide;
(E)-N-(3-Chloro-phenyl)-3-(3-hydroxy-phenyl)-acrylamide;
(E)-N-(3-Chloro-phenyl)-3-(3-hydroxy-4-methoxy-phenyl)-acrylamide;
(E)-N-(2-Chloro-phenyl)-3-(3-hydroxy-4-methoxy-phenyl)-acrylamide;
(E)-N-(4-Chloro-phenyl)-3-(3-hydroxy-4-methoxy-phenyl)-acrylamide;
(E)-3-(3-Hydroxy-1-ethoxy-phenyl)-N-(3-iodo-phenyl)-acrylamide;
(E)-N-(3-Bromo-phenyl)-3-(3-Hydroxy-4-methoxy-phenyl)-acrylamide;
(E)-3-(3-Hydroxy-4-methoxy-phenyl)-N-(3-isopropoxy-phenyl)-acylamide;
(E)-3-(3-Hydroxy-4-methoxy-phenyl)-N-(3-phenoxy-phenyl-acrylamide;
(E)-N-(3-Benzyloxy-phenyl)-3-(3-hydroxy-4-methoxy-phenyl)-acrylamide;
(E)-3-(3-Hydroxy-4-methoxy-phenyl)-N-(3-methoxy-phenyl)-acrylamide;
(E)-3-(3-Hydroxy-4-methoxy-phenyl)-N-(3-trifluoromethyl-phenyl)-acrylamide;
(E)-3-(3-Hydroxy-4-methoxy-phenyl)-N-[3-(pyridin-4-ylmethoxy)-phenyl]-acrylamide
(E)-3-(3-Hydroxy-4-methoxy-phenyl)-N-[3-(1-methyl-piperidin-3-ylmethoxy)-phenyl]-acrylamide;
(E)-3-(3-Hydroxy-4-methoxy-phenyl)-N-[3-(pyridin-4-yloxy)-phenyl]-acrylamide
(E)-N-(3,5-Dichloro-phenyl)-3-(3-hydroxy-4-methoxy-phenyl)-acrylamide;
(E)-3-Hydroxy-4-methoxy-phenyl)-N-[3-(1-methyl-piperidin-4-yloxy)-phenyl]-acrylamide;
(E)-N-(4-Benzyloxy-phenyl)-3-(3-hydroxy-4-methoxy-phenyl)-acrylamide;
(E)-N-(3-Chloro-phenyl)-3-(3-hydroxy-4-methyl-phenyl)-acrylamide;
(E)-3-(4-Fluoro-3-hydroxy-phenyl)-N-naphthalen-1-yl-acrylamide;
(E)-3-(3-Hydroxy-4-methoxy-phenyl)-N-(4-methoxy-pyrimidin-2-yl)-acrylamide;
(E)-3-(3-Hydroxy-4-methoxy-phenyl)-N-[3-(1H-tetrazol-5-ylmethoxy)phenyl]-acrylamide;
(E)-N-(3-Chloro-phenyl)-3-(4-fluoro-3-hydroxy-phenyl)-acrylamide;
(E)-3-(3-Hydroxy-4-methoxy-phenyl)-N-(2-phenethyloxy-phenyl)-acrylamide;
(E)-3-(3-Hydroxy-4-methoxy-phenyl)-N-[2-(pyridin-4-ylmethoxy)-phenyl]-acrylamide hydrochloride;
(E)-3-(4-Fluoro-3-hydroxy-phenyl)-N-[3-(pyridin-4-ylmethoxy)-phenyl]-acrylamide hydrochloride;
(E)-3-(3-Hydroxy-4-methoxy-phenyl)-N-[2-(pyridin-4-ylmethylsulfanyl)-phenyl]-acrylamide hydrochloride;
(E)-N-1,3-Benzodioxol-5-yl-3-(3-hydroxy-4-methoxy-phenyl)-acrylamide;
(E)-3-(3-Hydroxy-4-methoxy-phenyl)-N-(1-methyl-1H-indazol-7-yl)-acrylamide;
(E)-N-(4-Ethoxy-1-methyl-1H-indazol-7-yl)-3-(3-hydroxy-4-methoxy-phenyl)-acrylamide;
(E)-3-(3-Hydroxy-4-methoxy-phenyl)-N-(1-methyl-1H-indazol-4-yl)-acrylamide;
(E)-3-(3-Hydroxy-4-methoxy-phenyl)-N-[3-(5-methyl-furan-2-ylmethoxy)-phenyl]-acrylamide;
(E)-3-(3-Hydroxy-4-methoxy-phenyl)-N-[3-(pyridin-3-ylmethoxy)-phenyl]-acrylamide;
(E)-3-(3-Hydroxy-1-ethoxy-phenyl)-N-(3-phenethyloxy-phenyl)-acylamide;
(E)-3-(3-Hydroxy-4-methoxy-phenyl)-N-[3-(pyridin-2-ylmethoxy)-phenyl]-acrylamide;
(E)-N-(5-Chloro-2-phenoxymethyl-phenyl)-3-(3-hydroxy-4-methoxy-phenyl)-acrylamide;
(E)-3-(3-Hydroxy-4-methoxy-phenyl)-N-[4-(4-methyl-piperazin-1-yl)-2-phenoxymethyl-phenyl]-acrylamide hydrochloride;
(E)-3-(3-Hydroxy-4-methoxy-phenyl)-N-[2-(3-trifluoromethyl-phenoxymethyl)-phenyl]-acrylamide;
(E)-3-(3-Hydroxy-4-methoxy-phenyl)-N-[2-(3-chloro-phenoxymethyl)-phenyl]-acrylamide;
(E)-3-(3-Hydroxy-4-methoxy-phenyl)-N-[2-(4-morpholin-4-ylmethyl-phenoxymethyl)-phenyl]-acrylamide hydrochloride;
(E)-3-(4-Fluoro-3-hydroxy-phenyl)-N-{2-[4-(1-methyl-piperidin-4-yloxy)-phenoxymethyl]-phenyl}-acrylamide trifluoroacetate;
(E)-3-(3-Hydroxy-4-methoxy-phenyl)-N-[2-(2-trifluoromethyl-phenoxymethyl)-phenyl]-acrylamide;
(E)-3-(3-Hydroxy-4-methoxy-phenyl)-N-{2-[3-piperidin-4-yloxy)-phenoxymethyl]-phenyl}-acrylamide;

(E)-3-(3-Hydroxy-4-methoxy-phenyl)-N-{2-[4-piperidin-4-yloxy)-phenoxymethyl]-phenyl}-acrylamide hydrochloride;

(E)-3-(4-Chloro-3-hydroxy-phenyl)-N-{2-[3-piperidin-4-yloxy)-phenoxymethyl]-phenyl}-acrylamide;

(E)-3-(3-Hydroxy-4-methoxy-phenyl)-N-{2-[4-(1-methyl-piperidin-4-yl)-phenoxymethyl]-phenyl}-acrylamide;

(E)-3-(3-Hydroxy-4-methoxy-phenyl)-N-{2-[2-(4-methyl-piperazin-1-yl)-phenoxymethyl]-phenyl}-acrylamide;

(E)-3-(3-Hydroxy-4-methoxy-phenyl)-N-{2-[3-(1-methyl-piperidin-4-yloxy)phenoxymethyl]-phenyl}-acrylamide hydrochloride;

(E)-3-(4-Chloro-3-hydroxy-phenyl)-N-(3-chloro-phenyl)-acrylamide;

(E)-3-(3-Hydroxy-4-methoxy-phenyl)-N-{2-[3-(4-methyl-imidazol-1-yl)-phenoxymethyl]-phenyl}-acrylamide;

(E)-3-(2-Chloro-3-hydroxy-methoxy-phenyl)-N-(3-chloro-phenyl)-acrylamide;

(E)-3-(4-Fluoro-3-hydroxy-phenyl)-N-[3-(pyridin-4-ylmethylsulfanyl)-phenyl]-acrylamide;

(E)-N-(1-Benzyl-1H-indazol-7-yl)-3-(4-fluoro-3-hydroxy-phenyl)-acrylamide;

(E)-3-(3-Hydroxy-4-methoxy-phenyl)-N-{2-[4-(1-methyl-piperidin-4-yloxy)-phenoxymethyl]-phenyl}-acrylamide hydrochloride;

(E)-N-(3-Benzyl-3H-benzimidazol-4-yl)-3-(4-fluoro-3-hydroxy-phenyl)-acylamide;

(E)-3-(3-Hydroxy-4-methoxy-phenyl)-N-[2-(4-trifluoromethyl-phenoxymethyl)-phenyl]-acrylamide;

(E)-N-[2-(2-Chloro-phenoxymethyl)-phenyl]-3-(3-hydroxy-4-methoxy-phenyl)-acrylamide; acrylamide;

(E)-3-(4-Fluoro-3-hydroxy-phenyl)-N-[1-(4-imidazol-1-yl-benzyl)-1H-indol-7-yl]-acrylamide;

(E)-3-(3-Hydroxy-4-methoxy-phenyl)-N-{2-[4-(1-methyl-piperidin-4-ylmethyl)-phenoxymethyl]-phenyl}-acrylamide;

(E)-3-(3-Hydroxy-4-methoxy-phenyl)-N-{2-[3-(4-methyl-piperazin-1-yl)-phenoxymethyl]-phenyl}-acrylamide hydrochloride;

(E)-3-(3-Hydroxy-4-methoxy-phenyl)-N-{2-[4-(4-methyl-imidazol-1-yl)-phenoxymethyl]-phenyl}-acrylamide hydrochloride;

(E)-N-(1-Benzyl-2-oxo-2,3-dihydro-1H-indol-7-yl)-3-(3-hydroxy-4-methoxy-phenyl)-acrylamide;

(E)-N-(3-Chloro-naphthalen-1-yl)-3-(3-hydroxy-4-methoxy-phenyl)-acrylamide;

(E)-3-(3-Hydroxy-4-methoxy-phenyl)-N-[2-(2-methyl-2-pyrazol-3-yloxymethyl)-phenyl]-acrylamide;

(E)-3-(3-Hydroxy-4-methoxy-phenyl)-N-[2-(3-piperazin-1-yl-phenoxymethyl)-phenyl]-acrylamide;

(E)-3-(3-Hydroxy-4-methoxy-phenyl)-N-[1-(1-methyl-1H-imidazol-4-ylmethyl)-1H-indol-7-yl]-acrylamide;

(E)-3-(3-Hydroxy-4-methoxy-phenyl)-N-[1-(1-methyl-1H-pyrazol-3-ylmethyl)-1H-indol-7-yl]-acrylamide;

(E)-3-(3-Hydroxy-phenyl)-N-(2-phenoxymethyl-phenyl)-acrylamide;

(E)-N-(3-Chloro-phenyl)-3-(2,4-difluoro-3-hydroxy-phenyl)-acrylamide;

(E)-3-(3-Hydroxy-4-methoxy-phenyl)-N-[2-(4-pyrrolidin-1-ylmethyl-phenoxymethyl)-phenyl]-acrylamide hydrochloride;

(E)-3-(3-Hydroxy-4-methoxy-phenyl)-N-{2-[4-(4-methyl-piperazin-1-ylmethyl)-phenoxymethyl]-phenyl}-acrylamide;

(E)-3-(3-Hydroxy-4-methoxy-phenyl)-N-[2-(4-piperidin-1-ylmethyl-phenoxymethyl)-phenyl]-acrylamide trifluoroacetate;

(E)-3-(3-Hydroxy-4-methoxy-phenyl)-N-{1-[3-(1-methyl-piperidin-4-yloxy)-benzyl]-1H-indol-7-yl}-acrylamide;

(E)-3-(3-Hydroxy-4-methoxy-phenyl)-N-{2-[2-(1-methyl-piperidin-4-yloxy)-phenoxymethyl]-phenyl}-acrylamide (E)-3-(3-Hydroxy-4-methoxy-phenyl)-N-(2-[3-(1-methyl-piperidin-4-yl)-phenoxymethyl]-phenyl)-acrylamide;

(E)-3-(3-Hydroxy-4-methoxy-phenyl)-N-{2-[4-(4-methyl-piperazin-1-yl)-phenoxymethyl]-phenyl}-acrylamide trifluoroacetate;

(E)-3-(4-Fluoro-3-hydroxy-phenyl)-N-[2-(4-imidazol-1-yl-phenoxymethyl)-phenyl]-acrylamide;

(E)-3-(2,4-Difluoro-3-hydroxy-phenyl)-N-{2-[3-(1-methyl-piperidin-4-yloxy)-phenoxymethyl]-phenyl}-acrylamide;

(E)-3-(2-Chloro-3-hydroxy-4-methoxy-phenyl)-N-{2-[3-(1-ethyl-piperidin-4-yloxy)-phenoxymethyl]-phenyl}-acrylamide;

(E)-N-(3-Chloro-phenyl)-3-(4-cyano-3-hydroxy-phenyl)-acrylamide;

(E)-3-(4-Cyano-3-hydroxy-phenyl)-N-{2-[3-(1-methyl-piperidin-4-yloxy)-phenoxymethyl]-phenyl}-acrylamide;

(E)-3-(2,4-Difluoro-3-hydroxy-phenyl)-N-{2-[3-(piperidin-4-yloxy)-phenoxymethyl]-phenyl)}-acrylamide;

(E)-3-(2,4-Difluoro-3-hydroxy-phenyl)-N-{2-[4-(1-methyl-piperidin-4-yloxy)-phenoxymethyl]-phenyl}-acrylamide;

(E)-3-(2,4-Difluoro-3-hydroxy-phenyl)-N-{2-[4-(piperidin-4-yloxy)-phenoxymethyl]-phenyl}-acrylamide;

(E)-3-(2-Chloro-3-hydroxy-4-methoxy-phenyl)-N-{2-[3-(piperidin-4-yloxy)-phenoxymethyl]-phenyl}-acrylamide;

(E)-3-(4-Cyano-3-hydroxy-phenyl)-N-{2-[3-(piperidin-4-yloxy)-phenoxymethyl]-phenyl}-acrylamide;

(E)-3-(4-Cyano-3-hydroxy-phenyl)-N-{2-[4-(1-methyl-piperidin-4-yloxy)-phenoxymethyl]-phenyl}-acrylamide;

(E)-N-(3-Benzyl-3H-benzoimidazol-4-yl)-3-(3-hydroxy-4-methoxy-phenyl)-acrylamide;

(E)-N-[2-(4-Chloro-phenoxymethyl)-phenyl]-3-(3-hydroxy-4-methoxy-phenyl)-acrylamide;

(E)-N-(3-Chloro-phenyl)-3-(3-hydroxy-4-sulfamoyl-phenyl)-acrylamide;

Sodium (E)-5-(3-(3-chlorophenylamino)-3-oxoprop-1-enyl)-2-methoxyphenyl phosphate;

(E)-3-(3-Hydroxy-4-methoxy-phenyl)-N-[1-(3-methyl-3H-imidazol-4-ylmethyl)-1H-indol-7-yl]-acrylamide;

(E)-N-(3-Chloro-phenyl)-3-(4-amino-3-hydroxy-phenyl)-acrylamide.

As well as isomers, tautomers, racemic forms, enantiomers, diastereomers, polymorphs, mixtures, prodrugs and the pharmaceutically acceptable salts thereof.

The present invention also relates to processes for the preparation of a compound of general formula (I), as defined above, according to the following methods (Method A and Method B), that can be carried out according to methods well known to a person skilled in the art.

The following processes are given for representative purposes. Depending on the nature of the compounds of the formula (I) to be obtained, the methodologies presented may be adapted by a person skilled in the art by selecting the appropriate starting materials, in which the nature of the substituents R, R', R" and W may be modified.

A further object of the present invention is represented by the process for preparing the compounds of formula (I), prodrugs and the pharmaceutically acceptable salts thereof (Method A), which process comprises:

(a) reacting a hydroxycinnamic acid of formula (II), wherein R and R' are as defined above in formula (I), with an hydroxyl protecting agent, to give the corresponding protected compound of formula (III),

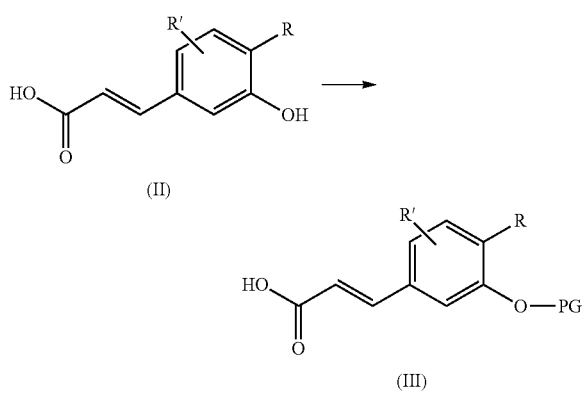

wherein R and R' are as defined above and PG is the said protecting group;

(b) activating the carboxyl moiety of a compound formula (III) towards amidation to give a compound of formula (V),

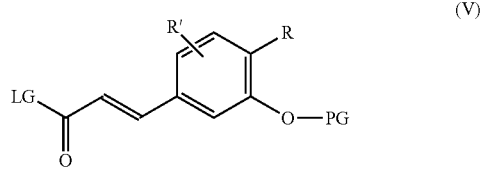

wherein LG represents any suitable activation group of the carboxyl moiety and R, R' and PG are as defined above in formula (III);

(c) acylating the amino compound of formula (IV), wherein W, R" and a are as defined above in formula (I), with a compound of formula (V) to give a compound of formula (VI), wherein R, R', R", W, a and PG are as defined above

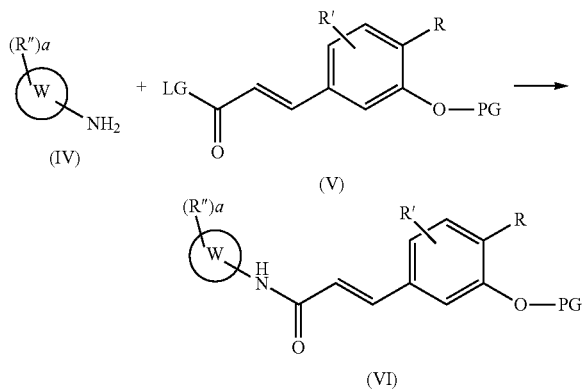

(d) removing the protecting group PG from a compound of formula (VI) to obtain a compound of formula (I) and, whenever desired, converting a compound of formula (I) into another compound of formula (I), or converting a compound of formula (I) into a pharmaceutically acceptable salt or converting the salt thereof into the free compound of formula (I).

According to step (a) of the process, the protection of the phenolic hydroxyl of a compound of formula (II) can be accomplished with different methods well known to a person skilled in the art (Theodora W. Greene, Peter G. M. Wuts, Protective Groups in Organic Synthesis, Wiley-Interscience). As an example, a compound of formula (II) can be treated with an acyl chloride or a carboxylic anhydride in the presence of a base, to obtain the corresponding phenolic ester. The reaction is carried out in a suitable solvent such as polar aprotic solvents, for instance, dichloromethane, tetrahydrofuran, 1,4-dioxane, N,N'-dimethylformamide, in the presence of a base, such as sodium or potassium hydride or potassium tert-butylate, at a temperature ranging from room temperature to the reflux temperature of the solvent, for a time varying from about 30 minutes to 18 hours.

Preferably, step (a) is carried out by reaction of a compound of formula (II) with acetic anhydride in the presence of a metallic hydride, such as sodium or potassium hydride, in tetrahydrofuran or 1,4-dioxane, at a temperature ranging from room temperature to reflux temperature.

According to step (b) of the process, the thus obtained phenol-protected carboxylic acid derivative of formula (III) is coupled with an aniline of formula (IV), by working according to methods well known to a person skilled in the art for the preparation of carboxamido derivatives. For example, the carboxylic acid (III) is intermediately converted into a suitable acylating agent (V), such as an acyl chloride, which is then used in the amidation reaction. Typically, within the compounds of formula (V), R" represents a halogen atom and, even more preferably, a chlorine atom.

The coupling reaction is carried out in a suitable solvent such as polar aprotic solvents, for instance, tetrahydrofuran, 1,4-dioxane, dimethylformamide, dichloromethane, or mixtures thereof, at a temperature ranging from about 0° C. to reflux and for a time varying from about 30 minutes up to 96 hours, if needed in the presence of a suitable proton scavenger, such as triethylamine, N,N-diisopropylethylamine or pyridine.

According to step (d) of the process, the phenolic protecting group of a compound of formula (VI) is selectively removed to yield the corresponding phenol of formula (I).

Depending on the nature of the protecting group, its removal can be carried out in different conditions, such as, for example, acid or alkaline hydrolisis, hydrogenolysis, or treatment with fluoride salts. Preferably, within the compounds of formula (VI), PG represents a phenolic ester that is conveniently hydrolised either in acid or basic conditions. Typically, acid hydrolisis can be carried out by treatment with hydrochloric, methansulfonic, trifluoroacetic acid and the like in a suitable solvent, such as polar aprotic solvents, for instance, dichloromethane, or polar protic solvents, for instance, methanol, or ethanol at a temperature ranging from about 0° C. to room temperature for a time varying from about 15 minutes up to 24 hours.

Alternatively, the compound of formula (VI) is deprotected under basic conditions and by working according to conventional techniques, for instance, by treatment with aqueous sodium or potassium hydroxide in the presence of a suitable co-solvent, such as polar protic solvents, for instance, methanol, ethanol, or polar aprotic solvents, for instance, dimethylformamide, 1,4-dioxane, or by treatment with a tertiary amine, such as triethylamine or N,N-diisopropylethylamine and by using an alcohol, like methanol or ethanol, as the solvent.

Deprotection may occur at a temperature ranging from about 0° C. to reflux temperature of the solvent, for a time varying from about 30 minutes up to 72 hours.

As said above, it is clear to the skilled person that, depending on the chemical reactivity of the derivatives of formulae (II) and (IV), the above protection/deprotection steps, step (a) and step (d), of the phenolic moiety can be in certain cases conveniently avoided, thus allowing the direct coupling of a carboxylic acid (II) with an aniline (IV), in the conditions above described for step (b), to directly produce the corresponding derivative of formula (I).

So, according to a further embodiment of the present invention, the process for preparing the compounds of formula (I), prodrugs and the pharmaceutically acceptable salts thereof comprises:

(a) activating the carboxyl moiety of a compound formula (II), as defined above, towards amidation, to give a compound of formula (Va),

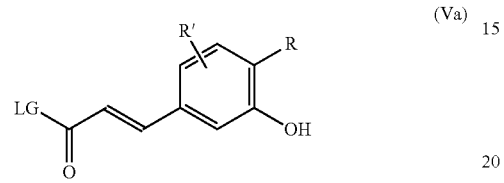

wherein R, R' and LG are as defined above;

(b) acylating the amino compound of formula (IV), as defined above, with a compound of formula (Va) to give a compound of formula (I), as defined above,

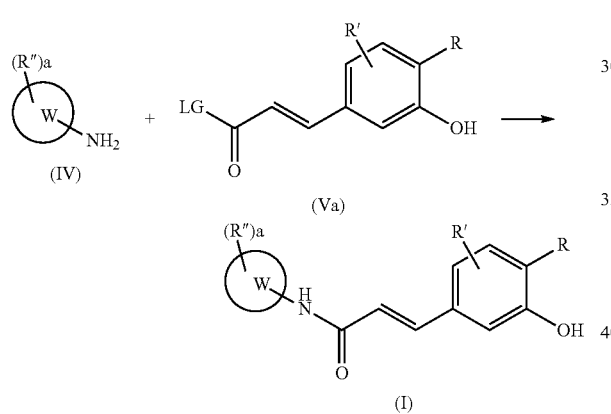

and, if desired, converting a compound of formula (I) into another compound of formula (I), or converting a compound of formula (I) into a pharmaceutically acceptable salt or converting the salt thereof into the free compound of formula (I).

According to a further embodiment of the present invention, an alternative process for preparing a compound of formula (I), prodrugs and the pharmaceutically acceptable salts thereof (Method B) is provided, comprising:

(a) acylating an amino compound of formula (VII), wherein W, R" are as defined above in formula (I), a is 0, 1 or 2 and X is O or S, with a compound of formula (V), as defined above, to give a compound of formula (VIII), wherein R, R', R", W, a, X and PG are as defined above

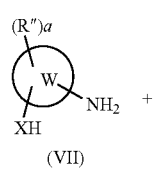

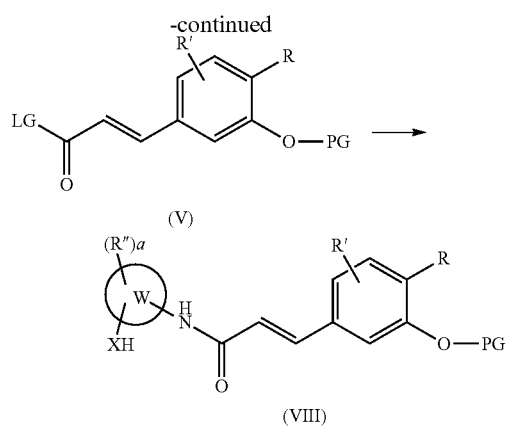

(b) alkylating a compound of formula (VIII) with a compound of formula (IX), wherein Y is any suitable leaving group or a hydroxy group, m and Q are as defined above in formula (I), to give a compound of formula (X), wherein R, R', R", W, a, m, X, Q and PG are as defined above

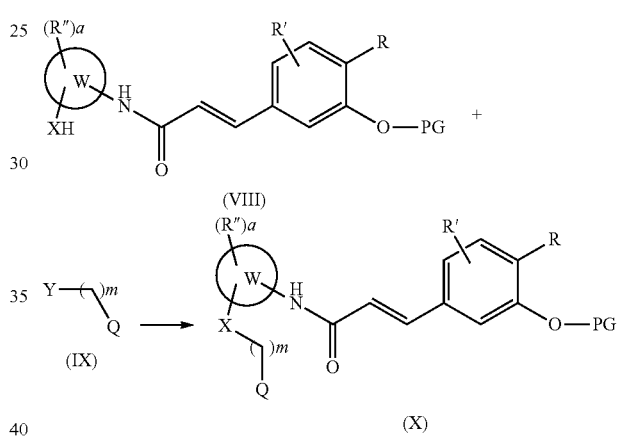

(c) removing the protecting group from a compound of formula (X) to give a compound of formula (Ia), wherein R, R', R", W, a, m, X and Q are as defined above, and, whenever desired, converting a compound of formula (Ia) into another compound of formula (Ia), or converting a compound of formula (Ia) into a pharmaceutically acceptable salt or converting the salt thereof into the free compound of formula (Ia).

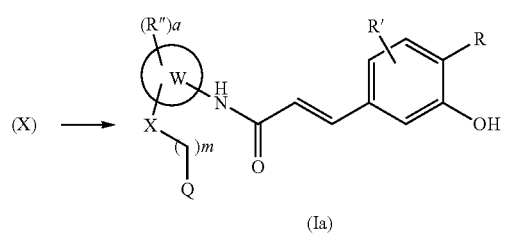

According to step (a) of the process, the coupling of a carboxylic acid of formula (V) with an aniline of formula (VII) can be carried out as described above for Method A, step (c).

According to step (b) of the process, the alkylation of the phenol or thiophenol moiety of a compound of formula (VIII)

can be carried out, for example, by reaction with a suitable halide derivative (IX) in the presence of a base, or, alternatively, by reaction with a suitable hydroxy derivative (IX) under Mitsunobu conditions as described in. Organic Syntheses, Coll. Vol. 7, p. 501 (1990); Vol. 62, p. 48 (1984) and Organic Syntheses, Coll. Vol. 10, p. 482 (2004); Vol. 79, p. 186 (2002). Typically, a compound of formula (VIII) is treated with a suitable halide derivative (IX) in the presence of a base, such as, for example, lithium, sodium or potassium hydrides, hydroxides, or carbonates, in a suitable solvent, such as polar aprotic solvents, for instance, N,N'-dimethylformamide, tetrahydrofuran, or 1,4-dioxane, at a temperature ranging from about 0° C. to reflux temperature of the solvent, for a time varying from about 30 minutes up to 48 hours.

Alternatively, step (b) can be accomplished by coupling a phenol or thiophenol compound of formula (VIII) with a suitable activated alcohol (IX) under the standard conditions of the Mitsunobu reaction, for instance by reaction with triphenylphosphine and diethylazodicarboxylate, at a temperature ranging from about 0° C. to 80° C., in a suitable solvent, such as polar aprotic or non polar solvents, for instance, tetrahydrofuran or toluene, for a time varying from about 30 minutes up to 48 hours.

According to step (c) of the process, the phenolic protecting group of a compound of formula (X) can be selectively removed to yield the corresponding phenol of formula (Ia) as described above for Method A, step (d).

If desired, the salification of a compound of formula (I) or the conversion of a corresponding salt thereof into the free compound (I), according to step (d) of the process, can be easily carried out according to well-known methods to a person skilled in the art.

It is clear to the person skilled in the art that if a compound of formula (I), prepared according to the above processes (Method A or Method B), is obtained as an admixture of isomers, their separation into the single isomers of formula (I), carried out according to conventional techniques, is still within the scope of the present invention.

As it will be appreciated by the person skilled in the art, when, during the syntheses of compounds of formula (I) certain functional groups could give rise to unwanted side reactions, these groups need to be properly protected according to conventional techniques. Likewise, the conversion of these latter into the corresponding de-protected compounds may be carried out according to procedures well known to the person skilled in the art.

All of the compounds of formula (II), (III), (IV), (VII), (IX) are known or commercially available, or can be obtained from known compounds according to standard procedures.

As an example, the starting materials of formula (IV), wherein W is phenyl, can be easily obtained as outlined in the Scheme 1(A-D) below, by starting from the suitable commercially available building blocks.

Scheme 1: Example of synthesis of the starting materials of formula (IV), wherein W is phenyl.

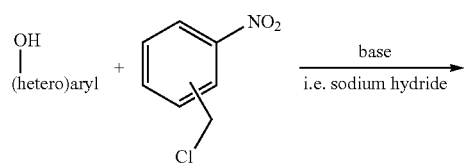

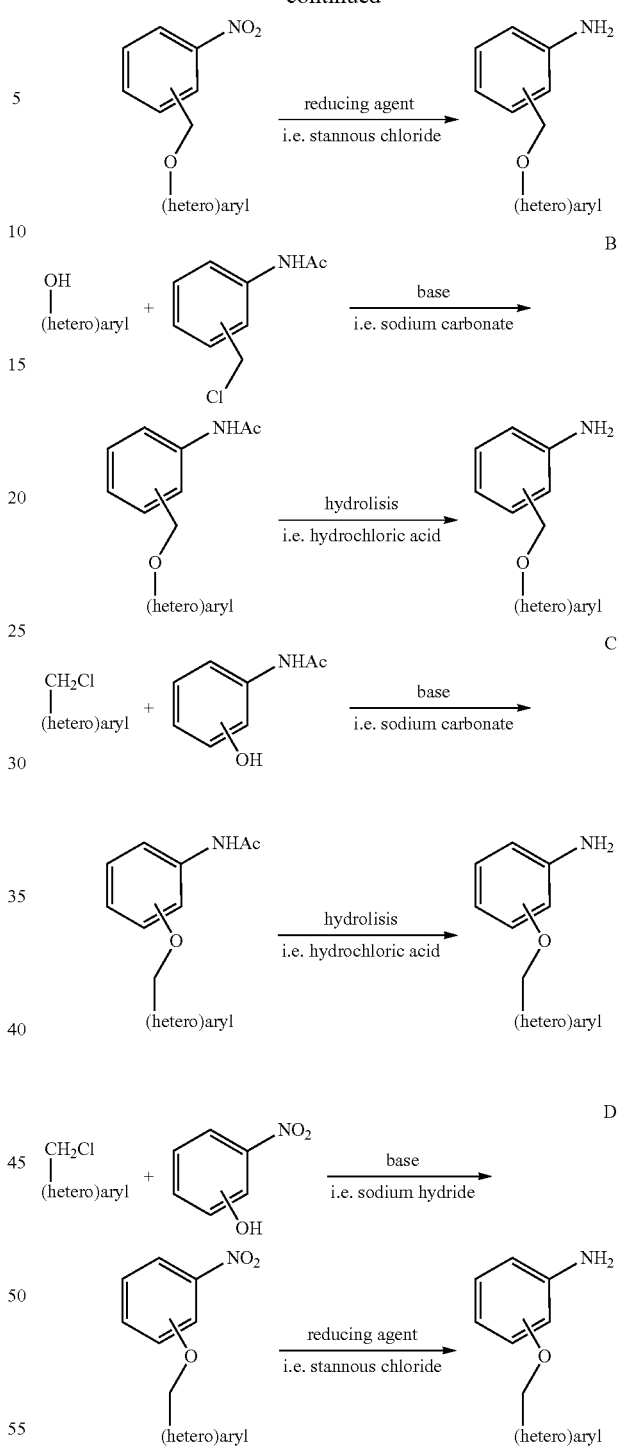

When needed, the intermediate derivatives in Scheme 1 can be further manipulated using standard synthetic procedures.

As an additional example, when (hetero)aryl-OH in Scheme 1 is resorcinol, the corresponding intermediates can be further treated with an alcohol Rx-OH, wherein Rx is an alkyl, cycloalkyl, heterocycloalkyl, aryl-alkyl, or heteroaryl-alkyl group under standard Mitsunobu conditions, to obtain the starting materials of formula (IV) outlined in Scheme 2.

Scheme 2: Example of synthesis of the starting materials of formula (IV), wherein W is phenyl substituted with a resorcinol derivative.

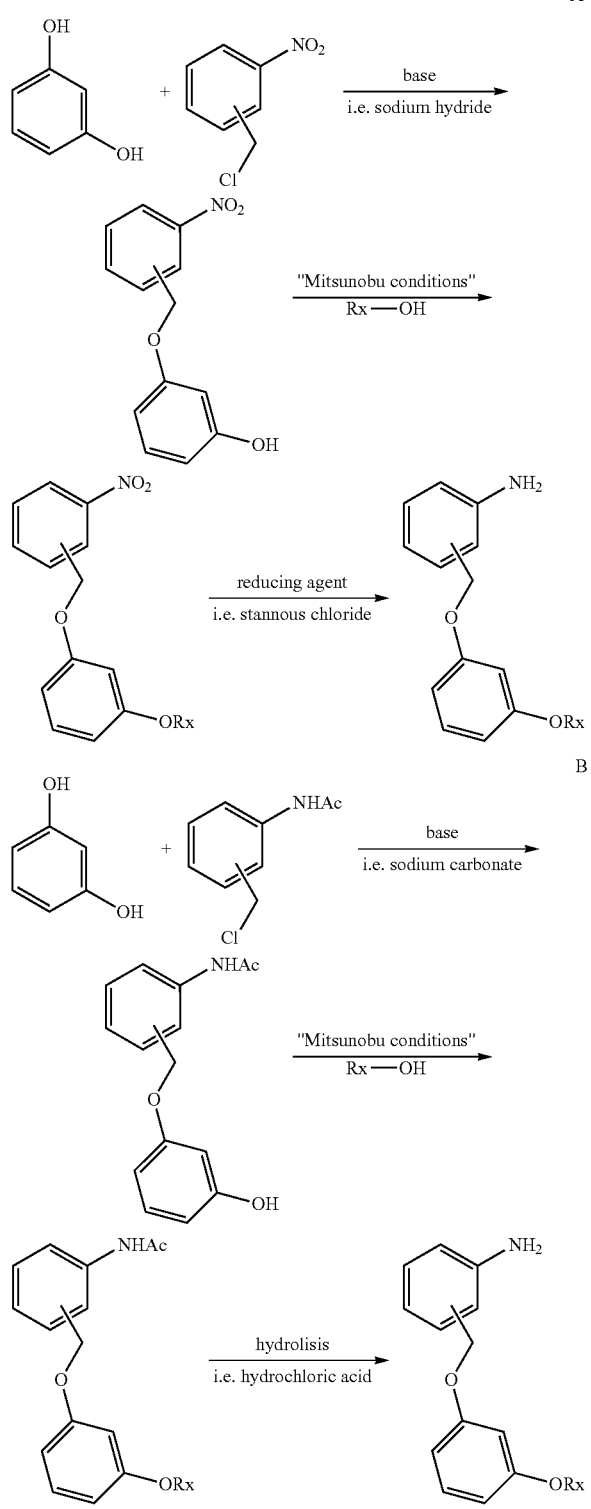

Scheme 3: Example of synthesis of the starting materials of formula (II).

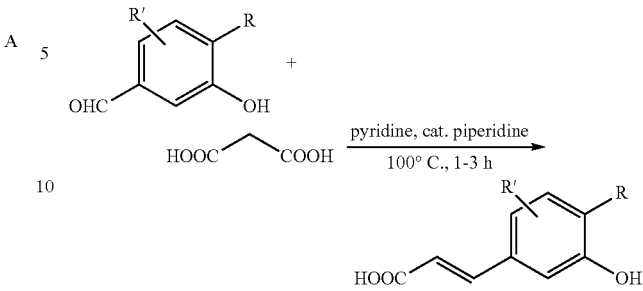

As a further example, the phosphate ester pro-drugs of compounds of formula (I) can be obtained following the known synthetic procedure (*J. Med. Chem.* 2000, 43, 2731-2737) outlined in Scheme 4.

Scheme 4: Example of synthesis of the phosphate ester of compounds of formula (I)

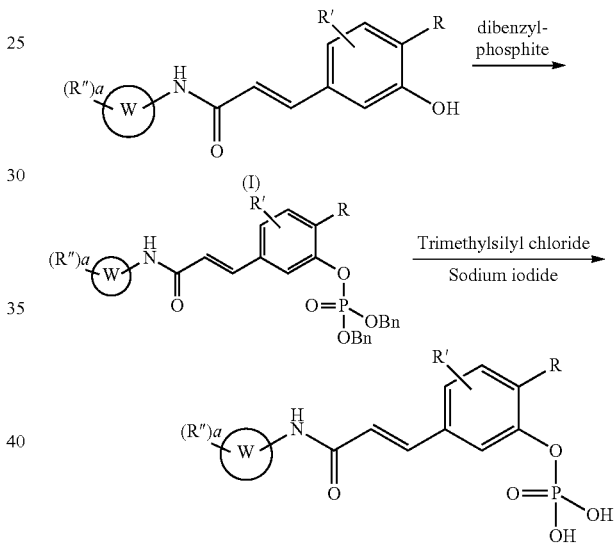

As a further example, the starting materials of formula (II) can be easily obtained as outlined in the Scheme 3 below by coupling commercially available or known benzaldehydes with malonic acid, under basic conditions.

The compounds of formula (I), as defined above, are useful in therapy as agents against a host of MPTP related diseases.

More specifically, the compounds of this invention are useful for the preparation of a medicament for the treatment of a variety of diseases such as those resulting from ischemia and reperfusion damage or oxidative damage, age-related diseases, degenerative and neurodegenerative diseases, including, but not limited to: heart disease (acute myocardial infarction, heart failure), transplantation surgery (organ ischemia), ischemic (stroke) and traumatic brain damage, Duchenne muscular dystrophy, Ullrich congenital muscular dystrophy, Bentham myopathy, amyotrophic lateral sclerosis, Huntington's disease, Alzheimer's disease, Parkinson's disease, diabetes type I and type II, diabetic complications (diabetic retinopathy, nephropathy), hyperglycemic tissue damage, hypoglycemic tissue damage, cholestasis, alcohol-induced damage.

The present invention also relates to methods for inhibiting MPTP and provides a method for treating diseases and conditions associated with the activity of the mitochondrial permeability transition pore (MPTP). Such method comprises administering to a mammal in need thereof an effective amount of a compound of formula (I).

The above method enables treatment of disorders characterized by ischemia/reperfusion, oxidative or degenerative tissue damage, age-related diseases, degenerative and neurodegenerative diseases.

In a preferred embodiment of the method described above, the disorders are acute myocardial infarction and diabetic retinopathy.

The inhibiting activity and the potency of selected compounds are determined through an in vitro assay that evaluates the ability of the invention compounds to interfere with MPT on isolated mitochondria.

Mitochondrial In Vitro Assay: Method and Results

The mitochondrial in vitro assay is based on studying physiological processes in isolated and functional mitochondrial organelles. It is possible to investigate many mitochondrial processes, including calcium retention and respiration, in isolated mitochondrial suspensions prepared from different tissues.

The ability of isolated mitochondria to uptake calcium from outside is a direct measure of mitochondrial integrity and function. Calcium overload causes MPT, which then disrupts mitochondrial integrity, impairs the ability of mitochondria to upload calcium and causes a release of stored calcium from the mitochondrial matrix. The assay takes advantage of this phenomenon of calcium uptake, overload and release in isolated mitochondria to evaluate the ability of the invention compounds to inhibit the MPTP and prevent MPT.

Mouse Liver Mitochondrial Preparation

Mitochondria were prepared from the livers of male 129 or C57/B6 mouse weighing 20-25 g. The animals were sacrificed by cervical dislocation. The livers were isolated and placed in ice-cold isolation medium (0.25 M sucrose, 10 mM Tris-HCl, 0.1 mM ethylene-bis(oxoethylenenitrilo)tetraacetic acid (EGTA), pH 7.4). The livers were rinsed three-four times with ice-cold medium, minced with scissors and passed through a manual Potter homogenizer kept in an ice-water bath. The homogenate was diluted to 50 ml per liver, and unbroken cells and nuclei were sedimented by centrifugation at 900×g in a Beckman Avanti™ 1-25 refrigerated centrifuge kept at 4° C. for 10 min. The supernatant was carefully decanted and centrifuged at 7000×g in the same centrifuge for 10 min. The supernatant was discarded and the mitochondrial pellets were carefully resuspended in ice-cold isolation medium and spun as above. The resulting mitochondrial pellets were resuspended in a small amount of ice-cold isolation medium, and stored on ice. Mitochondria protein content was determined with the biuret assay.

Calcium Retention Capacity (CRC)

The mitochondrial Calcium Retention Capacity (CRC) is a sensitive measure of the propensity of mitochondria to open the MPTP after calcium uptake. In the presence of extra-mitochondrial calcium, isolated mitochondria take up calcium into the matrix via the calcium uniporter. Continued addition of extra-mitochondrial calcium and subsequent uptake leads to the calcium-induced opening of the MPTP, loss of mitochondrial integrity and release of stored calcium. The concentration of calcium that can be retained until calcium-induced MPTP opening is termed the calcium retention capacity and is expressed as nMol calcium per mg of mitochondria.

The CRC of mitochondrial preparations (200 µL of a 0.5 mg/ml suspension) was measured fluorimetrically in the presence of a fluorescent $Ca^{2+}$ indicator (0.3 µM Calcium Green-5N) using a Tecan Infinite F200 fluorescence plate reader (excitation: 505 nm; emission: 535 nm) (Ichas, F.; Jouaville, L. S.; Mazat, J. P. Mitochondria are excitable organelles capable of generating and conveying electrical and calcium signal. Cell. 1997, 89, 1145-1153). Calcium Green-5N is a fluorometric probe that is not permeable to membranes and when added to a mitochondrial suspension is able to detect the presence of $Ca^{2+}$ in the extra-mitochondrial medium. Mitochondria were loaded with successive 10 µM pulses of calcium (1 µl of 2 mM $CaCl_2$ in 200 µL of mitochondrial suspension) at 1 min intervals, mixed and the extra-mitochondrial calcium signal was measured approximately 1 min after each addition to facilitate mitochondrial uptake (performed on Tecan Freedom Evo 200 automated workstation). Under these conditions mitochondria actively took up and retained $Ca^{2+}$ until a point at which mitochondria underwent a fast process of $Ca^{2+}$ release due to the opening of the MPTP. The final concentration of calcium required to open the MPTP and release the stored calcium is the mitochondrial CRC. This $Ca^{2+}$ loading protocol thus provides a convenient and sensitive assay for measuring MPTP opening and it is used to assess the ability of the compounds of the invention to inhibit MPTP opening. Compounds (1 µM final concentration) were added directly to the mitochondrial solution 1 min. prior to the start of calcium pulsing and the number of calcium pulses required to open the PTP was determined. The ratio between the amount of calcium required to trigger MPT in the presence of the compound ($CRC_i$) with respect to that required to induce MPT in the absence of the compound ($CRC_o$) is a measure of the inhibitory effect of the compound on the MPTP. This value is called the CRC efficacy and the results obtained from several compounds of the invention are reported in the biological example 1. Compound efficacies have been ranked by comparing inhibitory activity at 1 µM.

Further object of the present invention is represented by the use of a compound of general formula (I) as defined above, as well as its isomers, racemic forms, tautomers, enantiomers, diastereomers, epimers, polymorphs, mixtures thereof, prodrugs, and the pharmaceutically acceptable salts thereof, for the preparation of a medicament, for the prevention and/or treatment of diseases and conditions associated with the activity of the MPT pore.

A method is provided for using a compound according to the present invention in order to manufacture a medicament for use in the treatment of a disease state that is known to be mediated by MPTP, or that is known to be treated by MPTP inhibitors.

Further object of the present invention are pharmaceutical composition containing as active ingredient one or more compounds of formula (I), as defined above, and/or prodrugs, and/or a pharmaceutically acceptable salt thereof, in combination with one or several pharmaceutically acceptable excipients. A person skilled in the art is aware of a whole variety of such excipients suitable to formulate a pharmaceutical composition.

Suitable pharmaceutically acceptable excipients are well known to those skilled in the art. Excipients include, by way of illustration and not limitation, diluents, fillers, agglutinants, disintegrants, disintegration inhibitors, absorption accelerators, adjuvant, binders, carriers, suspensing/dispersing agents, film formers/coatings, adhesives, antiadherents, wetting agents, lubricants, glidants, preservatives, sorbents, surface active agents, substances added to mask or counteract a disagreeable taste or odor, flavorings, colorants, fragrances, aromatising agents, sweeteners and substances added to improve appearance of the composition.

The choice of excipient will to a large extent depend on factors such as the particular mode of administration, the effect of the excipient on solubility and stability, and the nature of the dosage form.

The pharmaceutical compositions of the present invention can be administered by a variety of routes including oral, parenteral, intravenous, subcutaneous, intramuscular, transmucosal (including buccal, sublingual, transurethral and rectal), topical, transdermal, by inhalation, permucous or percutaneous or using any other route of administration.

They will thus be presented in the form of injectable solutions or suspensions or multi-dose bottles, in the form of plain or coated tablets, sugar or film coated tablets, wafer capsules, gel capsules, pills, cachets, sachets, powders, granules, bolus, electuary, past, suppositories or rectal capsules, syrups, emulsions, solutions or suspensions, for percutaneous use in a polar solvent, or for permucous use.

For example, the solid oral forms may contain, together with the active compound, diluents, e.g., alkaline-earth metal carbonates, magnesium phosphate, lactose, dextrose, saccharose, sucrose, cellulose, microcrystalline cellulose derivatives, starches, corn starch or potato starch, modified starches and the like; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

The above described components for pharmaceutical composition administered are merely representative. Further materials as well as processing techniques and the like are set out in Part 5 of Remington's Pharmaceutical Sciences, 20$^{th}$ Edition, 2000, Merck Publishing Company, Easton, Pa., which is incorporated herein by reference. Compound of this invention of formula (I) can also be administered in sustained release forms or from sustained release drug delivery systems. A description of representative sustained release materials can also be found in the incorporated materials in Remington's Pharmaceutical Sciences.

The pharmaceutical compositions containing the compounds of the invention are usually prepared following conventional methods and are administered in a suitable pharmaceutical form.

Solid oral compositions can be prepared by conventional mixing, filling or compression. It is possible to repeat the mixing operations in order to disperse the active agent in compositions containing high amounts of fillers. These operations are conventional.

Liquid oral preparations can be formulated e.g. as aqueous or oily suspensions or solutions, emulsions, syrups or elixir, or can be presented as freeze dried product to be regenerated by addition of water or a suitable vehicle before use. Said liquid preparations can contain conventional additives such as suspending agents, e.g. sorbitol, syrup, methylcellulose, gelatine, hydroxyethylcellulose, carboxymethylcellulose, alluminium stearate gel or hydrogenated edible fats, emulsifying agents, e.g. lecithin, sorbitan monooleate, or acacia; non-aqueous vehicles (which may include edible oils), e.g. almond oil, fractionated coconut oil, oily esters such as glycerin esters, propylene glycol, or ethyl alcohol; preservatives, e.g. methyl or propyl p-hydroxybenzoate or sorbic acid and, if desired, conventional flavours and dyes.

For parenteral administration, it is possible to prepare fluid dosage units, containing the compound and a sterile vehicle. The compound, depending on the chosen vehicle and concentration, can be suspended or dissolved. Parenteral solutions are normally prepared by dissolving the compound in a vehicle, sterilising by filtration, filling suitable vials and sealing. Advantageously it is also possible to dissolve in the vehicle suitable adjuvants such as local anaesthetic, preservatives and buffering agents. In order to increase stability, the composition can be frozen after filling the vial and removing water under vacuum. Parenteral suspensions are prepared substantially in the same way, with the difference that the compound can be suspended rather than dissolved in the vehicle, and they can be sterilised by treatment with ethylene oxide before being suspended in the sterile vehicle. Advantageously, it is possible to include a surfactant or a wetting agent in the composition with the aim of easing the uniform distribution of the compound of the invention.

The compounds of the invention can also be administered topically. Topical formulations may comprise, for example, an ointment, cream, gel, lotion, solution, paste or the like, and/or may be prepared so as to contain liposomes, micelles, and/or microspheres. Ointments, as it is well known in the art of pharmaceutical formulation, are semisolid preparations that are typically based on petrolatum or other petroleum derivatives. Examples of ointments include leaginous ointment bases, for example, vegetable oils, fats obtained from animals, and semisolid hydrocarbons obtained from petroleum, emulsifiable ointment bases, for example, hydroxystearin sulfate, anhydrous lanolin and hydrophilic petrolatum, emulsion ointment bases, for example, cetyl alcohol, glyceryl monostearate, lanolin and stearic acid and water-soluble ointment bases prepared from polyethylene glycols of varying molecular weight. Creams, as also well known to those skilled in the art, are viscous liquids or semisolid emulsions, and contain an oil phase, an emulsifier and an aqueous phase. The oil phase is generally comprised of petrolatum and a fatty alcohol such as cetyl or stearyl alcohol. The aqueous phase usually contains a humectant. The emulsifier in a cream formulation is chosen among non-ionic, anionic, cationic or amphoteric surfactants. Single-phase gels contain organic macromolecules distributed substantially uniformly throughout the carrier liquid, which is typically aqueous, but also, preferably, contain an alcohol and, optionally, an oil. Preferred gelling agents are crosslinked acrylic acid polymers (such as "carbomer" polymers, e.g., carboxypolyalkylenes that may be obtained commercially under the Carbopol trademark). Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. For the preparation of uniform gels, dispersing agents such as alcohol or glycerin can be added, or the gelling agent can be dispersed by trituration, mechanical mixing, and/or stirring. The compounds of the invention may also be administered via transdermal release. Typical transdermal formulations include conventional aqueous and non aqueous vectors, such as creams, oils, lotions or pastes or can be provided as membranes or medicated plasters. In an embodiment, a compound of the invention is dispersed in a pressure-sensible plaster adhering to the skin. This formulation allows the compound to be spread from the plaster to the patient through the skin. In order to obtain a sustained drug release through the cutis, natural rubber and silicon can be used as pressure-sensitive adhesives.

The compounds of formula (I) of the present invention, suitable for administration to a mammal, e.g., to humans, can be administered by the usual routes and the dosage level depends on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

For example, a suitable dosage adopted for oral administration of a compound of formula (I) may range from about 30 to 500 mg per dose, from 1 to 5 times daily. In general lower doses will be administered when a parental route is employed. Thus, for example, for intravenous administration a dose in the range, for example, 0.5 mg to 30 mg per kg body weight will be generally used.

The compounds of the invention can be administered in a variety of dosage forms, e.g., orally, in the form of tablets, sugar or film coated tablets, capsules, cachets, as a powder or granules; as a syrups, emulsions, solution or a suspension in an aqueous or non-aqueous liquid, as an oil-in-water liquid emulsion or a water-in-oil liquid emulsion, as a bolus, electuary or paste; rectally, in the form of suppositories; parenterally, e.g., intramuscularly, or through intravenous injection or infusion.

With the aim to better illustrate the present invention, without posing any limitation to it, the following examples are now given.

EXAMPLES

Methods

Unless otherwise indicated, all the starting reagents were found to be commercially available or easily obtainable following standard described procedures, and were used without any prior purification.

The $^1$H-NMR spectra were acquired with a Bruker 400 MHz. The chemical shifts are expressed in parts per million (ppm, δ units) The coupling constants are expressed in Hertz (Hz) and the splitting patterns are described as s (singlet), bs (broad singlet), d (doublet), t (triplet), q (quartet), quint (quintet), m (multiplet).

The LC-MS experiments were performed according to the following methods.

Method_A—220: Waters Acquity UPLC, Waters SQD single quadrupole. Column Acquity UPLC-BEH C18 50×2.1 mm×1.7 µm. Flow rate: 0.6 ml/min. Mobile phase: A phase=water/$CH_3CN$ 95/5+0.07% TFA; B phase=$CH_3CN$+0.05% TFA. Gradient: 0 min (A: 98%, B: 2%), 3 min (A: 0%, B: 100%), 3.5 min (A: 0%, B: 100%). UV detection wavelength: 220 nm. Injection volume: 0.5 µL.

Method_N—254: Waters Acquity UPLC, Micromass ZQ 2000 Single quadrupole (Waters). Column Acquity UPLC-BEH C18 50×2.1 mm×1.7 µm. Flow rate: 0.6 ml/min splitting ratio MS: waste/1:4. Mobile phase: A phase=water/$CH_3CN$ 95/5+0.1% TFA; B phase=water/$CH_3CN$ 5/95+0.1% TFA. Gradient: 0-0.25 min (A: 95%, B: 5%), 0.25-3.30 min (A: 0%, B: 100%), 3.30-4.00 min (A: 0%, B: 100%). UV detection wavelength: 254 nm. Injection volume: 2 µL.

Method_N1: Waters Acquity UPLC, Micromass ZQ 2000 Single quadrupole (Waters). Column Acquity UPLC-BEH C18 50×2.1 mm×1.7 µm. Flow rate: 0.6 ml/min splitting ratio MS: waste/1:4. Mobile phase: A phase=water/MeOH 95/5+0.1% formic acid; B phase=water/$CH_3CN$ 5/95+0.1% formic acid. Gradient: 0-0.25 min (A: 95%, B: 5%), 0.25-3.30 min (A: 0%, B: 100%), 3.30-4.00 min (A: 0%, B: 100%). UV detection wavelength: 254 nm.

Injection volume: 2 µL.

Method_N2: Waters 1525 HPLC pump coupled with a PDA (996 Waters) detector and a single quadrupole ZQ (Waters). UV detection wavelength 254 nm or BPI; ESI+ detection 3.2 KV, 25V, 350° C. Flow rate: 2.0 ml/min Column XBridge C8 3.5 um 50×4.6 mm. Mobile phase: A phase=water+0.1% TFA; B phase=$CH_3CN$+0.1% TFA. Gradient: 0-1 min (A: 95%, B: 5%), 1-7.5 min (A: 0%, B: 100%), 7.5-8.5 min (A: 0%, B: 100%). UV detection wavelength: 254 nm.

Injection volume: 2 µL.

Method_N3: Waters Acquity UPLC, Micromass ZQ 2000 Single quadrupole (Waters). Column Acquity UPLC-BEH C18 50×2.1 mm×1.7 µm. Flow rate: 0.6 ml/min. Mobile phase: A phase=water/$CH_3CN$ 95/5+0.1% TFA; B phase=water/$CH_3CN$ 5/95+0.1% TFA. Gradient: 0-0.50 min (A: 95%, B: 5%), 0.50-6.00 min (A: 0%, B: 100%), 6.00-7.00 min (A: 0%, B: 100%). Injection volume: 2 µL. UV detection wavelength 254 nm or BPI; ESI+ detection 3.2 KV, 25V, 350° C.

Method_N4: Waters Acquity UPLC, Micromass ZQ 2000 Single quadrupole (Waters). Column Acquity UPLC-BEH C18 50×2.1 mm×1.7 µm. Flow rate: 0.6 ml/min splitting ratio MS: waste/1:4. Mobile phase: A phase=water/MeOH 95/5+0.1% formic acid; B phase=water/$CH_3CN$ 5/95+0.1% formic acid. Gradient: 0-0.5 min (A: 95%, B: 5%), 0.5-6.0 min (A: 0%, B: 100%), 6.0-7.0 min (A: 0%, B: 100%). UV detection wavelength: 254 nm. Injection volume: 2 µL.

Method_N5: Waters 1525 HPLC pump coupled with a PDA (996 Waters) detector and a single quadrupole ZQ (Waters) UV detection wavelength 254 nm or BPI; ESI+ detection 3.2 KV, 25V, 350° C. Flow rate: 0.4 ml/min Column Synergy 2.5 um 20×2.0 mm. Mobile phase: A phase=water/$CH_3CN$ 95/5+0.1% TFA; B phase=water/$CH_3CN$ 5/95+0.1% TFA. Gradient: 0-0.2 min (A: 95%, B: 5%), 0.2-5 min (A: 0%, B: 100%), 5-6 min (A: 0%, B: 100%). UV detection wavelength: 254 nm. Injection volume: 2 µL.

The following abbreviations refer respectively to the definitions below:

AcOEt (ethyl acetate); DIPEA (diisopropylethyl amine); DCM (dichloromethane); DMF (dimethylformamide); h (hour); hrs (hours); EDC (1-Ethyl-3-(3-dimethylaminopropyl)carbodiimide); EtOH (ethanol); HOBT (hydroxybenzotriazole); MeOH (methanol); min. (minutes); RT (room temperature); rt (retention time); SCX (Strong Cation Exchanger); TEA (triethylamine); THF (tetrahydrofuran).

Example 1

Preparation of substituted (E)-3-(3-hydroxy-phenyl)-acrylic anilides from the corresponding (E)-3-(3-acetoxy-phenyl)-derivatives by alkaline hydrolisis

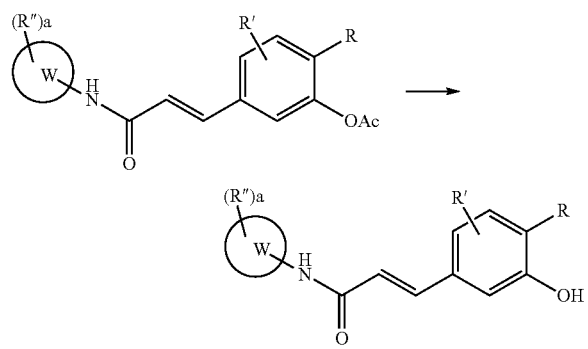

(1) (E)-3-(3-Hydroxy-4-methoxy-phenyl)-N-naphthalen-1-yl-acrylamide

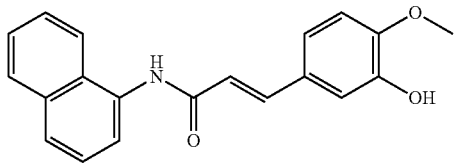 [SMILES: COc1ccc(/C=C/C(=O)Nc2cccc3ccccc23)cc1O]

A suspension of (E)-3-(3-acetoxy-4-methoxy-phenyl)-N-naphthalen-1-yl-acrylamide (254 mg, 0.70 mmol) in a mixture of MeOH (4.5 mL) and 50%$_{w/w}$ aqueous NaOH (74 μL) was heated under stirring for 40 min at the reflux temperature. The mixture was then concentrated under reduced pressure to give a light yellow oil that was taken up and triturated with 4 mL of aqueous HCl 0.5N. After filtration and drying 213 mg of the title (E)-3-(3-hydroxy-4-methoxy-phenyl)-N-naphthalen-1-yl-acrylamide were obtained as a white powder.

$^1$H NMR (DMSO-d6) δ (ppm): 10.04 (s, 1H), 9.24 (s, 1H), 8.16 (d, J=8.4 Hz, 1H), 7.96-7.94 (m, 1H), 7.90 (d, J=7.2 Hz, 1H), 7.76 (d, J=8.4 Hz, 1H), 7.60-7.47 (m, 4H), 7.10-7.06 (m, 2H), 6.99 (d, J=8.0 Hz, 1H), 6.93 (d, J=15.6 Hz, 1H), 3.83 (s, 3H).

LC-MS: Method_A—220, rt=1.68

(ES+) [2M+Na]+: 661

By analogously hydrolising the suitable (E)-3-(3-acetoxy-phenyl)-acrylic anilides, the following compounds were prepared:

(2) (E)-N-(2-Benzyloxy-phenyl)-3-(3-hydroxy-4-methoxy-phenyl)-acrylamide

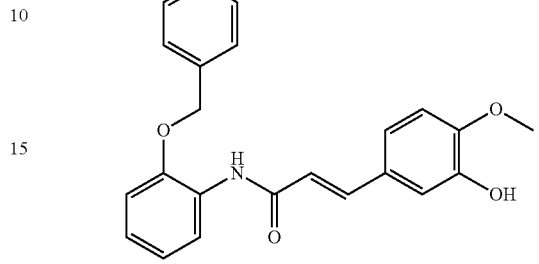

(purification by silica gel column chromatography, eluant n-hexane/AcOEt 65:35)

$^1$H NMR (DMSO-d6) δ (ppm): 9.25 (s, 1H), 9.17 (s, 1H), 8.06 (d, J=7.2 Hz, 1H), 7.52-7.50 (m, 2H), 7.43-7.36 (m, 3H), 7.32-7.28 (m, 1H), 7.09-7.00 (m, 4H), 6.98-6.89 (m, 3H), 5.25 (s, 2H), 3.81 (s, 3H).

LC-MS: Method_A—220, rt=2.08

(ES+) [2M+Na]+: 773

(3) (E)-3-(3-Hydroxy-4-methoxy-phenyl)-N-[3-(4-methyl-piperazin-1-yl)-phenyl]-acrylamide

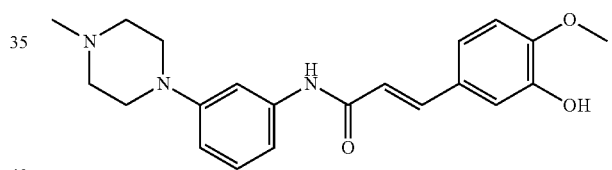

(following neutralization of the hydrochloride)

$^1$H NMR (DMSO-d6) δ (ppm): 9.97 (s, 1H), 9.23 (s, 1N), 7.40 (d, J=15.6 Hz, 1H), 7.36 (s, 1H), 7.16-7.12 (m, 1H), 7.10 (d, J=8.0 Hz, 1H), 7.02 (d, J=8.4 Hz, 2H), 6.97 (d, J=8.0 Hz, 1H), 6.66 (d, J=8.0 Hz, 1H), 6.59 (d, J=15.6 Hz, 1H), 3.81 (s, 3H), 3.15 (bs, 4H), 2.59 (bs, 4H), 2.32 (bs, 3H).

LC-MS: Method_A—220, rt=0.98

(ES+) [M+H]+: 368.

(4) (E)-N-(2-Chloro-pyridin-4-yl)-3-(3-hydroxy-4-methoxy-phenyl)-acrylamide

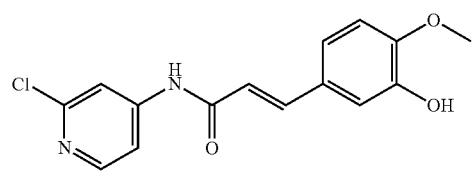 [SMILES: COc1ccc(/C=C/C(=O)Nc2ccnc(Cl)c2)cc1O]

(following neutralization of the hydrochloride)

$^1$H NMR (DMSO-d6) δ (ppm): 10.70 (s, 1H), 9.30 (s, 1H), 8.27 (d, J=5.6 Hz, 1H), 7.85 (d, J=1.6 Hz, 1H), 7.55-7.51 (m, 2H), 7.09-7.07 (m, 2H), 6.98 (d, J=8.0 Hz, 1H), 6.56 (d, J=15.6 Hz, 1H), 3.81 (s, 3H).

LC-MS: Method_A—220, rt=1.44

(ES+) [M+H]+: 305.

(5) (E)-N-(3-Chloro-2-methoxy-phenyl)-3-(3-hydroxy-4-methoxy-phenyl)-acrylamide

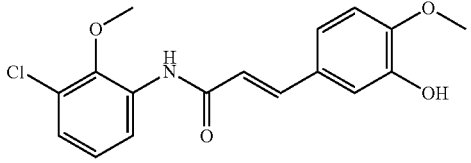 [SMILES: COc1ccc(/C=C/C(=O)Nc2cccc(Cl)c2OC)cc1O]

¹H NMR (DMSO-d6) δ (ppm): 9.56 (s, 1H), 9.20 (s, 1H), 8.21-8.19 (m, 1H), 7.45 (d, J=15.6 Hz, 1H), 7.20 (dd, J=8.4 Hz, J=2.0 Hz, 1H), 7.13 (t, J=8.4 Hz, 1H), 7.08-6.97 (m, 4H), 3.82 (s, 3H), 3.80 (s, 3H).

LC-MS: Method_A—220, rt=1.83

(ES+) [2M+Na]+: 689.

(6) (E)-N-(3,4-Dichloro-phenyl)-3-(3-hydroxy-4-methoxy-phenyl)-acrylamide

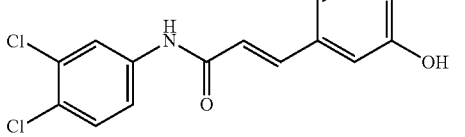

¹H NMR (DMSO-d6) δ (ppm): 10.39 (s, 1H), 9.26 (s, 1H), 8.10 (d, J=2.0 Hz, 1H), 7.60-7.54 (m, 2H), 7.47 (d, J=15.6 Hz, 1H), 7.06-7.04 (m, 2H), 6.98 (d, J=8.8 Hz, 1H), 6.54 (d, J=15.6 Hz, 1H), 3.81 (s, 3H).

LC-MS: Method_A—220, rt=1.83

(ES+) [2M+Na]+: 699.

(7) (E)-N-(3-Chloro-4-methoxy-phenyl)-3-(3-hydroxy-4-methoxy-phenyl)-acrylamide

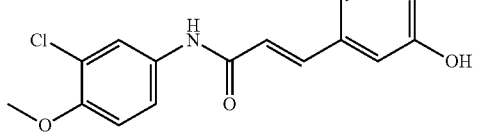

¹H NMR (DMSO-d6) δ (ppm): 10.11 (s, 1H), 9.24 (s, 1H), 7.89 (d, J=2.4 Hz, 1H), 7.50 (dd, J=8.8 Hz, J=2.4 Hz, 1H), 7.42 (d, J=15.6 Hz, 1H), 7.13 (d, J=9.2 Hz, 1H), 7.04-7.02 (m, 2H), 6.97 (d, J=8.8 Hz, 1H), 6.53 (d, J=15.6 Hz, 1H), 3.82 (s, 3H), 3.81 (s, 3H).

LC-MS: Method_A—220, rt=1.72

(ES+) [2M+Na]+: 689.

(8) (E)-N-(2,3-Dichloro-phenyl)-3-(3-hydroxy-4-methoxy-phenyl)-acrylamide

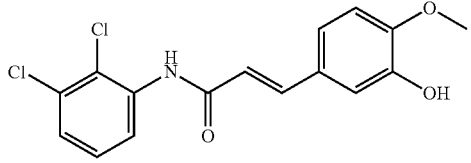 [SMILES: COc1ccc(/C=C/C(=O)Nc2cccc(Cl)c2Cl)cc1O]

¹H NMR (DMSO-d6) δ (ppm): 7.88 (dd, J=8.4 Hz, J=1.6 Hz, 1H), 7.45-7.41 (m, 2H), 7.35 (t, J=8.4 Hz, 1H), 7.02 (s, 1H), 6.86 (s, 2H), 6.80 (d, J=15.6 Hz, 1H), 3.77 (s, 3H).

LC-MS: Method_A—220, rt=2.01

(ES+) [M+H]+: 338.

(9) (E)-N-(3-Benzylamino-phenyl)-3-(3-hydroxy-4-methoxy-phenyl)-acrylamide

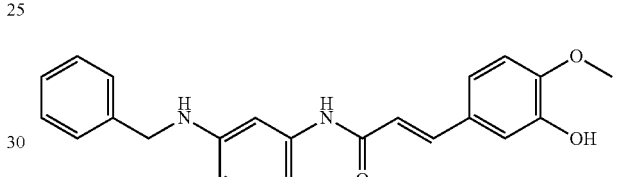

¹H NMR (DMSO-d6) δ (ppm): 9.78 (s, 1H), 9.20 (s, 1H), 7.40-7.30 (m, 5H), 7.23-7.20 (m, 1H), 7.02-7.00 (m, 3H), 6.97-6.93 (m, 2H), 6.86 (d, J=8.0 Hz, 1H), 6.58 (d, J=15.6 Hz, 1H), 6.30-6.27 (m, 2H), 4.25 (d, J=6.0 Hz, 2H), 3.80 (s, 3H).

LC-MS: Method_A—220, rt=1.89

(ES+) [M+H]+: 375

(10) (E)-N-[3-(Benzyl-methyl-amino)-phenyl]-3-(3-hydroxy-4-methoxy-phenyl)-acrylamide

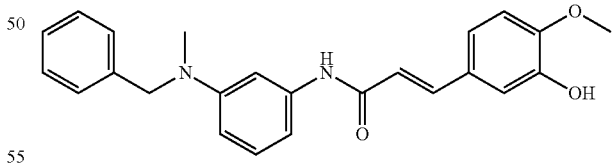

¹H NMR (DMSO-d6) δ (ppm): 9.87 (s, 1H), 9.21 (s, 1H), 7.39 (d, J=15.2 Hz, 1H), 7.34-7.30 (m, 2H), 7.24-7.21 (m, 3H), 7.15 (s, 1H), 7.07 (t, J=8.0 Hz, 1H), 7.02-6.99 (m, 3H), 6.96 (d, J=8.8 Hz, 1H), 6.57 (d, J=15.6 Hz, 1H), 6.44 (dd, J=8.0 Hz, J=2.0 Hz, 1H), 4.55 (s, 2H), 3.80 (s, 3H), 2.99 (s, 3H).

LC-MS: Method_A—220, rt=2.07

(ES+) [M+H]+: 389.

Example 2

Preparation of substituted (E)-3-(3-hydroxy-phenyl)-acrylic anilides from the corresponding (E)-3-(3-acetoxy-phenyl)-derivatives by acid hydrolisis

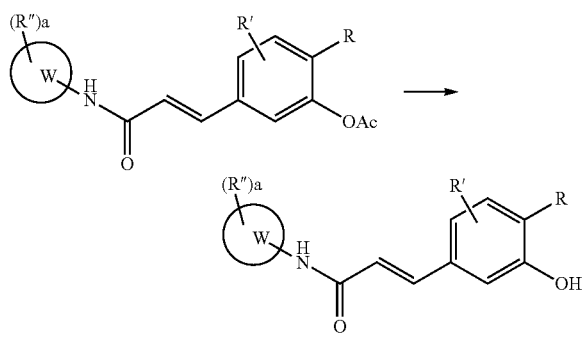

(11) (E)-N-[2-Chloro-3-(pyridin-4-ylmethoxy)-phenyl]-3-(3-hydroxy-4-methoxy-phenyl)-acrylamide hydrochloride

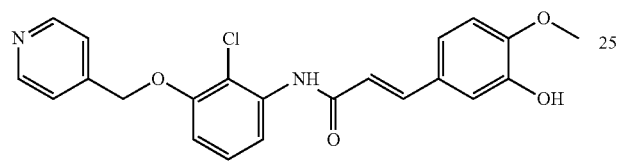

A 3N methanolic solution of hydrochloric acid (10 ml, 30 mmols) is added to a solution of (E)-N-[2-chloro-3-(pyridin-4-ylmethoxy)-phenyl]-3-(3-acetoxy-4-methoxy-phenyl)-acrylamide hydrochloride (240 mg, 0.53 mmol) in THF (5 mL). The resulting mixture was stirred at RT for 16 hrs, concentrated under reduced pressure, taken up with solvent an re-evaporated (3 times with MeOH and once with acetone) to give a light yellow residue that was triturated with ethyl ether. After filtration and drying, 232 mg of the title (E)-N-[2-chloro-3-(pyridin-4-ylmethoxy)-phenyl]-3-(3-hydroxy-4-methoxy-phenyl)-acrylamide hydrochloride were obtained as a light yellow powder.

$^1$H NMR (DMSO-d6) δ (ppm): 9.57 (s, 1H), 9.25 (bs, NH+), 8.88 (d, J=4.4 Hz, 2H), 7.97 (d, bs, 2H), 7.64 (d, J=8 Hz, 1H), 7.47 (d, J=15.6 Hz, 1H), 7.32 (t, J=8 Hz, 1H), 7.09-6.98 (m, 4H), 6.92 (d, J=15.6 Hz, 1H), 5.55 (s, 2H), 3.83 (s, 3H).
LC-MS: Method_A—220, rt=1.17
(ES+) [M+H]+: 411

By analogously hydrolising the suitable (E)-3-(3-acetoxy-phenyl)-acrylic anilides, the following compounds were prepared:

(12) (E)-3-(3-Hydroxy-4-methoxy-phenyl)-N-{3-[(pyridin-4-ylmethyl)-amino]-phenyl}-acrylamide

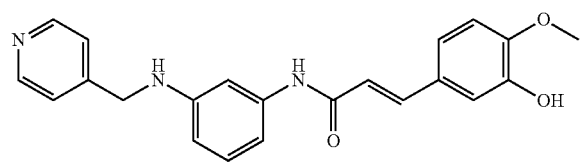 [SMILES: COc1ccc(/C=C/C(=O)Nc2cccc(NCc3ccncc3)c2)cc1O]

$^1$H NMR (DMSO-d6) δ (ppm): 9.80 (s, 1H), 9.20 (s, 1H), 8.51-8.49 (m, 2H), 7.39-7.35 (m, 3H), 7.01-6.95 (m, 5H), 6.86 (d, J=8.4 Hz, 1H), 6.57 (d, J=15.6 Hz, 1H), 6.47-6.44 (m, 1H), 6.25-6.23 (m, 1H), 4.30 (bs, 2H), 3.80 (s, 3H).
LC-MS: Method_A—220, rt=1.01
(ES+) [M+H]+: 376.

(13) (E)-N-(3-Benzyloxy-2-chloro-phenyl)-3-(3-hydroxy-4-methoxy-phenyl)-acrylamide

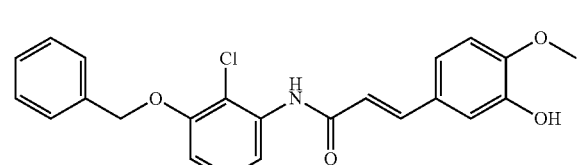

$^1$H NMR (DMSO-d6) δ (ppm): 9.50 (s, 1H), 9.21 (s, 1H), 7.60-6.97 (m, 12H), 6.90 (d, J=15.6 Hz, 1H), 5.23 (s, 2H), 3.82 (s, 3H).
LC-MS: Method_A—220, rt=2.08
(ES+) [M+H]+: 410.

(14) (E)-N-(2-Benzyloxy-3-chloro-phenyl)-3-(3-hydroxy-4-methoxy-phenyl)-acrylamide

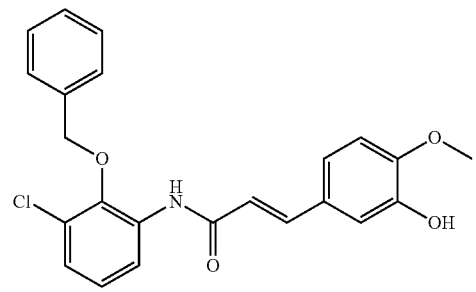 [SMILES: COc1ccc(/C=C/C(=O)Nc2cccc(Cl)c2OCc2ccccc2)cc1O]

(purification by silica gel column chromatography, eluant n-hexane/AcOEt 70:30)
$^1$H NMR (DMSO-d6) δ (ppm): 9.46 (s, 1H), 9.23 (s, 1H), 8.04 (m, 1H), 7.55-6.98 (m, 11H), 6.83 (d, J=16 Hz, 1H), 5.01 (s, 2H), 3.83 (s, 3H).
LC-MS: Method_A—220, rt=2.21
(ES+) [M+H]+: 410.

(15) (E)-N-(1-Benzyl-1H-indol-4-yl)-3-(3-hydroxy-4-methoxy-phenyl)-acrylamide

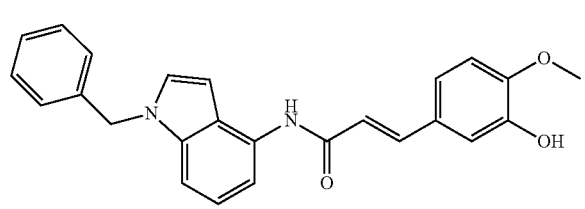 [SMILES: COc1ccc(/C=C/C(=O)Nc2cccc3c2ccn3Cc2ccccc2)cc1O]

$^1$H NMR (DMSO-d6) δ (ppm): 9.70 (s, 1H), 9.22 (s, 1H), 7.85 (m, 1H), 7.55-6.85 (m, 14H), 5.42 (s, 2H), 3.83 (s, 3H).
LC-MS: Method_A—220, rt=1.96
(ES+) [M+H]+: 399.

(16) (E)-N-[3-Chloro-2-(pyridin-4-ylmethoxy)-phenyl]-3-(3-hydroxy-4-methoxy-phenyl)-acrylamide

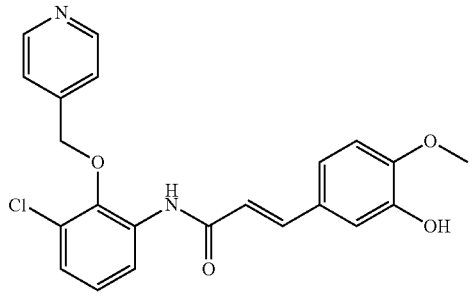 [SMILES: COc1ccc(/C=C/C(=O)Nc2cccc(Cl)c2OCc2ccncc2)cc1O]

(purification by silica gel column chromatography, eluant DCM/MeOH/aqueous ammonium hydroxide 98:2:0.2)
$^1$H NMR (DMSO-d6) δ (ppm): 9.58 (s, 1H), 9.22 (s, 1H), 8.59 (d, J=5.4 Hz, 2H), 8.08 (m, 1H), 7.56 (d, J=5.4 Hz, 2H), 7.44 (d, J=15.4 Hz, 1H), 7.28 (m, 1H), 7.19 (t, J=8.2 Hz, 1H), 7.06-6.97 (m, 3H), 6.85 (d, J=15.4 Hz, 1H), 5.05 (s, 2H), 3.82 (s, 3H).
LC-MS: Method_A—220, rt=1.33
(ES+) [M+H]+: 411.

(17) (E)-N-[4-Chloro-3-(pyridin-4-ylmethoxy)-phenyl]-3-(3-hydroxy-4-methoxy-phenyl)-acrylamide

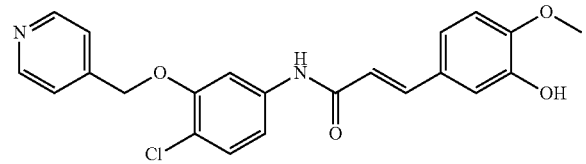 [SMILES: COc1ccc(/C=C/C(=O)Nc2ccc(Cl)c(OCc3ccncc3)c2)cc1O]

$^1$H NMR (DMSO-d6) δ (ppm): 9.58 (s, 1H), 9.22 (s, 1H), 8.59 (d, J=5.4 Hz, 2H), 8.08 (m, 1H), 7.56 (d, J=5.4 Hz, 2H), 7.44 (d, J=15.4 Hz, 1H), 7.28 (m, 1H), 7.19 (t, J=8.2 Hz, 1H), 7.06-6.97 (m, 3H), 6.85 (d, J=15.4 Hz, 1H), 5.05 (s, 2H), 3.82 (s, 3H).
LC-MS: Method_A—220, rt=1.30
(ES+) [M+H]+: 411.

(18) (E)-3-(3-Hydroxy-4-methoxy-phenyl)-N-(1-methyl-1H-indol-4-yl)-acrylamide

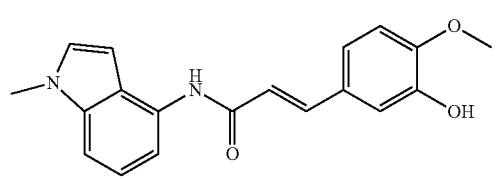

(purification by silica gel column chromatography, eluant DCM/MeOH 100:1)
$^1$H NMR (DMSO-d6) δ (ppm): 9.69 (s, 1H), 9.22 (s, 1H), 7.88 (m, 1H), 7.46 (d, J=15.6 Hz, 1H), 7.30 (m, 1H), 7.20-6.92 (min, 6H), 6.78 (m, 1H), 3.83 (s, 3H), 3.79 (s, 3H).
LC-MS: Method_A—220, rt=1.56
(ES+) [M+H]+: 323.

(19) (E)-N-(1-Benzyl-1H-indol-7-yl)-3-(3-hydroxy-4-methoxy-phenyl)-acrylamide

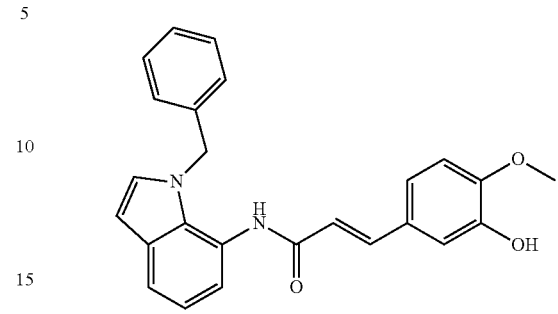

(purification by silica gel column chromatography, eluant DCM/MeOH 100:1)
$^1$H NMR (DMSO-d6) δ (ppm): 9.76 (s, 1H), 9.22 (s, 1H), 7.49-6.92 (m, 13H), 6.57 (min, 2H), 5.46 (s, 2H), 3.82 (s, 3H).
LC-MS: Method_A—220, rt=1.83
(ES+) [M+H]+: 399.

(20) (E)-3-(3-Hydroxy-4-methoxy-phenyl)-N-[3-(3-methyl-3H-imidazol-4-ylmethoxy)-phenyl]-acrylamide

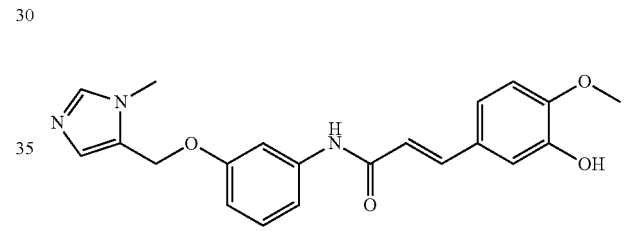

(purification by silica gel column chromatography, eluant DCM/MeOH/aqueous ammonium hydroxide 90:10:1)
$^1$H NMR (DMSO-d6) δ (ppm): 10.09 (s, 1H), 9.24 (s, 1H), 7.65 (s, 1H), 7.51 (m, 1H), 7.44 (d, J=15.6 Hz, 1H), 7.26-7.2 (m, 2H), 7.05-6.97 (m, 4H), 6.77-6.74 (m, 1H), 6.59 (d, J=15.6 Hz, 1H), 5.08 (s, 2H), 3.82 (s, 3H), 3.66 (s, 3H).
LC-MS: Method_A—220, rt=1.01
(ES+) [M+H]+: 380.

(21) (E)-3-(4-Fluoro-3-hydroxy-phenyl)-N-(2-phenoxymethyl-phenyl)-acrylamide

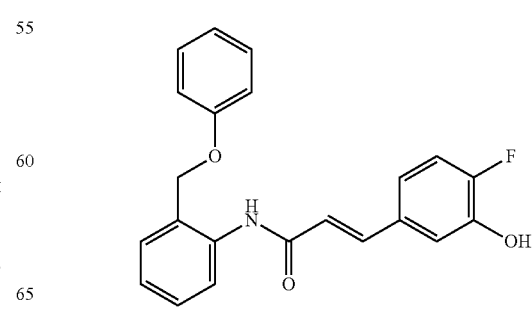

(purification by silica gel column chromatography, eluant DCM/MeOH/AcOEt 97:3)

¹H NMR (DMSO-d6) δ (ppm): 10.1 (s, 1H), 9.71 (s, 1H), 7.62-7.47 (m, 3H), 7.37-7.18 (m, 6H), 7.08-6.92 (m, 4H), 6.77 (d, J=15.2 Hz, 1H), 5.14 (s, 2H).

LC-MS: Method_A—220, rt=1.95

(ES+) [M+H]+: 364.

(22) (E)-3-(3-Hydroxy-4-methoxy-phenyl)-N-[3-(1H-imidazol-4-ylmethoxy)-phenyl]-acrylamide hydrochloride

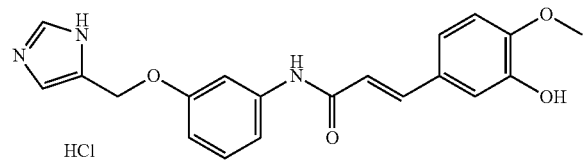 [SMILES: COc1ccc(/C=C/C(=O)Nc2cccc(OCc3cnc[nH]3)c2)cc1O ; Cl]

¹H NMR (DMSO-d6) δ (ppm): 10.1 (s, 1H), 9.71 (s, 1H), 7.62-7.47 (m, 3H), 7.37-7.18 (m, 6H), 7.08-6.92 (m, 4H), 6.77 (d, J=15.2 Hz, 1H), 5.14 (s, 2H).

LC-MS: Method_A—220, rt=1.00

(ES+) [M+H]+: 366.

(23) (E)-3-(3-Hydroxy-4-methoxy-phenyl)-N-[3-(pyridin-4-yloxymethyl)-phenyl]-acrylamide hydrochloride

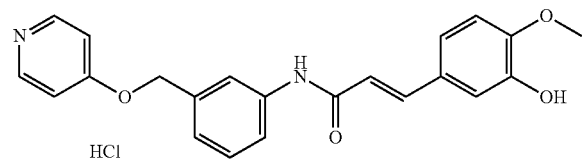 [SMILES: COc1ccc(/C=C/C(=O)Nc2cccc(COc3ccncc3)c2)cc1O ; Cl]

¹H NMR (DMSO-d6) δ (ppm): 10.32 (s, 1H), 8.75-8.73 (m, 2H), 7.74 (s, 1H), 7.63 (d, J=8.0 Hz, 1H), 7.45-7.36 (m, 4H), 7.07 (d, J=8.0 Hz, 1H), 7.04-7.02 (m, 2H), 6.97 (d, J=8.0 Hz, 1H), 6.61 (d, J=15.6 Hz, 1H), 5.61 (s, 2H), 3.81 (s, 3H).

LC-MS: Method_A—220, rt=1.05

(ES+) [2M+H]+: 753.

(24) (E)-3-(3-Hydroxy-4-methoxy-phenyl)-N-(3-oxazol-5-yl-phenyl)-acrylamide

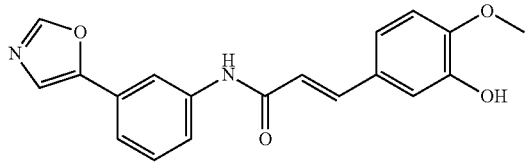 [SMILES: COc1ccc(/C=C/C(=O)Nc2cccc(-c3cnco3)c2)cc1O]

¹H NMR (DMSO-d6) δ (ppm): 10.33 (s, 1H), 8.47 (s, 1H), 8.13 (s, 1H), 7.66-7.64 (m, 2H), 7.48-7.41 (m, 3H), 7.06-7.04 (m, 2H), 6.98 (d, J=8.4 Hz, 1H), 6.63 (d, J=15.6 Hz, 1H), 3.81 (s, 3H).

LC-MS: Method_A—220, rt=1.44

(ES+) [2M+Na]+: 695.

(25) (E)-3-(3-Hydroxy-4-methoxy-phenyl)-N-indan-1-yl-acrylamide

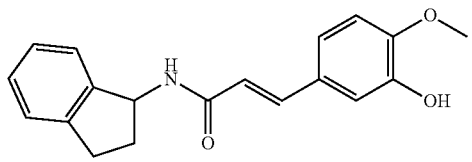 [SMILES: COc1ccc(/C=C/C(=O)NC2CCc3ccccc32)cc1O]

¹H NMR (DMSO-d6) δ (ppm): 8.39 (d, J=8.4 Hz, 1H), 7.35 (d, J=15.6 Hz, 1H), 7.27-7.17 (m, 4H), 6.98-6.93 (m, 3H), 6.44 (d, J=16.0 Hz, 1H), 5.39 (q, J=7.6 Hz, 1H), 3.79 (s, 3H), 2.99-2.92 (m, 1H), 2.86-2.78 (m, 1H), 2.47-2.39 (m, 1H), 1.86-1.80 (m, 1H).

LC-MS: Method_A—220, rt=1.59

(ES+) [2M+Na]+: 641.

(26) (E)-N-(2-Benzylsulfanyl-phenyl)-3-(3-hydroxy-4-methoxy-phenyl)-acrylamide

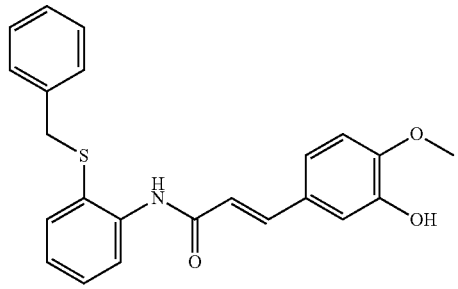 [SMILES: COc1ccc(/C=C/C(=O)Nc2ccccc2SCc2ccccc2)cc1O]

¹H NMR (DMSO-d6) δ (ppm): 9.32 (s, 1H), 9.19 (s, 1H), 7.71 (d, J=7.6 Hz, 1H), 7.42-7.39 (m, 2H), 7.32-7.19 (m, 6H), 7.12 (t, J=7.6 Hz, 1H), 7.07-7.04 (m, 2H), 6.97 (d, J=8.0 Hz, 1H), 6.75 (d, J=15.2 Hz, 1H), 4.14 (s, 2H), 3.81 (s, 3H).

LC-MS: Method_A—220, rt=2.13

(ES+) [M+H]+: 392.

(27) (E)-3-(3-Hydroxy-4-methoxy-phenyl)-N-(1-methyl-1H-benzimidazol-2-yl)-acrylamide hydrochloride

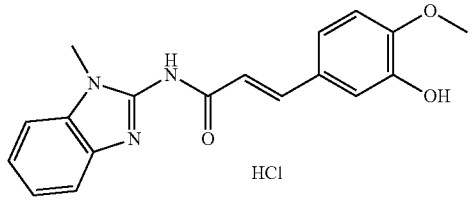 [SMILES: COc1ccc(/C=C/C(=O)Nc2nc3ccccc3n2C)cc1O ; Cl]

¹H NMR (DMSO-d6) δ (ppm): 9.42 (bs, 1H), 7.78-7.72 (m, 3H), 7.51-7.44 (m, 2H), 7.19-7.11 (m, 31H), 7.03 (d, J=8.4 Hz, 1H), 3.96 (s, 31H), 3.84 (s, 3H).

LC-MS: Method_A—220, rt=1.09

(ES+) [M+H]+: 324.

(28) (E)-3-(3-Hydroxy-4-methoxy-phenyl)-N-(2-phenoxymethyl-phenyl)-acrylamide

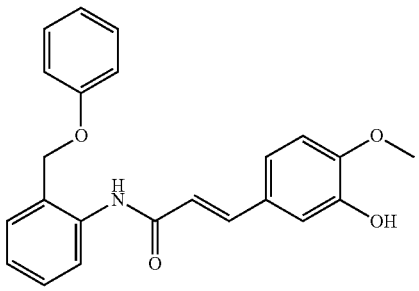 [SMILES: COc1ccc(/C=C/C(=O)Nc2ccccc2COc2ccccc2)cc1O]

LC-MS: Method_A—220, rt=1.92
(ES+) [M+H]+: 376.

(29) (E)-N-Benzoxazol-4-yl-3-(3-hydroxy-4-methoxy-phenyl)-acrylamide

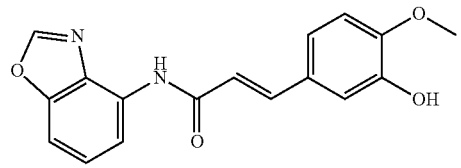 [SMILES: COc1ccc(/C=C/C(=O)Nc2cccc3ocnc23)cc1O]

LC-MS: Method_A—220, rt=1.47
(ES+) [M+H]+: 311.

(30) (E)-N-(1-Benzyl-1H-benzimidazol-4-yl)-3-(3-hydroxy-4-methoxy-phenyl)-acrylamide

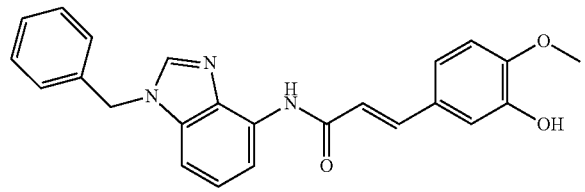 [SMILES: COc1ccc(/C=C/C(=O)Nc2cccc3c2ncn3Cc2ccccc2)cc1O]

$^1$H NMR (DMSO-d6) δ (ppm): 9.99 (s, 1H), 9.20 (bs, 1H), 8.44 (s, 1H), 8.12 (d, J=7.6 Hz, 1H), 7.44 (d, J=15.2 Hz, 2H), 7.32 (m, 5H), 7.23 (m, 1H), 7.16 (m, 2H), 7.07 (m, 2H), 6.98 (m, 1H), 5.52 (s, 2H), 3.82 (s, 3H).
LC-MS: Method_A—220, rt=1.54
(ES+) [M+H]+: 400.

(31) (E)-3-(3-Hydroxy-4-methoxy-phenyl)-N-(1-methyl-1H-benzimidazol-4-yl)-acrylamide hydrochloride

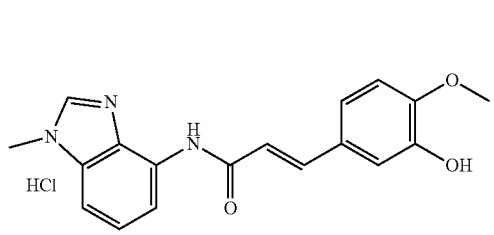

$^1$H NMR (DMSO-d6) δ (ppm): 10.88 (bs, 1H), 9.39 (bs, 1H), 7.98 (d, J=7.6 Hz, 1H), 7.65 (d, J=8.0 Hz, 1H), 7.56 (m, 2H), 7.10 (m, 2H), 7.00 (d, J=8.0 Hz, 1H), 6.93 (d, J=7.6 Hz, 1H), 4.04 (s, 3H), 3.83 (s, 3H).
LC-MS: Method_A—220, rt=0.93
(ES+) [M+H]+: 324.

(32) (E)-N-(1-Benzyl-1H-indazol-7-yl)-3-(3-hydroxy-4-methoxy-phenyl)-acrylamide

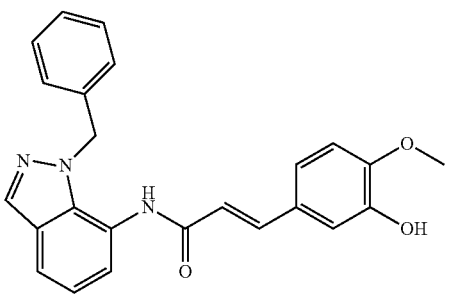 [SMILES: COc1ccc(/C=C/C(=O)Nc2cccc3cnn(Cc4ccccc4)c23)cc1O]

$^1$H NMR (DMSO-d6) δ (ppm): 10.04 (s, 1H), 9.25 (s, 1H), 8.18 (s, 1H), 7.70 (d, J=7.6 Hz, 1H), 7.43 (d, J=15.6 Hz, 1H), 7.10 (m, 2H), 7.00-7.22 (m, 10H), 6.64 (d, J=15.6 Hz, 1H), 3.82 (s, 3H).
LC-MS: Method_A—220, rt=1.59
(ES+) [M+H]+: 400.

(33) (E)-3-(3-Hydroxy-4-methoxy-phenyl)-N-(1-methyl-1H-benzotriazol-4-yl)-acrylamide

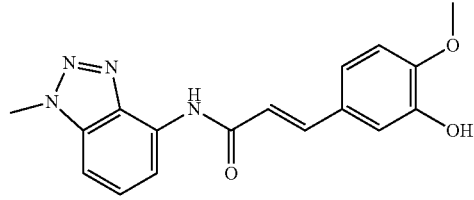 [SMILES: COc1ccc(/C=C/C(=O)Nc2cccc3c2nnn3C)cc1O]

$^1$H NMR (DMSO-d6) δ (ppm): 10.65 (s, 1H), 9.23 (bs, 1H), 8.29 (dd, J=2.8 Hz, 1H), 7.48-7.52 (m, 3H), 7.18 (d, J=15.6 Hz, 1H), 7.07 (m, 2H), 6.99 (d, J=8.0 Hz, 1H), 4.32 (s, 3H), 3.83 (s, 3H).
LC-MS: Method_A—220, rt=1.39
(ES+) [M+H]+: 325.

(34) (E)-N-(1-Benzyl-1H-indazol-4-yl)-3-(3-hydroxy-4-methoxy-phenyl)-acrylamide hydrochloride

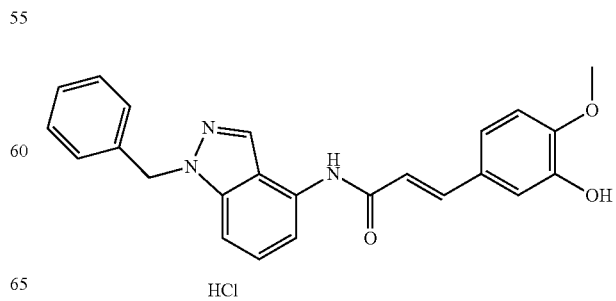

¹H NMR (DMSO-d6) δ (ppm): 10.16 (s, 1H), 8.41 (s, 1H), 7.87 (d, J=7.2 Hz, 1H), 7.50 (d, J=15.2 Hz, 1H), 7.40 (d, J=8.4 Hz, 1H), 7.34-7.29 (m, 3H), 7.26-7.21 (m, 3H), 7.09-7.07 (m, 2H), 6.99 (d, J=8.0 Hz, 1H), 6.88 (d, J=15.6 Hz, 1H), 5.64 (s, 2H), 3.82 (s, 3H).
LC-MS: Method_A—220, rt=1.83
(ES+) [M+H]+: 400.

(35) (E)-N-(2-Benzyl-2H-indazol-7-yl)-3-(3-hydroxy-4-methoxy-phenyl)-acrylamide

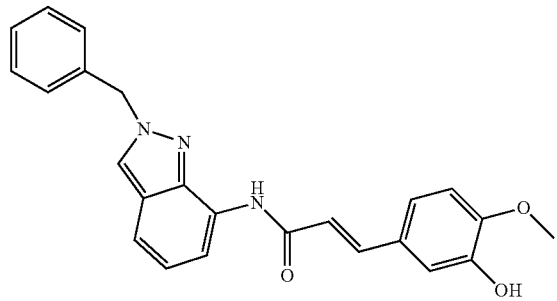 [SMILES: COc1ccc(/C=C/C(=O)Nc2cccc3cn(Cc4ccccc4)nc23)cc1O]

¹H NMR (DMSO-d6) δ (ppm): 9.86 (s, 1H), 9.16 (s, 1H), 8.51 (s, 1H), 8.10 (d, J=7.6 Hz, 1H), 7.29-7.45 (m, 7H), 7.15 (d, J=15.2 Hz, 1H), 6.96-7.07 (m, 4H), 5.72 (s, 2H), 3.82 (s, 3H).
LC-MS: Method_A—220, rt=1.86
(ES+) [M+H]+: 400.

(36) (E)-3-(3-Hydroxy-4-methoxy-phenyl)-N-(2-methyl-2H-indazol-7-yl)-acrylamide

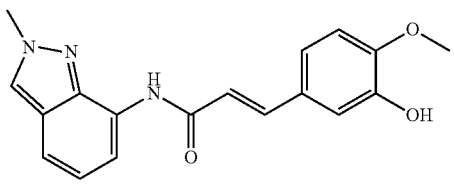

¹H NMR (DMSO-d6) δ (ppm): 9.89 (s, 1H), 9.17 (s, 1H), 8.36 (s, 1H), 8.10 (d, J=7.2 Hz, 1H), 7.40 (m, 2H), 7.16 (d, J=15.6 Hz, 1H), 7.07 (m, 2H), 7.00 (m, 2H), 4.22 (s, 3H), 3.82 (s, 3H).
LC-MS: Method_A—220, rt=1.41
(ES+) [M+H]+: 324.

(37) (E)-N-[3-(2,5-Dimethyl-2H-pyrazol-3-ylmethoxy)-phenyl]-3-(3-hydroxy-4-methoxy-phenyl)-acrylamide

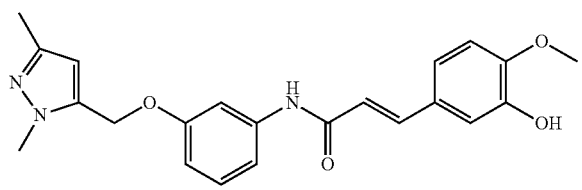 [SMILES: COc1ccc(/C=C/C(=O)Nc2cccc(OCc3cc(C)nn3C)c2)cc1O]

¹H NMR (DMSO-d6) δ (ppm): 10.12 (s, 1H), 7.50 (m, 1H), 7.44 (d, J=16.0 Hz, 1H), 7.24 (m, 2H), 7.05 (s, 1H), 7.03 (m, 1H), 6.97 (d, J=8.8 Hz, 1H), 6.75 (m, 1H), 6.60 (d, J=15.6 Hz, 1H), 6.16 (s, 1H), 5.08 (s, 2H), 3.81 (s, 3H), 3.75 (s, 3H), 2.12 (s, 3H).
LC-MS: Method_A—220, rt=1.54
(ES+) [M+H]+: 394.

(38) (E)-3-(3-Hydroxy-4-methoxy-phenyl)-N-[3-(1-methyl-1H-imidazo-2-ylmethoxy)-phenyl]-acrylamide

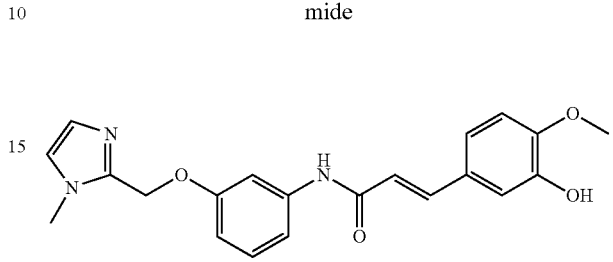

¹H NMR (DMSO-d6) δ (ppm): 10.35 (s, 1H), 7.77 (d, J=2.0 Hz, 1H), 7.72 (d, J=2.0 Hz, 1H), 7.68 (s, 1H), 7.44 (d, J=15.2 Hz, 1H), 7.32-7.24 (m, 2H), 7.06-7.02 (m, 2H), 6.97 (d, J=8.4 Hz, 1H), 6.82 (dd, J=8.0 Hz, J=1.6 Hz, 1H), 6.65 (d, J=15.6 Hz, 1H), 5.46 (s, 2H), 3.90 (s, 3H), 3.81 (s, 3H).
LC-MS: Method_A—220, rt=1.02
(ES+) [M+H]+: 380.

(39) (E)-3-(3-Hydroxy-4-methoxy-phenyl)-N-[2-(3-methoxy-phenoxymethyl)-phenyl]-acrylamide

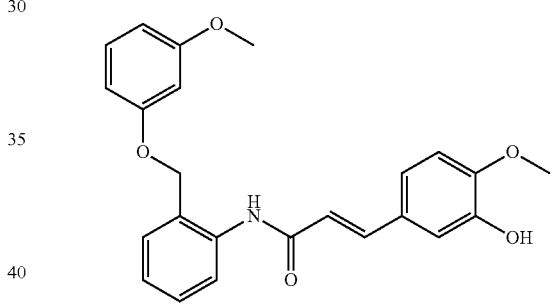

¹H NMR (DMSO-d6) δ (ppm): 9.58 (s, 1H), 9.16 (br. s., 1H), 7.61 (d, 1H), 7.44-7.53 (m, 1H), 7.45 (d, 1H), 7.34 (td, 1H), 7.10-7.27 (m, 2H), 7.00-7.08 (m, 2H), 6.90-7.00 (m, 1H), 6.68 (d, 1H), 6.38-6.63 (m, 3H), 5.12 (s, 2H), 3.81 (s, 3H), 3.71 (s, 3H).
LC-MS: Method_N—254, rt=2.28
(ES+) [M+H]+: 406.

(40) (E)-3-(3-Hydroxy-4-methoxy-4-methoxy-phenyl)-N-[2-(2-methoxy-phenoxymethyl)-phenyl]-acrylamide

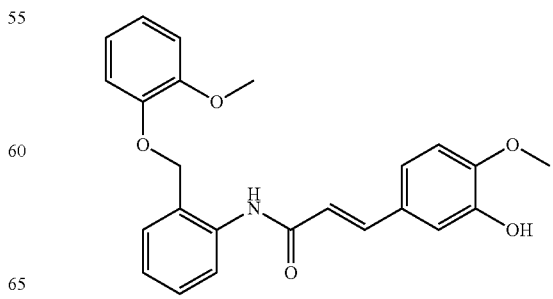

¹H NMR (DMSO-d6) δ (ppm): 9.55 (s, 1H), 9.17 (br. s., 1H), 7.72 (d, 1H), 7.41-7.54 (m, 2H), 7.34 (td, 1H), 7.11-7.27 (m, 1H), 6.82-7.11 (m, 7H), 6.65 (d, 1H), 5.13 (s, 2H), 3.81 (s, 3H), 3.77 (s, 3H).

LC-MS: Method_N—254, rt=2.27

(ES+) [M+H]+: 406.

(41) (E)-3-(3-Hydroxy-4-methoxy-phenyl)-N-[2-(4-methoxy-phenoxymethyl)-phenyl]-acrylamide

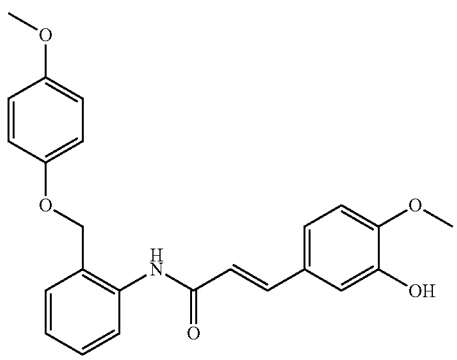 [SMILES: COc1ccc(OCc2ccccc2NC(=O)/C=C/c2ccc(OC)c(O)c2)cc1]

¹H NMR (DMSO-d6) δ (ppm): 9.55 (s, 1H), 9.18 (br. s., 1H), 7.61 (d, 1H), 7.39-7.54 (m, 2H), 7.33 (td, 1H), 7.14-7.27 (m, 1H), 6.81-7.08 (m, 7H), 6.68 (d, 1H), 5.07 (s, 2H), 3.81 (s, 3H), 3.68 (s, 3H).

LC-MS: Method_N—254, rt=2.24

(ES+) [M+H]+: 406.

(42) (E)-N-(2-Cyclobutoxymethyl-phenyl)-3-(3-hydroxy-4-methoxy-phenyl)-acrylamide

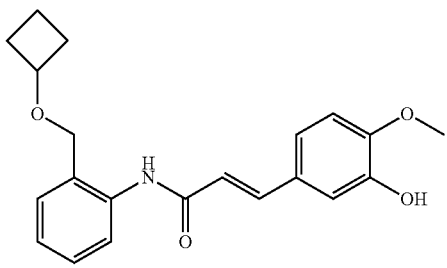 [SMILES: COc1ccc(/C=C/C(=O)Nc2ccccc2COC2CCC2)cc1O]

¹H NMR (DMSO-d6) δ (ppm): 9.37 (s, 1H), 9.17 (s, 1H), 7.63 (d, 1H), 7.43 (d, 1H), 7.35-7.42 (m, 1H), 7.29 (td, 1H), 7.11-7.23 (m, 1H), 7.01-7.09 (m, 2H), 6.97 (d, 1H), 6.66 (d, 1H), 4.42 (s, 2H), 3.90-4.10 (m, 1H), 3.82 (s, 3H), 2.04-2.23 (m, 2H), 1.76-2.00 (m, 2H), 1.54-1.74 (m, 1H), 1.28-1.54 (m, 1H)

LC-MS: Method_N—254, rt=2.19

(ES+) [M+H]+: 354.

(43) (E)-3-(3-Hydroxy-4-methoxy-phenyl)-N-[2-(pyridin-4-yloxymethyl)-phenyl]-acrylamide hydrochloride

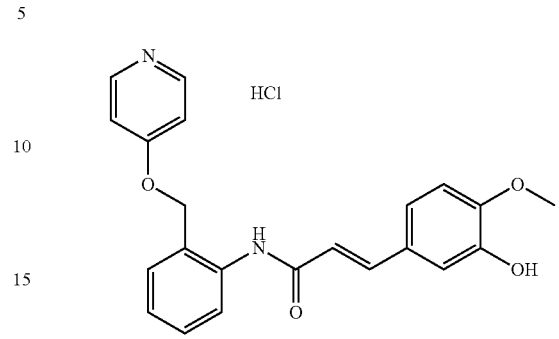

¹H NMR (DMSO-d6) δ (ppm): 9.92 (s, 1H), 9.22 (br. s., 1H), 8.03-8.14 (m, 2H), 7.47-7.53 (m, 1H), 7.43 (d, 1H), 7.35-7.44 (m, 1H), 7.27 (td, 1H), 7.15-7.22 (m, 1H), 7.01-7.10 (m, 2H), 6.98 (d, 1H), 6.67 (d, 1H), 6.52-6.79 (m, 2H), 5.37 (s, 2H), 3.82 (s, 3H).

LC-MS: Method_N—254, rt=1.26

(ES+) [M+H]+: 377.

(44) (E)-N-[2-(4-Fluoro-phenoxymethyl)-phenyl]-3-(3-hydroxy-4-methoxy-phenyl)-acrylamide

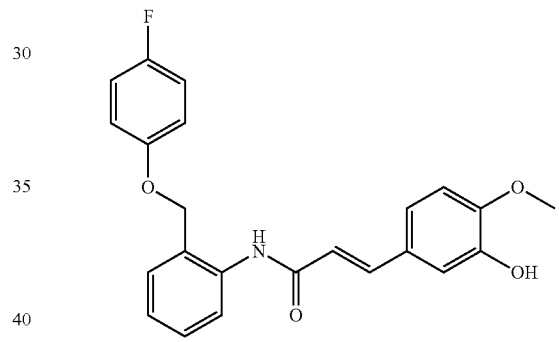

¹H NMR (DMSO-d6) δ (ppm): 9.57 (s, 1H), 9.17 (s, 1H), 7.61 (d, 1H), 7.45-7.53 (m, 1H), 7.45 (d, 1H), 7.34 (td, 1H), 7.17-7.26 (m, 1H), 6.86-7.17 (m, 7H), 6.68 (d, 1H), 5.11 (s, 2H), 3.81 (s, 3H).

LC-MS: Method_N—254, rt=2.26

(ES+) [M+H]+: 394.

(45) (E)-3-(3-Hydroxy-4-methoxy-phenyl)-N-[2-(4-imidazol-1-yl-phenoxymethyl)-phenyl]-acrylamide

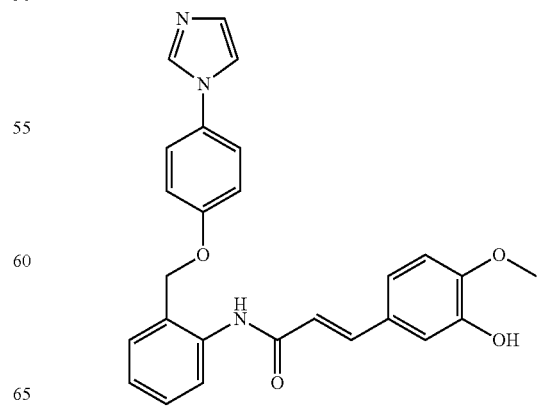

¹H NMR (DMSO-d6) δ (ppm): 9.61 (s, 1H), 9.17 (s, 1H), 8.09 (s, 1H), 7.41-7.66 (m, 6H), 7.35 (td, 1H), 7.23 (td, 1H), 7.08-7.16 (m, 2H), 7.01-7.08 (m, 3H), 6.88-7.00 (m, 1H), 6.69 (d, 1H), 5.19 (s, 2H), 3.81 (s, 3H).
LC-MS: Method_N—254, rt=1.55
(ES+) [M+H]+: 442.

(46) (E)-N-[2-(2-Fluoro-phenoxymethyl)-phenyl]-3-(3-hydroxy-4-methoxy-phenyl)-acrylamide

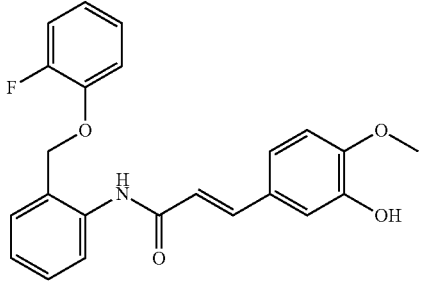 [SMILES: COc1ccc(/C=C/C(=O)Nc2ccccc2COc2ccccc2F)cc1O]

¹H NMR (DMSO-d6) δ (ppm): 9.62 (s, 1H), 9.17 (s, 1H), 7.63 (d, 1H), 7.50 (dd, 1H), 7.45 (d, 1H), 7.35 (td, 1H), 6.88-7.29 (m, 8H), 6.68 (d, 1H), 5.21 (s, 2H), 3.81 (s, 3H).
LC-MS: Method_N—254, rt=2.25
(ES+) [M+H]+: 394.

(47) (E)-3-(3-Hydroxy-4-methoxy-phenyl)-N-(2-methoxymethyl-phenyl)-acrylamide

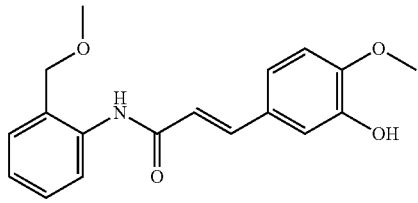 [SMILES: COCc1ccccc1NC(=O)/C=C/c1ccc(OC)c(O)c1]

¹H NMR (DMSO-d6) δ (ppm): 9.35 (s, 1H), 9.16 (s, 1H), 7.66 (d, 1H), 7.43 (d, 1H), 7.36-7.40 (m, 1H), 7.30 (td, 1H), 7.12-7.24 (m, 1H), 7.02-7.10 (m, 2H), 6.97 (d, 1H), 6.69 (d, 1H), 4.46 (s, 2H), 3.82 (s, 3H), 3.31 (s, 3H).
LC-MS: Method_N—254, rt=1.81
(ES+) [M+H]+: 314.

(48) (E)-N-[2-(3-Fluoro-phenoxymethyl)-phenyl]-3-(3-hydroxy-4-methoxy-phenyl)-acrylamide

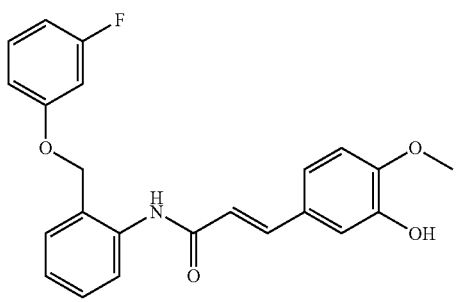 [SMILES: COc1ccc(/C=C/C(=O)Nc2ccccc2COc2cccc(F)c2)cc1O]

¹H NMR (DMSO-d6) δ (ppm): 9.58 (s, 1H), 9.17 (s, 1H), 7.62 (d, 1H), 7.44-7.53 (m, 1H), 7.45 (d, 1H), 7.26-7.39 (m, 2H), 7.22 (td, 1H), 6.92-7.12 (m, 3H), 6.81-6.91 (m, 2H), 6.72-6.81 (m, 1H), 6.68 (d, 1H), 5.16 (s, 2H), 3.81 (s, 3H).
LC-MS: Method_N—254, rt=2.34
(ES+) [M+H]+: 394.

(49) (E)-N-(3-Bromo-phenyl)-3-(4-fluoro-3-hydroxy-phenyl)-acrylamide

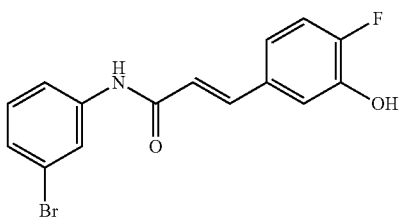 [SMILES: O=C(/C=C/c1ccc(F)c(O)c1)Nc1cccc(Br)c1]

¹H NMR (DMSO-d6) δ (ppm): 10.32 (s, 1H), 10.08 (br. s., 1H), 8.06 (t, 1H), 7.57 (dt, 1H), 7.49 (d, 1H), 7.13-7.41 (m, 4H), 6.90-7.13 (m, 1H), 6.64 (d, 1H).
LC-MS: Method_N—254, rt=2.20
(ES+) [M+H]+: 336.

(50) (E)-N-(2-Benzyloxy-phenyl)-3-(4-fluoro-3-hydroxy-phenyl)-acrylamide

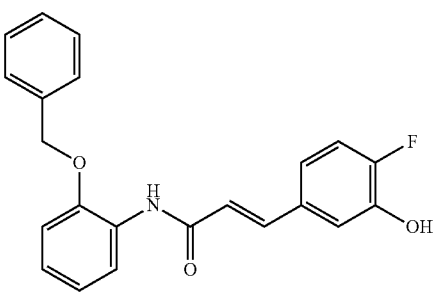 [SMILES: O=C(/C=C/c1ccc(F)c(O)c1)Nc1ccccc1OCc1ccccc1]

¹H NMR (DMSO-d6) δ (ppm): 10.10 (br. s., 1H), 9.32 (s, 1H), 8.06 (d, 1H), 7.49-7.56 (m, 2H), 7.45 (d, 1H), 7.34-7.41 (m, 2H), 7.25-7.34 (m, 1H), 7.15-7.25 (m, 2H), 6.99-7.14 (m, 3H), 7.01 (d, 1H), 6.87-6.96 (m, 1H), 5.26 (s, 2H).
LC-MS: Method_N—254, rt=2.41
(ES+) [M+H]+: 364.

(51) (E)-N-(2,3-Dichloro-phenyl)-3-(4-fluoro-3-hydroxy-phenyl)-acrylamide

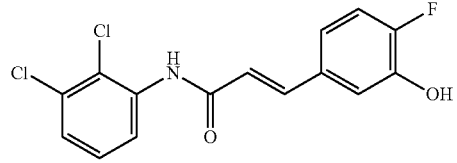 [SMILES: O=C(/C=C/c1ccc(F)c(O)c1)Nc1cccc(Cl)c1Cl]

¹H NMR (DMSO-d6) δ (ppm): 10.08 (br. s., 1H), 9.79 (s, 1H), 7.89 (d, 1H), 7.51 (d, 1H), 7.44-7.50 (m, 1H), 7.38 (t, 1H), 7.14-7.30 (m, 2H), 7.03-7.14 (m, 1H), 6.94 (d, 1H).
LC-MS: Method_N—254, rt=2.27
(ES+) [M+H]+: 326.

(52) (E)-N-(1-Benzyl-1H-indol-7-yl)-3-(4-fluoro-3-hydroxy-phenyl)-acrylamide

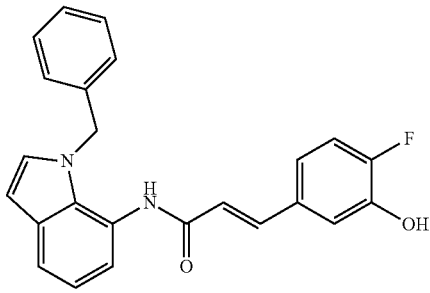 [SMILES: O=C(/C=C/c1ccc(F)c(O)c1)Nc1cccc2ccn(Cc3ccccc3)c12]

¹H NMR (DMSO-d6) δ (ppm): 10.07 (s, 1H), 9.81 (s, 1H), 7.31-7.57 (m, 3H), 7.09-7.30 (m, 5H), 6.77-7.09 (m, 5H), 6.63 (d, 1H), 6.55 (d, 1H), 5.47 (s, 2H).
LC-MS: Method_N—254, rt=2.25
(ES+) [M+H]+: 387.

(53) (E)-N-(3-Fluoro-phenyl)-3-(3-hydroxy-4-methoxy-phenyl)-acrylamide

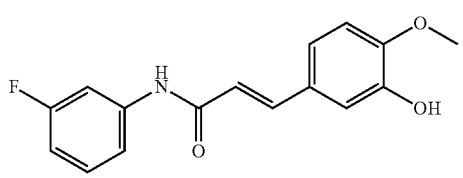 [SMILES: COc1ccc(/C=C/C(=O)Nc2cccc(F)c2)cc1O]

¹H NMR (DMSO-d6) δ (ppm): 10.28 (s, 1H), 9.22 (s, 1H), 7.72 (ddd, J=12.32 Hz, J=1.91 Hz, J=1.61 Hz, 1H), 7.47 (d, J=15.85 Hz, 1H), 7.41-7.27 (m, 2H), 7.05 (d, J=2.05 Hz, 1H), 7.05 (dd, J=8.80 Hz, J=2.05 Hz, 1H), 6.98 (d, J=8.80 Hz, 1H), 6.93-6.80 (m, 1H), 6.58 (d, J=15.85 Hz, 1H), 3.82 (s, 3H).
(ES+) [M+H]+: 288.

Example 3

Preparation of substituted (E)-3-(3-hydroxy-phenyl)-acrylic anilides from the corresponding (E)-3-(3-hydroxy-phenyl)-acrylic acids

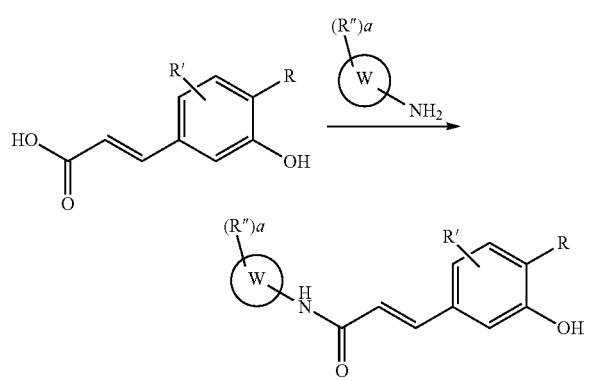

(54) (E)-N-(3-Chloro-phenyl)-3-(3-hydroxy-phenyl)-acrylamide

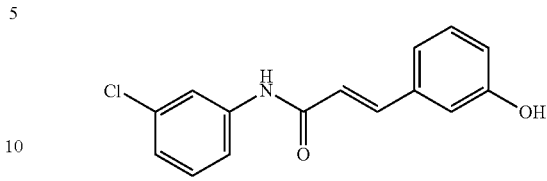

A solution of (E)-3-(3-hydroxy-phenyl)-acrylic acid (1.0 g, 6.1 mmol) and thionyl chloride (0.53 mL, 7.32 mmol) in dry THF (15 mL) was stirred at 55° C. for 3 hrs. Then a further aliquot of thionyl chloride (0.1 mL, 1.38 mmol) is added and the mixture is stirred at reflux temperature for additional 1.5 hrs. After cooling to about 5° C., a solution of 3-chloro-aniline (0.65 mL, 6.1 mmol) and triethylamine (3.4 mL, 24.4 mmol) in dry THF (5 mL) was added dropwise. After stirring at RT for 16 hrs the reaction mixture was diluted with DCM and washed with water, aqueous hydrochloric acid, and brine. The organic layer was dried over sodium sulphate and evapored. The resulting raw material was purified first by column chromatography (eluant petroleum ether/AcOEt 45/55) and then by trituration in DCM, yielding 140 mg of the title compound as a white solid.
¹H NMR (DMSO-d6) δ (ppm): 10.37 (s, 1H), 9.64 (s, 1H), 7.93 (m, 1H), 7.53-7.49 (m, 2H), 7.37 (m, 1H), 7.25 (m, 1H), 7.13 (m, 1H), 7.05 (m, 1H), 6.70 (m, 1H), 6.83 (m, 1H), 6.72 (d, J=15.6 Hz, 1H).
LC-MS: Method_A—220, rt=1.81
(ES+) [M+H]+: 274
By analogously coupling the suitable acrylic acid with the suitable aniline, the following compounds were prepared:

(55) (E)-N-(3-Chloro-phenyl)-3-(3-hydroxy-4-methoxy-phenyl)-acrylamide

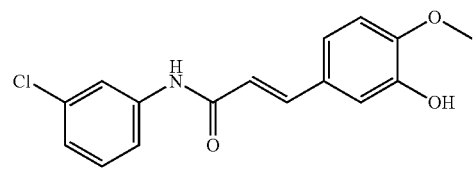 [SMILES: COc1ccc(/C=C/C(=O)Nc2cccc(Cl)c2)cc1O]

¹H NMR (DMSO-d6) δ (ppm): 10.28 (s, 1H), 9.26 (s, 1H), 7.93 (m, 1H), 7.50 (m, 1H), 7.46 (d, J=15.4 Hz, 1H), 7.35 (m, 1H), 7.12 (m, 1H), 7.10-6.97 (m, 3H), 6.57 (d, J=15.4 Hz, H), 3.81 (s, 3H).
LC-MS: Method_N—254, rt=1.78
(ES+) [2M+Na]+: 629

(56) (E)-N-(2-Chloro-phenyl)-3-(3-hydroxy-4-methoxy-phenyl)-acrylamide

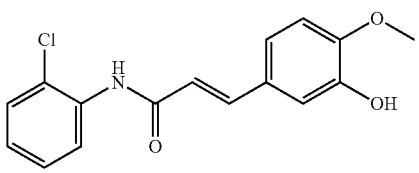 [SMILES: COc1ccc(/C=C/C(=O)Nc2ccccc2Cl)cc1O]

¹H NMR (DMSO-d6) δ (ppm): 8.53 (m, 1H), 7.74 (m, 1H), 7.68 (d, J=15, 1H), 7.39 (m, 1H), 7.30 (m, 1H), 7.19 (m, 1H), 7.06 (m, 2H), 6.44 (d, J=15, 1H), 3.94 (s, 3H).

(ES+) [M+H]+: 304.

(57) (E)-N-(4-Chloro-phenyl)-3-(3-hydroxy-4-methoxy-phenyl)-acrylamide

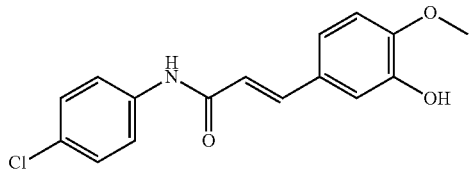 [SMILES: COc1ccc(/C=C/C(=O)Nc2ccc(Cl)cc2)cc1O]

¹H NMR (DMSO-d6) δ (ppm): 10.23 (s, 1H), 9.25 (s, 1H), 7.71 (AB system, 2H), 7.44 (d, J=15.6, 1H), 7.38 (AB system, 2H), 7.05-7.03 (m, 2H), 6.98-6.96 (m, 1H), 6.57 (d, J=15.6, 1H), 3.81 (s, 3H).

LC-MS: Method_A—220, rt=1.78

(ES+) [2M+Na]+: 629.

(58) (E)-3-(3-Hydroxy-4-methoxy-phenyl)-N-(3-iodo-phenyl)-acrylamide

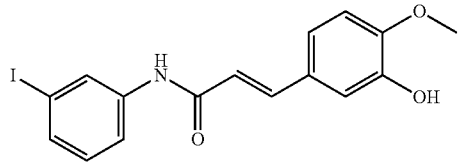 [SMILES: COc1ccc(/C=C/C(=O)Nc2cccc(I)c2)cc1O]

¹H NMR (DMSO-d6) δ (ppm): 10.19 (s, 1H), 9.25 (s, 1H), 8.21 (m, 1H), 7.61 (m, 1H), 7.47-7.40 (m, 2H), 7.15-6.97 (m, 4H), 6.55 (d, J=15.6 Hz, 1H), 3.81 (s, 3H).

LC-MS: Method_A—220, rt=1.92

(ES+) [2M+Na]+: 813.

(59) (E)-N-(3-Bromo-phenyl)-3-(3-hydroxy-4-methoxy-phenyl)-acrylamide

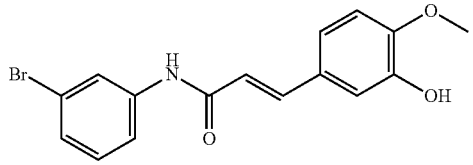

¹H NMR (DMSO-d6) δ (ppm): 10.26 (s, 1H), 9.24 (s, 1H), 8.06 (t, J=2.0 Hz, 1H), 7.56-7.54 (m, 1H), 7.46 (d, J=15.6 Hz, 1H), 7.31-7.22 (m, 2H), 7.06-7.03 (m, 2H), 6.97 (d, J=8.8 Hz, 1H), 6.56 (d, J=15.6 Hz, 1H), 3.81 (s, 3H).

LC-MS: Method_A—220, rt=1.98

(ES+) [2M+Na]+: 719.

(60) (E)-3-(3-Hydroxy-4-methoxy-phenyl)-N-(3-isopropoxy-phenyl)-acrylamide

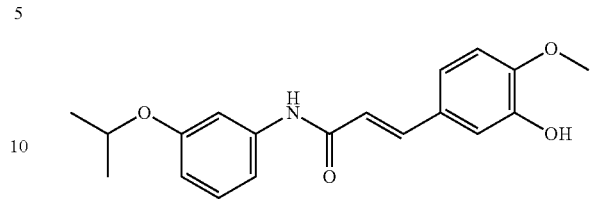

¹H NMR (DMSO-d6) δ (ppm): 10.04 (s, 1H), 9.23 (s, 1H), 7.45-7.39 (m, 2H), 7.21-7.13 (m, 2H), 7.04-7.02 (m, 2H), 6.97 (d, J=8.8 Hz, 1H), 6.62-6.56 (m, 2H), 4.54 (ep, J=6.0 Hz, 1H), 3.81 (s, 3H), 1.27 (d, J=6.0 Hz, 6H).

LC-MS: Method_A—220, rt=1.95

(ES+) [2M+Na]+: 677.

(61) (E)-3-(3-Hydroxy-4-methoxy-phenyl)-N-(3-phenoxy-phenyl)-acrylamide

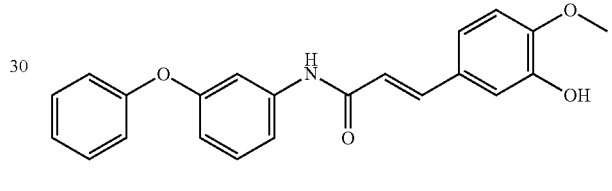

¹H NMR (DMSO-d6) δ (ppm): 10.16 (s, 1H), 9.23 (s, 1H), 7.45-7.41 (m, 2H), 7.40-7.38 (m, 3H), 7.32 (t, J=8.4 Hz, 1H), 7.19-7.14 (m, 1H), 7.06-7.05 (m, 1H), 7.04-7.00 (m, 3H), 6.96 (d, J=8.8 Hz, 1H), 6.71 (ddd, J=8.0 Hz, J=2.4 Hz, J=0.8 Hz, 1H), 6.55 (d, J=15.6 Hz, 1H), 3.80 (s, 3H).

LC-MS: Method_A—220, rt=2.17

(ES+) [2M+Na]+: 745.

(62) (E)-N-(3-Benzyloxy-phenyl)-3-(3-hydroxy-4-methoxy-phenyl)-acrylamide

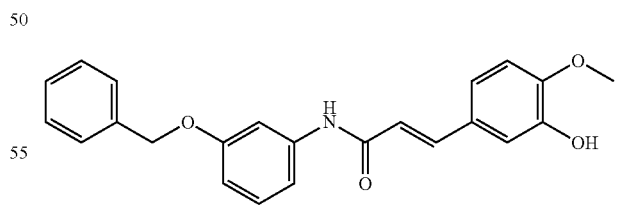

¹H NMR (DMSO-d6) δ (ppm): 10.08 (s, 1H), 9.23 (s, 1H), 7.50 (s, 1H), 7.47-7.38 (m, 5H), 7.35-7.31 (m, 1H), 7.24-7.18 (m, 2H), 7.04-7.02 (m, 2H), 6.97 (d, J=8.8 Hz, 1H), 6.73-6.70 (m, 1H), 6.58 (d, J=16.0 Hz, 1H), 5.09 (s, 2H), 3.81 (s, 3H).

LC-MS: Method_A—220, rt=2.15

(ES+) [2M+Na]+: 773.

(63) (E)-3-(3-Hydroxy-4-methoxy-phenyl)-N-(3-methoxy-phenyl)-acrylamide

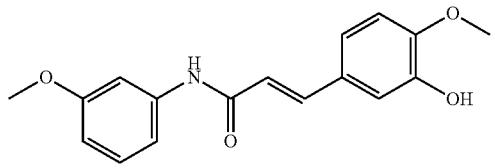

¹H NMR (DMSO-d6) δ (ppm): 10.07 (s, 1H), 9.24 (s, 1H), 7.45-7.41 (m, 2H), 7.24-7.18 (m, 2H), 7.04-7.02 (m, 2H), 6.98-6.96 (m, 1H), 6.65-6.62 (m, 1H), 6.58 (d, J=15.6 Hz, 1H), 3.81 (s, 3H), 3.74 (s, 3H).
LC-MS: Method_A—220, rt=1.52
(ES+) [2M+Na]+: 621.

(64) (E)-3-(3-Hydroxy-4-methoxy-phenyl)-N-(3-trifluoromethyl-phenyl)-acrylamide

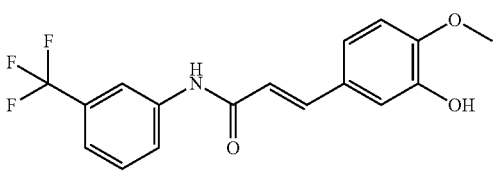 [SMILES: COc1ccc(/C=C/C(=O)Nc2cccc(C(F)(F)F)c2)cc1O]

¹H NMR (DMSO-d6) δ (ppm): 10.43 (s, 1H), 9.26 (s, 1H), 8.20 (s, 1H), 7.85 (d, J=8.8 Hz, 1H), 7.57 (t, J=8.0 Hz, 1H), 7.48 (d, J=16.0 Hz, 1H), 7.40 (d, J=8.0 Hz, 1H), 7.06-7.04 (m, 2H), 6.99-6.97 (m, 1H), 6.58 (d, J=15.6 Hz, 1H), 3.81 (s, 3H).
LC-MS: Method_A—220, rt=1.89
(ES+) [2M+Na]+: 697.

(65) (E)-3-(3-Hydroxy-4-methoxy-phenyl)-N-[3-(pyridin-4-ylmethoxy)-phenyl]-acrylamide

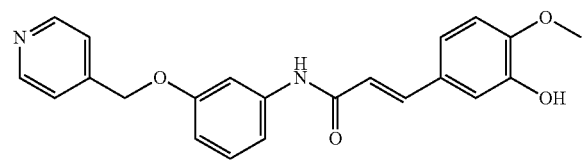 [SMILES: COc1ccc(/C=C/C(=O)Nc2cccc(OCc3ccncc3)c2)cc1O]

¹H NMR (DMSO-d6) δ (ppm): 10.09 (s, 1H), 9.22 (s, 1H), 8.59-8.57 (m, 2H), 7.52 (t, J=2.0 Hz, 1H), 7.45-7.41 (m, 3H), 7.26-7.19 (m, 2H), 7.04-7.02 (m, 2H), 6.97 (d, J=8.8 Hz, 1H), 6.72 (ddd, J=7.6 Hz, J=2.4 Hz, J=1.6 Hz, 1H), 6.58 (d, J=15.6 Hz, 1H), 5.17 (s, 2H), 3.81 (s, 3H).
LC-MS: Method_A—220, rt=1.13
(ES+) [2M+Na]+: 775.

(66) (E)-3-(3-Hydroxy-4-methoxy-phenyl)-N-[3-(1-methyl-piperidin-3-ylmethoxy)-phenyl]-acrylamide

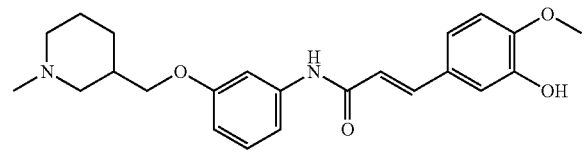

¹H NMR (DMSO-d6) δ (ppm): 10.04 (s, 1H), 9.21 (s, 1H), 7.45-7.41 (m, 2H), 7.22-7.15 (m, 2H), 7.04-7.02 (m, 2H), 6.97 (d, J=8.8 Hz, 1H), 6.62 (ddd, J=7.6 Hz, J=2.4 Hz, J=1.2 Hz, 1H), 6.58 (d, J=15.6 Hz, 1H), 3.86-3.78 (m, 5H), 2.79 (d, J=8.0 Hz, 1H), 2.62-2.60 (m, 1H), 2.16 (s, 3H), 2.02-1.97 (m, 1H), 1.93-1.88 (m, 1H), 1.79 (t, J=10.4 Hz, 1H), 1.73-1.69 (m, 1H), 1.66-1.61 (m, 1H), 1.54-1.44 (m, 1H), 1.11-1.05 (m, 1H).
LC-MS: Method_A—220, rt=1.11
(ES+) [M+H]+: 397.

(67) (E)-3-(3-Hydroxy-4-methoxy-phenyl)-N-[3-(pyridin-4-yloxy)-phenyl]-acrylamide

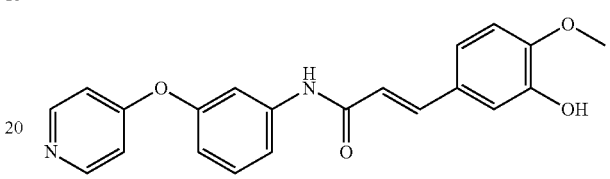

¹H NMR (DMSO-d6) δ (ppm): 10.39 (s, 1H), 9.25 (s, 1H), 7.97-7.95 (m, 3H), 7.64 (d, J=7.6 Hz, 1H), 7.53-7.46 (m, 2H), 7.24 (dd, J=7.6 Hz, J=1.6 Hz, 1H), 7.06-7.05 (m, 2H), 6.98 (d, J=9.2 Hz, 1H), 6.60 (d, J=15.6 Hz, 1H), 6.26-6.24 (m, 2H), 3.82 (s, 3H).
LC-MS: Method_A—220, rt=1.07
(ES+) [2M+H]+: 725.

(68) (E)-N-(3,5-Dichloro-phenyl)-3-(3-hydroxy-4-methoxy-phenyl)-acrylamide

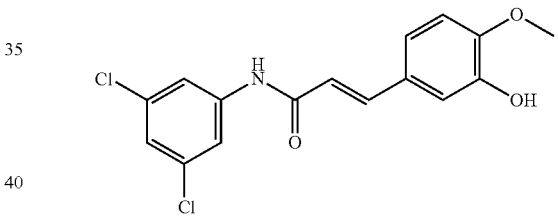

¹H NMR (DMSO-d6) δ (ppm): 10.42 (s, 1H), 9.25 (s, 1H), 7.75 (d, J=1.6, 2H), 7.48 (d, J=15.6 Hz, 1H), 7.27 (t, J=1.6 Hz, 1H), 7.07-7.05 (m, 2H), 6.99-6.97 (m, 1H), 6.52 (d, J=15.6 Hz, 1H), 3.81 (s, 3H).
LC-MS: Method_A—220, rt=1.07
(ES+) [2M+Na]+: 699.

(69) (E)-3-(3-Hydroxy-4-methoxy-phenyl)-N-[3-(1-methyl-piperidin-4-yloxy)-phenyl]-acrylamide

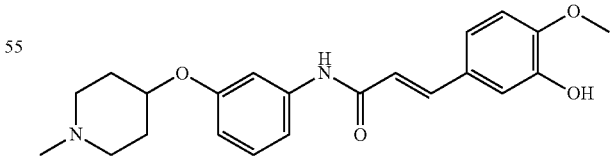

¹H NMR (DMSO-d6) δ (ppm): 10.02 (s, 1H), 7.45-7.41 (m, 2H), 7.21-7.14 (m, 2H), 7.04-7.02 (m, 2H), 6.97 (d, J=8.4 Hz, 1H), 6.65-6.62 (m, 1H), 6.57 (d, J=15.6 Hz, 1H), 4.29 (qn, J=4.0 Hz, 1H), 3.81 (s, 3H), 2.62-2.60 (m, 2H), 2.18-2.13 (m, 5H), 1.94-1.91 (m, 2H), 1.68-1.59 (m, 2H).
LC-MS: Method_A—220, rt=1.05
(ES+) [2M+Na]+: 687.

(70) (E)-N-(4-Benzyloxy-phenyl)-3-(3-hydroxy-4-methoxy-phenyl)-acrylamide

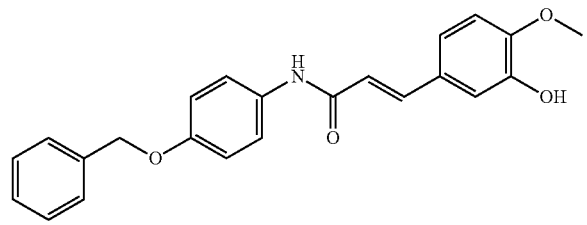 [SMILES: COc1ccc(/C=C/C(=O)Nc2ccc(OCc3ccccc3)cc2)cc1O]

$^1$H NMR (DMSO-d6) δ (ppm): 9.96 (s, 1H), 9.20 (s, 1H), 7.61-7.58 (m, 2H), 7.46-7.37 (m, 5H), 7.35-7.30 (m, 1H), 7.03-6.95 (m, 5H), 6.56 (d, J=15.6 Hz, 1H), 5.07 (s, 2H), 3.81 (s, 3H).

LC-MS: Method_A—220, rt=1.99

(ES+) [2M+Na]+: 773.

(71) (E)-N-(3-Chloro-phenyl)-3-(3-hydroxy-4-methyl-phenyl)-acrylamide

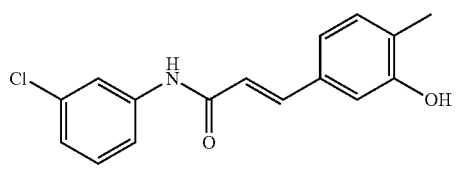 [SMILES: Cc1ccc(/C=C/C(=O)Nc2cccc(Cl)c2)cc1O]

$^1$H NMR (DMSO-d6) δ (ppm): 10.35 (s, 1H), 9.56 (s, 1H), 7.93 (s, 1H), 7.49 (m, 2H), 7.36 (m, 1H), 7.13 (m, 2H), 6.98 (m, 2H), 6.65 (d, J=16 Hz, 1H), 2.15 (s, 3H).

LC-MS: Method_A—220, rt=1.88

(ES+) [M+H]+: 288.

(72) (E)-3-(4-Fluoro-3-hydroxy-phenyl)-N-naphthalen-1-yl-acrylamide

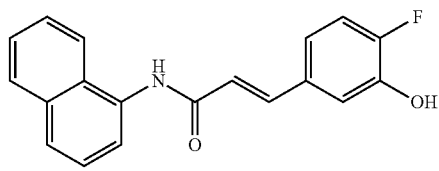 [SMILES: O=C(/C=C/c1ccc(F)c(O)c1)Nc1cccc2ccccc12]

$^1$H NMR (DMSO-d6) δ (ppm): 10.13 (s, 2H), 8.16 (min, 1H), 7.98-7.90 (m, 2H), 7.79 (d, J=8 Hz, 1H), 7.61-7.52 (m, 4H), 7.24 (m, 2H), 7.18 (m, bs, 1H), 7.01 (d, J=15.2 Hz, 1H).

LC-MS: Method_A—220, rt=1.72

(ES+) [M+H]+: 308.

Example 4

Preparation of substituted (E)-3-(3-hydroxy-phenyl)-acrylic anilides from the corresponding (E)-3-(3-acetoxy-phenyl)-acrylic acids

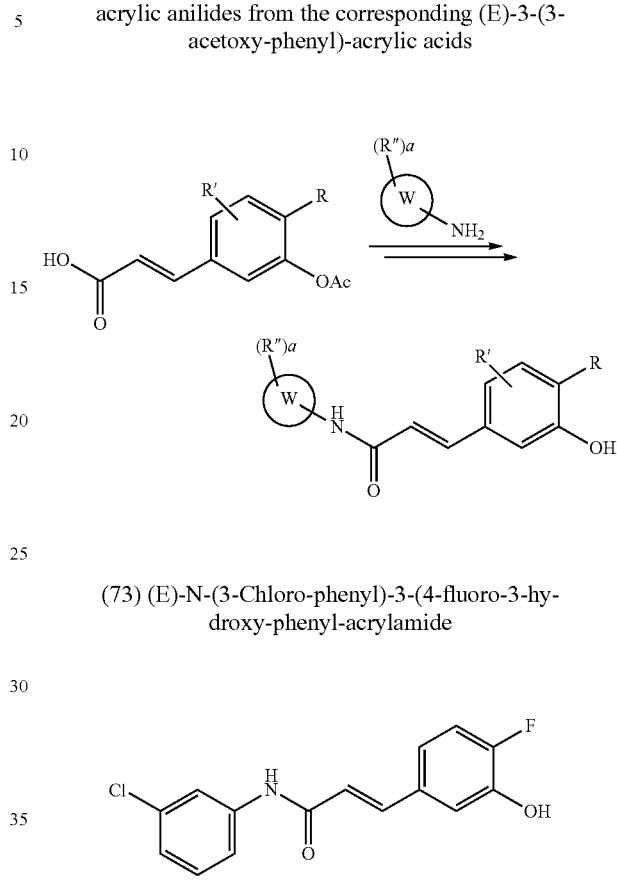

(73) (E)-N-(3-Chloro-phenyl)-3-(4-fluoro-3-hydroxy-phenyl-acrylamide

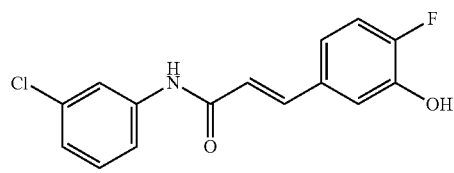 [SMILES: O=C(/C=C/c1ccc(F)c(O)c1)Nc1cccc(Cl)c1]

A solution (E)-3-(3-acetoxy-4-fluoro-phenyl)-acrylic acid (0.17 g, 0.76 mmol) and thionyl chloride (0.069 mL, 0.95 mmol) in dry THF (2 mL) was stirred at 55° C. for 3 hrs. Then a further aliquot of thionyl chloride (0.008 mL, 0.11 mmol) was added and the mixture was stirred at reflux temperature for additional 1.5 hrs. After cooling to about 35° C., a solution of 3-chloro-aniline (0.204 mL, 1.90 mmol) dry THF (0.5 mL) was added dropwise. After stirring at RT for 16 hrs, the reaction mixture was diluted with DCM and washed with water, aqueous hydrochloric acid, and brine. The organic layer was then dried over sodium sulphate and evaporated. The resulting raw material was taken up without further purification with THF (2 mL), and a 3N methanolic solution of hydrochloric acid (4 mL-12 mmols) was added to the so obtained solution. The resulting mixture was stirred at RT for 16 hrs, concentrated under reduced pressure, taken up with solvent an re-evaporated (3 times with MeOH and once with acetone) to give a light yellow residue that was sequentially triturated with toluene, ethyl ether and dichlorometane. After the last filtration and drying, 75 mg of the title (E)-N-(3-chloro-phenyl)-3-(4-fluoro-3-hydroxy-phenyl)-acrylamide were obtained, as a light yellow powder.

$^1$H NMR (DMSO-d6) δ (ppm): 10.38 (s, 1H), 10.15 (s, 1H), 7.94 (bs, 1H), 7.54-7.49 (m, 2H), 7.39-7.35 (m, 1H), 7.22-7.20 (m, 2H), 7.15-7.08 (m, 2H), 6.64 (d, J=15.6 Hz, H).

LC-MS: Method_A—220, rt=1.78

(ES+) [M+H]+: 292.

By analogously coupling the suitable acrylic acid with the suitable aniline, and performing the adequate chromatographic purification when needed, the following compounds were prepared:

(74) (E)-3-(3-Hydroxy-4-methoxy-phenyl)-N-[3-(1H-tetrazol-5-ylmethoxy)-phenyl]-acrylamide

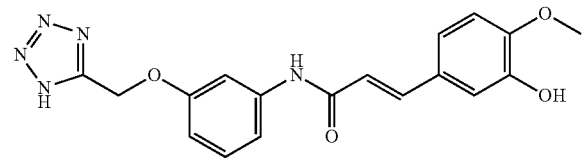 [SMILES: COc1ccc(/C=C/C(=O)Nc2cccc(OCc3nnn[nH]3)c2)cc1O]

¹H NMR (DMSO-d6) δ (ppm): 10.14 (s, 1H), 9.25 (s, 1H), 7.53 (s, 1H), 7.44 (d, J=15.6 Hz, 1H), 7.29-7.23 (m, 2H), 7.04-7.03 (m, 2H), 6.97 (d, J=8.8 Hz, 1H), 6.78-6.76 (m, 1H), 6.58 (d, J=15.6 Hz, 1H), 5.46 (s, 2H), 3.81 (s, 3H).

LC-MS: Method_A—220, rt=1.24

(ES+) [M+H]+: 368.

(75) (E)-3-(3-Hydroxy-4-methoxy-phenyl)-N-(4-methoxy-pyrimidin-2-yl)-acrylamide

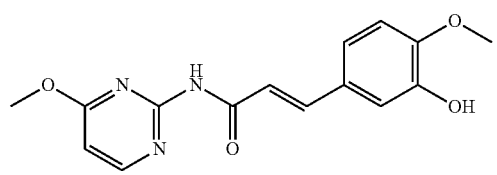

¹H NMR (DMSO-d6) δ (ppm): 8.42 (d, J=6.4 Hz, 1H), 7.65 (d, J=16.0 Hz, 1H), 7.13-7.11 (m, 2H), 7.01 (d, J=7.6, 1H), 6.91-6.86 (m, 2H), 4.04 (s, 3H), 3.83 (s, 3H).

LC-MS: Method_A—220, rt=0.95

(ES+) [2M+Na]+: 625.

(76) (E)-3-(3-Hydroxy-4-methoxy-phenyl)-N-(2-phenethyloxy-phenyl)-acrylamide

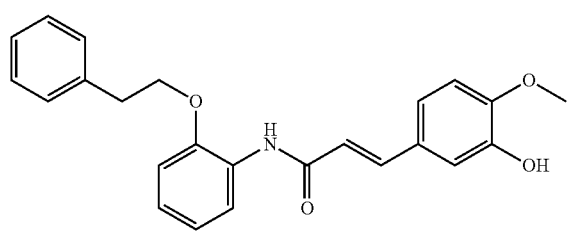 [SMILES: COc1ccc(/C=C/C(=O)Nc2ccccc2OCCc2ccccc2)cc1O]

¹H NMR (DMSO-d6) δ (ppm): 10.38 (s, 1H), 10.15 (s, 1H), 7.94 (bs, 1H), 7.54-7.49 (m, 2H), 7.39-7.35 (m, 1H), 7.22-7.20 (m, 2H), 7.15-7.08 (m, 2H), 6.64 (d, J=15.6 Hz, H).

LC-MS: Method_A—220, rt=2.09

(ES+) [M+H]+: 390.

(77) (E)-3-(3-Hydroxy-4-methoxy-phenyl)-N-[2-(pyridin-4-ylmethoxy)-phenyl]-acrylamide hydrochloride

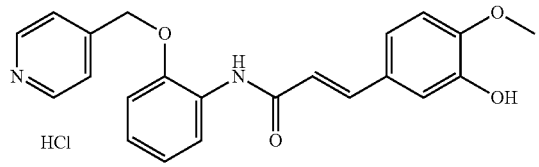 [SMILES: COc1ccc(/C=C/C(=O)Nc2ccccc2OCc2ccncc2)cc1O ; Cl]

¹H NMR (DMSO-d6) δ (ppm): 9.47 (s, 1H), 8.85 (d, J=6.4 Hz, 2H), 8.07-8.00 (m, 3H), 7.44 (d, J=16 Hz, 1H), 7.09-7.05 (m, 4H), 7.01-6.91 (m, 3H), 5.52 (s, 2H), 3.82 (s, 3H).

LC-MS: Method_A—220, rt=1.11

(ES+) [M+H]+: 377.

(78) (E)-3-(4-Fluoro-3-hydroxy-phenyl)-N-[3-(pyridin-4-ylmethoxy)-phenyl]-acrylamide hydrochloride

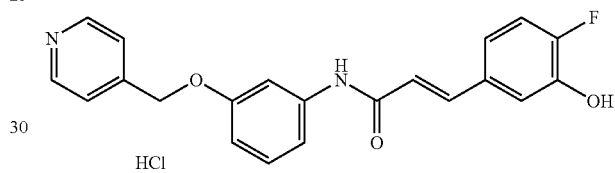

LC-MS: Method_A—220, rt=1.14

(ES+) [M+H]+: 365.

(79) (E)-3-(3-Hydroxy-4-methoxy-phenyl)-N-[3-(pyridin-4-ylmethylsulfanyl)-phenyl]-acrylamide hydrochloride

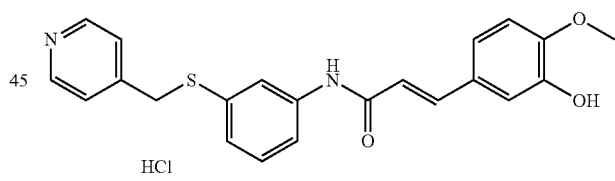

LC-MS: Method_A—220, rt=1.20

(ES+) [M+H]+: 393.

(80) (E)-N-1,3-Benzodioxol-5-yl-3-(3-hydroxy-4-methoxy-phenyl)-acrylamide

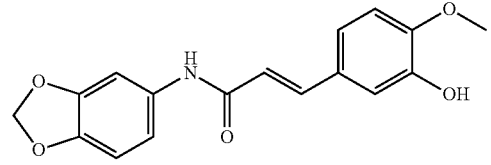 [SMILES: COc1ccc(/C=C/C(=O)Nc2ccc3c(c2)OCO3)cc1O]

LC-MS: Method_A—220, rt=1.44

(ES+) [M+H]+: 314.

(81) (E)-3-(3-Hydroxy-4-methoxy-phenyl)-N-(1-methyl-1H-indazol-7-yl)-acrylamide

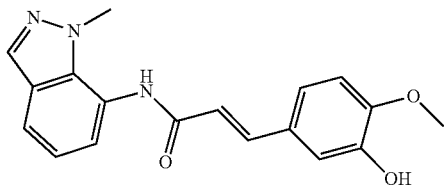 [SMILES: COc1ccc(/C=C/C(=O)Nc2cccc3cnn(C)c23)cc1O]

$^1$H NMR (DMSO-d6) δ (ppm): 10.04 (s, 1H), 9.24 (s, 1H), 8.06 (s, 1H), 7.67 (d, J=8.0 Hz, 1H), 7.49 (d, J=16.0 Hz, 1H), 7.21 (d, J=6.8 Hz, 1H), 7.10 (m, 3H), 6.99 (d, J=8.0 Hz, 1H), 6.70 (d, J=16.0 Hz, 1H), 4.09 (s, 3H), 3.82 (s, 3H).

LC-MS: Method_A—220, rt=1.23

(ES+) [M+H]+: 324.

(82) (E)-N-(4-Ethoxy-1-methyl-1H-indazol-7-yl)-3-(3-hydroxy-4-methoxy-phenyl)-acrylamide

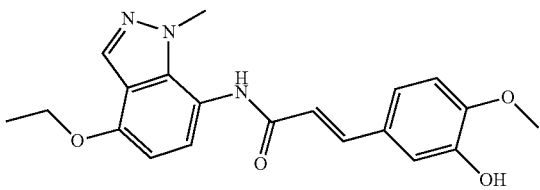 [SMILES: CCOc1ccc(NC(=O)/C=C/c2ccc(OC)c(O)c2)c2c1cnn2C]

$^1$H NMR (DMSO-d6) δ (ppm): 9.83 (s, 1H), 9.23 (s, 1H), 7.97 (s, 1H), 7.46 (d, J=15.6 Hz, 1H), 7.07 (m, 3H), 6.98 (d, J=7.6 Hz, 1H), 6.66 (d, J=15.6 Hz, 1H), 6.53 (d, J=7.6 Hz, 1H), 4.20 (q, J=6.8 Hz, 21-H), 4.03 (s, 3H), 3.82 (s, 3H), 1.43 (t, J=6.8 Hz, 3H).

LC-MS: Method_A—220, rt=1.43

(ES+) [M+H]+: 368.

(83) (E)-3-(3-Hydroxy-4-methoxy-phenyl)-N-(1-methyl-1H-indazol-4-yl)-acrylamide

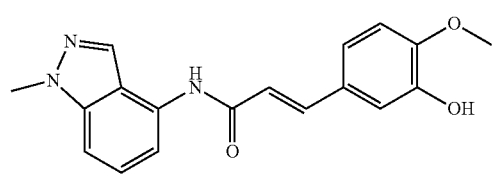

$^1$H NMR (DMSO-d6) δ (ppm): 10.10 (s, 1H), 9.24 (s, 1H), 8.31 (s, 1H), 7.88 (dd, J=6.0 Hz, J=2.0, 1H), 7.50 (d, J=15.6 Hz, 1H), 7.37-7.32 (m, 2H), 7.09-7.06 (m, 2H), 6.99 (d, J=8.0 Hz, 1H), 6.86 (d, J=15.6 Hz, 1H), 4.03 (s, 3H), 3.82 (s, 3H).

LC-MS: Method_A—220, rt=1.38

(ES+) [M+H]+: 324.

Example 5

(84) (E)-3-(3-Hydroxy-4-methoxy-phenyl)-N-[3-(5-methyl-furan-2-ylmethoxy)-phenyl]-acrylamide

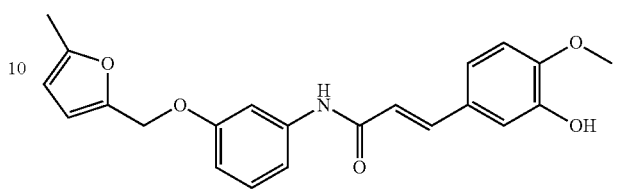

Diethylazodicarboxylate (1.13 mL 5.83 mmol) was added dropwise to a solution of (E)-3-(3-acetoxy-4-methoxy-phenyl)-N-(3-hydroxy-phenyl)-acrylamide (0.763 g, 2.33 mmol), (5-methyl-furan-2-yl)-methanol (0.392 g, 3.5 mmol) and triphenylphosphine (1.53 g, 5.83 mmol) in dry THF (20 mL) at 0° C. The resulting solution was allowed to reach RT and stirred for 16 hrs. The reaction mixture was then diluted with DCM and washed with water, aqueous hydrochloric acid, and brine. The organic layer was then dried over sodium sulphate and evapored. The resulting raw material was taken up, without further purification, with a 3N methanolic solution of hydrochloric acid (5 mL-15 mmols) and stirred at RT for 16 hrs, concentrated under reduced pressure, taken up with solvent an re-evaporated (3 times with MeOH and once with acetone) to give a residue that was purified by silica gel column chromatography (eluant DCM/MeOH 98/2) to obtain 15 mg of the title (E)-3-(3-hydroxy-4-methoxy-phenyl)-N-[3-(5-methyl-furan-2-ylmethoxy)-phenyl]-acrylamide.

$^1$H NMR (DMSO-d6) δ (ppm): 9.32 (s, 1H), 9.27 (s, 1H), 9.20 (s, 1H), 7.39 (d, J=15.6 Hz, 1H), 7.12 (s, 1H), 7.04-7.02 (m, 2H), 6.96 (d, J=8.4 Hz, 1H), 6.92 (d, J=8.4 Hz, 1H), 6.70 (d, J=15.6 Hz, 1H), 6.52 (d, J=8.4 Hz, 1H), 5.89 (s, 1H), 5.86 (s, 1H), 3.84 (s, 2H), 3.81 (s, 3H), 2.16 (s, 3H).

LC-MS: Method_A—220, rt=1.60

(ES+) [M+H]+: 380.

Example 6

(85) (E)-3-(3-Hydroxy-4-methoxy-phenyl)-N-[3-(pyridin-3-ylmethoxy)-phenyl]-acrylamide

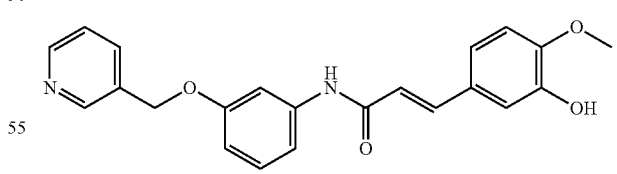

3-Chloromethyl-pyridine hydrochloride (0.59 g 3.6 mmol) was added to a mixture of (E)-3-(3-hydroxy-4-methoxy-phenyl)-N-(3-hydroxy-phenyl)-acrylamide (0.39 g, 1.2 mmol) and potassium carbonate (0.83 g, 6.0 mmol) in dry DMF (5 mL) at RT. After stirring at 40° C. for 5 hrs, the resulting mixture was poured into ice, and the resulting precipitate was filtered, washed with water and dried. The resulting raw material was taken up, without further purification, with a 3N methanolic solution of hydrochloric acid (5 mL-15 mmols)

and stirred at RT for 2.5 hrs, concentrated under reduced pressure, taken up with solvent an re-evaporated (3 times with MeOH and once with acetone) to give a residue that, after neutralization, was purified by silica gel column chromatography (eluant DCM/MeOH 98/2) to obtain 50 mg of the title (E)-3-(3-hydroxy-4-methoxy-phenyl)-N-[3-(pyridin-3-yl-methoxy)-phenyl]-acrylamide.

$^1$H NMR (DMSO-d6) δ (ppm): 9.97 (s, 1H), 9.38 (s, 1H), 8.69 (s, 1H), 8.57 (d, J=5.2 Hz, 1H), 7.89 (d, J=7.6 Hz, 1H), 7.52-7.44 (m, 2H), 7.35 (s, 1H), 7.29 (s, 1H), 7.23 (d, J=8.0 Hz, 1H), 7.11-7.03 (m, 3H), 6.69 (d, J=15.6 Hz, 1H), 6.45 (d, J=8.4 Hz, 1H), 5.19 (s, 2H), 3.82 (s, 3H).

LC-MS: Method_A—220, rt=1.11

(ES+) [2M+H]+: 753.

By analogous reaction of (E)-3-(3-hydroxy-4-methoxy-phenyl)-N-(3-hydroxy-phenyl)-acrylamide with the suitable alkylating agent and subsequent acetyl removal, the following compounds were obtained:

(86) (E)-3-(3-Hydroxy-4-methoxy-phenyl)-N-(3-phenethyloxy-phenyl)-acrylamide

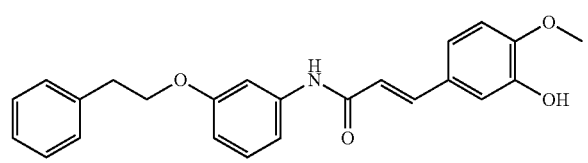 [SMILES: COc1ccc(/C=C/C(=O)Nc2cccc(OCCc3ccccc3)c2)cc1O]

$^1$H NMR (DMSO-d6) δ (ppm): 9.91 (s, 1H), 9.37 (s, 1H), 7.47 (d, J=15.6 Hz, 1H), 7.37-7.31 (m, 4H), 7.27-7.22 (m, 3H), 7.17 (d, J=8.4 Hz, 1H), 7.09-7.01 (m, 3H), 6.66 (d, J=15.6 Hz, 1H), 6.44 (d, J=8.0 Hz, 1H), 4.21 (t, J=7.2 Hz, 2H), 3.80 (s, 3H), 3.08 (t, J=7.2 Hz, 2H).

LC-MS: Method_A—220, rt=1.95

(ES+) [2M+Na]+: 801.

(87) (E)-3-(3-Hydroxy-4-methoxy-phenyl)-N-[3-(pyridin-2-ylmethoxy)-phenyl]-acrylamide

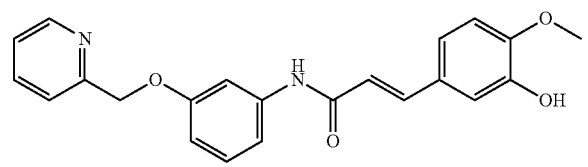 [SMILES: COc1ccc(/C=C/C(=O)Nc2cccc(OCc3ccccn3)c2)cc1O]

$^1$H NMR (DMSO-d6) δ (ppm): 10.24 (s, 1H), 10.04 (s, 1H), 8.76 (t, J=6.0 Hz, 2H), 8.26-8.17 (m, 2H), 7.86-7.80 (m, 2H), 7.70 (t, J=6.0 Hz, 1H), 7.65 (t, J=6.4 Hz, 1H), 7.60 (s, 1H), 7.48 (d, J=15.6 Hz, H), 7.43 (d, J=15.6 Hz, 1H), 7.35 (d, J=1.6 Hz, 1H), 7.29-7.23 (m, 4H), 7.11-7.02 (m, 5H), 6.97 (d, J=8.4 Hz, 1H), 6.77-6.70 (m, 2H), 6.62 (d, J=15.6 Hz, 1H), 6.47-6.44 (m, 1H), 5.35 (s, 2H), 5.34 (s, 2H), 3.84 (s, 3H), 3.81 (s, 3H).

LC-MS: Method_A—220, rt=1.11

(ES+) [2M+Na]+: 775.

Example 7

Preparation of substituted (E)-3-(3-acetoxy-phenyl)-acrylic anilides front the corresponding (E)-3-(3-acetoxy-phenyl)-acrylic acids

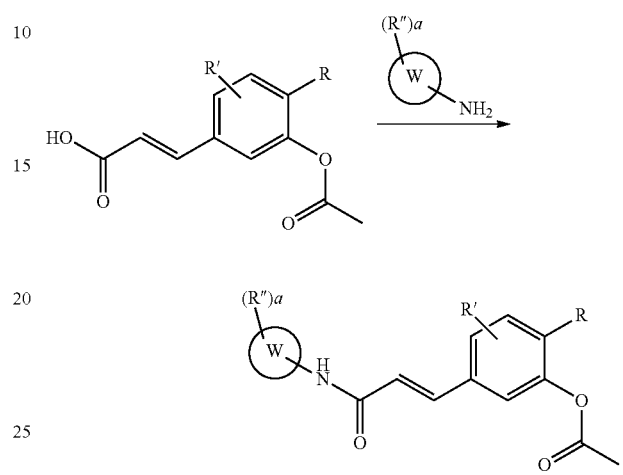

(88) (E)-N-[4-Chloro-3-(pyridin-4-ylmethoxy)-phenyl]-3-(3-acetoxy-4-methoxy-phenyl)-acrylamide

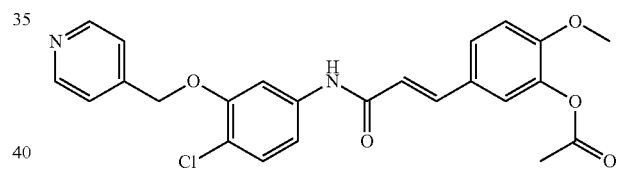

A solution (E)-3-(3-acetoxy-4-methoxy-phenyl)-acrylic acid (0.20 g, 0.76 mmol) and thionyl chloride (0.069 mL, 0.95 mmol) in dry THF (4 mL) was stirred at reflux temperature for 2.5 hrs. Then a further aliquot of thionyl chloride (0.008 mL, 0.11 mmol) was added and the mixture was stirred at reflux temperature for additional 5 hrs. After cooling to about 35° C., a solution of 4-chloro-3-(pyridin-4-ylmethoxy)-phenylamine (0.232 mg, 0.99 mmol) and diisopropylethylamine (0.54 mL, 3.04 mmol) in dry THF (0.5 mL) was added dropwise. After stirring at reflux temperature for 2 hrs, the reaction mixture was diluted with DCM and washed with water, aqueous sodium hydrogencarbonate, and brine. The organic layer was then dried over sodium sulphate and evaporated. The resulting raw material was purified by column chromatography over silica gel (eluant DCM/MeOH 98/2) to give 250 mg of the title (E)-N-[4-chloro-3-(pyridin-4-ylmethoxy)-phenyl]-3-(3-acetoxy-4-methoxy-phenyl)-acrylamide as a light brown solid.

$^1$H NMR (DMSO-d6) δ (ppm): 10.27 (s, 1H), 8.62 (m, 2H), 7.70 (s, 1H), 7.55-7.02 (m, 8H), 6.66 (d, J=15.6 Hz, 1H), 5.27 (s, 2H), 3.83 (s, 3H), 2.09 (s, 3H).

LC-MS: Method_A—220, rt=1.49

(ES+) [M+H]+: 453.

By analogously coupling the suitable acrylic acid with the suitable aniline, and performing the adequate chromatographic purification when needed, the following compounds were prepared:

(89) (E)-3-(3-acetoxy-4-methoxy-phenyl)-N-naphthalen-1-yl-acrylamide

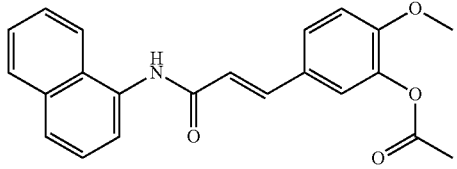 [SMILES: COc1ccc(/C=C/C(=O)Nc2cccc3ccccc23)cc1OC(C)=O]

¹H NMR (DMSO-d6) δ (ppm): 10.03 (s, 1H), 8.17-8.15 (m, 1H), 7.97-7.92 (m, 2H), 7.77 (d, J=8.4 Hz, 1H), 7.60-7.50 (m, 5H), 7.42 (d, J=1.6 Hz, 1H), 7.23 (d, J=8.4 Hz, 1H), 7.03 (d, J=15.6 Hz, 1H), 3.84 (s, 3H), 2.30 (s, 3H).
LC-MS: Method_A—220, rt=1.94
(ES+) [M+H]+: 362.

(90) (E)-N-(2-Benzyloxy-phenyl)-3-(3-acetoxy-4-methoxy-phenyl)-acrylamide

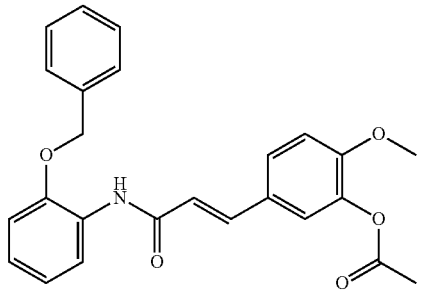 [SMILES: COc1ccc(/C=C/C(=O)Nc2ccccc2OCc2ccccc2)cc1OC(C)=O]

¹H NMR (DMSO-d6) δ (ppm): 9.22 (s, 1H), 8.11 (d, J=7.6 Hz, 1H), 7.52-7.48 (m, 4H), 7.41-7.36 (m, 3H), 7.32-7.28 (m, 1H), 7.20 (d, J=8.4 Hz, 1H), 7.09-7.00 (m, 3H), 6.93-6.90 (m, 1H), 5.37 (s, 2H), 3.82 (s, 3H), 2.28 (s, 3H).
LC-MS: Method_A—220, rt=2.21
(ES+) [M+H]+: 418.

(91) (E)-3-(3-acetoxy-4-methoxy-phenyl)-N-[3-(4-methyl-piperazin-1-yl)-phenyl]-acrylamide

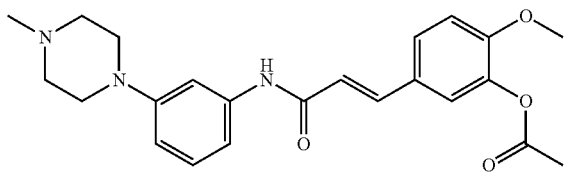 [SMILES: COc1ccc(/C=C/C(=O)Nc2cccc(N3CCN(C)CC3)c2)cc1OC(C)=O]

¹H NMR (DMSO-d6) δ (ppm): 9.96 (s, 1H), 7.52-7.46 (m, 2H), 7.36-7.34 (m, 2H), 7.20 (d, J=8.4 Hz, 1H), 7.16-7.12 (m, 1H), 7.08 (d, J=8.4 Hz, 1H), 6.70-6.64 (m, 2H), 3.82 (s, 3H), 3.12-3.10 (m, 41H), 2.47-2.44 (m, 4H), 2.28 (s, 3H), 2.22 (s, 3H).
LC-MS: Method_A—220, rt=1.21
(ES+) [M+H]+: 410.

(92) (E)-N-(2-Chloro-pyridin-4-yl)-3-(3-acetoxy-4-methoxy-phenyl)-acrylamide

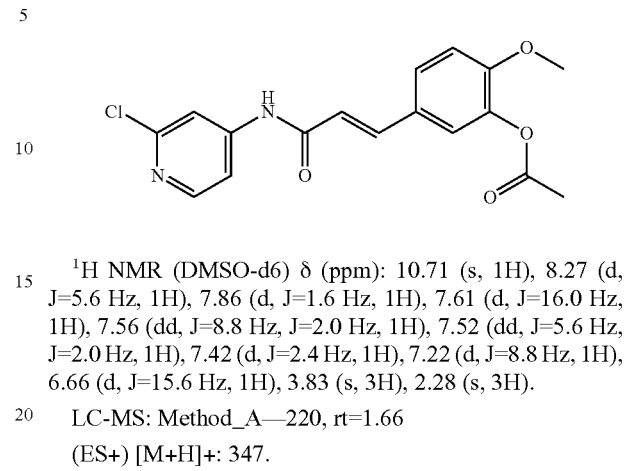

¹H NMR (DMSO-d6) δ (ppm): 10.71 (s, 1H), 8.27 (d, J=5.6 Hz, 1H), 7.86 (d, J=1.6 Hz, 1H), 7.61 (d, J=16.0 Hz, 1H), 7.56 (dd, J=8.8 Hz, J=2.0 Hz, 1H), 7.52 (dd, J=5.6 Hz, J=2.0 Hz, 1H), 7.42 (d, J=2.4 Hz, 1H), 7.22 (d, J=8.8 Hz, 1H), 6.66 (d, J=15.6 Hz, 1H), 3.83 (s, 3H), 2.28 (s, 3H).
LC-MS: Method_A—220, rt=1.66
(ES+) [M+H]+: 347.

(93) ((E)-N-(3-Chloro-2-methoxy-phenyl)-3-(3-acetoxy-4-methoxy-phenyl)-acrylamide

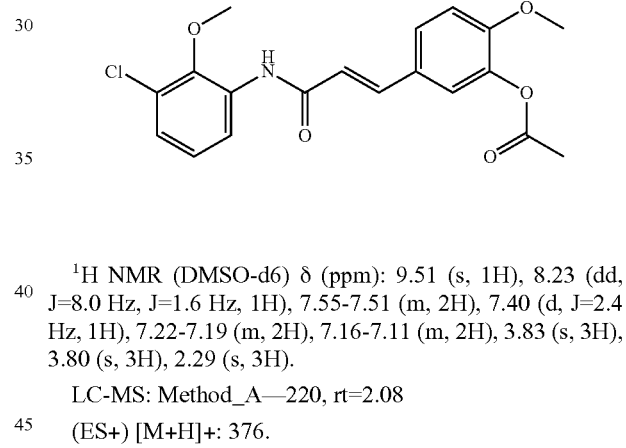

¹H NMR (DMSO-d6) δ (ppm): 9.51 (s, 1H), 8.23 (dd, J=8.0 Hz, J=1.6 Hz, 1H), 7.55-7.51 (m, 2H), 7.40 (d, J=2.4 Hz, 1H), 7.22-7.19 (m, 2H), 7.16-7.11 (m, 2H), 3.83 (s, 3H), 3.80 (s, 3H), 2.29 (s, 3H).
LC-MS: Method_A—220, rt=2.08
(ES+) [M+H]+: 376.

(94) (E)-N-(3,4-Dichloro-phenyl)-3-(3-acetoxy-4-methoxy-phenyl)-acrylamide

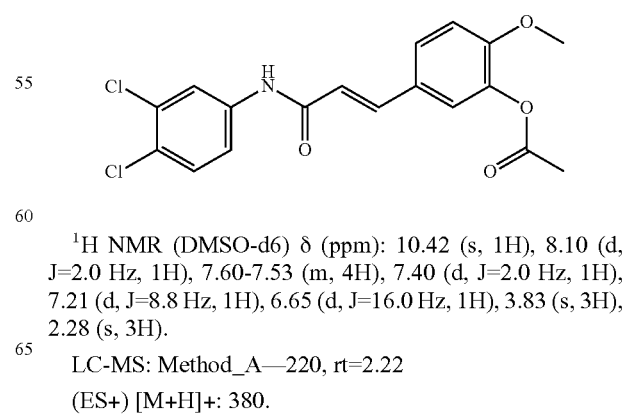

¹H NMR (DMSO-d6) δ (ppm): 10.42 (s, 1H), 8.10 (d, J=2.0 Hz, 1H), 7.60-7.53 (m, 4H), 7.40 (d, J=2.0 Hz, 1H), 7.21 (d, J=8.8 Hz, 1H), 6.65 (d, J=16.0 Hz, 1H), 3.83 (s, 3H), 2.28 (s, 3H).
LC-MS: Method_A—220, rt=2.22
(ES+) [M+H]+: 380.

67

(95) (E)-N-(3-Chloro-4-methoxy-phenyl)-3-(3-acetoxy-4-methoxy-phenyl)-acrylamide

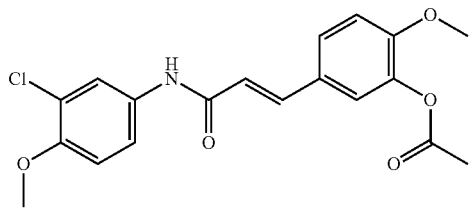 [SMILES: COc1ccc(NC(=O)/C=C/c2ccc(OC)c(OC(C)=O)c2)cc1Cl]

$^1$H NMR (DMSO-d6) δ (ppm): 10.14 (s, 1H), 7.90 (d, J=2.0 Hz, 1H), 7.53-7.49 (m, 3H), 7.37 (d, J=2.4 Hz, 1H), 7.20 (d, J=8.4 Hz, 1H), 7.13 (d, J=9.2 Hz, 1H), 6.63 (d, J=15.6 Hz, 1H), 3.83 (s, 3H), 3.82 (s, 3H), 2.28 (s, 3H).

LC-MS: Method_A—220, rt=1.91

(ES+) [M+H]+: 376.

(96) (E)-N-(2,3-Dichloro-phenyl)-3-(3-acetoxy-4-methoxy-phenyl)-acrylamide

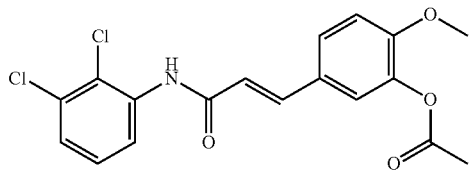 [SMILES: COc1ccc(/C=C/C(=O)Nc2cccc(Cl)c2Cl)cc1OC(C)=O]

$^1$H NMR (DMSO-d6) δ (ppm): 9.69 (s, 1H), 7.97-7.93 (m, 1H), 7.58-7.53 (m, 2H), 7.45 (dd, J=8.4 Hz, J=1.6 Hz, 1H), 7.41 (d, J=2.0 Hz, 1H), 7.38 (t, J=8.4 Hz, 1H), 7.21 (d, J=8.8 Hz, 1H), 7.02-6.97 (m, 1H), 3.83 (s, 3H), 2.29 (s, 3H).

LC-MS: Method_A—220, rt=2.20

(ES+) [M+H]+: 380.

(97) (E)-N-(3-Benzylamino-phenyl)-3-(3-acetoxy-4-methoxy-phenyl)-acrylamide

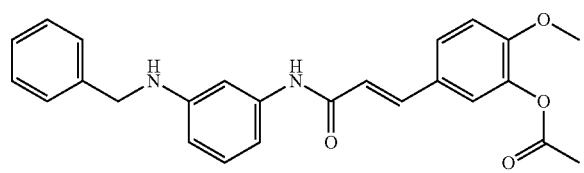 [SMILES: COc1ccc(/C=C/C(=O)Nc2cccc(NCc3ccccc3)c2)cc1OC(C)=O]

$^1$H NMR (DMSO-d6) δ (ppm): 9.79 (s, 1H), 7.50-7.43 (m, 2H), 7.37-7.30 (m, 5H), 7.23-7.18 (m, 2H), 7.00 (s, 1H), 6.98-6.94 (m, 1H), 6.86 (d, J=8.0 Hz, 1H), 6.68 (d, J=15.6 Hz, 1H), 6.32-6.27 (m, 2H), 4.25 (d, J=5.2 Hz, 2H), 3.82 (s, 3H), 2.28 (s, 3H).

LC-MS: Method_A—220, rt=2.03

(ES+) [M+H]+: 417.

68

(98) (E)-N-[3-(Benzyl-methyl-amino)-phenyl]-3-(3-acetoxy-4-methoxy-phenyl)-acrylamide

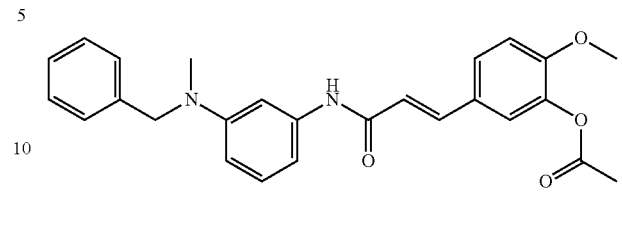

$^1$H NMR (DMSO-d6) δ (ppm): 9.89 (s, 1H), 7.50-7.47 (m, 2H), 7.34-7.30 (m, 3H), 7.27-7.18 (m, 4H), 7.14 (s, 1H), 7.09-7.05 (m, 1H), 7.00-6.97 (m, 1H), 6.67 (d, J=15.6 Hz, 1H), 6.44 (d, J=7.6 Hz, 1H), 4.55 (s, 2H), 3.82 (s, 3H), 2.99 (s, 3H), 2.28 (s, 3H).

LC-MS: Method_A—220, rt=2.19

(ES+) [M+H]+: 431.

(99) (E)-N-[2-Chloro-3-(pyridin-4-ylmethoxy)-phenyl]-3-(3-acetoxy-4-methoxy-phenyl)-acrylamide hydrochloride

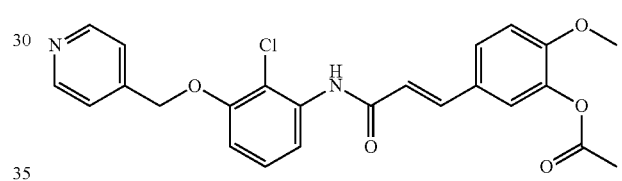

$^1$H NMR (DMSO-d6) δ (ppm): 9.49 (s, 1H), 8.61 (d, J=5.6 Hz, 2H), 7.67 (d, J=8 Hz, 1H), 7.57-7.42 (m, 5H), 7.30 (t, J=8 Hz, 1H), 7.22 (d, J=8 Hz, 1H), 7.06-7.01 (m, 2H), 5.32 (s, 2H), 3.84 (s, 3H), 2.29 (s, 3H).

LC-MS: Method_A—220, rt=1.40

(ES+) [M+H]+: 453.

(100) (E)-N-(3-Benzyloxy-2-chloro-phenyl)-3-(3-acetoxy-4-methoxy-phenyl)-acrylamide

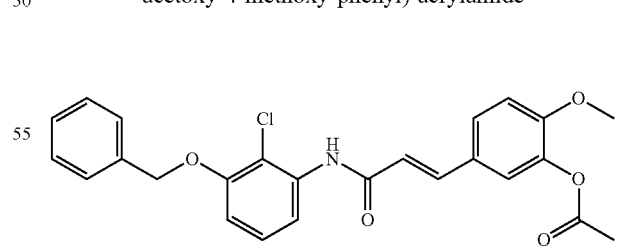

$^1$H NMR (DMSO-d6) δ (ppm): 9.45 (s, 1H), 7.65-7.01 (m, 13H), 5.24 (s, 2H), 3.84 (s, 3H), 2.28 (s, 3H).

LC-MS: Method_A—220, rt=2.26

(101) (E)-N-(2-Benzyloxy-3-chloro-phenyl)-3-(3-acetoxy-4-methoxy-phenyl)-acrylamide

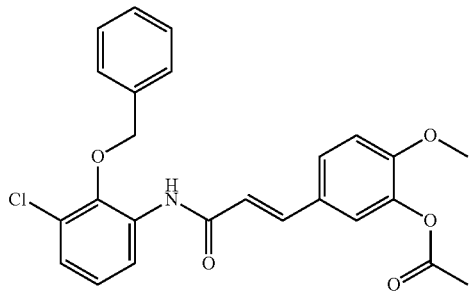 [SMILES: COc1ccc(/C=C/C(=O)Nc2cccc(Cl)c2OCc2ccccc2)cc1OC(C)=O]

¹H NMR (DMSO-d6) δ (ppm): 9.41 (s, 1H), 8.06 (m, 1H), 7.54-7.21 (m, 10H), 7.16 (t, J=8 Hz, 1H), 6.92 (d, J=15.6 Hz, 1H), 5.02 (s, 2H), 3.83 (s, 3H), 2.30 (s, 3H).
LC-MS: Method_A—220, rt=2.38
(ES+) [M+H]+: 452.

(102) (E)-N-(1-Benzyl-1H-indol-4-yl)-3-(3-acetoxy-4-methoxy-phenyl)-acrylamide

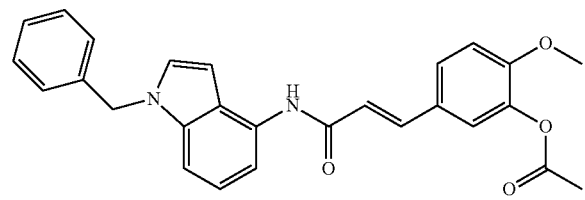 [SMILES: COc1ccc(/C=C/C(=O)Nc2cccc3c2ccn3Cc2ccccc2)cc1OC(C)=O]

¹H NMR (DMSO-d6) δ (ppm): 9.70 (s, 1H), 7.86 (m, 1H), 7.60-6.84 (m, 14H), 5.43 (s, 2H), 3.84 (s, 3H), 2.30 (s, 3H).
LC-MS: Method_A—220, rt=2.13
(ES+) [M+H]+: 441.

(103) (E)-N-[3-Chloro-2-(pyridin-4-ylmethoxy)-phenyl]-3-(3-acetoxy-4-methoxy-phenyl)-acrylamide

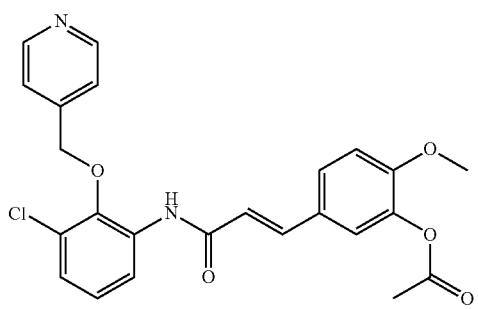 [SMILES: COc1ccc(/C=C/C(=O)Nc2cccc(Cl)c2OCc2ccncc2)cc1OC(C)=O]

¹H NMR (DMSO-d6) δ (ppm): 9.54 (s, 1H), 8.59 (d, J=4.8 Hz, 2H), 8.10 (m, 1H), 7.56-7.50 (m, 4H), 7.38-7.17 (m, 4H), 6.96 (d, J=16 Hz, 1H), 5.06 (s, 2H), 3.83 (s, 3H), 2.29 (s, 3H).
LC-MS: Method_A—220, rt=1.49
(ES+) [M+H]+: 453.

(104) (E)-3-(3-acetoxy-4-methoxy-phenyl)-N-(1-methyl-1H-indol-4-yl)-acrylamide

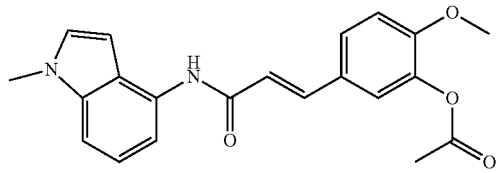

¹H NMR (DMSO-d6) δ (ppm): 9.68 (s, 1H), 7.89 (m, 1H), 7.56-7.52 (m, 21H), 7.39 (s, 1H), 7.31 (d, J=2.8 Hz, 1H), 7.24-7.19 (m, 2H), 7.12 (t, J=8 Hz, 1H), 7.04 (d, J=16 Hz, 1H), 6.78 (m, 1H), 3.84 (s, 3H), 3.79 (s, 3H), 2.3 (s, 3H).
LC-MS: Method_A—220, rt=1.77
(ES+) [M+H]+: 365.

(105) (E)-N-(1-Benzyl-1H-indol-7-yl)-3-(3-acetoxy-4-methoxy-phenyl)-acrylamide

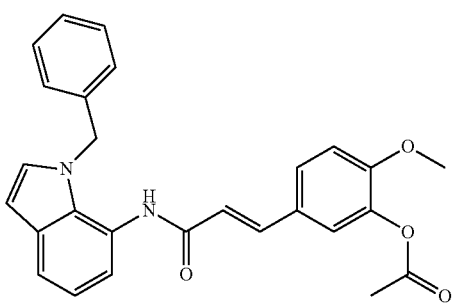 [SMILES: COc1ccc(/C=C/C(=O)Nc2cccc3ccn(Cc4ccccc4)c23)cc1OC(C)=O]

¹H NMR (DMSO-d6) δ (ppm): 9.78 (s, 1H), 7.52-7.38 (m, 5H), 7.23-7.16 (m, 4H), 7.01 (t, J=7.6 Hz, 1H), 6.92 (m, 3H), 6.67 (d, J=15.6 Hz, 1H), 6.55 (m, 1H), 5.45 (s, 2H), 3.84 (s, 3H), 2.30 (s, 3H).
LC-MS: Method_A—220, rt=2.01
(ES+) [M+H]+: 441.

(106) (E)-3-(3-Acetoxy-4-methoxy-phenyl)-N-[3-(3-methyl-3H-imidazol-4-ylmethoxy)-phenyl]-acrylamide

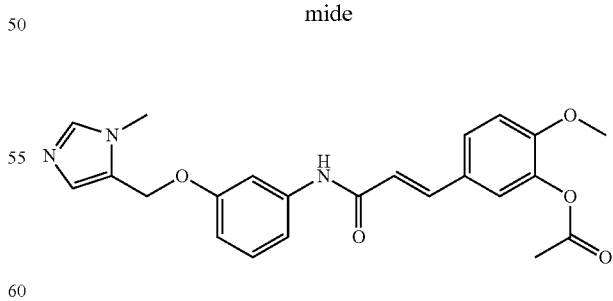

¹H NMR (DMSO-d6) δ (ppm): 10.11 (s, 1H), 7.65 (s, 1H), 7.53 (m, 3H), 7.38 (s, 1H), 7.27-7.2 (m, 3H), 7.05 (s, 1H), 6.77 (m, 1H), 6.79 (d, J=15.6 Hz, 1H), 5.08 (s, 2H), 3.83 (s, 3H), 3.66 (s, 3H), 2.29 (s, 3H).
LC-MS: Method_A—220, rt=1.22
(ES+) [M+H]+: 422.

(107) (E)-3-(4-Fluoro-3-acetoxy-phenyl)-N-(2-phenoxymethyl-phenyl)-acrylamide

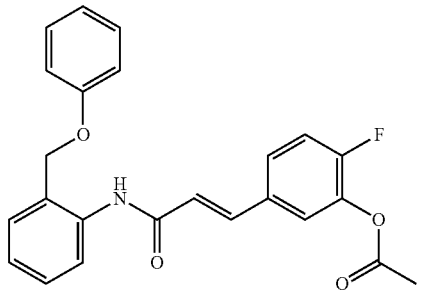 [SMILES: CC(=O)Oc1cc(/C=C/C(=O)Nc2ccccc2COc2ccccc2)ccc1F]

¹H NMR (DMSO-d6) δ (ppm): 9.70 (s, 1H), 7.64-6.88 (m, 14H), 5.14 (s, 2H), 2.36 (s, 3H).
LC-MS: Method_A—220, rt=2.18
(ES+) [M+H]+: 406.

(108) (E)-3-(3-Acetoxy-4-methoxy-phenyl)-N-[3-(1-trityl-1H-imidazol-4-ylmethoxy)-phenyl]-acrylamide

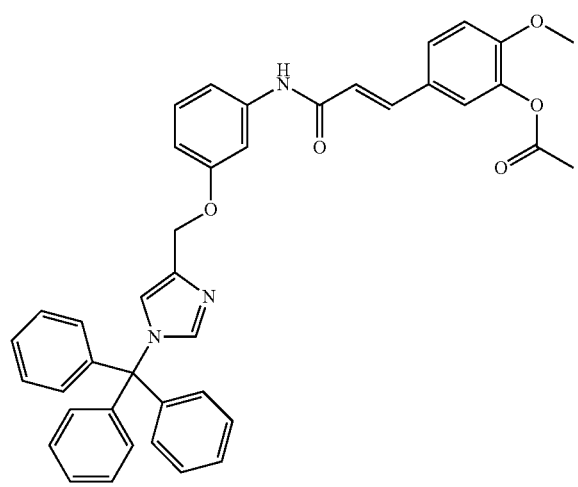 [SMILES: COc1ccc(/C=C/C(=O)Nc2cccc(OCc3cn(C(c4ccccc4)(c4ccccc4)c4ccccc4)cn3)c2)cc1OC(C)=O]

¹H NMR (DMSO-d6) δ (ppm): 10.07 (s, 1H), 7.53-7.48 (m, 2H), 7.43-7.36 (m, 12H), 7.22-7.19 (m, 3H), 7.10-7.07 (m, 6H), 7.03 (s, 1H), 6.73-6.65 (m, 2H), 4.91 (s, 2H), 3.82 (s, 3H), 2.28 (s, 3H).
LC-MS: Method_A—220, rt=2.19
(ES+) [M+H]+: 650.

(109) (E)-3-(3-Acetoxy-4-methoxy-phenyl)-N-[3-(pyridin-4-yloxymethyl)-phenyl]-acrylamide

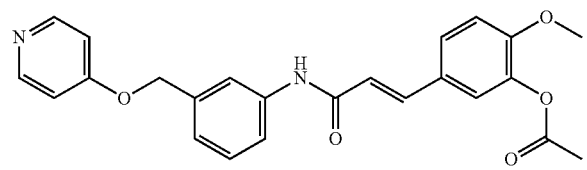 [SMILES: COc1ccc(/C=C/C(=O)Nc2cccc(COc3ccncc3)c2)cc1OC(C)=O]

¹H NMR (DMSO-d6) δ (ppm): 10.18 (s, 1H), 7.73-7.70 (m, 2H), 7.65 (d, J=8.0 Hz, 1H), 7.56 (s, 1H), 7.53-7.49 (m, 2H), 7.37-7.33 (m, 2H), 7.20 (d, J=8.8 Hz, 1H), 6.98 (d, J=7.2 Hz, 1H), 6.68 (d, J=15.6 Hz, 1H), 6.13-6.09 (m, 2H), 5.09 (s, 2H), 3.82 (s, 3H), 2.28 (s, 3H).
LC-MS: Method_A—220, rt=1.29
(ES+) [M+H]+: 419.

(110) (E)-3-(3-Acetoxy-4-methoxy-phenyl)-N-(3-oxazol-5-yl-phenyl)-acrylamide

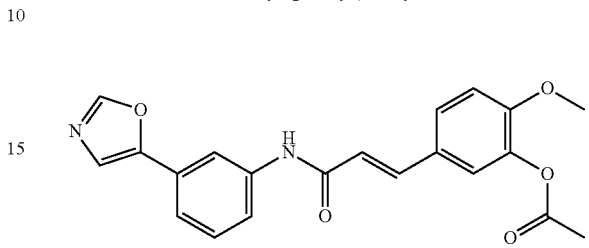

¹H NMR (DMSO-d6) δ (ppm): 10.29 (s, 1H), 8.47 (s, 1H), 8.12 (s, 1H), 7.65-7.63 (m, 2H), 7.56-7.52 (m, 2H), 7.45-7.43 (m, 2H), 7.39 (d, J=2.0 Hz, 1H), 7.22 (d, J=8.4 Hz, 1H), 6.71 (d, J=15.6 Hz, 1H), 3.81 (s, 3H), 2.29 (s, 3H).
LC-MS: Method_A—220, rt=1.61
(ES+) [M+H]+: 379.

(111) (E)-3-(3-Acetoxy-4-methoxy-phenyl)-N-indan-1-yl-acrylamide

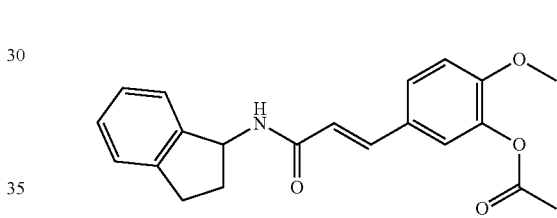

¹H NMR (DMSO-d6) δ (ppm): 8.39 (d, J=8.0 Hz, 1H), 7.46-7.41 (m, 2H), 7.30 (d, J=2.0 Hz, 1H), 7.28-7.26 (m, 1H), 7.24-7.16 (m, 4H), 6.54 (d, J=15.6 Hz, 1H), 5.40 (q, J=7.6 Hz; 1H), 3.81 (s, 3H), 2.99-2.92 (m, 1H), 2.87-2.79 (m, 1H), 2.48-2.40 (m, 1H), 2.27 (s, 3H), 1.86-1.82 (m, 1H).
LC-MS: Method_A—220, rt=1.77
(ES+) [M+H]+: 352.

(112) (E)-N-(2-Benzylsulfanyl-phenyl)-3-(3-acetoxy-4-methoxy-phenyl)-acrylamide

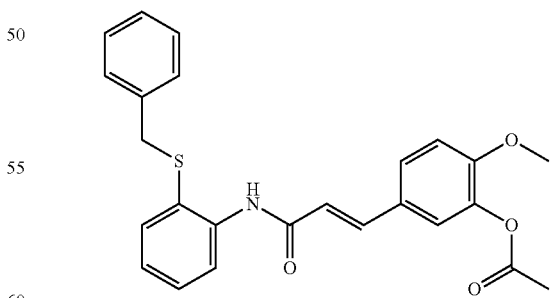

¹H NMR (DMSO-d6) δ (ppm): 9.28 (s, 1H), 7.78 (d, J=8.0 Hz, 1H), 7.54-7.47 (m, 2H), 7.43-7.41 (m, 2H), 7.31-7.19 (m, 7H), 7.14-7.10 (m, 1H), 6.89 (d, J=15.6 Hz, 1H), 4.14 (s, 2H), 3.83 (s, 3H), 2.29 (s, 3H).
LC-MS: Method_A—220, rt=2.32
(ES+) [M+H]+: 434.

(113) ((E)-3-(3-Acetoxy-4-methoxy-phenyl)-N-(1-methyl-1H-benzimidazol-2-yl)-acrylamide

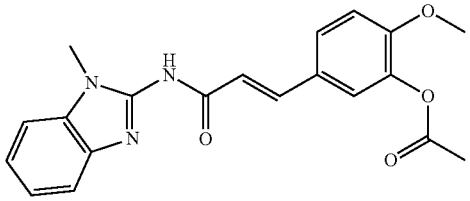 [SMILES: COc1ccc(/C=C/C(=O)Nc2nc3ccccc3n2C)cc1OC(C)=O]

¹H NMR (DMSO-d6) δ (ppm): 7.60-7.48 (m, 5H), 7.26-7.17 (m, 3H), 6.66 (d, J=15.2 Hz, 1H), 3.82 (s, 3H), 3.64 (s, 3H), 2.28 (s, 3H).
LC-MS: Method_A—220, rt=129
(ES+) [M+H]+: 366.

(114) (E)-3-(3-Acetoxy-4-methoxy-phenyl)-N-(2-phenoxymethyl-phenyl)-acrylamide

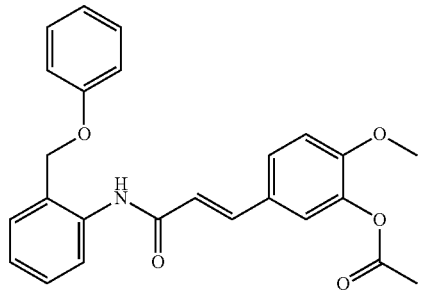 [SMILES: COc1ccc(/C=C/C(=O)Nc2ccccc2COc2ccccc2)cc1OC(C)=O]

LC-MS: Method_A—220, rt=2.11
(ES+) [M+H]+: 418.

(115) (E)-N-Benzoxazol-4-yl-3-(3-acetoxy-4-methoxy-phenyl)-acrylamide

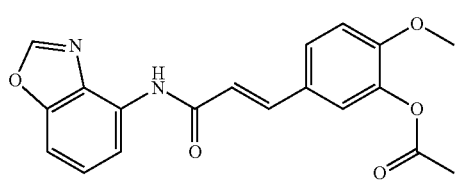 [SMILES: COc1ccc(/C=C/C(=O)Nc2cccc3ocnc23)cc1OC(C)=O]

LC-MS: Method_A—220, rt=1.69
(ES+) [M+H]+: 353.

(116) (E)-N-(1-Benzyl-1H-benzimidazol-4-yl)-3-(3-acetoxy-4-methoxy-phenyl)-acrylamide

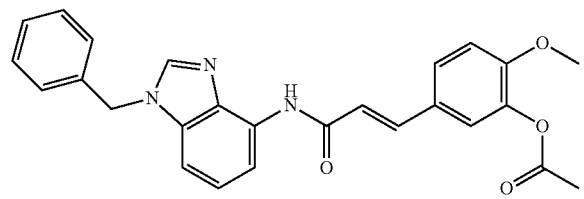 [SMILES: COc1ccc(/C=C/C(=O)Nc2cccc3c2ncn3Cc2ccccc2)cc1OC(C)=O]

¹H NMR (CDCl₃) δ (ppm): 10.48 (bs, 1H), 8.75 (d, J=8.4 Hz, 1H), 8.50 (s, 1H), 7.72 (s, 1H), 7.50 (m, 5H), 7.35 (m, 4H), 7.02 (m, 2H), 5.50 (s, 2H), 3.88 (s, 3H), 2.35 (s, 3H).
LC-MS: Method_A—220, rt=1.73
(ES+) [M+H]+: 442.

(117) (E)-3-(3-Acetoxy-4-methoxy-phenyl)-N-(1-methyl-1H-benzimidazol-4-yl)-acrylamide

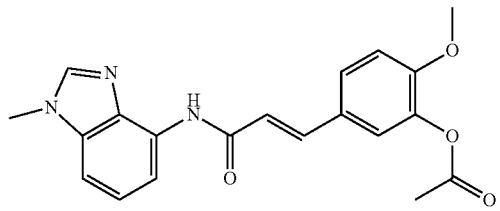 [SMILES: COc1ccc(/C=C/C(=O)Nc2cccc3c2ncn3C)cc1OC(C)=O]

¹H NMR (CDCl₃) δ (ppm): 9.69 (bs, 1H), 8.58 (d, J=8.0 Hz, 1H), 8.38 (bs, 1H), 7.72 (d, J=15.6 Hz, 1H), 7.48 (m, 2H), 7.34 (s, 1H), 7.19 (d, J=8.0 Hz, 1H), 7.00 (d, J=8.0 Hz, 1H), 6.86 (d, J=15.6 Hz, 1H), 3.99 (s, 3H), 3.89 (s, 3H), 2.37 (s, 3H).
LC-MS: Method_A—220, rt=1.14
(ES+) [M+H]+: 366.

(118) (E)-N-(1-Benzyl-1H-indazol-7-yl)-3-(3-acetoxy-4-methoxy-phenyl)-acrylamide

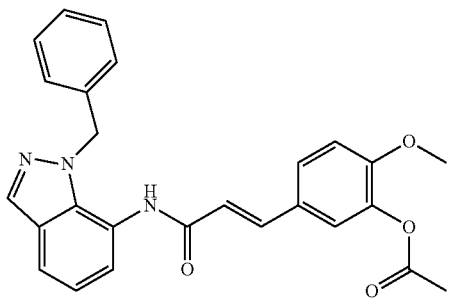 [SMILES: COc1ccc(/C=C/C(=O)Nc2cccc3cnn(Cc4ccccc4)c23)cc1OC(C)=O]

¹H NMR (CDCl₃) δ (ppm): 8.12 (s, 1H), 7.71 (m, 1H), 7.55 (m, 1H), 7.34 (m, 4H), 7.17 (m, 2H), 7.10 (m, 2H), 6.99 (m, 2H), 6.00 (d, J=15.6 Hz, 1H), 5.80 (s, 2H), 3.91 (s, 3H), 2.35 (s, 3H).
LC-MS: Method_A—220, rt=1.79
(ES+) [M+H]+: 442.

(119) (E)-3-(3-Acetoxy-4-methoxy-phenyl)-N-(1-methyl-1H-benzotriazol-4-yl)-acrylamide

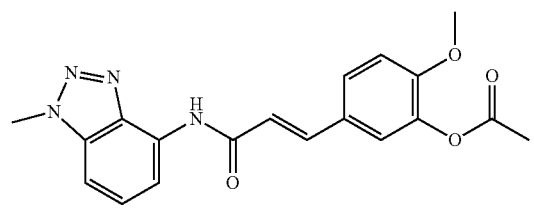 [SMILES: COc1ccc(/C=C/C(=O)Nc2cccc3c2nnn3C)cc1OC(C)=O]

¹H NMR (DMSO-d6) δ (ppm): 10.62 (s, 1H), 8.30 (dd, J=3.6, 2.0 Hz, 1H), 7.51-7.60 (m, 4H), 7.40 (d, J=2.0 Hz, 1H), 7.30 (d, J=15.6 Hz, 1H), 7.23 (d, J=3.6 Hz, 1H), 4.32 (s, 3H), 3.84 (s, 3H), 2.30 (s, 3H).
LC-MS: Method_A—220, rt=1.61
(ES+) [M+H]+: 366.

75

(120) (E)-N-(1-Benzyl-1H-indazol-4-yl)-3-(3-acetoxy-4-methoxy-phenyl)-acrylamide

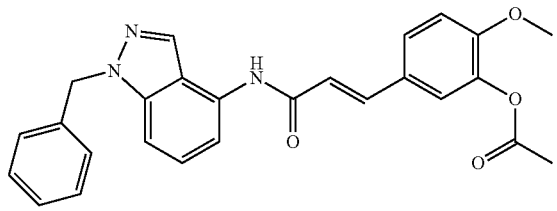 [SMILES: COc1ccc(/C=C/C(=O)Nc2cccc3c2cnn3Cc2ccccc2)cc1OC(C)=O]

¹H NMR (DMSO-d6) δ (ppm): 10.13 (s, 1N), 8.38 (s, 1H), 7.88 (d, J=7.6 Hz, 1H), 7.60-7.55 (m, 2H), 7.42-7.40 (m, 2H), 7.35-7.29 (m, 3H), 7.27-7.22 (m, 4H), 6.95 (d, J=16.0 Hz, 1H), 5.65 (s, 2H), 3.83 (s, 3H), 2.29 (s, 3H).
LC-MS: Method_A—220, rt=2.00
(ES+) [M+H]+: 442.

(121) (E)-N-(2-Benzyl-2H-indazol-7-yl)-3-(3-acetoxy-4-methoxy-phenyl)-acrylamide

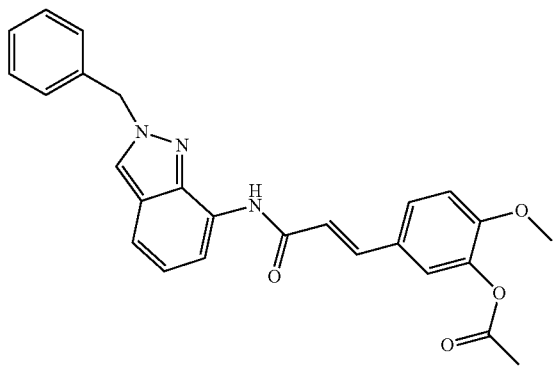 [SMILES: COc1ccc(/C=C/C(=O)Nc2cccc3cn(Cc4ccccc4)nc23)cc1OC(C)=O]

¹H NMR (CDCl₃) δ (ppm): 9.23 (bs, 1H), 8.32 (m, 1H), 7.96 (s, 1H), 7.75 (d, J=15.2 Hz, 1H), 7.25-7.47 (m, 9H), 7.00 (d, J=8.8 Hz, 1H), 6.79 (d, J=16.0 Hz, 1H), 5.73 (s, 2H), 3.90 (s, 3H), 2.36 (s, 3H).
LC-MS: Method_A—220, rt=2.07
(ES+) [M+H]+: 442.

(122) (E)-3-(3-Acetoxy-4-methoxy-phenyl)-N-(2-methyl-2H-indazol-7-yl)-acrylamide

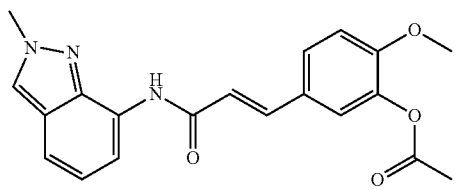 [SMILES: COc1ccc(/C=C/C(=O)Nc2cccc3cn(C)nc23)cc1OC(C)=O]

¹H NMR (CDCl₃) δ (ppm): 9.54 (bs, 1H), 8.67 (m, 1H), 7.96 (s, 1H), 8.06 (s, 1H), 7.75 (d, J=16.0 Hz, 1H), 7.50 (d, J=8.8 Hz, 1H), 7.45 (d, J=8.8 Hz, 1H), 7.36 (m, 2H), 7.00 (d, J=8.8 Hz, 1H), 6.85 (d, J=16.0 Hz, 1H), 4.42 (s, 3H), 3.90 (s, 3H), 2.36 (s, 3H).
LC-MS: Method_A—220, rt=1.63
(ES+) [M+H]+: 366.

76

(123) (E)-N-[3-(2,5-Dimethyl-2H-pyrazol-3-ylmethoxy)-phenyl]-3-(3-acetoxy-4-methoxy-phenyl)-acrylamide

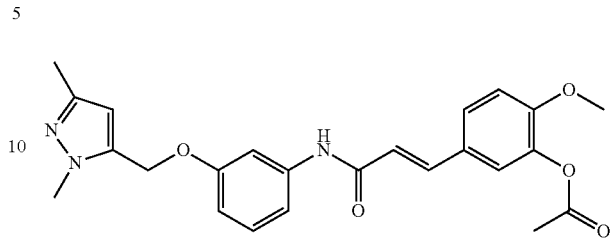

¹H NMR (CDCl₃) δ (ppm): 7.67 (m, 3H), 7.37 (d, J=8.4 Hz, 1H), 7.26 (m, 2H), 7.04 (d, J=8.0 Hz, 1H), 6.95 (d, J=8.4 Hz, 1H), 6.73 (d, J=8.0 Hz, 1H), 6.39 (d, J=15.6 Hz, 1H), 6.17 (s, 1H), 5.03 (s, 2H), 3.90 (s, 3H), 3.85 (s, 3H), 2.36 (s, 3H), 2.30 (s, 3H).
LC-MS: Method_A—220, rt=1.73
(ES+) [M+H]+: 436.

(124) (E)-3-(3-Acetoxy-4-methoxy-phenyl)-N-[3-(1-methyl-1H-imidazol-2-ylmethoxy)-phenyl]-acrylamide

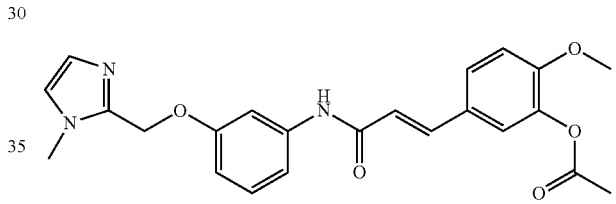

¹H NMR (CDCl₃) δ (ppm): 10.11 (s, 1H), 7.53-7.49 (m, 2H), 7.47 (s, 1H), 7.37 (d, J=2.0 Hz, 1H), 7.25-7.23 (m, 2H), 7.22-7.19 (m, 2H), 6.87 (s, 1H), 6.83-6.80 (m, 1H), 6.69 (d, J=15.6 Hz, 1H), 5.10 (s, 2H), 3.82 (s, 3H), 3.68 (s, 3H), 2.28 (s, 3H).
LC-MS: Method_A—220, rt=1.14
(ES+) [M+H]+: 422.

(125) (E)-3-(3-Acetoxy-4-methoxy-phenyl)-N-[2-(3-methoxy-phenoxymethyl)-phenyl]-acrylamide

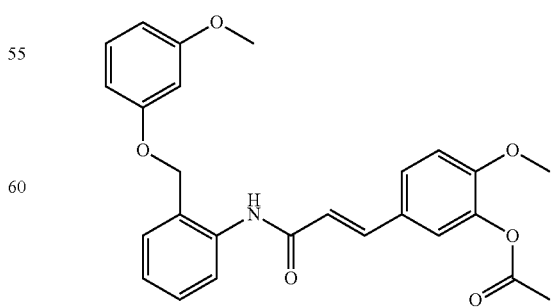

(ES+) [M+H]+: 448.

(126) (E)-3-(3-Acetoxy-4-methoxy-phenyl)-N-[2-(2-methoxy-phenoxymethyl)-phenyl]-acrylamide

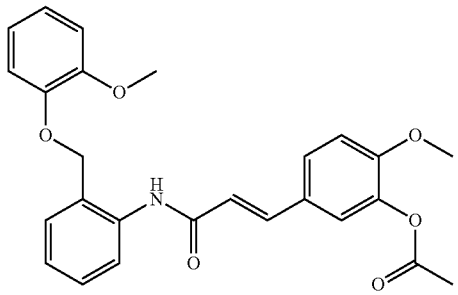 [SMILES: COc1ccccc1OCc1ccccc1NC(=O)/C=C/c1ccc(OC)c(OC(C)=O)c1]

(ES+) [M+H]+: 448.

(127) (E)-3-(3-Acetoxy-4-methoxy-phenyl)-N-[2-(4-methoxy-phenoxymethyl)-phenyl]-acrylamide

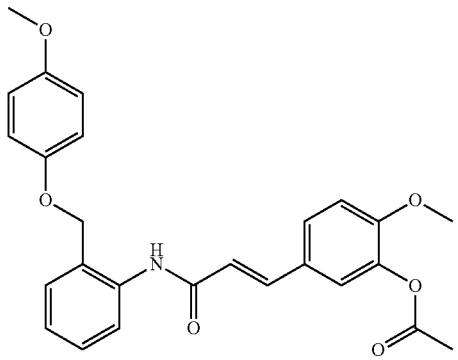 [SMILES: COc1ccc(OCc2ccccc2NC(=O)/C=C/c2ccc(OC)c(OC(C)=O)c2)cc1]

(ES+) [M+H]+: 448.

(128) (E)-N-(2-Cyclobutoxymethyl-phenyl)-3-(3-acetoxy-4-methoxy-phenyl)-acrylamide

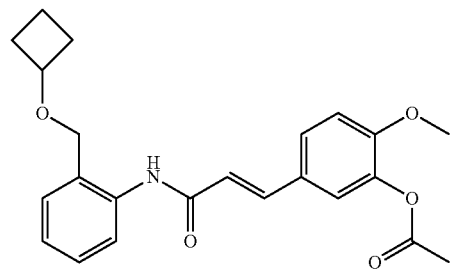 [SMILES: COc1ccc(/C=C/C(=O)Nc2ccccc2COC2CCC2)cc1OC(C)=O]

(ES+) [M+H]+: 396.

(129) (E)-3-(3-Acetoxy-4-methoxy-phenyl)-N-[2-(pyridin-4-yloxymethyl)-phenyl]-acrylamide

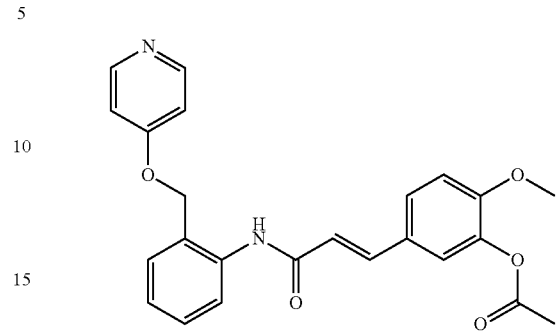

(ES+) [M+H]+: 419.

(130) (E)-N-[2-(4-Fluoro-phenoxymethyl)-phenyl]-3-(3-acetoxy-4-methoxy-phenyl)-acrylamide

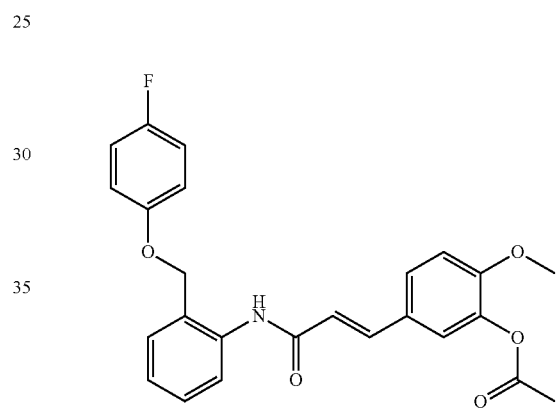

(ES+) [M+H]+: 436.

(131) (E)-3-(3-Acetoxy-4-methoxy-phenyl)-N-[2-(4-Imidazol-1-yl-phenoxymethyl)-phenyl]-acrylamide

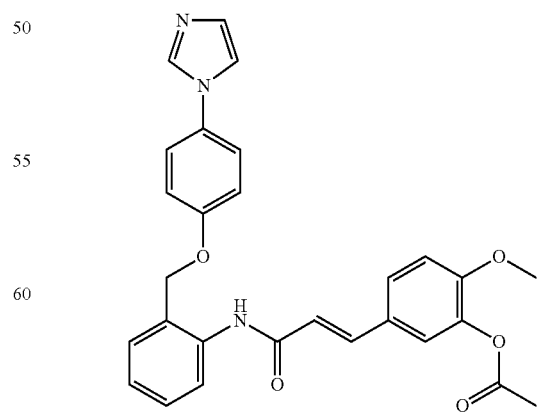

(ES+) [M+H]+: 484.

(132) (E)-N-[2-(2-Fluoro-phenoxymethyl)-phenyl]-3-(3-acetoxy-4-methoxy-phenyl)-acrylamide

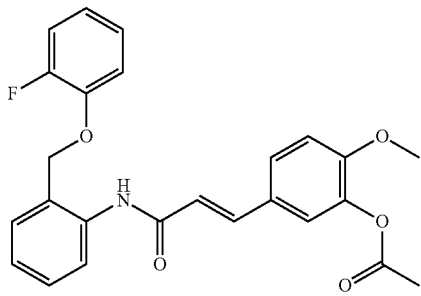 [SMILES: COc1ccc(/C=C/C(=O)Nc2ccccc2COc2ccccc2F)cc1OC(C)=O]

(ES+) [M+H]+: 436.

(133) (E)-3-(3-Acetoxy-4-methoxy-phenyl)-N-(2-methoxymethyl-phenyl)acrylamide

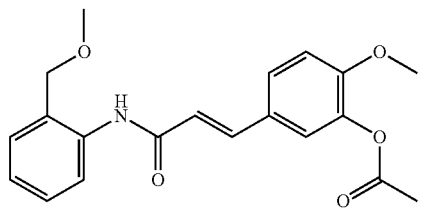 [SMILES: COCc1ccccc1NC(=O)/C=C/c1ccc(OC)c(OC(C)=O)c1]

(ES+) [M+H]+: 356.

(134) (E)-N-(3-Bromo-phenyl)-3-(4-fluoro-3-acetoxy-phenyl)acrylamide

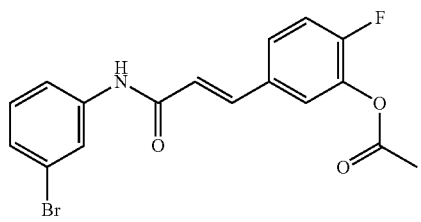 [SMILES: CC(=O)Oc1cc(/C=C/C(=O)Nc2cccc(Br)c2)ccc1F]

(ES+) [M+H]+: 379.

(135) (E)-N-(2-Benzyloxy-phenyl)-3-(4-fluoro-3-acetoxy-phenyl)-acrylamide

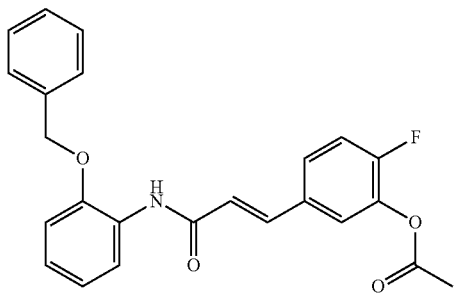 [SMILES: CC(=O)Oc1cc(/C=C/C(=O)Nc2ccccc2OCc2ccccc2)ccc1F]

(ES+) [M+H]+: 406.

(136) (E)-N-(2,3-Dichloro-phenyl)-3-(4-fluoro-3-acetoxy-phenyl)-acrylamide

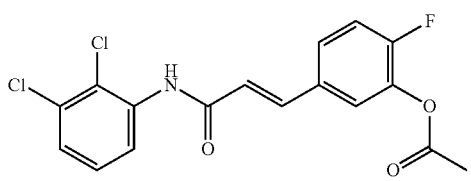 [SMILES: CC(=O)Oc1cc(/C=C/C(=O)Nc2cccc(Cl)c2Cl)ccc1F]

(ES+) [M+H]+: 369.

(137) (E)-N-(1)-Benzyl-1H-indol-7-yl)-3-(4-fluoro-3-acetoxy-phenyl)-acrylamide

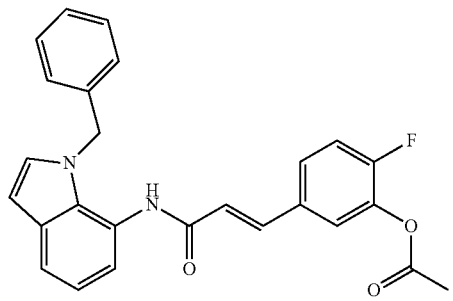 [SMILES: CC(=O)Oc1cc(/C=C/C(=O)Nc2cccc3ccn(Cc4ccccc4)c23)ccc1F]

(ES+) [M+H]+: 429.

(138) (E)-N-(3-Fluoro-phenyl)-3-(3-acetoxy-4-methoxy-phenyl)-acrylamide

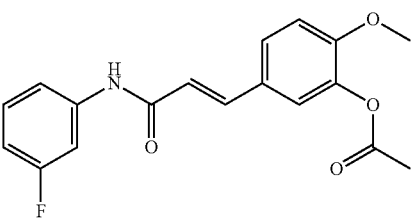 [SMILES: COc1ccc(/C=C/C(=O)Nc2cccc(F)c2)cc1OC(C)=O]

$^1$H NMR (DMSO-d6) δ (ppm): 10.30 (s, 1H), 7.71 (ddd, J=12.25 Hz, J=1.76 Hz, J=1.54 Hz, 1H), 7.55 (d, J=15.85 Hz, 1H), 7.53 (dd, J=8.51 Hz, J=2.35 Hz, 1H), 7.38 (d, J=2.05 Hz, 1H), 7.43-7.29 (m, 2H), 7.21 (d, J=8.80 Hz, 1H), 6.96-6.81 (m, 1H), 6.68 (d, J=15.55 Hz, 1H), 3.83 (s, 3H), 2.29 (s, 3H).

(ES+) [M+H]+: 331.

Example 8

Preparation of substituted (E)-3-(3-acetoxy-phenyl)-acrylic acids from the corresponding (E)-3-(3-hydroxy-phenyl)-acrylic acids

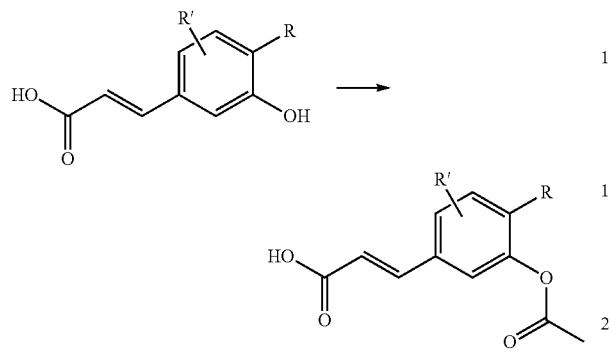

(139) (E)-3-(3-Acetoxy-4-methoxy-phenyl)-acrylic acid

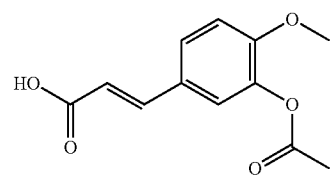 [SMILES: COc1ccc(/C=C/C(=O)O)cc1OC(C)=O]

Sodium hydride (1.40 g, 58 mmol) was added portionwise to a solution of (E)-3-(3-hydroxy-4-methoxy-phenyl)-acrylic acid (5.15 g, 26.5 mmol) in THF (100 mL) at 0° C. The resulting mixture was allowed to reach the RT, and acetic anhydride (4 mL, 42.4 mmol) was added. After stirring at reflux temperature for 6 hrs, the reaction mixture was concentrated under reduced pressure. The residue was taken up with AcOEt, and washed with water, aqueous sodium hydrogencarbonate, and brine. The organic layer was then dried over sodium sulphate and evaporated. The resulting raw material was triturated with AcOEt. After filtration and drying, 4.7 g of the title (E)-3-(3-acetoxy-4-methoxy-phenyl)-acrylic acid were obtained, as a white powder.

$^1$H NMR (DMSO-d6) δ (ppm): 12.25 (s, 1H), 7.58-7.50 (m, 3H), 7.16 (d, J=8.4 Hz, 1H), 6.41 (d, J=16.0 Hz, 1H), 3.82 (s, 3H), 2.29 (s, 3H).

LC-MS: Method_A—220, rt=1.14

(ES−) [M−H]−: 235.

By analogously coupling the suitable acrylic acid with acetic anhydride, the following (E)-3-(3-acetoxy-4-fluoro-phenyl)-acrylic acid was prepared:

(140) (E)-3-(3-Acetoxy-4-fluoro-phenyl)-acrylic acid

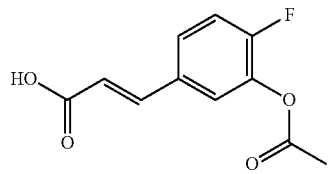 [SMILES: CC(=O)Oc1cc(/C=C/C(=O)O)ccc1F]

$^1$H NMR (DMSO-d6) δ (ppm): 12.41 (br. s., 1H), 7.70 (dd, 1H), 7.65 (ddd, 1H), 7.56 (d, 1H), 7.41 (dd, 1H), 6.52 (d, 1H), 2.34 (s, 3H)

LC-MS: Method_A—220, rt=1.32

(ES−) [M−H]−: 223.

Example 9

Preparation of substituted (E)-3-(3-hydroxy-phenyl)-acrylic anilides from the corresponding (E)-3-(3-acetoxy-phenyl)-derivatives by acid hydrolisis

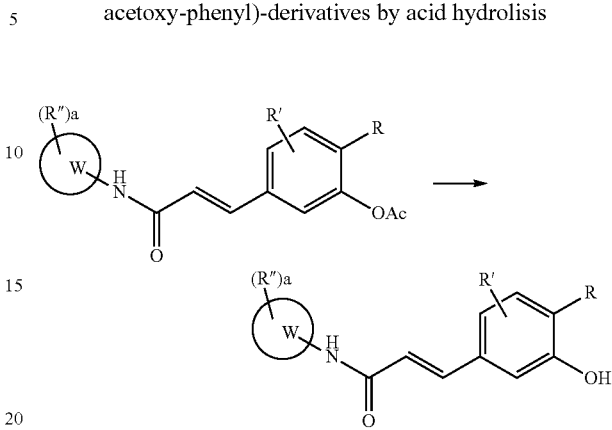

The following compounds were prepared by hydrolising the suitable (E)-3-(3-acetoxy-phenyl)-acrylic anilides according the procedure described in Example 2:

(141) (E)-N-(5-Chloro-2-phenoxymethyl-phenyl)-3-(3-hydroxy-4-methoxy-phenyl)-acrylamide

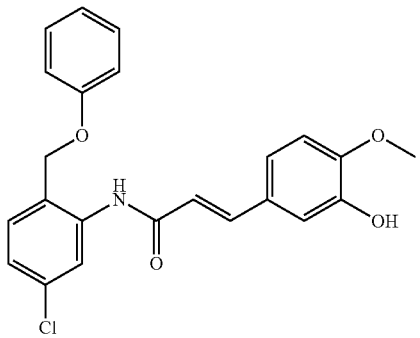 [SMILES: COc1ccc(/C=C/C(=O)Nc2cc(Cl)ccc2COc2ccccc2)cc1O]

$^1$H NMR (DMSO-d6) δ (ppm): 9.63 (s, 1H), 9.19 (s, 1H), 7.85 (d, J=2.05 Hz, 1H), 7.51 (d, J=7.92 Hz, 1H), 7.47 (d, J=15.85 Hz, 1H), 7.36-7.21 (m, 3H), 7.14-6.84 (m, 6H), 6.71 (d, J=15.85 Hz, 1H), 5.15 (s, 2H), 3.81 (s, 3H).

LC-MS: Method_N—254, rt=2.51

(ES+) [M+H]+: 410.

(142) (E)-3-(3-Hydroxy-4-methoxy-phenyl)-N-[4-(4-methyl-piperazin-1-yl)-2-phenoxymethyl-phenyl]-acrylamide hydrochloride

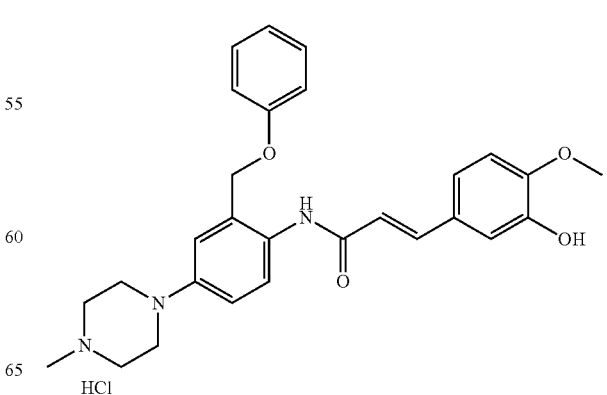

¹H NMR (DMSO-d6) δ (ppm): 10.35 (bs, 1H), 9.52 (s, 1H), 7.47-7.41 (m, 1H), 7.40 (d, J=15.55 Hz, 1H), 7.34-7.22 (m, 2H), 7.13 (d, J=2.64 Hz, 1H), 7.09-6.87 (m, 7H), 6.66 (d, J=16.14 Hz, 1H), 5.06 (s, 2H), 3.81 (s, 3H), 3.83-3.72 (m, 2H), 3.57-3.42 (m, 2H), 3.22-2.98 (m, 4H), 2.83 (d, J=4.70 Hz, 3H).

LC-MS: Method_N—254, rt=1.64

(ES+) [M+H]+: 474.

(143) (E)-3-(3-Hydroxy-4-methoxy-phenyl)-N-[2-(3-trifluoromethyl-phenoxymethyl)-phenyl]-acrylamide

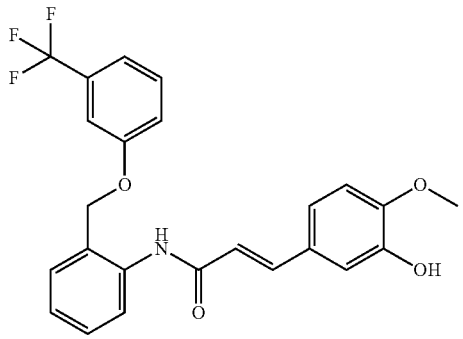 [SMILES: COc1ccc(/C=C/C(=O)Nc2ccccc2COc2cccc(C(F)(F)F)c2)cc1O]

¹H NMR (DMSO-d6) δ (ppm): 9.59 (s, 1H), 9.17 (s, 1H), 7.65 (dd, J=8.07 Hz, J=1.03 Hz, 1H), 7.57-7.49 (m, 2H), 7.45 (d, J=15.85 Hz, 1H), 7.36 (td, J=7.70 Hz, J=1.61 Hz, 1H), 7.33-7.27 (m, 3H), 7.23 (td, J=7.34 Hz, J=1.17 Hz, 1H), 7.05 (d, J=2.05 Hz, 1H), 7.03 (dd, J=8.51 Hz, J=2.05 Hz, 1H), 6.96 (d, J=8.51 Hz, 1H), 6.68 (d, J=15.85 Hz, 1H), 5.23 (s, 2H), 3.81 (s, 3H).

LC-MS: Method_N—254, rt=2.52

(ES+) [M+H]+: 444.

(144) (E)-3-(3-Hydroxy-4-methoxy-phenyl)-N-[2-(3-chloro-phenoxymethyl)-phenyl]-acrylamide

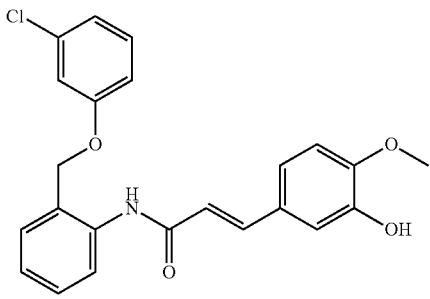 [SMILES: COc1ccc(/C=C/C(=O)Nc2ccccc2COc2cccc(Cl)c2)cc1O]

¹H NMR (DMSO-d6) δ (ppm): 9.57 (s, 1H), 9.17 (s, 1H), 7.64 (d, J=7.34 Hz, 1H), 7.49 (dd, J=7.63 Hz, J=1.17 Hz, 1H), 7.45 (d, J=15.55 Hz, 1H), 7.36 (td, J=7.63 Hz, J=1.47 Hz, 1H), 7.31 (t, J=8.22 Hz, 1H), 7.22 (td, J=7.63 Hz, J=1.17 Hz, 1H), 7.13-6.90 (m, 6H), 6.69 (d, J=15.55 Hz, 1H), 5.17 (s, 2H), 3.81 (s, 3H).

LC-MS: Method_N—254, rt=2.59

(ES+) [M+H]+: 410.

(145) (E)-3-(3-Hydroxy-4-methoxy-phenyl)-N-[2-(4-morpholin-4-ylmethyl-phenoxymethyl)-phenyl]-acrylamide hydrochloride

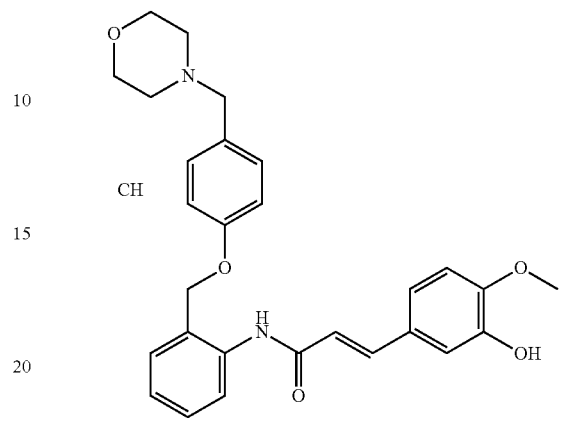

¹H NMR (DMSO-d6) δ (ppm): 9.70 (s, 1H), 9.17 (bs, 1H), 7.63-7.54 (m, 1H), 7.53-7.40 (m, 4H), 7.35 (td, J=7.70 Hz, J=1.61 Hz, 1H), 7.27-7.17 (m, 1H), 7.12-6.92 (m, 5H), 6.70 (d, J=15.55 Hz, 1H), 5.18 (s, 2H), 4.30-4.20 (m, 2H), 4.00-3.85 (m, 2H), 3.82 (s, 3H) 3.77-3.59 (m, 2H), 3.28-3.13 (m, 2H), 3.13-2.93 (m, 2H).

LC-MS: Method_N—254, rt=1.66

(ES+) [M+H]+: 475.

(146) (E)-3-(4-Fluoro-3-hydroxy-phenyl)-N-{2-[4-(1-methyl-piperidin-4-yloxy)-phenoxymethyl]-phenyl}-acrylamide trifluoroacetate

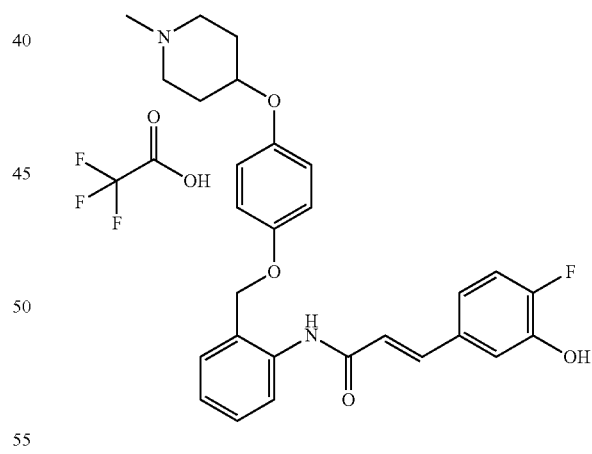

(purification by liquid chromatography, eluant water, acetonitrile, trifluoroacetic acid)

¹H NMR (DMSO-d6) δ (ppm): 9.65 (bs, 1H), 7.59 (d, J=7.34 Hz, 1H), 7.48 (dd, J=7.63 Hz, J=1.47 Hz, 1H), 7.43 (d, J=15.55 Hz, 1H), 7.33 (td, J=7.63 Hz, J=1.76 Hz, 1H), 7.27-7.17 (m, 1H), 7.17-7.00 (m, 2H), 6.95-6.79 (m, 5H), 6.71 (d, J=15.85 Hz, 1H), 5.06 (s, 2H), 4.17 (m, 1H), 2.64-2.54 (m, 2H), 2.15 (s, 3H), 2.14-2.02 (m, 2H), 1.97-1.74 (m, 2H), 1.74-1.44 (m, 2H).

LC-MS: Method_N—254, rt=2.63

(ES+) [M+H]+: 477.

(147) (E)-3-(3-Hydroxy-4-methoxy-phenyl)-N-[2-(2-trifluoromethyl-phenoxymethyl)-phenyl]-acrylamide

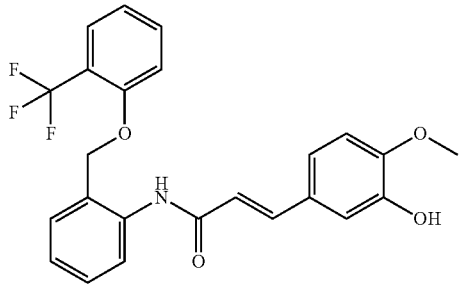 [SMILES: COc1ccc(/C=C/C(=O)Nc2ccccc2COc2ccccc2C(F)(F)F)cc1O]

¹H NMR (DMSO-d6) δ (ppm): 9.60 (s, 1H), 9.18 (s, 1H), 7.73-7.56 (m, 3H), 7.51 (dd, J=7.63 Hz, J=1.17 Hz, 1H), 7.46 (d, J=15.55 Hz, 1H), 7.35 (td, J=7.70 Hz, J=1.61 Hz, 1H), 7.31-7.19 (m, 2H), 7.17-6.91 (m, 4H), 6.68 (d, J=15.85 Hz, 1H), 5.29 (s, 2H), 3.82 (s, 3H).

LC-MS: Method_N—254, rt=2.49

(ES+) [M+H]+: 444.

(148) (E)-3-(3-Hydroxy-4-methoxy-phenyl)-N-{2-[3-(piperidin-4-yloxy)-phenoxy ethyl]-phenyl}-acrylamide

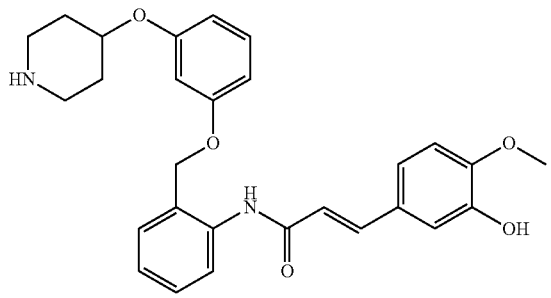 [SMILES: COc1ccc(/C=C/C(=O)Nc2ccccc2COc2cccc(OC3CCNCC3)c2)cc1O]

¹H NMR (DMSO-d6) δ (ppm): 9.57 (s, 1H), 7.62 (d, J=7.63 Hz, 1H), 7.51-7.45 (m, 1H), 7.45 (d, J=15.55 Hz, 1H), 7.34 (td, J=7.78 Hz, J=1.47 Hz, 1H), 7.21 (td, J=7.63 Hz, J=1.17 Hz, 1H), 7.19-7.12 (m, 1H), 7.09-7.00 (m, 2H), 6.97 (d, J=8.22 Hz, 1H), 6.69 (d, J=15.85 Hz, 1H), 6.60-6.45 (m, 3H), 5.12 (s, 2H), 4.50-4.21 (m, 1H), 3.81 (s, 3H), 2.96 (dt, J=12.91, J=4.40 Hz, 2H), 2.62 (ddd, J=12.62 Hz, J=9.83, J=2.79 Hz, 2H), 1.99-1.73 (m, 2H), 1.53-1.40 (m, 2H).

LC-MS: Method_N1, rt=2.06

(ES+) [M+H]+: 475.

(149) (E)-3-(3-Hydroxy-4-methoxy-phenyl)-N-{2-[4-(piperidin-4-yloxy)-phenoxymethyl]-phenyl}-acrylamide hydrochloride

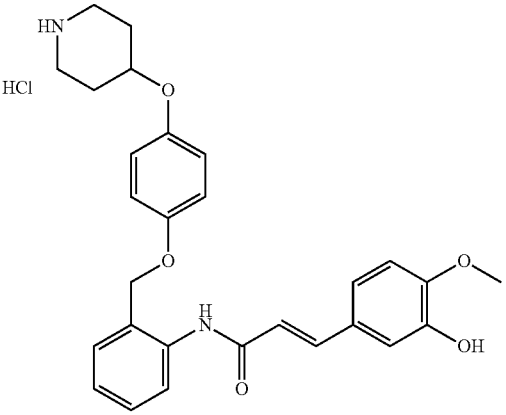 [SMILES: Cl ; COc1ccc(/C=C/C(=O)Nc2ccccc2COc2ccc(OC3CCNCC3)cc2)cc1O]

¹H NMR (DMSO-d6) δ (ppm): 9.60 (s, 1H), 9.14 (bs, 1H), 7.60 (d, J=7.92 Hz, 1H), 7.52-7.38 (m, 2H), 7.37-7.26 (m, 1H), 7.25-7.16 (m, 1H), 7.12-6.82 (m, 7H), 6.69 (d, J=15.85 Hz, 1H), 5.08 (s, 2H), 4.43-4.31 (min, 1H), 3.81 (s, 3H), 3.18-3.00 (m, 2H), 2.96-2.78 (m, 2H), 2.09-1.78 (m, 2H), 1.78-1.54 (m, 2H).

LC-MS: Method_N1, rt=1.98

(ES+) [M+H]+: 475.

(150) (E)-3-(4-Chloro-3-hydroxy-phenyl)-N-{2-[3-(piperidin-4-yloxy)-phenoxymethyl]-phenyl}-acrylamide

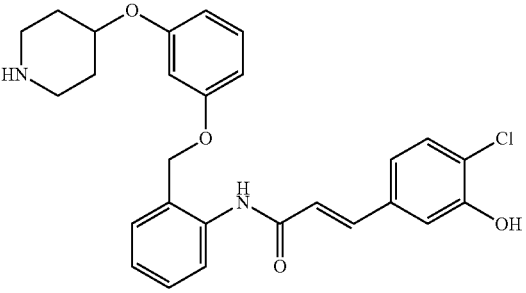 [SMILES: O=C(/C=C/c1ccc(Cl)c(O)c1)Nc1ccccc1COc1cccc(OC2CCNCC2)c1]

¹H NMR (DMSO-d6) δ (ppm): 9.70 (s, 1H), 7.62 (d, J=7.63 Hz, 1H), 7.52-7.46 (m, 1H), 7.48 (d, J=15.85 Hz, 1H), 7.39 (d, J=8.22 Hz, 1H), 7.34 (dd, J=7.92 Hz, J=1.47 Hz, 1H), 7.23 (td, J=7.34 Hz, J=0.88 Hz, 1H), 7.18-7.11 (m, 2H), 7.06 (dd, J=8.22 Hz, J=1.76 Hz, 1H), 6.82 (d, J=15.55 Hz, 1H), 6.67-6.47 (m, 3H), 5.12 (s, 2H), 4.55-4.25 (m, 1H), 3.05-2.88 (m, 2H), 2.60 (ddd, J=12.62 Hz, J=9.98 Hz, J=2.64 Hz, 2H), 1.97-1.76 (m, 2H), 1.55-1.34 (m, 2H)

LC-MS: Method_N2, rt=4.58

(ES+) [M+H]+: 479.

87

(151) (E)-3-(3-hydroxy-4-methoxy-phenyl)-N-{2-[4-(1-methyl-piperidin-4-yl)-phenoxymethyl]-phenyl}-acrylamide

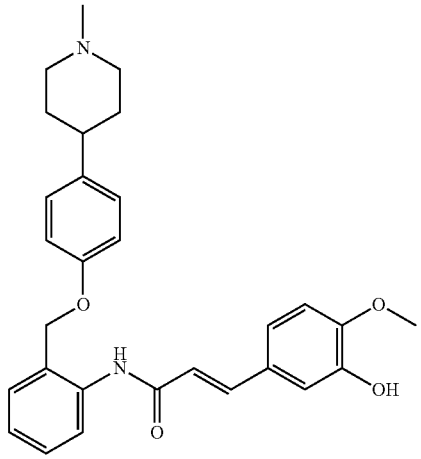 [SMILES: COc1ccc(/C=C/C(=O)Nc2ccccc2COc2ccc(C3CCN(C)CC3)cc2)cc1O]

¹H NMR (DMSO-d6) δ (ppm): 9.59 (s, 1H), 9.17 (bs, 1H), 7.61 (d, J=7.92 Hz, 1H), 7.48 (dd, J=8.51, J=1.47 Hz, 1H), 7.44 (d, J=15.55 Hz, 1H), 7.33 (td, J=7.70, J=1.61 Hz, 1H), 7.21 (td, J=7.63, 1.17 Hz, 1H), 7.17-7.09 (m, 2H), 7.08-7.01 (m, 2H), 6.97 (d, J=8.22 Hz, 1H), 6.94-6.86 (m, 2H), 6.68 (d, J=15.85 Hz, 1H), 5.10 (s, 2H), 3.81 (s, 3H), 2.97-2.77 (m, 2H), 2.46-2.30 (m, 1H), 2.21 (s, 3H), 2.09-1.86 (m, 2H), 1.74-1.52 (m, 4H)

LC-MS: Method_N—254, rt=1.80

(ES+) [M+H]+: 473.

(152) (E)-3-(3-Hydroxy-4-methoxy-phenyl)-N-{2-[2-(4-methyl-piperazin-1-yl)-phenoxymethyl]-phenyl}-acrylamide

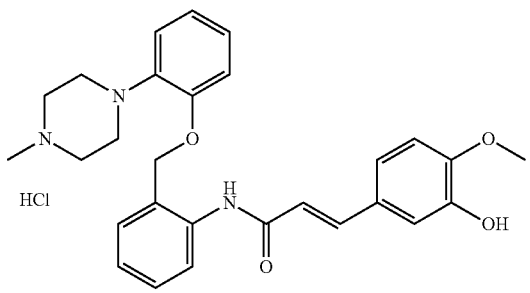

¹H NMR (DMSO-d6) δ (ppm): 10.46 (bs, 1H), 9.75 (s, 1H), 7.65 (d, J=7.34 Hz, 1H), 7.55 (dd, J=7.63, J=1.17 Hz, 1H), 7.45 (d, J=15.55 Hz, 1H), 7.37 (td, J=7.63, J=1.47 Hz, 1H), 7.25 (td, J=7.48, J=1.17 Hz, 1H), 7.11-6.82 (m, 7H), 6.72 (d, J=15.85 Hz, 1H), 5.18 (s, 2H), 3.81 (s, 3H), 3.60-3.45 (m, 2H), 3.45-3.31 (m, 2H), 3.21-3.01 (m, 2H), 3.01-2.87 (m, 2H), 2.78 (d, J=4.69 Hz, 3H)

LC-MS: Method_N—254, rt=1.70

(ES+) [M+H]+: 474.

88

(153) (E)-3-(3-Hydroxy-4-methoxy-phenyl)-N-{2-[3-(1-methyl-piperidin-4-yloxy)-phenoxymethyl]-phenyl}-acrylamide hydrochloride

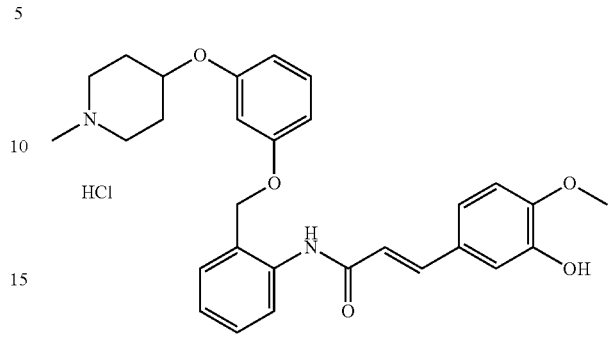

¹H NMR (DMSO-d6) δ (ppm): 9.52 (s, 1H), 9.17 (bs, 1H), 7.71 (d, J=7.63 Hz, 1H), 7.56 (dd, J=7.63, J=1.47 Hz, 1H), 7.45 (d, J=15.55 Hz, 1H), 7.34 (td, J=7.70, J=1.61 Hz, 1H), 7.27-7.16 (m, 1H), 7.11-6.82 (m, 7H), 6.67 (d, J=15.55 Hz, 1H), 5.14 (s, 2H), 4.27 (lt, J=7.89, J=3.85 Hz, 1H), 3.82 (s, 3H), 2.63-2.53 (m, 2H), 2.11 (s, 3H), 2.17-2.02 (m, 2H), 1.94-1.75 (m, 2H), 1.73-1.53 (m, 2H)

LC-MS: Method_N3, rt=2.64

(ES+) [M+H]+: 489.

(154) (E)-3-(4-Chloro-3-hydroxy-phenyl)-N-(3-chloro-phenyl)-acrylamide

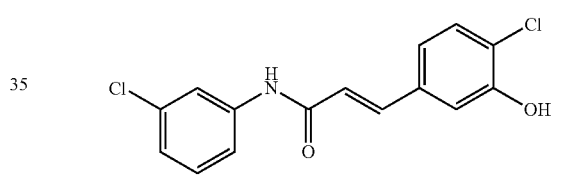

¹H NMR (DMSO-d6) δ (ppm): 10.41 (bs, 1H), 10.38 (s, 1H), 7.92 (t, J=2.05 Hz, 1H), 7.53 (ddd, J=8.22, J=1.91, J=1.03 Hz, 1H), 7.50 (d, J=15.85 Hz, 1H), 7.40 (d, J=8.22 Hz, 1H), 7.37 (t, J=8.22 Hz, 1H), 7.19 (d, J=1.76 Hz, 1H), 7.13 (ddd, J=7.92, J=2.05, J=0.88 Hz, 1H), 7.08 (dd, J=8.36, J=1.91 Hz, 1H), 6.71 (d, J=15.55 Hz, 1H).

LC-MS: Method_N4, rt=4.45

(ES+) [M+H]+: 308.

(155) (E)-3-(3-Hydroxy-4-methoxy-phenyl)-N-{2-[3-(4-methyl-imidazol-1-yl)-phenoxymethyl]-phenyl}-acrylamide

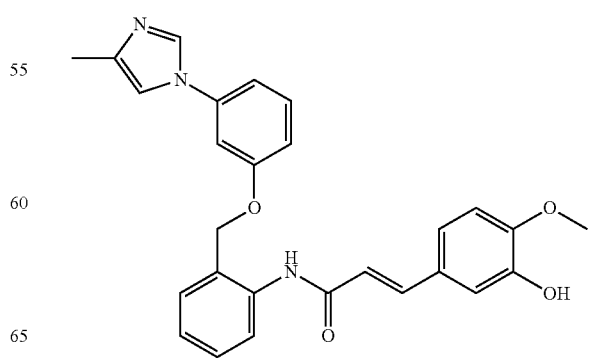

¹H NMR (DMSO-d6) δ (ppm): 9.76 (s, 1H), 9.61 (d, J=1.76 Hz, 1H), 8.01 (dd, J=1.76, J=1.17 Hz, 1H), 7.68-7.48 (m, 3H), 7.44 (d, J=15.85 Hz, 1H), 7.40-7.31 (m, 3H), 7.28-7.15 (m, 3H), 7.08-7.00 (m, 3H), 6.97 (t, J=8.80 Hz, 1H), 6.75 (d, J=15.85 Hz, 1H), 5.29 (s, 2H), 3.81 (s, 3H), 2.34 (d, J=1.17 Hz, 3H)

LC-MS: Method_N1, rt=1.85
(ES+) [M+H]+: 456.

(156) (E)-3-(2-Chloro-3-hydroxy-4-methoxy-phenyl)-N-(3-chloro-phenyl)-acrylamide

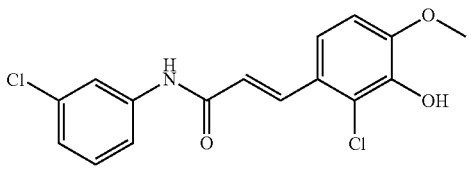 [SMILES: COc1ccc(/C=C/C(=O)Nc2cccc(Cl)c2)c(Cl)c1O]

¹H NMR (DMSO-d6) δ (ppm): 0.44 (s, 1H), 7.94 (t, J=2.05 Hz, 1H), 7.85 (d, J=15.55 Hz, 1H), 7.54 (ddd, J=8.29, J=1.98, J=0.88 Hz, 1H), 7.36 (t, J=8.07 Hz, 1H), 7.26 (d, J=8.51 Hz, 1H), 7.12 (ddd, J=8.00, J=2.13, J=1.03 Hz, 1H), 7.06 (d, J=8.80 Hz, 1H), 6.77 (d, J=15.55 Hz, 1H), 3.88 (s, 3H).

LC-MS: Method_N2, rt=1.85
(ES+) [M+H]+: 456.

(157) (E)-3-(4-Fluoro-3-hydroxy-phenyl)-N-[3-(pyridin-4-ylmethylsulfanyl)-phenyl]-acrylamide

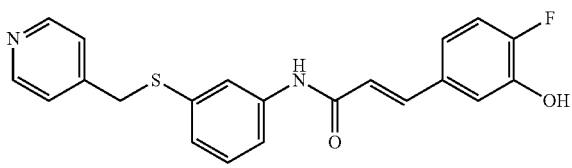 [SMILES: O=C(/C=C/c1ccc(F)c(O)c1)Nc1cccc(SCc2ccncc2)c1]

(Reaction carried out in MeOH, purification by column chromatography)

¹H NMR (DMSO-d6) δ (ppm): 10.17 (s, 1H), 10.08 (s, 1H), 8.42-8.55 (m, 2H), 7.77 (t, J=1.76 Hz, 1H), 7.40-7.52 (m, 2H), 7.33-7.40 (m, 2H), 7.14-7.30 (m, 3H), 6.99-7.12 (m, 2H), 6.64 (d, J=15.55 Hz, 1H), 4.25 (s, 2H).

LC-MS: Method_N—254, rt=1.55
(ES+) [M+H]+: 381.

(158) (E)-N-(1-Benzyl-1H-indazol-7-yl)-3-(4-fluoro-3-hydroxy-phenyl)-acrylamide

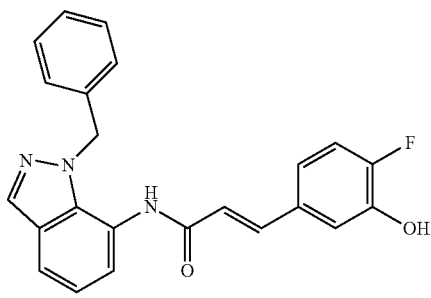 [SMILES: O=C(/C=C/c1ccc(F)c(O)c1)Nc1cccc2cnn(Cc3ccccc3)c12]

(Purification by liquid chromatography)

¹H NMR (DMSO-d6) δ (ppm): 10.11 (bs, 2H), 8.19 (s, 1H), 7.71 (d, J=7.63 Hz, 1H), 7.45 (d, J=15.55 Hz, 1H), 7.03-7.30 (m, 8H), 6.90-7.03 (m, 2H), 6.71 (d, J=15.55 Hz, 1H), 5.67 (s, 2H).

LC-MS: Method_N—254, rt=2.02
(ES+) [M+H]+: 388.

(159) (E)-3-(3-Hydroxy-4-methoxy-phenyl)-N-{2-[4-(1-methyl-piperidin-4-yloxy)-phenoxymethyl]-phenyl}-acrylamide hydrochloride

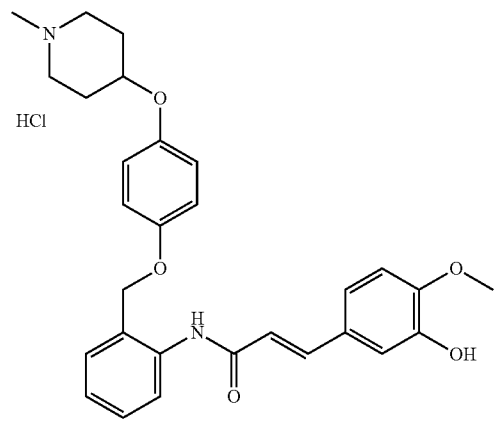

(Purification by liquid chromatography, eluant water, acetonitrile, trifluoroacetic acid. The obtained trifluoroacetate salt is treated with PS—HCO₃ cartridge and converted to the corresponding hydrochloride salt with HCl/Et₂O)

¹H NMR (DMSO-d₆+Na₂CO₃) δ (ppm): 9.58 (s, 1H), 7.61 (d, J=7.92 Hz, 1H), 7.48 (dd, J=7.63, 1.47 Hz, 1H), 7.44 (d, J=15.85 Hz, 1H), 7.33 (td, J=7.63, 1.76 Hz, 1H), 7.21 (td, J=7.63, 1.17 Hz, 1H), 7.06 (d, J=1.76 Hz, 1H), 7.03 (dd, J=8.51, 1.76 Hz, 1H), 6.96 (d, J=8.22 Hz, 1H), 6.79-6.93 (m, 4H), 6.68 (d, J=15.55 Hz, 1H), 5.07 (s, 2H), 4.17 (ddd, J=8.22, 4.55, 4.25 Hz, 1H), 3.81 (s, 3H), 2.54-2.68 (m, 2H), 2.15 (s, 3H), 2.05-2.14 (m, 2H), 1.75-1.99 (m, 2H), 1.42-1.74 (m, 2H).

LC-MS: Method_N3 rt=2.62
(ES+) [M+H]+: 489.

(160) (E)-N-(3-Benzyl-3H-benzoimidazol-4-yl)-3-(4-fluoro-3-hydroxy-phenyl)-acrylamide

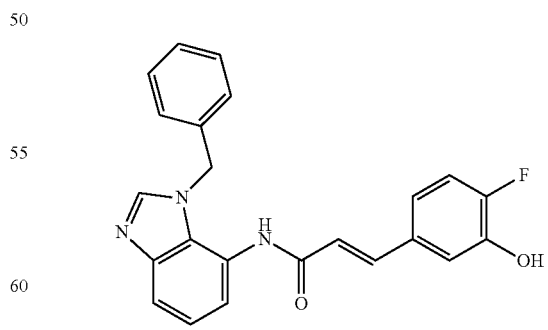

(Reaction carried out in MeOH, purification by trituration with acetonitrile)

¹H NMR (DMSO-d6) δ (ppm): 10.28 (bs, 1H), 10.15 (bs, 1H), 9.28 (s, 1H), 7.73 (d, J=7.92 Hz, 1H), 7.48 (dd, J=7.92

Hz, 1H), 7.40 (d, J=15.85 Hz, 1H), 7.15-7.35 (m, 6H), 7.02-7.15 (m, 3H), 6.67 (d, J=15.55 Hz, 1H), 5.77 (s, 2H).

LC-MS: Method_N rt=1.52

(ES+) [M+H]+: 388.

(161) (E)-3-(3-Hydroxy-4-methoxy-phenyl)-N-[2-(4-trifluoromethyl-phenoxymethyl)-phenyl]-acrylamide

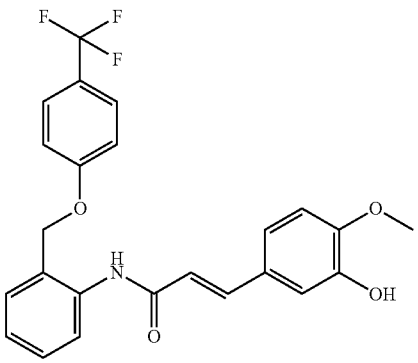 [SMILES: COc1ccc(/C=C/C(=O)Nc2ccccc2COc2ccc(C(F)(F)F)cc2)cc1O]

(Reaction carried out in MeOH, purification by column chromatography)

¹H NMR (DMSO-d6) δ (ppm): 9.62 (s, 1H), 9.16 (bs, 1H), 7.55-7.71 (m, 3H), 7.50 (dd, J=7.78, 1.32 Hz, 1H), 7.45 (d, J=15.55 Hz, 1H), 7.36 (td, J=7.70, 1.61 Hz, 1H), 7.23 (td, J=7.48, 1.17 Hz, 1H), 7.13-7.19 (m, 2H), 6.90-7.08 (m, 3H), 6.68 (d, J=15.55 Hz, 1H), 5.23 (s, 2H), 3.81 (s, 3H).

LC-MS: Method_N—254, rt=2.65

(ES+) [M+H]+: 444.

(162) (E)-N-[2-(2-Chloro-phenoxymethyl)-phenyl]-3-(3-hydroxy-4-methoxy-phenyl)-acrylamide

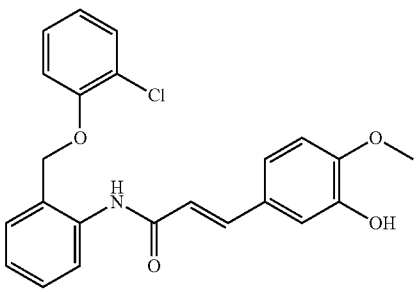 [SMILES: COc1ccc(/C=C/C(=O)Nc2ccccc2COc2ccccc2Cl)cc1O]

(Reaction carried out in DCM/MeOH)

¹H NMR (DMSO-d6) δ (ppm): 9.59 (s, 1H), 9.17 (s, 1H), 7.66 (d, J=7.04 Hz, 1H), 7.54 (dd, J=7.63, 1.47 Hz, 1H), 7.40-7.51 (m, 2H), 7.12-7.40 (m, 4H), 6.91-7.09 (m, 4H), 6.68 (d, J=15.55 Hz, 1H), 5.25 (s, 2H), 3.82 (s, 3H).

LC-MS: Method_N—254, rt=2.47

(163) (E)-3-(3-Hydroxy-4-methoxy-phenyl)-N-[1-(4-imidazol-1-yl-benzyl)-1H-indol-7-yl]-acrylamide

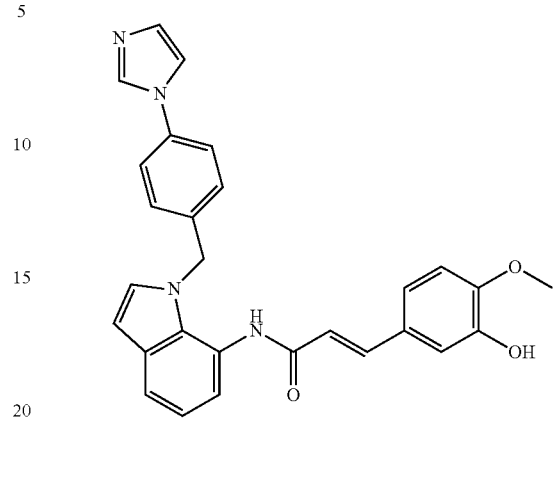

(Reaction carried out in MeOH, purification by column chromatography)

¹H NMR (DMSO-d6) δ (ppm): 9.77 (s, 1H), 9.19 (s, 1H), 8.10 (s, 1H), 7.29-7.69 (m, 6H), 6.86-7.12 (m, 8H), 6.48-6.67 (m, 2H), 5.50 (s, 2H), 3.82 (s, 3H).

LC-MS: Method_N—254, rt=1.60

(ES+) [M+H]+: 465.

(164) (E)-3-(4-Fluoro-3-hydroxy-phenyl)-N-[1-(4-imidazol-1-yl-benzyl)-1H-indol-7-yl]-acrylamide

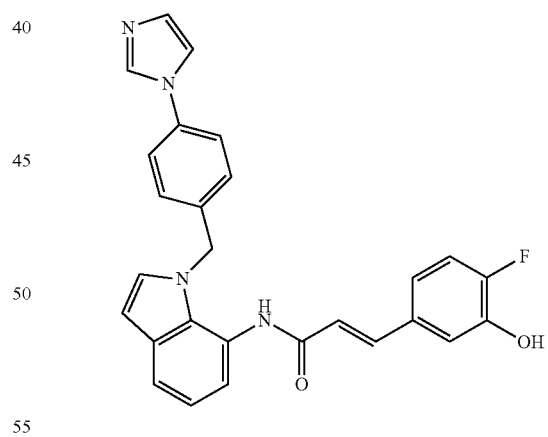

(Reaction carried out in MeOH, purification by column chromatography)

¹H NMR (DMSO-d6) δ (ppm): 10.14 (bs, 1H), 9.87 (s, 1H), 8.10 (s, 1H), 7.59 (s, 1H), 7.43-7.54 (m, 4H), 7.38 (d, J=15.81 Hz, 1H), 7.13-7.25 (m, 2H), 6.89-7.09 (m, 6H), 6.63 (d, J=15.81 Hz, 1H), 6.56 (d, J=3.12 Hz, 1H), 5.49 (s, 2H).

LC-MS: Method_N—254, rt=1.62

(ES+) [M+H]+: 453.

(165) (E)-3-(3-Hydroxy-4-methoxy-phenyl)-N-{(2-[4-(1-methyl-piperidin-4-ylmethyl)-phenoxymethyl]-phenyl}-acrylamide

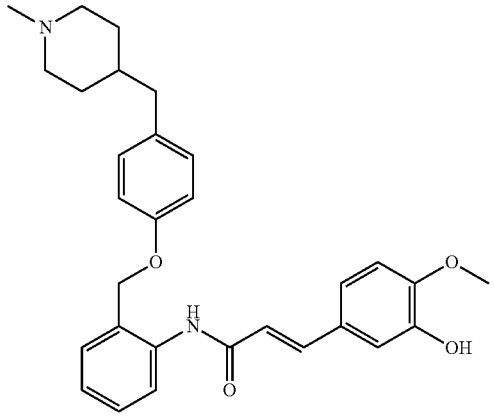

(Reaction carried out in MeOH, purification by column chromatography)

¹H NMR (DMSO-d6) δ (ppm): 9.57 (s, 1H), 9.16 (bs, 1H), 7.61 (d, J=7.92 Hz, 1H), 7.49 (dd, J=7.63, 1.47 Hz, 1H), 7.44 (d, J=15.85 Hz, 1H), 7.33 (td, J=7.70, 1.61 Hz, 1H), 7.14-7.26 (m, 1H), 6.81-7.14 (m, 7H), 6.68 (d, J=15.85 Hz, 1H), 5.09 (s, 2H), 3.81 (s, 3H), 2.59-2.81 (m, 2H), 2.40 (d, J=6.75 Hz, 2H), 2.10 (s, 3H), 1.63-1.85 (m, 2H), 1.43-1.53 (m, 2H), 1.23-1.41 (m, 1H), 1.07-1.21 (m, 2H).

LC-MS: Method_N3, rt=2.77

(ES+) [M+H]+: 487.

(166) (E)-3-(3-Hydroxy-4-methoxy-phenyl)-N-{2-[3-(4-methyl-piperazin-1-yl)-phenoxymethyl]-phenyl}-acrylamide hydrochloride

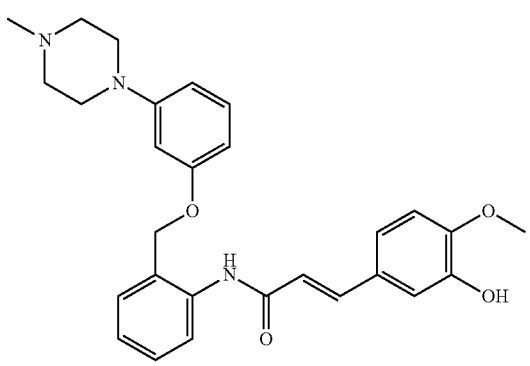

(Reaction carried out in MeOH, purification by trituration with ethyl ether)

¹H NMR (DMSO-d6) δ (ppm): 10.25 (bs, 1H), 9.65 (s, 1H), 7.61 (d, J=7.04 Hz, 1H), 7.48 (dd, J=7.63, 1.47 Hz, 1H), 7.45 (d, J=15.55 Hz, 1H), 7.34 (td, J=7.63, 1.47 Hz, 1H), 7.21 (td, J=7.34, 1.17 Hz, 1H), 7.15 (t, J=8.22 Hz, 1H), 7.01-7.10 (m, 2H), 6.97 (d, J=8.22 Hz, 1H), 6.71 (d, J=15.55 Hz, 1H), 6.55-6.64 (m, 2H), 6.51 (dd, J=7.92, 2.05 Hz, 1H), 5.13 (s, 2H), 3.82 (s, 3H), 3.74-3.85 (m, 2H), 3.41-3.54 (m, 2H), 2.91-3.20 (m, 4H), 2.81 (d, J=4.69 Hz, 3H).

LC-MS: Method_N—254, rt=1.67

(ES+) [M+H]+: 474.

(167) (E)-3-(3-Hydroxy-4-methoxy-phenyl)-N-{2-[4-(4-methyl-imidazol-1-yl)-phenoxymethyl]-phenyl}-acrylamide hydrochloride

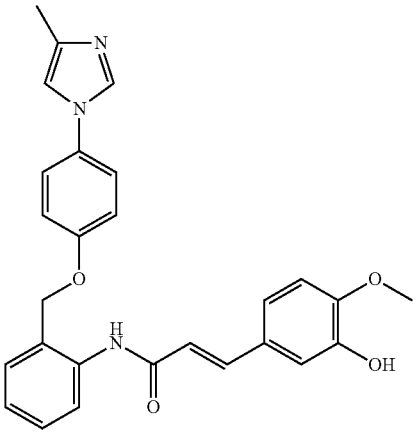 [SMILES: COc1ccc(/C=C/C(=O)Nc2ccccc2COc2ccc(-n3cnc(C)c3)cc2)cc1O]

(Reaction carried out in MeOH, purification by trituration with ethyl ether)

¹H NMR (DMSO-d6) δ (ppm): 9.72 (s, 1H), 9.38 (d, J=1.47 Hz, 1H), 9.19 (bs, 1H), 7.85 (t, J=1.32 Hz, 1H), 7.55-7.73 (m, 3H), 7.50 (dd, J=7.63, 1.47 Hz, 1H), 7.44 (d, J=15.55 Hz, 1H), 7.36 (td, J=7.63, 1.47 Hz, 1H), 7.14-7.30 (m, 3H), 7.00-7.09 (m, 2H), 6.96 (d, J=8.22 Hz, 1H), 6.71 (d, J=15.55 Hz, 1H), 5.25 (s, 2H), 3.81 (s, 3H), 2.33 (d, J=0.88 Hz, 3H).

LC-MS: Method_N—254, rt=1.61

(ES+) [M+H]+: 456.

(168) (E)-N-(1-Benzyl-2-oxo-2,3-dihydro-1H-indol-7-yl)-3-(3-hydroxy-4-methoxy-phenyl)-acrylamide

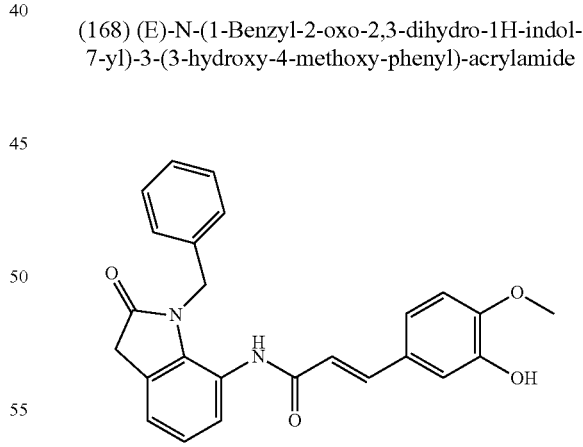

(Reaction carried out in MeOH, purification by liquid chromatography)

¹H NMR (DMSO-d6) δ (ppm): 9.49 (bs, 1H), 9.21 (bs, 1H), 7.27 (d, J=15.85 Hz, 1H), 7.11-7.24 (m, 4H), 6.88-7.10 (m, 7H), 6.40 (d, J=15.55 Hz, 1H), 5.00 (s, 2H), 3.82 (s, 3H), 3.77 (s, 2H).

LC-MS: Method_N—254, rt=1.77

(ES+) [M+H]+: 415.

(169) (E)-N-(3-Chloro-naphthalen-1-yl)-3-(3-hydroxy-4-methoxy-phenyl)-acrylamide

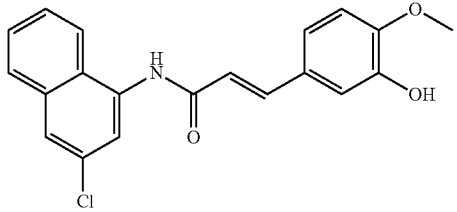 [SMILES: COc1ccc(/C=C/C(=O)Nc2cc(Cl)cc3ccccc23)cc1O]

(Reaction carried out in MeOH, purification by liquid chromatography)
¹H NMR (DMSO-d6) δ (ppm): 10.14 (bs, 1H), 9.22 (bs, 1H), 8.19-8.33 (m, 1H), 8.12 (d, J=2.05 Hz, 1H), 7.90-7.99 (m, 1H), 7.87 (d, J=2.05 Hz, 1H), 7.58-7.68 (m, 2H), 7.53 (d, J=15.55 Hz, 1H), 7.01-7.17 (m, 3H), 6.97 (d, J=15.55 Hz, 1H), 3.83 (s, 3H).
LC-MS: Method_N5, rt=2.33
(ES+) [M+H]+: 354.

(170) (E)-3-(3-Hydroxy-4-methoxy-phenyl)-N-[2-(2-methyl-2H-pyrazol-3-yloxymethyl)-phenyl]-acrylamide

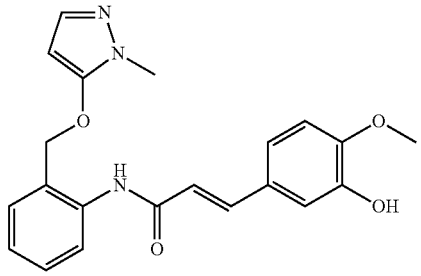 [SMILES: COc1ccc(/C=C/C(=O)Nc2ccccc2COc2ccnn2C)cc1O]

(Reaction carried out in MeOH, purification by column chromatography)
¹H NMR (DMSO-d6) δ (ppm): 9.65 (s, 1H), 9.20 (bs, 1H), 7.59 (dd, J=8.07, 1.03 Hz, 1H), 7.51 (dd, J=7.78, 1.32 Hz, 1H), 7.45 (d, J=15.85 Hz, 1H), 7.37 (td, J=7.70, 1.61 Hz, 1H), 7.20-7.28 (m, 1H), 7.18 (d, J=2.05 Hz, 1H), 7.00-7.10 (m, 2H), 6.97 (d, J=8.22 Hz, 1), 6.69 (d, J=15.55 Hz, 1H), 5.64 (d, J=2.05 Hz, 1H), 5.17 (s, 2H), 3.81 (s, 3H), 3.53 (s, 3H).
LC-MS: Method_N1, rt=2.23
(ES+) [M+H]+: 380.

(171) (E)-3-(3-Hydroxy-4-methoxy-phenyl)-N-[2-(3-piperazin-1-yl-phenoxymethyl)phenyl]-acrylamide

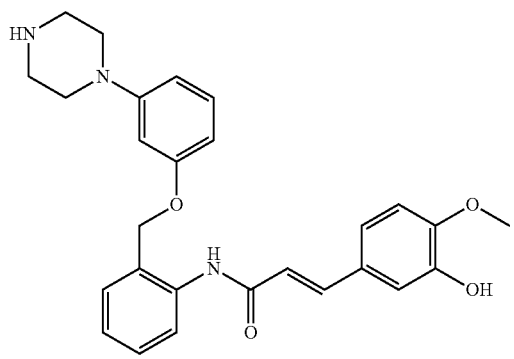 [SMILES: COc1ccc(/C=C/C(=O)Nc2ccccc2COc2cccc(N3CCNCC3)c2)cc1O]

(Reaction carried out in MeOH, purification by column chromatography column followed by trituration with DCM and ethyl ether)
¹H NMR (DMSO-d6) δ (ppm): 9.56 (s, 1H), 7.62 (d, J=7.34 Hz, 1H), 7.45-7.52 (m, 1H), 7.44 (d, J=15.55 Hz, 1H), 7.33 (td, J=7.70, 1.61 Hz, 1H), 7.16-7.26 (m, 1H), 7.00-7.15 (m, 3H), 6.97 (d, J=8.22 Hz, 1H), 6.68 (d, J=15.55 Hz, 1H), 6.48-6.57 (m, 2H), 6.35-6.45 (m, 1H), 5.10 (s, 2H), 3.81 (s, 3H), 2.94-3.12 (m, 4H), 2.78-2.91 (m, 4H).
LC-MS: Method_N1, rt=1.96
(ES+) [M+H]+: 460.

(172) (E)-3-(3-Hydroxy-4-methoxy-phenyl)-N-[1-(1-methyl-1H-imidazol-4-ylmethyl)-1H-indol-7-yl]-acrylamide

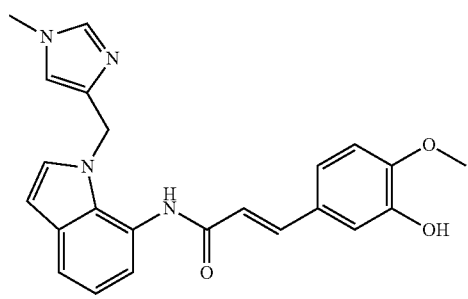

(Reaction carried out in MeOH, purification by column chromatography)
¹H NMR (DMSO-d6) δ (ppm): ¹H NMR (DMSO-d₆) δ (ppm): 11.64 (s, 1H), 9.17 (bs, 1H), 7.76 (s, 1H), 7.51 (d, J=15.55 Hz, 1H), 7.24-7.39 (m, 3H), 7.19 (s, 1H), 6.87-7.09 (m, 4H), 6.70 (d, J=15.55 Hz, 1H), 6.41 (d, J=2.93 Hz, 1H), 5.34 (s, 2H), 3.81 (s, 3H), 3.64 (s, 3H).
LC-MS: Method_N5, rt=1.43
(ES+) [M+H]+: 403.

(173) (E)-3-(3-Hydroxy-4-methoxy-phenyl)-N-[1-(1-methyl-1H-pyrazol-3-ylmethyl)-1H-indol-7-yl]-acrylamide

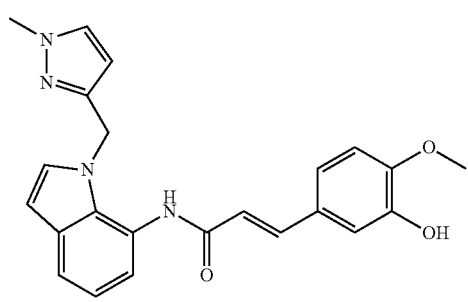

(Reaction carried out in MeOH, purification by column chromatography)
¹H NMR (DMSO-d6) δ (ppm): ¹H NMR (DMSO-d₆) δ (ppm): 10.10 (s, 1H), 9.20 (bs, 1H), 7.57 (d, J=1.76 Hz, 1H), 7.47 (d, J=15.85 Hz, 1H), 7.41 (d, J=7.63 Hz, 1H), 7.35 (d, J=3.23 Hz, 1H), 6.88-7.19 (m, 5H), 6.71 (d, J=15.85 Hz, 1H), 6.45 (d, J=2.93 Hz, 1H), 6.02 (d, J=2.05 Hz, 1H), 5.41 (s, 2H), 3.81 (s, 3H), 3.78 (s, 3H).
LC-MS: Method_N2, rt=4.52
(ES+) [M+H]+: 403.

(174) (E)-3-(3-Hydroxy-phenyl)-N-(2-phenoxymethyl-phenyl)-acrylamide

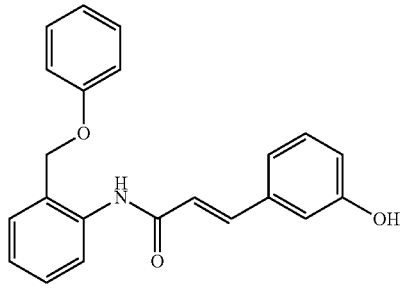 [SMILES: O=C(/C=C/c1cccc(O)c1)Nc1ccccc1COc1ccccc1]

(Reaction carried out in MeOH, purification by liquid chromatography)

$^1$H NMR (DMSO-d6) δ (ppm): 9.68 (s, 1H), 9.58 (s, 1H), 7.61 (d, J=7.34 Hz, 1H), 7.50 (dd, J=7.63, 1.47 Hz, 1H), 7.49 (d, J=15.55 Hz, 1H), 7.35 (td, J=7.92, 1.47 Hz, 1H), 7.18-7.32 (m, 4H), 7.02-7.07 (m, 1H), 6.90-7.02 (m, 4H), 6.84 (d, J=15.85 Hz, 1H), 6.81 (ddd, J=7.92, 2.35, 0.88 Hz, 1H), 5.14 (s, 2H).

LC-MS: Method_N2, rt=5.26

(ES+) [M+H]+: 346.

(175) (E)-N-(3-Chloro-phenyl)-3-(2,4-difluoro-3-hydroxy-phenyl)-acrylamide

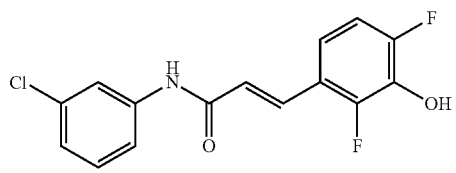 [SMILES: O=C(/C=C/c1ccc(F)c(O)c1F)Nc1cccc(Cl)c1]

(Reaction carried out in MeOH/DCM, purification by trituration with AcOEt and ethyl ether)

$^1$H NMR (DMSO-d6) δ (ppm): 10.44 (s, 1H), 10.36 (bs, 1H), 7.93 (s, 1H), 7.49-7.58 (m, 1H), 7.58 (d, J=16.14 Hz, 1H), 7.37 (t, J=7.92 Hz, 1H), 7.05-7.27 (m, 3H), 6.85 (d, J=16.14 Hz, 1H).

(ES+) [M+H]+: 310.

Example 10

Preparation of substituted (E)-3-(3-hydroxy-phenyl)-acrylic anilides from the corresponding (E)-3-(3-acetoxy-phenyl)-acrylic acids

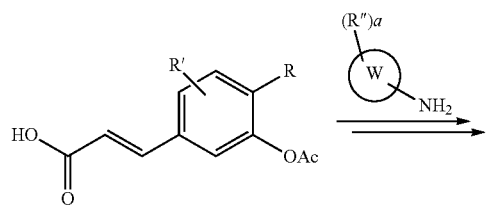

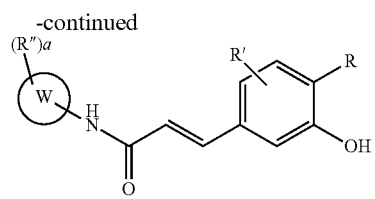

According to the procedure described in Example 4, the following compounds were prepared by coupling the suitable acrylic acid with the suitable aniline and performing the adequate chromatographic purifications when needed:

(176) (E)-3-(3-Hydroxy-4-methoxy-phenyl)-N-[2-(4-pyrrolidin-1-ylmethyl-phenoxymethyl)-phenyl]-acrylamide hydrochloride

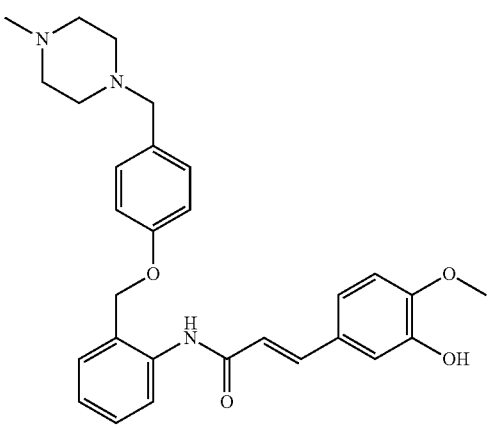

$^1$H NMR (DMSO-d6) δ (ppm): 9.61 (bs, 1H), 7.61 (d, J=7.92 Hz, 1H), 7.49 (dd, J=7.63 Hz, J=1.17 Hz, 1H), 7.44 (d, J=15.85 Hz, 1H), 7.34 (td, J=7.56 Hz, J=1.61 Hz, 1H), 7.28-7.12 (m, 3H), 7.12-6.83 (m, 5H), 6.68 (d, J=16.14 Hz, 1H), 5.11 (s, 2H), 3.81 (s, 3H), 3.47 (s, 2H), 2.44-2.31 (m, 4H), 1.77-1.54 (m, 4H).

LC-MS: Method_N—254, rt=2.51

(ES+) [M+H]+: 459.

(177) (E)-3-(3-Hydroxy-4-methoxy-phenyl)-N-{2-[4-(4-methyl-piperazin-1-ylmethyl)-phenoxymethyl]-phenyl}-acrylamide ¹H NMR (DMSO-d6) δ (ppm): 9.58 (s, 1H), 9.20 (s, 1H), 7.61 (d, J=7.34 Hz, 1H), 7.49 (dd, J=7.63 Hz, J=1.17 Hz, 1H), 7.44 (d, J=15.55 Hz, 1H), 7.34 (td, J=7.70 Hz, J=1.61 Hz, 1H), 7.28-7.11 (m, 3H), 7.10-6.99 (m, 2H), 6.99-6.88 (m, 3H), 6.67 (d, J=15.55 Hz, 1H), 5.11 (s, 2H), 3.81 (s, 3H), 3.35 (s, 2H), 2.44-2.20 (m, 8H), 2.13 (s, 3H).

LC-MS: Method_N—254, rt=1.46

(ES+) [M+H]+: 488.

(178) (E)-3-(3-Hydroxy-4-methoxy-phenyl)-N-[2-(4-piperidin-1-ylmethyl-phenoxymethyl)-phenyl]-acrylamide trifluoroacetate

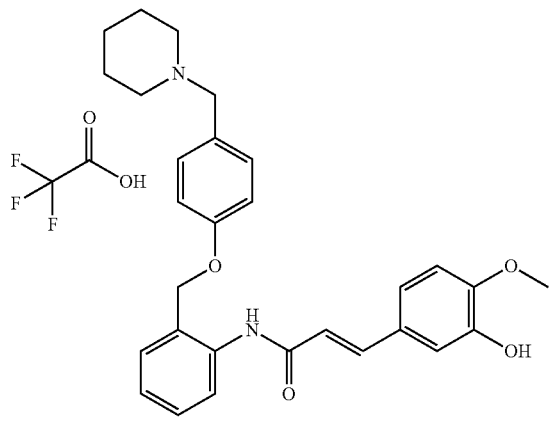

(Purification by liquid chromatography, eluant water, acetonitrile, trifluoroacetic acid)

¹H NMR (DMSO-d6) δ (ppm): 9.64 (s, 1H), 9.16 (s, 1H), 9.08 (bs, 1H), 7.61-7.56 (m, 1H), 7.52-7.47 (m, 1H), 7.44-7.33 (m, 3H), 7.23 (td, J=7.63 Hz, J=1.17 Hz, 1H), 7.1-6.89 (m, 5H), 6.68 (d, J=15.55 Hz, 1H), 5.17 (s, 2H), 4.19 (d, J=5.28 Hz, 2H), 3.82 (s, 3H), 3.27-3.21 (m, 2H), 2.97-2.66 (m, 2H), 1.90-1.75 (m, 2H), 1.75-1.46 (m, 3H), 1.46-1.20 (m, 1H)

LC-MS: Method_N—254, rt=1.71

(ES+) [M+H]+: 473.

(179) (E)-3-(3-Hydroxy-4-methoxy-phenyl)-N-{1-[3-(1-methyl-piperidin-4-yloxy)-benzyl]-1H-indol-7-yl}-acrylamide

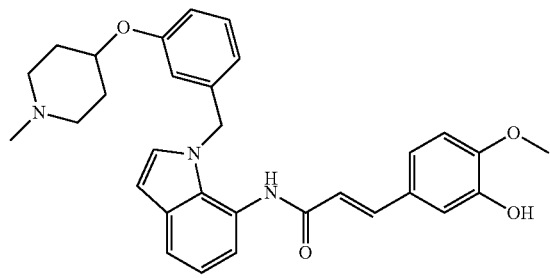

¹H NMR (DMSO-d6) δ (ppm): 9.71 (s, 1H), 7.55-7.28 (m, 3H), 7.19-6.86 (m, 6H), 6.78-6.65 (m, 1H), 6.64-6.49 (m, 2H), 6.46-6.31 (m, 2H), 5.42 (s, 2H), 4.23-3.98 (m, 1H), 3.81 (s, 3H), 2.47-2.40 (m, 2H), 2.09 (s, 3H), 2.04-1.89 (m, 2H), 1.79-1.64 (m, 2H), 1.55-1.35 (m, 2H).

LC-MS: Method_N1, rt=2.00

(ES+) [M+H]+: 512.

(180) (E)-3-(3-Hydroxy-4-methoxy-phenyl)-N-{2-[2-(1-methyl-piperidin-4-yloxy)-phenoxymethyl]-phenyl}-acrylamide

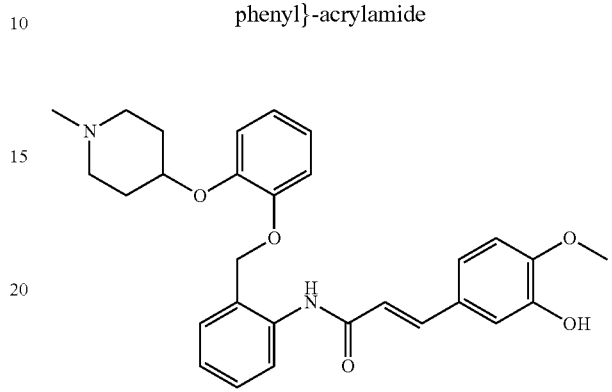

¹H NMR (DMSO-d6) δ (ppm): 9.52 (s, 1H), 9.17 (bs, 1H), 7.71 (d, J=7.63 Hz, 1-1H), 7.56 (dd, J=7.63, J=1.47 Hz, 1H), 7.45 (d, J=15.55 Hz, 1H), 7.34 (td, J=7.70, J=1.61 Hz, 1H), 7.27-7.16 (m, 1H), 7.11-6.82 (m, 7H), 6.67 (d, J=15.55 Hz, 1H), 5.14 (s, 2H), 4.27 (tt, J=7.89, J=3.85 Hz, 1H), 3.82 (s, 3H), 2.63-2.53 (m, 2H), 2.11 (s, 3H), 2.17-2.02 (m, 2H), 1.94-1.75 (m, 2H), 1.73-1.53 (m, 2H).

LC-MS: Method_N3, rt=2.64

(ES+) [M+H]+: 489.

(181) (E)-3-(3-Hydroxy-4-methoxy-phenyl)-N-{2-[3-(1-methyl-piperidin-4-yl)-phenoxymethyl]-phenyl}-acrylamide

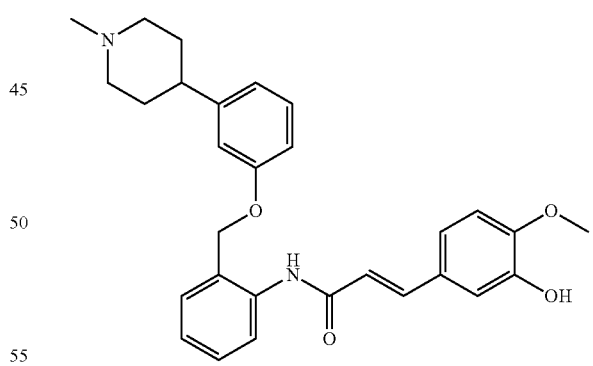

¹H NMR (DMSO-d6) δ (ppm): 9.58 (s, 1H), 9.16 (bs, 1H), 7.62 (d, J=7.92 Hz, 1H), 7.49 (dd, J=7.92, J=1.47 Hz, 1H), 7.45 (d, J=15.55 Hz, 1H), 7.34 (td, J=7.56, J=1.61 Hz, 1H), 7.21 (td, J=7.63, J=1.17 Hz, 1H), 7.20 (t, J=7.92 Hz, 1H), 7.08-7.01 (m, 2H), 6.97 (d, J=8.51 Hz, 1H), 6.89-6.77 (m, 3H), 6.69 (d, J=15.55 Hz, 1H), 5.12 (s, 2H), 3.81 (s, 3H), 3.01-2.83 (m, 2H), 2.47-2.36 (m, 1H), 2.27 (s, 3H), 2.18-2.03 (m, 2H), 1.83-1.68 (m, 2H), 1.68-1.52 (m, 2H).

LC-MS: Method_N1, rt=1.97

(ES+) [M+H]+: 473.

(182) (E)-3-(3-Hydroxy-4-methoxy-phenyl)-N-{2-[4-(4-methyl-piperazin-1-yl)-phenoxymethyl]-phenyl}-acrylamide trifluoroacetate

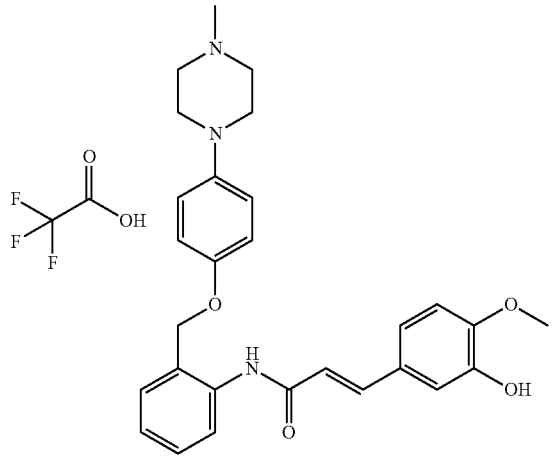

(Deacetylation carried out in MeOH. Final purification by liquid chromatography, eluant water, acetonitrile, trifluoroacetic acid)

$^1$H NMR (DMSO-d6) δ (ppm): 9.57 (s, 1H), 9.48 (bs, 1H), 9.16 (s, 1H), 7.59 (d, J=7.63 Hz, 1H), 7.40-7.50 (m, 2H), 7.27-7.37 (m, 1H), 7.17-7.25 (m, 1H), 7.00-7.08 (m, 2H), 6.94-7.00 (m, 1H), 6.93 (s, 4H), 6.67 (d, J=15.85 Hz, 1H), 5.08 (s, 2H), 3.82 (s, 3H), 3.62 (bs, 2H), 3.46 (bs, 2H), 3.15 (bs, 2H), 2.76-2.99 (m, 5H).

LC-MS: Method_N—254, rt=1.64

(ES+) [M+H]+: 474.

(183) (E)-3-(4-Fluoro-3-hydroxy-phenyl)-N-[2-(4-imidazol-1-yl-phenoxymethyl)-phenyl]-acrylamide

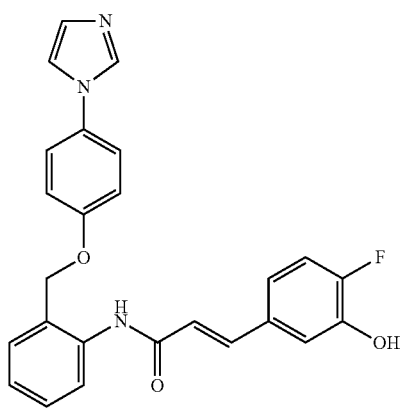 [SMILES: O=C(/C=C/c1ccc(F)c(O)c1)Nc1ccccc1COc1ccc(-n2ccnc2)cc1]

(Deacetylation carried out in MeOH. Final purification by liquid chromatography followed by crystallization from ethyl ecetate/2-propanol)

$^1$H NMR (DMSO-d6) δ (ppm): 10.06 (bs, 1H), 9.70 (s, 1H), 8.09 (s, 1H), 7.43-7.69 (m, 6H), 7.36 (td, J=7.63, 1.47 Hz, 1H), 7.02-7.30 (m, 7H), 6.77 (d, J=15.85 Hz, 1H), 5.19 (s, 2H).

LC-MS: Method_N—254, rt=1.63

(ES+) [M+H]+: 430.

(184) (E)-3-(2,4-Difluoro-3-hydroxy-phenyl)-N-{2-[3-(1-methyl-piperidin-4-yloxy)-phenoxymethyl]-phenyl}-acrylamide

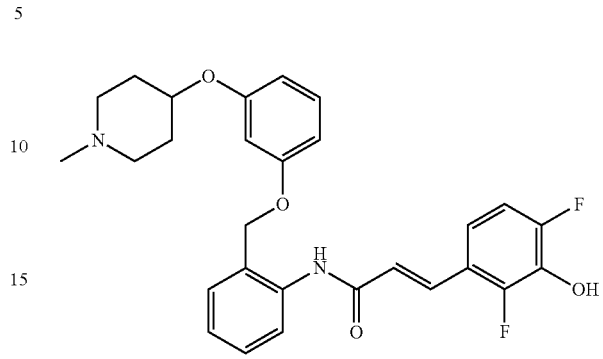

(Deacetylation carried out in MeOH. Final purification by liquid chromatography)

(ES+) [M+H]+: 495.

(185) (E)-3-(2-Chloro-3-hydroxy-4-methoxy-phenyl)-N-{2-[3-(1-methyl-piperidin-4-yloxy)-phenoxymethyl]-phenyl}-acrylamide

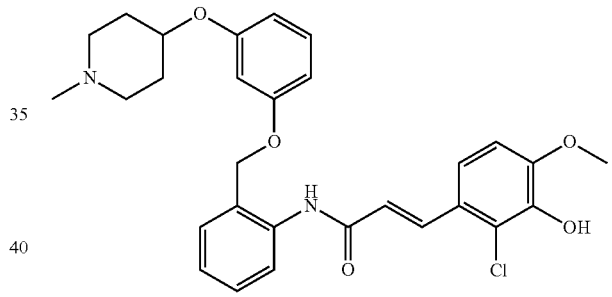

(Deacetylation carried out in MeOH. Final purification by liquid chromatography)

(ES+) [M+H]+: 523.

(186) (E)-N-(3-Chloro-phenyl)-3-(4-cyano-3-hydroxy-phenyl)-acrylamide

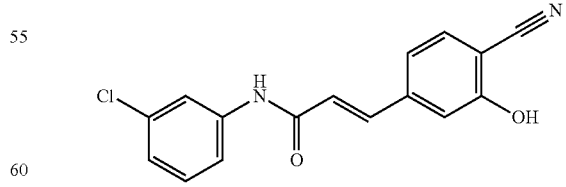

(Deacetylation carried out in MeOH. Final purification by liquid chromatography)

(ES+) [M+H]+: 299.

(187) (E)-3-(4-Cyano-3-hydroxy-phenyl)-N-{2-[3-(1-methyl-piperidin-4-yloxy)-phenoxymethyl]-phenyl}-acrylamide

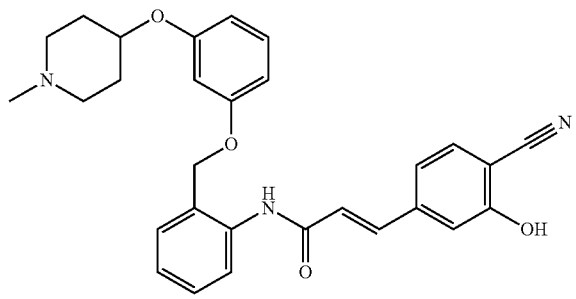 [SMILES: CN1CCC(Oc2cccc(OCc3ccccc3NC(=O)/C=C/c3ccc(C#N)c(O)c3)c2)CC1]

(Deacetylation carried out in MeOH. Final purification by liquid chromatography)
(ES+) [M+H]+: 484.

(188) (E)-3-(2,4-Difluoro-3-hydroxy-phenyl)-N-{2-[3-(piperidin-4-yloxy)-phenoxymethyl]-phenyl})-acrylamide

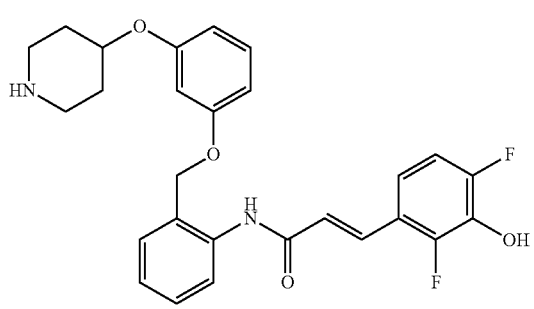 [SMILES: O=C(/C=C/c1ccc(F)c(O)c1F)Nc1ccccc1COc1cccc(OC2CCNCC2)c1]

(Deacetylation carried out in MeOH. Final purification by liquid chromatography)
(ES+) [M+H]+: 481.

(189) (E)-3-(2,4-Difluoro-3-hydroxy-phenyl)-N-{2-[4-(1-methyl-piperidin-4-yloxy)-phenoxymethyl]-phenyl}-acrylamide

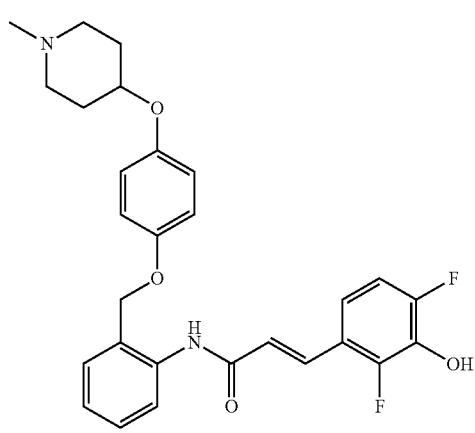 [SMILES: CN1CCC(Oc2ccc(OCc3ccccc3NC(=O)/C=C/c3ccc(F)c(O)c3F)cc2)CC1]

(Deacetylation carried out in MeOH. Final purification by liquid chromatography)
(ES+) [M+H]+: 495.

(190) (E)-3-(2,4-Difluoro-3-hydroxy-phenyl)-N-{2-[4-(piperidin-4-yloxy)-phenoxymethyl]-phenyl}-acrylamide

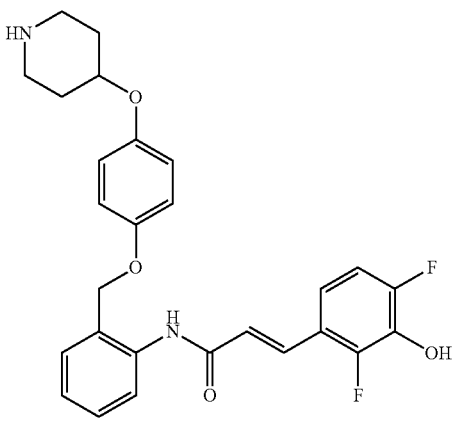 [SMILES: O=C(/C=C/c1ccc(F)c(O)c1F)Nc1ccccc1COc1ccc(OC2CCNCC2)cc1]

(Deacetylation carried out in MeOH. Final purification by liquid chromatography)
(ES+) [M+H]+: 481.

(191) (E)-3-(2-Chloro-3-hydroxy-4-methoxy-phenyl)-N-{2-[3-(piperidin-4-yloxy)-phenoxymethyl]-phenyl}-acrylamide

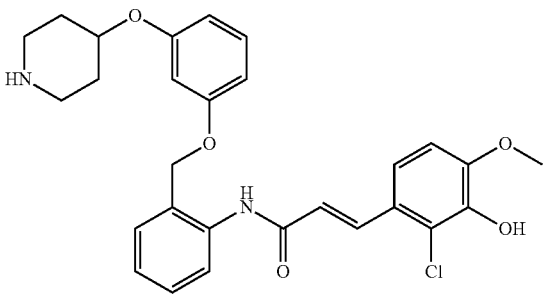 [SMILES: COc1ccc(/C=C/C(=O)Nc2ccccc2COc2cccc(OC3CCNCC3)c2)c(Cl)c1O]

(Deacetylation carried out in MeOH. Final purification by liquid chromatography)
(ES+) [M+H]+: 509.

(192) (E)-3-(4-Cyano-3-hydroxy-phenyl)-N-{2-[3-(piperidin-4-yloxy)-phenoxymethyl]-phenyl}-acrylamide

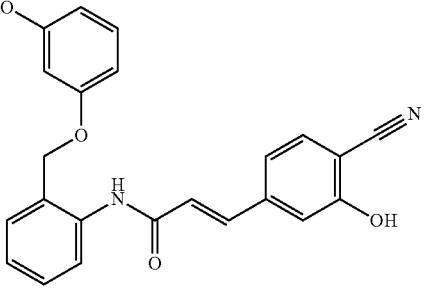

(Deacetylation carried out in MeOH. Final purification by liquid chromatography)
(ES+) [M+H]+: 470.

105

(193) (E)-3-(4-Cyano-3-hydroxy-phenyl)-N-{2-[4-(1-methyl-piperidin-4-yloxy)-phenoxymethyl]-phenyl}-acrylamide

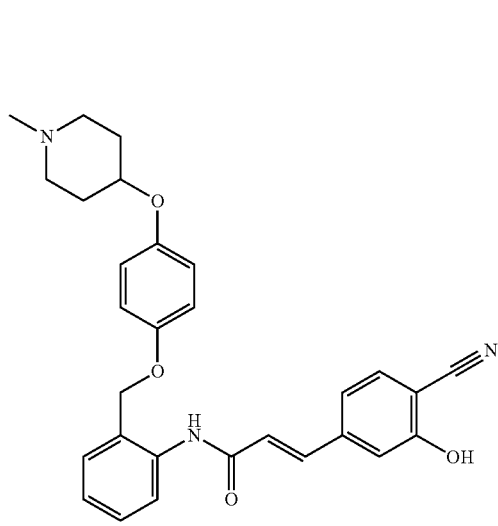 [SMILES: CN1CCC(Oc2ccc(OCc3ccccc3NC(=O)/C=C/c3ccc(C#N)c(O)c3)cc2)CC1]

(Deacetylation carried out in MeOH. Final purification by liquid chromatography)

(ES+) [M+H]+: 484.

(194) (E)-N-(3-Benzyl-3H-benzoimidazol-4-yl)-3-(3-hydroxy-4-methoxy-phenyl)-acrylamide

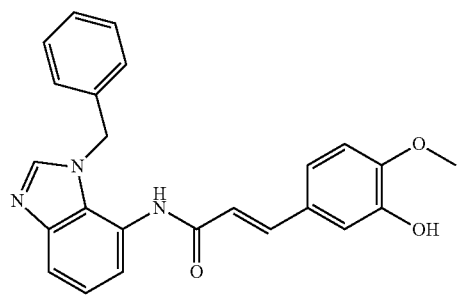 [SMILES: COc1ccc(/C=C/C(=O)Nc2cccc3ncn(Cc4ccccc4)c23)cc1O]

(Deacetylation carried out in MeOH. Final purification by trituration with acetonitrile)

$^1$H NMR (DMSO-d6) δ (ppm): 10.28 (bs, 1H), 9.36 (s, 1H), 7.73 (d, J=7.92 Hz, 1H), 7.49 (t, J=7.92 Hz, 1H), 7.20-7.43 (m, 5H), 7.03-7.18 (m, 4H), 7.00 (t, J=8.36 Hz, 1H), 6.63 (d, J=15.26 Hz, 1H), 5.79 (s, 2H), 3.83 (s, 3H).

LC-MS: Method_N—254, rt=1.46

(ES+) [M+H]+: 400.

106

(195) (E)-N-[2-(4-Chloro-phenoxymethyl)-phenyl]-3-(3-hydroxy-4-methoxy-phenyl)-acrylamide

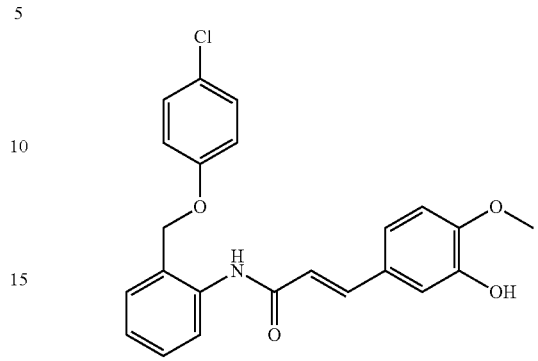

(Deacetylation carried out in MeOH. Final purification by column chromatography)

$^1$H NMR (DMSO-d6) δ (ppm): 9.59 (s, 1H), 9.17 (bs, 1H), 7.61 (d, J=7.34 Hz, 1H), 7.48 (dd, J=7.63, 1.47 Hz, 1H), 7.45 (d, J=15.55 Hz, 1H), 7.28-7.39 (m, 3H), 7.22 (td, J=7.63, 1.17 Hz, 1H), 6.88-7.14 (m, 5H), 6.68 (d, J=15.85 Hz, 1H), 5.14 (s, 2H), 3.82 (s, 3H).

LC-MS: Method_N3, rt=3.99

(ES+) [M+H]+: 410.

Example 11

Preparation of substituted (E)-3-(3-acetoxy-phenyl)-acrylic anilides from the corresponding (E)-3-(3-acetoxy-phenyl)-acrylic acids

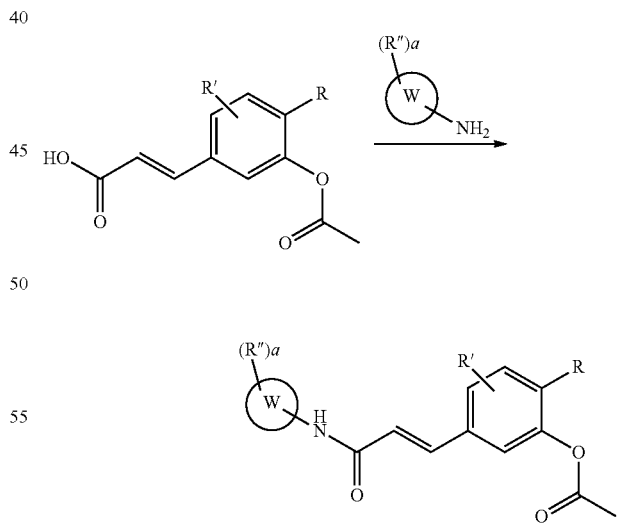

According to the procedure described in Example 7, the following compounds were prepared by coupling the suitable acrylic acid with the suitable aniline and performing the adequate chromatographic purification when needed:

(196) (E)-3-(3-Acetoxy-4-methoxy-phenyl)-N-[3-(pyridin-2-ylmethoxy)-phenyl]-acrylamide

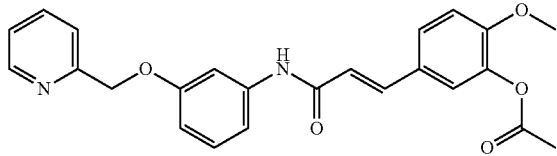 [SMILES: COc1ccc(/C=C/C(=O)Nc2cccc(OCc3ccccn3)c2)cc1OC(C)=O]

¹H NMR (DMSO-d6) δ (ppm): 10.27 (s, 1H), 10.12 (s, 1H), 8.61-8.59 (m, 2H), 7.89-7.83 (m, 2H), 7.63-7.44 (m, 8H), 7.37-7.35 (m, 5H), 7.25-7.20 (m, 4H), 7.08 (d, J=8.4 Hz, H), 6.84-6.65 (m, 4H), 5.24 (s, 2H), 5.17 (s, 2H), 3.85 (s, 3H), 3.83 (s, 3H), 2.29 (s, 6H).

LC-MS: Method_A—220, rt=1.55

(ES+) [M+H]+: 419.

(197) (E)-N-(5-Chloro-2-phenoxymethyl-phenyl)-3-(3-acetoxy-4-methoxy-phenyl)-acrylamide

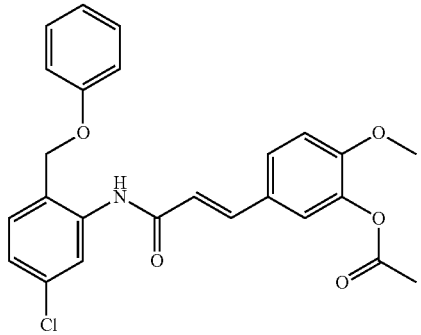 [SMILES: COc1ccc(/C=C/C(=O)Nc2cc(Cl)ccc2COc2ccccc2)cc1OC(C)=O]

¹H NMR (DMSO-d6) δ (ppm): 9.61 (s, 1H), 7.87 (d, J=2.05 Hz, 1N), 7.59-7.49 (m, 3H), 7.40 (d, J=2.35 Hz, 1H), 7.35-7.24 (m, 3H), 7.20 (d, J=8.80 Hz, 1H), 7.07-6.90 (m, 3H), 6.82 (d, J=15.55 Hz, 1H), 5.16 (s, 2H), 3.83 (s, 3H), 2.28 (s, 3H).

(ES+) [M+H]+: 452.

(198) (E)-3-(3-Acetoxy-4-methoxy-phenyl)-N-[4-(4-methyl-piperazin-1-yl)-2-phenoxymethyl-phenyl]-acrylamide hydrochloride

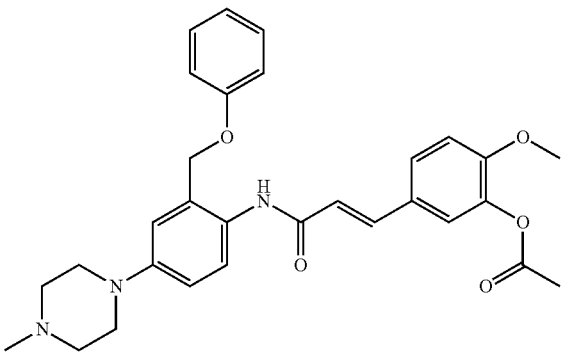 [SMILES: COc1ccc(/C=C/C(=O)Nc2ccc(N3CCN(C)CC3)cc2COc2ccccc2)cc1OC(C)=O]

¹H NMR (DMSO-d6) δ (ppm): 9.40 (s, 1H), 7.54-7.44 (m, 2H), 7.42-7.34 (m, 2H), 7.32-7.22 (m, 2H), 7.18 (d, J=8.80 Hz, 1H), 7.05 (d, J=2.64 Hz, 1H), 7.02-6.84 (m, 4H), 6.74 (d, J=16.14 Hz, 1H), 5.04 (s, 2H), 3.82 (s, 3H), 3.20-3.02 (m, 4H), 2.47-2.35 (m, 4H), 2.28 (s, 3H), 2.22 (s, 3H).

(ES+) [M+H]+: 516.

(199) (E)-3-(3-Acetoxy-4-methoxy-phenyl)-N-[2-(3-trifluoromethyl-phenoxymethyl)-phenyl]-acrylamide

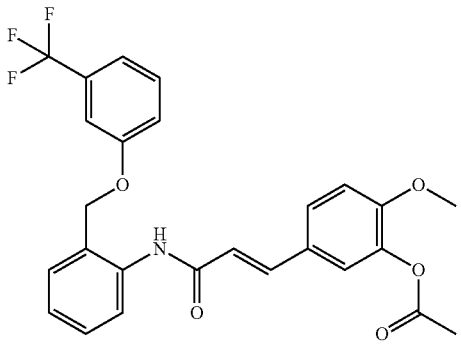 [SMILES: COc1ccc(/C=C/C(=O)Nc2ccccc2COc2cccc(C(F)(F)F)c2)cc1OC(C)=O]

¹H NMR (DMSO-d6) δ (ppm): 9.58 (s, 1H), 7.67 (d, J=7.34 Hz, 1H), 7.60-7.45 (m, 4H), 7.42-7.27 (m, 5H), 7.23 (td, J=7.63 Hz, J=1.17 Hz, 1H), 7.19 (d, J=8.51 Hz, 1H), 6.79 (d, J=15.85 Hz, 1H), 5.24 (s, 2H), 3.83 (s, 3H), 2.28 (s, 3H).

(ES+) [M+H]+: 486.

(200) (E)-3-(3-Acetoxy-4-phenyl)-N-[2-(3-chloro-phenoxymethyl)-phenyl]-acrylamide

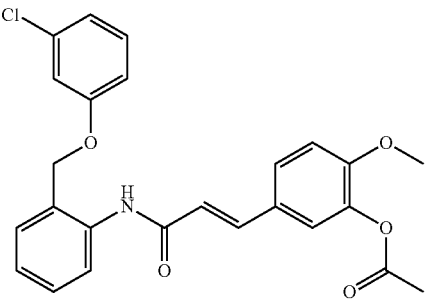 [SMILES: COc1ccc(/C=C/C(=O)Nc2ccccc2COc2cccc(Cl)c2)cc1OC(C)=O]

¹H NMR (DMSO-d6) δ (ppm): 9.56 (s, 1H), 7.66 (d, J=7.34 Hz, 1H), 7.53 (d, J=15.85 Hz, 1H), 7.54-7.45 (m, 2H), 7.41-7.35 (m, 2H), 7.31 (t, J=8.07 Hz, 1H), 7.22 (td, J=7.34 Hz, J=1.17 Hz, 1H), 7.20 (d, J=8.51 Hz, 1H), 7.09 (d, J=8.51 Hz, 1H), 7.05-6.91 (m, 2H), 6.79 (d, J=15.55 Hz, 1H), 5.17 (s, 2H), 3.83 (s, 3H), 2.28 (s, 3H).

(ES+) [M+H]+: 452.

(201) (E)-3-(3-Acetoxy-4-methoxy-phenyl)-N-[2-(4-morpholin-4-ylmethyl-phenoxymethyl)-phenyl]-acrylamide

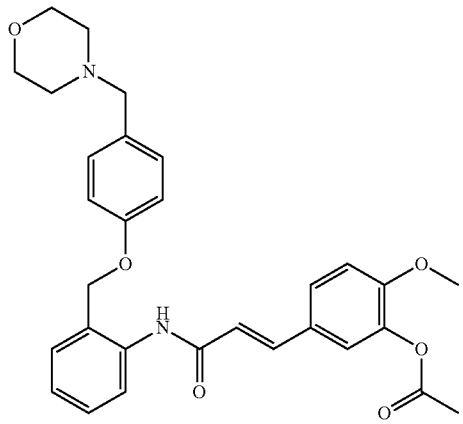 [SMILES: COc1ccc(/C=C/C(=O)Nc2ccccc2COc2ccc(CN3CCOCC3)cc2)cc1OC(C)=O]

¹H NMR (DMSO-d6) δ (ppm): 9.57 (s, 1H) 7.63 (dd, J=8.07 Hz, J=1.03 Hz, 1H) 7.58-7.44 (m, 3H) 7.38 (d, J=2.05 Hz, 1H) 7.34 (td, J=7.70 Hz, J=1.61 Hz, 1H) 7.26-7.13 (m, 4H) 6.94 (m, 2H) 6.79 (d, J=15.85 Hz, 1H) 5.12 (s, 2H) 3.83 (s, 3H) 3.59-3.48 (m, 4H) 3.37 (s, 2H) 2.33-2.28 (m, 4H) 2.28 (s, 3H).

(ES+) [M+H]+: 517.

(202) 4-(4-{2-[(E)-3-(3-Acetoxy-4-methoxy-phenyl)-acryloylamino]-benzyloxy}-phenoxy)-piperidine-1-carboxylic acid tert-butyl ester

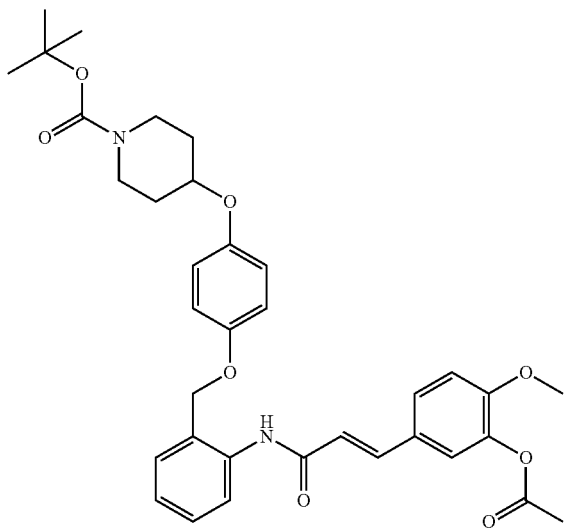 [SMILES: COc1ccc(/C=C/C(=O)Nc2ccccc2COc2ccc(OC3CCN(C(=O)OC(C)(C)C)CC3)cc2)cc1OC(C)=O]

¹H NMR (DMSO-d6) δ (ppm): 9.54 (s, 1H), 7.64 (d, J=8.22 Hz, 1H), 7.52 (d, J=15.26 Hz, 1H), 7.54-7.46 (m, 2H), 7.39 (d, J=1.76 Hz, 1H), 7.34 (td, J=7.63 Hz, J=1.47 Hz, 1H), 7.25-7.18 (m, 1H), 7.20 (d, J=8.51 Hz, 1H), 6.97-6.85 (m, 4H), 6.79 (d, J=15.85 Hz, 1H), 5.07 (s, 2H), 4.44-4.34 (m, 1H), 3.83 (s, 3H), 3.70-3.55 (m, 2H), 3.19-3.09 (m, 2H), 2.28 (s, 3H), 1.98-1.74 (m, 2H), 1.55-1.45 (m, 2H), 1.40 (s, 9H).

(ES+) [M+H]+: 617.

(203) (E)-3-(4-Fluoro-3-acetoxy-phenyl)-N-{2-[4-(1-methyl-piperidin-4-yloxy)-phenoxymethyl]-phenyl}-acrylamide

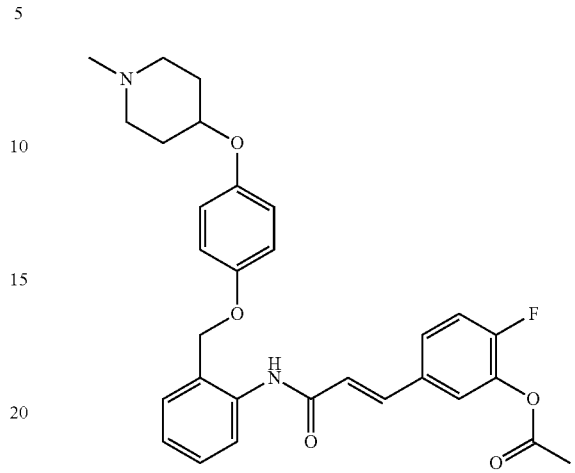

¹H NMR (DMSO-d6) δ (ppm): 9.64 (s, 1H), 7.65-7.40 (m, 5H), 7.35 (td, J=7.70 Hz, J=1.61 Hz, 1H), 7.29-7.19 (m, 1H), 7.04-6.76 (m, 5H), 6.63 (bs, 1H), 5.07 (s, 2H), 4.28-4.14 (m, 1H), 2.83-2.60 (m, 2H), 2.36 (s, 3H), 2.33-2.14 (m, 2H), 2.26 (bs, 3H), 1.98-1.80 (m, 2H), 1.72-1.48 (m, 2H).

(ES+) [M+H]+: 519.

(204) (E)-3-(3-Acetoxy-4-methoxy-phenyl)-N-[2-(2-trifluoromethyl-phenoxymethyl)-phenyl]-acrylamide

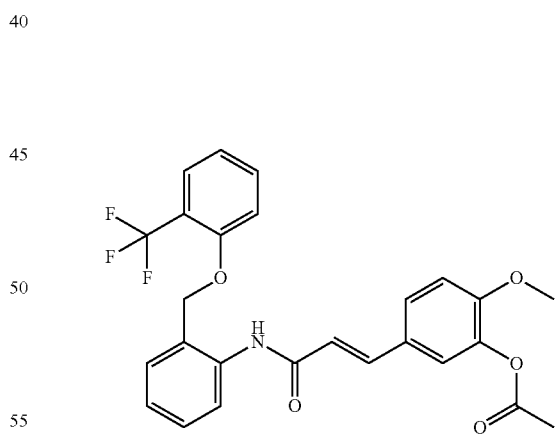

¹H NMR (DMSO-d6) δ (ppm): 9.60 (s, 1H), 7.75-7.46 (m, 6H), 7.41-7.32 (m, 2H), 7.32-7.24 (m, 2H), 7.21 (d, J=8.80 Hz, 1H), 7.15-7.08 (m, 1H), 6.78 (d, J=15.85 Hz, 1H), 5.29 (s, 2H), 3.83 (s, 3H), 2.29 (s, 3H).

(ES+) [M+H]+: 486.

(205) (E)-3-(3-Acetoxy-4-methoxy-phenyl)-N-{2-[4-(1-methyl-piperidin-4-yloxy)-phenoxymethyl]-phenyl}-acrylamide

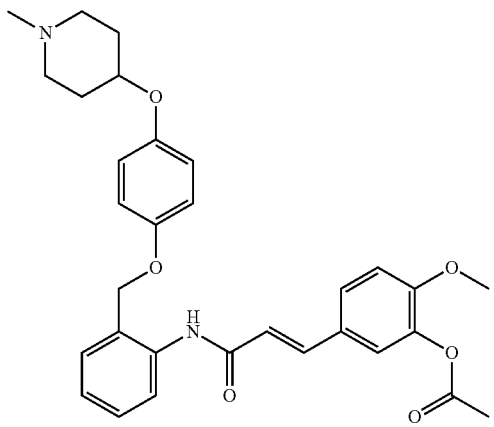

¹H NMR (DMSO-d6) δ (ppm 9.53 (s, 1H), 7.64 (d, J=7.63 Hz, 1H), 7.59-7.43 (m, 3H), 7.43-7.27 (m, 2H), 7.27-7.09 (m, 2H), 6.96-6.84 (m, 4H), 6.79 (d, J=15.85 Hz, 1H), 5.07 (s, 2H), 4.22-4.12 (m, 1H), 3.83 (s, 3H), 2.69-2.55 (m, 2H), 2.28 (s, 3H), 2.15 (s, 3H), 2.14-2.03 (m, 2H), 2.00-1.77 (m, 2H), 1.71-1.48 (m, 2H).

(ES+) [M+H]+: 531.

(206) 4-(3-{2-[(E)-3-(3-Acetoxy-4-methoxy-phenyl)-acryloylamino]-benzyloxy}-phenoxy)-piperidine-1-carboxylic acid tert-butyl ester

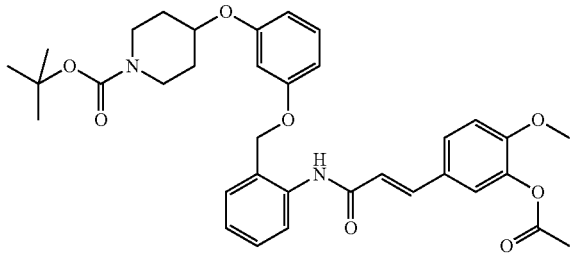 [SMILES: COc1ccc(/C=C/C(=O)Nc2ccccc2COc2cccc(OC3CCN(C(=O)OC(C)(C)C)CC3)c2)cc1OC(C)=O]

¹H NMR (DMSO-d6) δ (ppm): 9.55 (s, 1H), 7.65 (dd, J=8.07 Hz, J=0.73 Hz, 1H), 7.52 (d, J=15.85 Hz, 1H), 7.53-7.45 (m, 2H), 7.38 (d, J=2.05 Hz, 1H), 7.34 (td, J=7.63 Hz, J=1.76 Hz, 1H), 7.26-7.10 (m, 3H), 6.79 (d, J=15.55 Hz, 1H), 6.65-6.48 (m, 3H), 5.12 (s, 2H), 4.55-4.43 (m, 1H), 3.83 (s, 3H), 3.74-3.49 (m, 2H), 3.120-3.06 (m, 2H), 2.28 (s, 3H), 1.96-1.73 (m, 2H), 1.54-1.43 (m, 2H), 1.40 (s, 9H).

(ES+) [M+H]+: 617.

(207) 4-(3-{2-[(E)-3-(3-Acetoxy-4-chloro-phenyl)-acryloylamino]-benzyloxy}-phenoxy)-piperidine-1-carboxylic acid tert-butyl ester

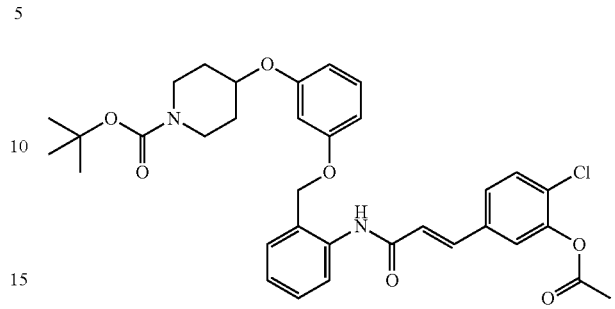

¹H NMR (DMSO-d6) δ (ppm): 0.68 (s, 1H), 7.71-7.52 (m, 5H), 7.49 (dd, J=7.63 Hz, J=1.47 Hz, 1H), 7.35 (td, J=7.70 Hz, J=1.61 Hz, 1H), 7.23 (td, J=7.34 Hz, J=1.17 Hz, 1H), 7.19-7.13 (m, 1H), 6.95 (d, J=15.85 Hz, 1H), 6.62-6.50 (m, 3H), 5.12 (s, 2H), 4.57-4.42 (m, 1H), 3.73-3.56 (m, 2H), 3.21-3.06 (m, 2H), 2.36 (s, 3H), 1.93-1.75 (m, 2H), 1.57-1.42 (m, 2H), 1.40 (s, 9H).

(ES+) [M+H]+: 621.

(208) (E)-3-(3-Acetoxy-4-methoxy-phenyl)-N-{2-[4-(1-methyl-piperidin-4-yl)-phenoxymethyl]-phenyl}-acrylamide

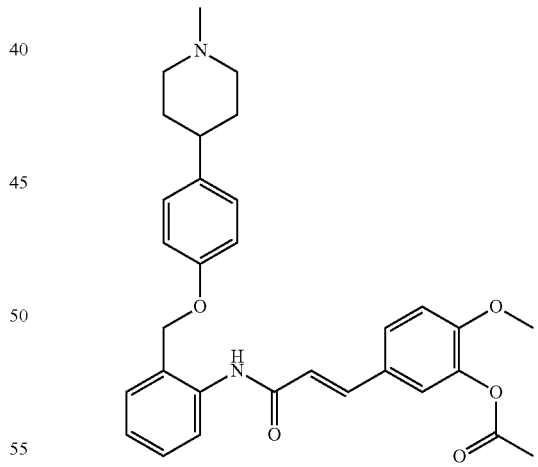

¹H NMR (DMSO-d6) δ (ppm): 9.56 (s, 1H), 7.64 (d, J=7.34 Hz, 1H), 7.52 (d J=15.85, 1H), 7.54-7.45 (m, 2H), 7.39 (d, J=2.05 Hz, 1H), 7.34 (td, J=7.63, 1.76 Hz, 1H), 7.20 (d, J=8.51 Hz, 1H), 7.26-7.17 (m, 2H), 6.99-6.86 (m, 2H), 6.79 (d, J=15.55 Hz, 1H), 5.11 (s, 2H), 3.83 (s, 3H), 2.97-2.78 (m, 2H), 2.46-2.31 (m, 1H), 2.28 (s, 3H), 2.09-1.85 (m, 2H), 1.77-1.47 (m, 4H).

LC-MS: Method_N2, rt=4.57

(ES+) [M+H]+: 515.

(209) (E)-3-(3-Acetoxy-4-methoxy-phenyl)-N-{2-[2-(4-methyl-piperazin-1-yl)-phenoxymethyl]-phenyl}-acrylamide

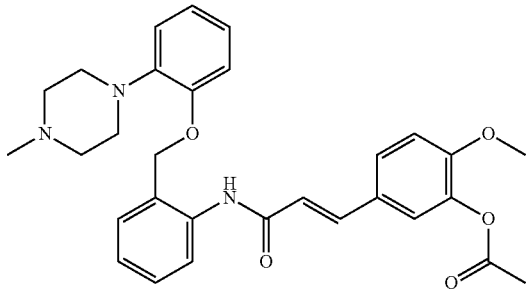

$^1$H NMR (DMSO-d6) δ (ppm): 9.54 (s, 1H), 7.74 (d, J=6.46 Hz, 1H), 7.63-7.45 (m, 3H), 7.43-7.29 (m, 2H), 7.27-7.23 (m, 1H), 7.20 (d, J=8.51 Hz, 1H), 7.08-6.87 (m, 4H), 6.75 (d, J=15.85 Hz, 1H), 5.16 (s, 2H), 3.83 (s, 3H), 3.10-2.89 (m, 4H), 2.47-2.35 (m, 4H), 2.28 (s, 3H), 2.17 (s, 3H).
LC-MS: Method_N5—254, rt=1.28
(ES+) [M+H]+: 516.

(210) (E)-3-(3-Acetoxy-4-methoxy-phenyl)-N-{2-[3-(1-methyl-piperidin-4-yloxy)-phenoxymethyl]-phenyl}-acrylamide

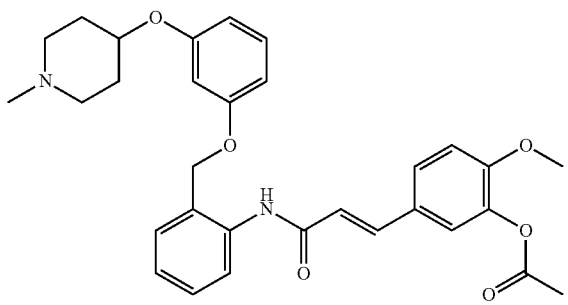

$^1$H NMR (DMSO-d6) δ (ppm): 9.54 (s, 1H), 7.75-7.58 (m, 1H), 7.58-7.28 (m, 4H), 7.28-7.10 (m, 3H), 7.09-6.93 (m, 1H), 6.79 (d, J=15.85 Hz, 1H), 6.60-6.42 (m, 3H), 5.12 (s, 2H), 4.41-4.18 (m, 1H), 3.83 (s, 3H), 2.67-2.56 (m, 2H), 2.28 (s, 3H), 2.15 (s, 3H), 2.14-2.04 (m, 2H), 1.98-1.78 (m, 2H), 1.69-1.40 (m, 2H).
LC-MS: Method_N5—254, rt=1.30
(ES+) [M+H]+: 531.

(211) (E)-3-(4-Chloro-3-acetoxy-phenyl)-N-(3-chloro-phenyl)-acrylamide

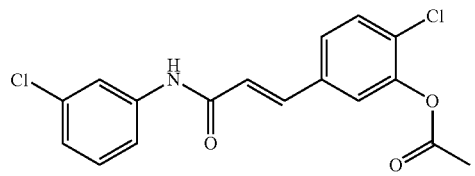 [SMILES: CC(=O)Oc1cc(/C=C/C(=O)Nc2cccc(Cl)c2)ccc1Cl]

$^1$H NMR (DMSO-d6) δ (ppm): 7.73 (t, J=1.76 Hz, 1H), 7.67 (d, J=15.55 Hz, 1H), 7.79-7.42 (m, 3H), 7.39-7.24 (m, 2H), 7.13 (ddd, J=7.92 Hz, J=1.76 Hz, J=0.88 Hz, 1H), 6.48 (d, J=15.55 Hz, 1H), 2.40 (s, 3H).
LC-MS: Method_N2, rt=5.81
(ES+) [M+H]+: 350.

(212) (E)-3-(3-Acetoxy-4-methoxy-phenyl)-N-{2-[3-(4-methyl-imidazol-1-yl)-phenoxymethyl]-phenyl}-acrylamide

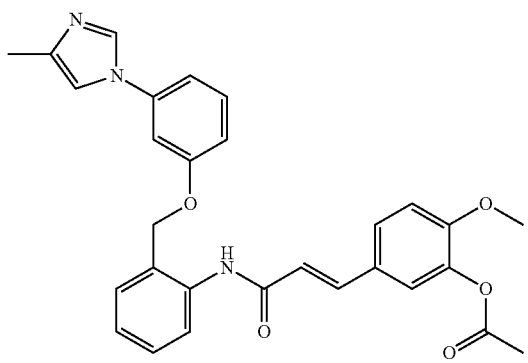

$^1$H NMR (DMSO-d6) δ (ppm): 9.58 (s, 1H), 8.11 (d, J=1.17 Hz, 1H), 7.41 (d, J=1.17 Hz, 1H), 7.40-7.32 (m, 2H), 7.26 (t, J=2.35 Hz, 1H), 7.61-7.13 (m, 9H), 6.95 (ddd, J=8.36 Hz, J=2.35 Hz, J=0.73 Hz, 1H), 5.22 (s, 2H), 3.82 (s, 3H), 2.28 (s, 3H), 2.15 (d, J=0.88 Hz, 3H).
LC-MS: Method_N1, rt=1.97
(ES+) [M+H]+: 498.

(213) (E)-3-(2-Chloro-3-acetoxy-4-methoxy-phenyl)-N-(3-chloro-phenyl)-acrylamide

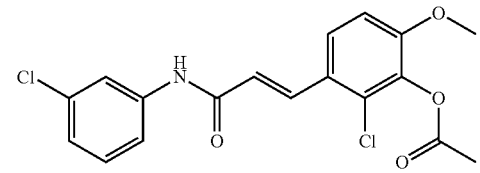 [SMILES: COc1ccc(/C=C/C(=O)Nc2cccc(Cl)c2)c(Cl)c1OC(C)=O]

$^1$H NMR (DMSO-d6) δ (ppm): 10.42 (s, 1H), 7.93 (t, J=1.91 Hz, 1H), 7.81 (d, J=15.85 Hz, 1H), 7.71 (d, J=8.80 Hz, 1H), 7.54 (ddd, J=8.22, J=2.05, J=1.17 Hz, 1H), 7.37 (t, J=7.92 Hz, 1H), 7.28 (d, J=8.80 Hz, 1H), 7.14 (ddd, J=7.92, J=2.05, J=0.88 Hz, 1H), 6.81 (d, J=15.55 Hz, 1H), 3.88 (s, 3H), 2.36 (s, 3H).
LC-MS: Method_N2, rt=5.81
(ES+) [M+H]+: 380.

(214) (E)-3-(4-Fluoro-3-acetoxy-phenyl)-N-[3-(pyridin-4-ylmethylsulfanyl)-phenyl]-acrylamide

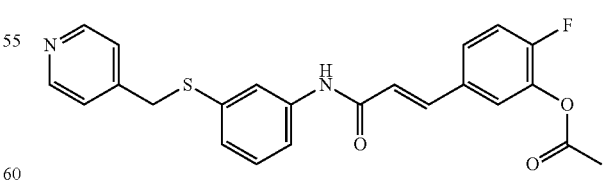

$^1$H NMR (DMSO-d6) δ (ppm): 10.20 (s, 1H), 8.33-8.61 (m, 2H), 7.77 (t, J=1.76 Hz, 1H), 7.51-7.63 (m, 3H), 7.40-7.51 (m, 2H), 7.32-7.40 (m, 2H), 7.26 (t, J=7.92 Hz, 1H), 7.00-7.08 (m, 1H), 6.75 (d, J=15.55 Hz, 1H), 4.25 (s, 2H), 2.36 (s, 3H).
(ES+) [M+H]+: 423.

(215) (E)-N-(3-Benzyl-3H-benzoimidazol-4-yl)-3-(4-fluoro-3-acetoxy-phenyl)-acrylamide

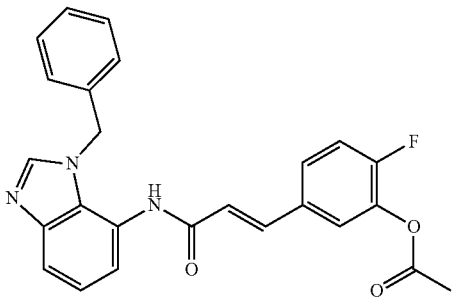 [SMILES: CC(=O)Oc1cc(/C=C/C(=O)Nc2cccc3ncn(Cc4ccccc4)c23)ccc1F]

$^1$H NMR (DMSO-d6) δ (ppm): 9.94 (s, 1H), 8.34 (s, 1H), 7.55-7.71 (m, 3H), 7.36-7.55 (m, 2H), 7.13-7.31 (m, 4H), 7.07 (d, J=7.63 Hz, 1H), 6.92-7.03 (m, 2H), 6.73 (d, J=15.55 Hz, 1H), 5.55 (s, 2H), 2.37 (s, 3H).

(ES+) [M+H]+: 430.

(216) (E)-3-(3-acetoxy-4-methoxy-phenyl)-N-[2-(4-trifluoromethyl-phenoxymethyl)-phenyl]-acrylamide

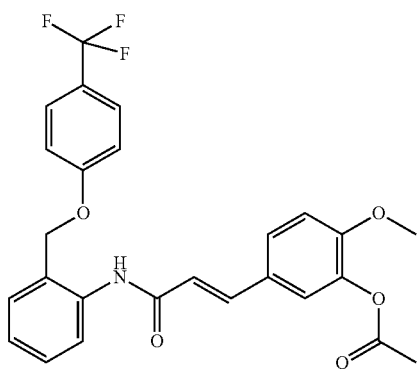 [SMILES: COc1ccc(/C=C/C(=O)Nc2ccccc2COc2ccc(C(F)(F)F)cc2)cc1OC(C)=O]

$^1$H NMR (DMSO-d6) δ (ppm): 9.61 (s, 1H), 7.60-7.76 (m, 3H), 7.44-7.59 (m, 3H), 7.31-7.43 (m, 2H), 7.07-7.30 (m, 4H), 6.79 (d, J=15.55 Hz, 1H), 5.24 (s, 2H), 3.83 (s, 3H), 2.28 (s, 3H).

(ES+) [M+H]+: 486.

(217) (E)-N-[2-(2-Chloro-phenoxymethyl)-phenyl]-3-(3-acetoxy-4-methoxy-phenyl)-acrylamide

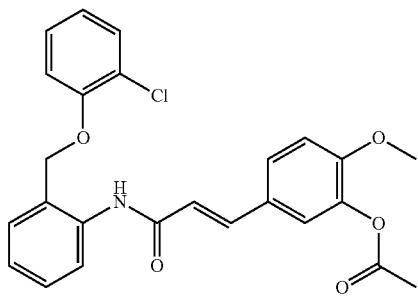 [SMILES: COc1ccc(/C=C/C(=O)Nc2ccccc2COc2ccccc2Cl)cc1OC(C)=O]

$^1$H NMR (DMSO-d6) δ (ppm): 9.60 (s, 1H), 7.64-7.72 (m, 1H), 7.47-7.58 (m, 3H), 7.44 (dd, J=7.78, 1.61 Hz, 1H), 7.14-7.41 (m, 6H), 6.97 (td, J=7.56, 1.61 Hz, 1H), 6.79 (d, J=15.55 Hz, 1H), 5.25 (s, 2H), 3.83 (s, 3H), 2.29 (s, 3H).

(ES+) [M+H]+: 452.

(218) (E)-3-(3-Acetoxy-4-methoxy-phenyl)-N-[1-(4-imidazol-1-yl-benzyl)-1H-indol-7-yl]-acrylamide

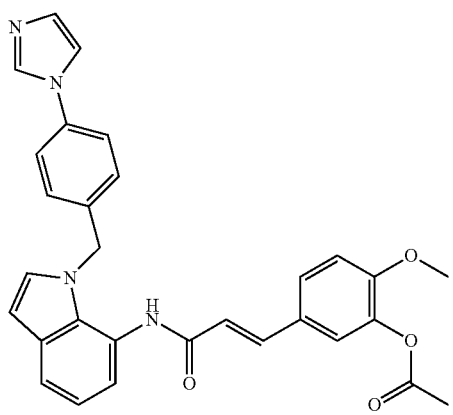 [SMILES: COc1ccc(/C=C/C(=O)Nc2cccc3ccn(Cc4ccc(-n5ccnc5)cc4)c23)cc1OC(C)=O]

$^1$H NMR (DMSO-d6) δ (ppm):): 9.44 (s, 1H), 8.00 (t, J=1.17 Hz, 1H), 7.51 (dd, J=7.78, 1.32 Hz, 1H), 7.48 (t, J=1.32 Hz, 1H), 7.34-7.45 (m, 5H), 7.23-7.30 (m, 1H), 7.16 (d, J=8.51 Hz, 1H), 7.08 (m, 2H), 7.05 (dd, J=1.17 Hz, 1H), 7.03 (d, J=7.63 Hz, 1H), 6.95-7.00 (m, 1H), 6.57 (d, J=3.23 Hz, 1H), 6.58 (d, J=15.55 Hz, 1H), 5.56 (s, 2H), 3.84 (s, 3H), 2.28 (s, 3H).

(ES+) [M+H]+: 507.

(219) (E)-3-(4-Fluoro-3-acetoxy-phenyl)-N-[1-(4-imidazol-1-yl-benzyl)-1H-indol-7-yl]-acrylamide

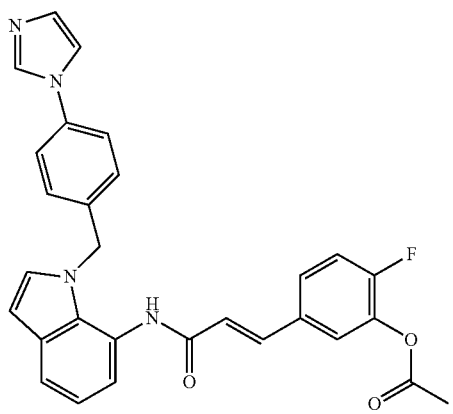 [SMILES: CC(=O)Oc1cc(/C=C/C(=O)Nc2cccc3ccn(Cc4ccc(-n5ccnc5)cc4)c23)ccc1F]

$^1$H NMR (DMSO-d6) δ (ppm):): 9.86 (s, 1H), 8.10 (s, 1H), 7.36-7.64 (m, 9H), 6.86-7.11 (m, 5H), 6.75 (d, J=15.85 Hz, 1H), 6.58 (d, J=3.23 Hz, 1H), 5.52 (s, 2H), 2.37 (s, 3H).

(ES+) [M+H]+: 495.

(220) (E)-3-(3-acetoxy-4-methoxy-phenyl)-N-{2-[4-(1-methyl-piperidin-4-ylmethyl)-phenoxymethyl]-phenyl}-acrylamide

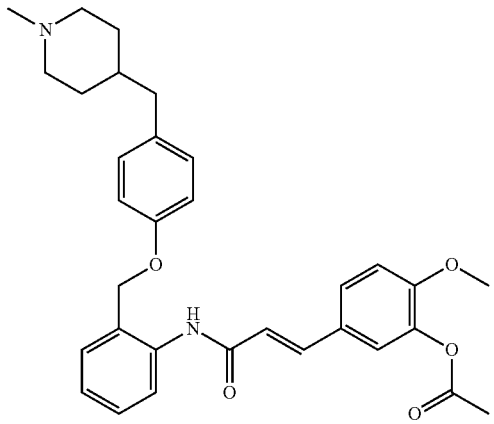

¹H NMR (DMSO-d6) δ (ppm): 9.56 (s, 1H), 7.63 (d, J=7.04 Hz, 1H), 7.44-7.58 (m, 3H), 7.38 (d, J=2.05 Hz, 1H), 7.34 (td, J=7.63, 1.76 Hz, 1H), 7.15-7.27 (m, 2H), 6.99-7.12 (m, 2H), 6.85-6.97 (m, 2H), 6.79 (d, J=15.55 Hz, 1H), 5.10 (s, 2H), 3.83 (s, 3H), 2.68-2.86 (m, 2H), 2.41 (d, J=7.04 Hz, 2H), 2.28 (s, 3H), 2.17 (s, 3H), 1.71-2.02 (m, 2H), 1.29-1.60 (m, 3H), 0.99-1.29 (m, 2H).

(ES+) [M+H]+: 529.

(221) (E)-3-(3-acetoxy-4-methoxy-phenyl)-N-{2-[3-(4-methyl-piperazin-1-yl)-phenoxymethyl]-phenyl}-acrylamide

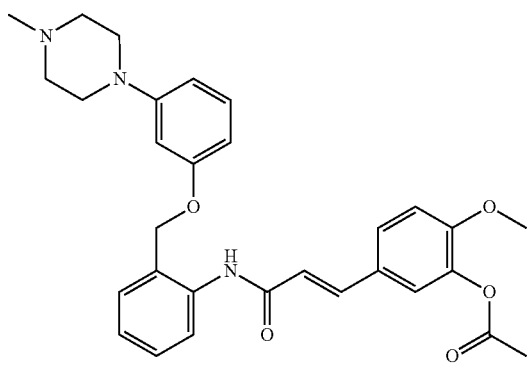

¹H NMR (DMSO-d6) δ (ppm): 9.54 (s, 1H), 7.65 (d, J=7.04 Hz, 1H), 7.46-7.57 (m, 3H), 7.38 (d, J=2.05 Hz, 1H), 7.34 (td, J=7.70, 1.61 Hz, 1H), 7.15-7.27 (m, 2H), 7.00-7.15 (m, 1H), 6.79 (d, J=15.55 Hz, 1H), 6.47-6.60 (m, 2H), 6.42 (dd, J=7.78, 1.91 Hz, 1H), 5.11 (s, 2H), 3.83 (s, 3H), 2.99-3.19 (m, 4H), 2.38-2.48 (m, 4H), 2.28 (s, 3H), 2.24 (s, 3H).

(ES+) [M+H]+: 516.

(222) (E)-3-(3-Acetoxy-4-methoxy-phenyl)-N-{2-[4-(4-methyl-imidazol-1-yl)-phenoxymethyl]-phenyl}-acrylamide

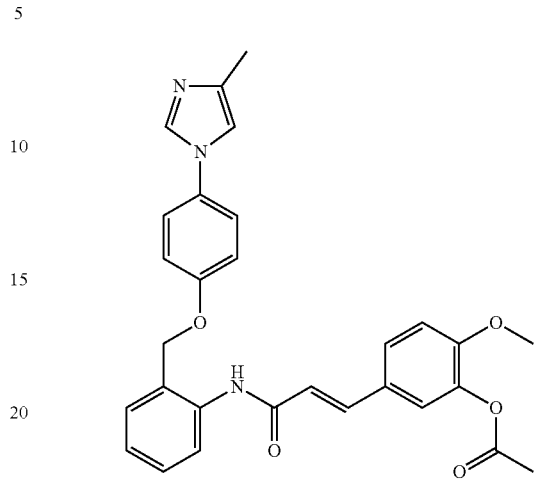

¹H NMR (DMSO-d6) δ (ppm): 9.59 (s, 1H), 7.95 (d, J=1.47 Hz, 1H), 7.65 (d, J=7.34 Hz, 1H), 7.43-7.59 (m, 5H), 7.39 (d, J=2.05 Hz, 1H), 7.34 (dd, J=7.92, 1.47 Hz, 1H), 7.29 (t, J=1.17 Hz, 1H), 7.24 (dd, J=7.34, 1.17 Hz, 1H), 7.19 (d, J=8.80 Hz, 1H), 7.00-7.14 (m, 2H), 6.80 (d, J=15.55 Hz, 1H), 5.19 (s, 2H), 3.83 (s, 3H), 2.28 (s, 3H), 2.15 (s, 3H).

(ES+) [M+H]+: 498.

(223) (E)-N-(1-Benzyl-2-oxo-2,3-dihydro-1H-indo-7-yl)-3-(3-acetoxy-4-methoxy-phenyl)-acrylamide

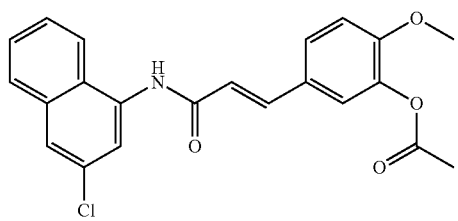 [SMILES: COc1ccc(/C=C/C(=O)Nc2cc(Cl)cc3ccccc23)cc1OC(C)=O]

¹H NMR (DMSO-d6) δ (ppm): 9.51 (s, 1H), 7.41-7.59 (m, 1H), 7.26-7.41 (m, 2H), 7.10-7.26 (m, 5H), 6.86-7.10 (m, 4H), 6.50 (d, J=15.85 Hz, 1H), 5.02 (s, 2H), 3.83 (s, 3H), 3.77 (s, 2H), 2.29 (s, 3H).

(ES+) [M+H]+: 457.

(224) (E)-N-(3-Chloro-naphthalen-1-yl)-3-(3-acetoxy-4-methoxy-phenyl)-acrylamide ¹H NMR (DMSO-d6) δ (ppm): 10.13 (s, 1H), 8.19-8.36 (m, 1H), 8.13 (d, J=2.35 Hz, 1H), 7.90-8.01 (m, 1H), 7.88 (d, J=2.05 Hz, 1H), 7.51-7.72 (m, 4H), 7.43 (d, J=2.05 Hz, 1H), 7.24 (d, J=8.51 Hz, 1H), 7.07 (d, J=15.85 Hz, 1H), 3.85 (s, 3H), 2.30 (s, 3H).

(ES+) [M+H]+: 396.

(225) (E)-3-(3-Acetoxy-4-methoxy-phenyl)-N-[2-(2-methyl-2H-pyrazol-3-yloxymethyl)-phenyl]-acrylamide

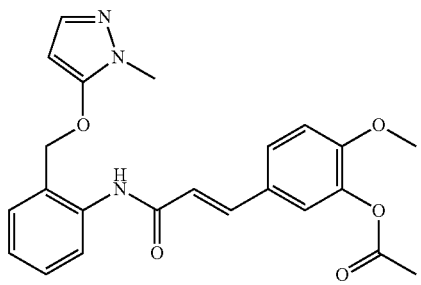 [SMILES: COc1ccc(/C=C/C(=O)Nc2ccccc2COc2ccnn2C)cc1OC(C)=O]

¹H NMR (DMSO-d6) δ (ppm): 9.64 (s, 1H), 7.61 (dd, J=8.07, 1.03 Hz, 1H), 7.48-7.55 (m, 2H), 7.53 (d, J=15.55 Hz, 1H), 7.39 (d, J=2.05 Hz, 1H), 7.38 (td, J=7.92, 1.76 Hz, 1H), 7.25 (dd, J=7.48, 1.32 Hz, 1H), 7.20 (d, J=8.80 Hz, 1H), 7.18 (d, J=2.05 Hz, 1H), 6.80 (d, J=15.55 Hz, 1H), 5.65 (d, J=2.05 Hz, 1H), 5.17 (s, 2H), 3.83 (s, 3H), 3.53 (s, 3H), 2.28 (s, 3H).

(ES+) [M+H]+: 422.

(226) 4-(3-{2-[(E)-3-(3-Acetoxy-4-methoxy-phenyl)-acryloylamino]-benzyloxy}-phenyl)-piperazine-1-carboxylic acid tert-butyl ester

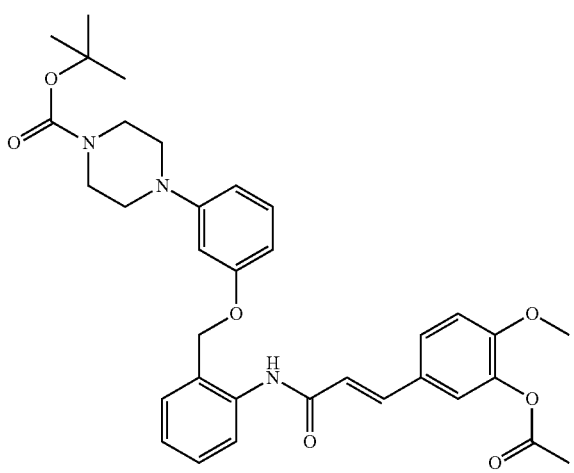 [SMILES: COc1ccc(/C=C/C(=O)Nc2ccccc2COc2cccc(N3CCN(C(=O)OC(C)(C)C)CC3)c2)cc1OC(C)=O]

¹H NMR (DMSO-d6) δ (ppm): 9.55 (s, 1H), 7.65 (d, J=7.63 Hz, 1H), 7.52 (d, J=14.08 Hz, 1H), 7.45-7.54 (m, 2H), 7.38 (d, J=2.05 Hz, 1H), 7.34 (td, J=7.70, 1.61 Hz, 1H), 7.19 (d, J=8.80 Hz, 1H), 7.21 (td, J=7.63, 1.17 Hz, 1H), 7.05-7.15 (m, 1H), 6.79 (d, J=15.55 Hz, 1H), 6.49-6.57 (m, 2H), 6.45 (dd, J=7.78, 2.20 Hz, 1H), 5.11 (s, 2H), 3.83 (s, 3H), 3.35-3.53 (m, 4H), 2.96-3.12 (m, 4H), 2.28 (s, 3H), 1.41 (s, 9H).

(227) (E)-3-(3-Acetoxy-4-methoxy-phenyl)-N-[1-(1-methyl-1H-imidazol-4-ylmethyl)-1H-indol-7-yl]-acrylamide

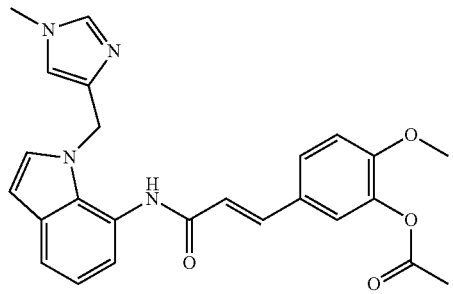 [SMILES: COc1ccc(/C=C/C(=O)Nc2cccc3ccn(Cc4cn(C)cn4)c23)cc1OC(C)=O]

¹H NMR (DMSO-d6) δ (ppm): 11.65 (s, 1H), 7.74 (s, 1H), 7.59 (d, J=15.55 Hz, 1H), 7.51 (dd, J=8.66, 1.32 Hz, 1H), 7.25-7.43 (m, 4H), 7.13-7.22 (m, 2H), 6.98 (t, J=7.63 Hz, 1H), 6.79 (d, J=15.55 Hz, 1H), 6.41 (d, J=2.93 Hz, 1H), 5.33 (s, 2H), 3.82 (s, 3H), 3.63 (s, 3H), 2.28 (s, 3H).

(ES+) [M+H]+: 445.

(228) (E)-3-(3-Acetoxy-4-methoxy-phenyl)-N-[1-(1-methyl-1H-pyrazol-3-ylmethyl)-1H-indol-7-yl]-acrylamide

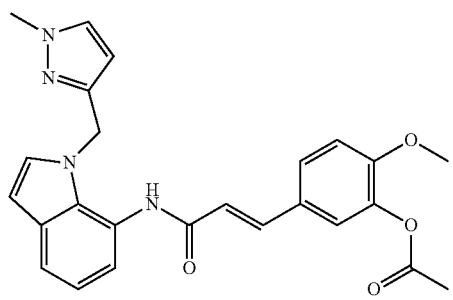 [SMILES: COc1ccc(/C=C/C(=O)Nc2cccc3ccn(Cc4ccn(C)n4)c23)cc1OC(C)=O]

¹H NMR (DMSO-d6) δ (ppm): 10.09 (s, 1H), 7.48-7.62 (m, 3H), 7.38-7.46 (m, 2H), 7.34 (d, J=3.23 Hz, 1H), 7.20 (d, J=8.80 Hz, 1H), 7.11 (d, J=7.34 Hz, 1H), 6.94-7.05 (m, 1H), 6.80 (d, J=15.85 Hz, 1H), 6.45 (d, J=3.23 Hz, 1H), 6.01 (d, J=2.05 Hz, 1H), 5.41 (s, 2H), 3.83 (s, 3H), 3.76 (s, 3H), 2.28 (s, 3H).

(ES+) [M+H]+: 445.

(229) (E)-3-(3-Acetoxy-phenyl)-N-(2-phenoxymethyl-phenyl)-acrylamide

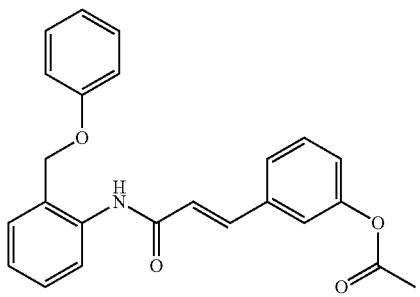 [SMILES: CC(=O)Oc1cccc(/C=C/C(=O)Nc2ccccc2COc2ccccc2)c1]

¹H NMR (DMSO-d6) δ (ppm): 9.41 (bs, 1H) 7.65 (dd, 1H) 7.57 (d, 1H) 7.49-7.54 (m, 1H) 7.43-7.49 (m, 2H) 7.13-7.39 (m, 6H) 6.93-7.05 (m, 3H) 6.89 (d, 1H) 5.17 (s, 2H) 2.29 (s, 3H).

(ES+) [M+H]+: 388.

(230) (E)-N-(3-Chloro-phenyl)-3-(2,4-difluoro-3-acetoxy-phenyl)-acrylamide

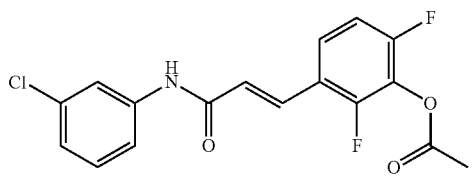 [SMILES: CC(=O)Oc1c(F)ccc(/C=C/C(=O)Nc2cccc(Cl)c2)c1F]

¹H NMR (DMSO-d6) δ (ppm): 10.48 (s, 1H), 7.93 (t, J=2.05 Hz, 1H), 7.71 (td, J=8.58, 6.02 Hz, 1H), 7.60 (d, J=16.14 Hz, 1H), 7.54 (ddd, J=8.22, 2.05, 0.88 Hz, 1H), 7.40 (td, J=9.39, 1.76 Hz, 1H), 7.38 (t, J=7.92 Hz, 1H), 7.15 (ddd, J=7.92, 2.05, 0.88 Hz, 1H), 6.91 (d, J=16.14 Hz, 1H), 2.44 (s, 3H).

(ES+) [M+H]+: 352.

Example 12

(231) (E)-N-(1-Benzyl-1H-indazol-7-yl)-3-(4-fluoro-3-acetoxy-phenyl)-acrylamide

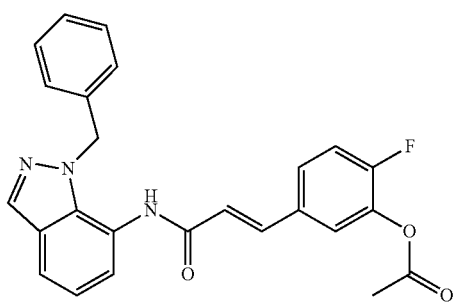 [SMILES: CC(=O)Oc1cc(/C=C/C(=O)Nc2cccc3cnn(Cc4ccccc4)c23)ccc1F]

A mixture of (E)-3-(3-acetoxy-4-fluoro-phenyl)-acrylic acid (119 mg, 0.53 mmol), 1-benzyl-1H-indazol-7-ylamine (118 mg, 0.53 mmol), EDC (123 mg, 0.64 mmol) and HOBT (36 mg, 0.27 mmol) in DMF (3 ml) was stirred at RT for 48 hrs. The mixture was then diluted with water and extracted with AcOEt. The organic layer was dried over sodium sulphate and evaporated to dryness. The crude was purified by column chromatography (petroleum ether:AcOEt from 9:1 to 1:1) to give the title (E)-N-(1-benzyl-1H-indazol-7-yl)-3-(4-fluoro-3-acetoxy-phenyl)-acrylamide (19 mg).

¹H NMR (DMSO-d6) δ (ppm): 10.12 (s, 1H), 8.19 (s, 1H), 7.71 (d, J=7.92 Hz, 1H), 7.33-7.66 (m, 4H), 7.06-7.33 (m, 51H), 6.91-7.06 (m, 2H), 6.83 (d, J=16.14 Hz, 1H), 5.68 (s, 2H), 2.37 (s, 3H).

(ES+) [M+H]+: 430.

Example 13

(232) (E)-N-(3-Chloro-phenyl)-3-(3-methoxy-4-sulfamoyl-phenyl)-acrylamide

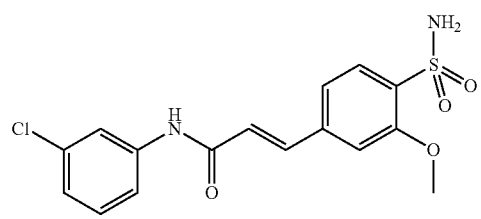 [SMILES: COc1cc(/C=C/C(=O)Nc2cccc(Cl)c2)ccc1S(N)(=O)=O]

A solution of (E)-3-(3-methoxy-4-sulfamoyl-phenyl)-acrylic acid (0.291 g, 1.13 mmol) and thionyl chloride (0.100 mL, 1.36 mmol) in dry THF (15 mL) was stirred at reflux temperature for 1 h. Then a further aliquot of thionyl chloride (0.050 mL, 0.68 mmol) was added and the mixture was stirred at reflux temperature for additional 2 hrs. The mixture was then concentrated under reduced pressure, taken up with dry THF (3 mL) and added dropwise to a solution of 3-chlorophenylamine (0.109 mL, 1.03 mmol) and diisopropylethylamine (0.705 mL, 4.12 mmol) in dry THF (13 mL). After stirring at RT for 16 hrs, the reaction mixture was concentrated under reduced pressure, taken up with DCM and washed with aqueous sodium hydrogencarbonate, and brine. The organic layer was then dried over sodium sulphate and evaporated. The resulting raw material was purified by column chromatography over silica gel (eluant DCM/acetone 9/1) to give 100 mg of the title (E)-N-(3-chloro-phenyl)-3-(3-methoxy-4-sulfamoyl-phenyl)-acrylamide as a white powder.

1H NMR (DMSO-d6) δ (ppm): 10.46 (s, 1H), 7.94 (t, J=2.05 Hz, 1H), 7.78 (d, J=8.22 Hz, 1H), 7.64 (d, J=15.85 Hz, 1H), 7.58-7.51 (m, 1H), 7.46 (d, J=0.88 Hz, 1H), 7.38 (t, J=8.07 Hz, 1H), 7.33 (dd, J=7.92 Hz, J=1.17 Hz, 1H), 7.15 (ddd, J=7.92 Hz, J=2.05 Hz, J=0.88 Hz, 1H), 7.12 (s, 2H), 6.92 (d, J=15.85 Hz, 1H), 3.97 (s, 3H), (ES+) [M+H]+: 367.

Example 14

(233) (E)-N-(3-Chloro-phenyl)-3-(3-hydroxy-4-sulfamoyl-phenyl)-acrylamide

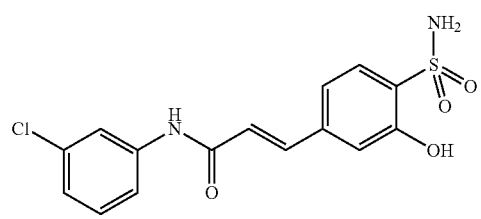 [SMILES: NS(=O)(=O)c1ccc(/C=C/C(=O)Nc2cccc(Cl)c2)cc1O]

BBr₃ (0.680 mL, 0.68 mmol) was added to a suspension of (E)-N-(3-chloro-phenyl)-3-(3-methoxy-4-sulfamoyl-phenyl)-acrylamide (0.045 g, 0.12 mmol) in dry DCM (12 mL) at 0° and under nitrogen atmosphere. The resulting mixture was allowed to reach RT, stirred at reflux temperature for 4 hrs and then poured into ice/water. The aqueous phase was concentrated under reduced pressure and the resulting residue was triturated with water, filtered and dried to give 13 mg of the title (E)-N-(3-chloro-phenyl)-3-(3-hydroxy-4-sulfamoyl-phenyl)-acrylamide as a white solid.

1H NMR (DMSO-d6) δ (ppm): 10.86 (s, 1H), 10.45 (s, 1H), 7.93 (t, J=2.05 Hz, 1H), 7.71 (d, J=8.51 Hz, 1H), 7.60-7.47 (m, 2H), 7.38 (t, J=8.07 Hz, 1H), 7.22-7.10 (m, 3H), 7.01 (s, 2H), 6.80 (d, J=15.55 Hz, 1H).

LC-MS: Method_N2, rt=4.62
(ES+) [M+H]+: 353.

Example 15

(234) Sodium (E)-5-(3-(3-chlorophenylamino)-3-oxoprop-1-enyl)-2-methoxyphenyl phosphate

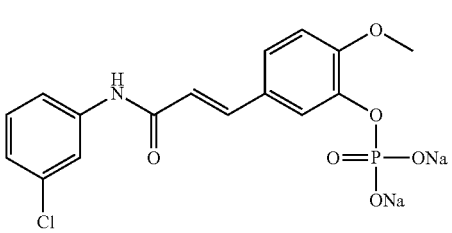

Step A (E)-N-(3-Chloro-phenyl)-3-(3-hydroxy-4-methoxy-phenyl)-acrylamide (compound 55, 1.608 g, 5.31 mmol) was dissolved in dry CH$_3$CN (80 ml) and CCl$_4$ (5.13 ml, 53.1 mmol) and the resulting solution was cooled at 0° C. Dimethyl amino pyridine (65 mg, 0.53 mmol), DIPEA (2.88 ml, 22.3 mmol) and then dibenzyl phosphite (3.52 ml, 15.93 mmol) were added and the mixture was stirred at RT for 1 h. The reaction was quenched with 0.5M KH$_2$PO$_4$ and extracted with AcOEt. The organic layer was dried over sodium sulphate and evaporated to dryness. The crude was purified by column chromatography (eluent DCM/MeOH from 100:1 to 99:1) to give phosphoric acid dibenzyl ester 5-[(E)-2-(3-chloro-phenylcarbamoyl)-vinyl]-2-methoxy-phenyl ester (1.87 g).

1H NMR (DMSO-d$_6$) δ (ppm): 10.34 (s, 1H), 7.93 (t, J=1.91 Hz, 1H), 7.31-7.57 (m, 15H), 7.20 (d, J=9.10 Hz, 1H), 7.12 (ddd, J=7.92, 2.05, 0.88 Hz, 1H), 6.65 (d, J=15.85 Hz, 1H), 5.20 (d, J=8.22 Hz, 4H), 3.84 (s, 3H).

Step B

Trimethylsilylchloride (1.68 ml, 13.3 mmol) was added dropwise to a stirred solution of phosphoric acid dibenzyl ester 5-[(E)-2-(3-chloro-phenylcarbamoyl)-vinyl]-2-methoxy-phenyl ester (1.87 g, 3.32 mmol) and NaI (1.99 g, 13.3 mmol) in dry CH$_3$CN (40 ml). The mixture was stirred for 1 h at RT and then diluted with water and extracted with AcOEt. The organic phase was dried over sodium sulphate and evaporated in vacuo. The crude was triturated with AcOEt and Et$_2$O, filtered and dissolved in EtOH (100 ml). NaOMe (714 mg, 13.3 mmol) was added and the resulting mixture was stirred for 2 hrs at RT. The solvent was evaporated to dryness and the residue was crystallized from water to give the title sodium (E)-5-(3-(3-chlorophenylamino)-3-oxoprop-1-enyl)-2-methoxyphenyl phosphate (1.1 g).

$^1$H NMR (DMSO-d$_6$+TFA) δ (ppm): 10.40 (s, 1H), 7.93 (t, J=1.91 Hz, 1H), 7.64 (m, 1H), 7.46-7.60 (m, 2H), 7.36 (d, J=8.22 Hz, 1H), 7.35 (t, J=7.92 Hz, 1H), 7.04-7.20 (m, 2H), 6.64 (d, J=15.85 Hz, 1H), 3.83 (s, 3H).

LC-MS: Method_N—254, rt=1.66

(ES+) [M+H]+: 384
C,H,N: C, 40.10%; H, 3.77%; N, 2.87%; Cl, 7.52%; P, 6.53%; Na, 9.89% in agreement as C$_{16}$H$_{13}$ClNPO$_6$Na$_2$+ 3H$_2$O.

Example 16

(235) (E)-3-(3-Hydroxy-4-methoxy-phenyl)-N-[1-(3-methyl-3H-imidazol-4-ylmethyl)-1H-indol-7-yl]-acrylamide

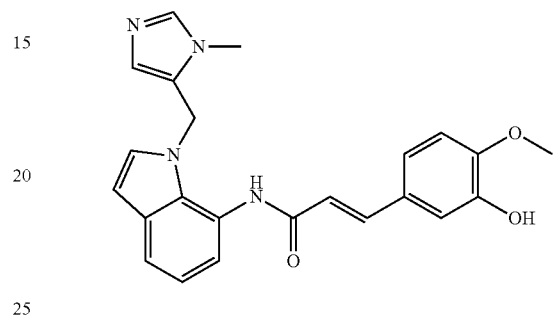

(E)-3-(3-Acetoxy-4-methoxyphenyl)acrylic acid (0.099 g, 0.420 mmol) was suspended in dry THF (8 ml). SOCl$_2$ (0.037 ml, 0.504 mmol) was added and the mixture was stirred at RT for 1 h. The solvent was evaporated to dryness and the residue was dissolved in dry THF (8.00 ml). TEA (0.059 ml, 0.420 mmol) and 1-(3-methyl-3H-imidazol-4-ylmethyl)-1H-indol-7-ylamine (0.095 g, 0.420 mmol) were added. The mixture was stirred at RT for 18 hrs, heated at reflux for 5 hrs and then at RT for 48 hrs. The solvent was removed in vacuo and the residue was partitioned between EtOAc (10 ml) and H$_2$O (2×10 ml). Organic phase was dried over sodium sulphate and concentrated to dryness. The crude was charged onto a SCX cartridge and eluted firstly with MeOH and then with NH$_3$/MeOH. The title (E)-3-(3-hydroxy-4-methoxy-phenyl)-N-[1-(3-methyl-3H-imidazol-4-ylmethyl)-1H-indol-7-yl]-acrylamide (56 mg) was obtained after column chromatography (eluent: DCM 100% to DCM/MeOH 98:2).

$^1$H NMR (DMSO-d$_6$) δ (ppm): 9.97 (s, 1H), 9.20 (s, 1H), 7.81 (s, 1H), 7.49 (d, J=8.22 Hz, 1H), 7.44 (d, J=15.85 Hz, 1H), 7.20 (d, J=2.93 Hz, 1H), 6.91-7.11 (m, 5H), 6.64-6.79 (m, 2H), 6.53 (d, J=2.93 Hz, 1H), 5.50 (s, 2H), 3.82 (s, 3H), 3.48 (s, 3H).

LC-MS: Method_N1, rt=1.67
(ES+) [M+H]+: 403.

Example 17

(236) (E)-N-(3-Chloro-phenyl)-3-(3-hydroxy-4-nitro-phenyl)-acrylamide

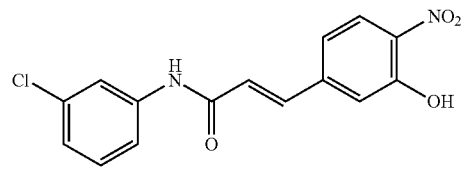 [SMILES: O=C(/C=C/c1ccc([N+](=O)[O-])c(O)c1)Nc1cccc(Cl)c1]

Thionyl chloride (0.83 mL, 6.6 mmol) was added portionwise to a suspension of (E)-3-(3-hydroxy-4-nitro-phenyl)- acrylic acid (1.05 g, 5.0 mmol) in DCM-DMF (20-2 mL). After stirring the resulting solution at RT for 1.5 hrs, 3-chloroaniline (2.12 mL, 20 mmol) was added dropwise and the mixture was stirred at RT for additional 2 hrs. Then the reaction mixture was diluted with DCM and washed with water, aqueous hydrochloric acid, and brine. The organic layer was dried over sodium sulphate and evapored. The resulting raw material was purified first by column chromatography (eluant DCM/MeOH), yielding 1.25 g of the title compound.

$^1$H NMR (CDCl$_3$) δ (ppm): 10.64 (s, 1H), 8.16 (d, J=9.2 Hz, 1H), 7.77 (bs, 1H), 7.73 (d, J=16.0 Hz, 1H), 7.39 (m, 1H), 7.32 (s, 1H), 7.30 (m, 2H), 7.17 (m, 2H), 6.65 (t, J=15.6 Hz, 1H), (ES+) [M+H]+: 319.

Example 18

(237) (E)-N-(3-Chloro-phenyl)-3-(4-amino-3-hydroxy-phenyl)-acrylamide

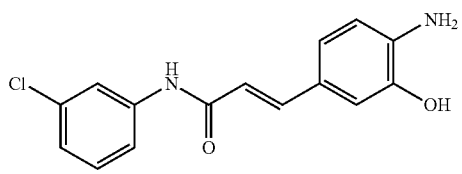 [SMILES: Nc1ccc(/C=C/C(=O)Nc2cccc(Cl)c2)cc1O]

(E)-N-(3-Chloro-phenyl)-3-(3-hydroxy-4-nitro-phenyl)-acrylamide (159 mg, 0.5 mmol) was suspended in EtOH (10 ml); SnCl$_2$ (562 g, 2.5 mmol) was added and the mixture refluxed for 1.5 hrs. After cooling to RT, the solvent was evaporated. The residue was worked up with 5% sodium bicarbonate and 10% sodium potassium tartrate solutions, extracted with AcOEt, which was separated, dried and evaporated. The residue was triturated with a 1:1 diethyl ether-petroleum ether mixture, giving 89 mg of (E)-N-(3-chlorophenyl)-3-(4-amino-3-hydroxy-phenyl)-acrylamide as a yellow solid.

$^1$H NMR (DMSO-d6) δ (ppm): 10.16 (s, 1H), 9.34 (s, 1H), 7.93 (t, J=1.6 Hz, 1H), 7.50 (m, 1H), 7.34 (m, 2H), 7.08 (m, 1H), 6.92 (s, 1H), 6.87 (m, 1H), 6.59 (d, J=8.0 Hz, 1H), 6.38 (t, J=15.6 Hz, 1H), 5.15 (s, 2H).

LC-MS: Method_A—220, rt=1.47
(ES+) [M+H]+: 289.

Example 19

(238) (E)-3-(4-chloro-3-hydroxy-phenyl)-acrylic acid

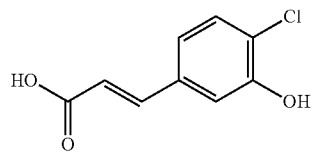 [SMILES: O=C(O)/C=C/c1ccc(Cl)c(O)c1]

Step A
Sodium hydride (60% suspension in mineral oil) (1.44 g, 36 mmol) was added in small portions at 0° C. to a solution of triethyl phosphonoacetate (5.94 ml, 30 mmol) in dry THF (60 ml). 3-hydroxy-4-nitrobenzaldehyde (5.01 g, 30 mmol) was dissolved in THF (50 ml), cooled to 0° C. and sodium hydride (1.44 g, 36 mmol) was added in small portions to it. After 15 min., this solution was added dropwise at 0° C. to the previously described solution and the resulting suspension was stirred at RT for 1.5 hrs. Then it was poured in HCl solution (150 ml, 0.5 N) and extracted with AcOEt. This was dried and evaporated and the crude residue was treated with SnCl$_2$ (25 g, 111 mmol) in AcOEt (200 ml) and refluxed for 2.5 hrs. After cooling to RT, the reaction was worked up with 5% sodium bicarbonate and 10% sodium potassium tartrate solutions, AcOEt was separated, dried and evaporated. The residue was crystallized with diethyl ether and petroleum ether, giving 4.85 g of (E)-3-(4-amino-3-hydroxy-phenyl)-acrylic acid ethyl ester as a brown solid.

Step B
(E)-3-(4-Amino-3-hydroxy-phenyl)-acrylic acid ethyl ester (2.76 g, 13.3 mmol) was suspended in HCl solution (6N, 4 ml), and sodium nitrite solution in water (960 mg, 14 mmol) was added at 0° C. The resulting suspension was added at 0° C. to a solution of copper (I) chloride (2 g, 16 mmol) in concentrated HCl (4 ml). The mixture was slowly warmed to RT and heated to 60° C. for 30 min., shaking occasionally. Then it was cooled to RT, diluted with water and extracted with DCM, which was dried and evaporated. The residue was purified by silica gel column chromatography, eluant petroleum ether/AcOEt 90:10, to give 1.46 g of (E)-3-(4-chloro-3-hydroxy-phenyl)-acrylic acid ethyl ester as a white solid.

Step C
(E)-3-(4-Chloro-3-hydroxy-phenyl)-acrylic acid ethyl ester (1.45 g, 6.4 mmol) was dissolved in a mixture of 6N HCl (8 ml) and acetic acid (8 ml) and heated at 85° C. for 3.5 hrs. Solvents were evaporated, giving 1.23 g of (E)-3-(4-chloro-3-hydroxy-phenyl)-acrylic acid as a light yellow solid.

Example 20

(239) (E)-3-(2-Chloro-3-hydroxy-4-methoxy-phenyl)-acrylic acid

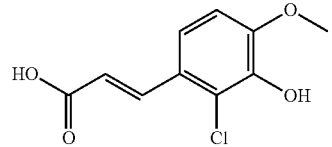

2-Chloro-3-hydroxy-4-methoxybenzaldehyde (1.86 g, 10 mmol) was dissolved in pyridine (7 ml), malonic acid (1.25 g, 10 mmol) and piperidine (0.1 ml) were added and the mixture was heated at 100° C. for 2 hrs, then it was poured in 100 ml HCl 1N and extracted with AcOEt. This was dried and evaporated, and the residue was triturated with diethyl ether and filtered, giving 2.10 g of (E)-3-(2-chloro-3-hydroxy-4-methoxy-phenyl)-acrylic acid as a white solid, which was used without further purification.

Example 21

(240) (E)-3-(2,4-difluoro-3-hydroxyphenyl)acrylic acid

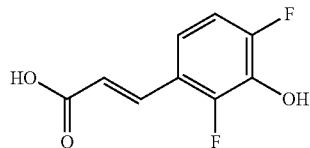 [SMILES: O=C(O)/C=C/c1ccc(F)c(O)c1F]

Step A

1M BBr₃ in DCM (2.179 ml) was added dropwise in about 30 min. to a stirred solution of 2,4-difluoro-3-methoxybenzaldehyde (0.25 g, 1.452 mmol) in DCM, cooled at −10° C. and under nitrogen atmosphere The solution was stirred for 4 hrs at RT and then diluted with a mixture of THF/H₂O (9/1) and heated for 30 min. at 80° C. The solvent was removed and the residue was partitioned between 10N NaOH and Et₂O. The aqueous layer was acidified with 10 N HCl and extracted with Et₂O/EtOAc (2/1). Organic layers were dried over sodium sulphate and evaporated to give 2,4-difluoro-3-hydroxybenzaldehyde (225 mg) as pale brown powder.

¹H NMR (DMSO-d6) δ (ppm): 10.73 (s, 1H), 10.12 (s, 1H), 7.33 (m, J=8.80, 7.04, 5.87 Hz, 1H), 7.18-7.27 (m, 1H).

Step B

A mixture of 2,4-difluoro-3-hydroxybenzaldehyde (0.255 g, 1.613 mmol) and malonic acid (0.168 g, 1.613 mmol) in pyridine (6 ml) and piperidine (0.06 ml) was heated to reflux for 1 h. All the volatile were removed and the residue was partitioned between NaHCO₃ sat. and Et₂O. The aqueous phase was acidified with 37% HCl until pH<3 and extracted with AcOEt. The organic layer was dried over sodium sulphate and evaporated to give (E)-3-(2,4-difluoro-3-hydroxyphenyl)acrylic acid (280 mg) as pale a brown solid. The compound was used in the next step without further purification.

¹H NMR (DMSO-d₆) δ (ppm): 12.51 (bs, 1H), 10.43 (s, 1H), 7.58 (d, J=16.14 Hz, 1H), 7.29 (td, J=8.29, 6.02 Hz, 1H), 7.03-7.20 (m, 1H), 6.52 (d, J=16.14 Hz, 1H).

Example 22

Preparation of substituted (E)-3-(3-acetoxy-phenyl)-acrylic acids from the corresponding (E)-3-(3-hydroxy-phenyl)-acrylic acids

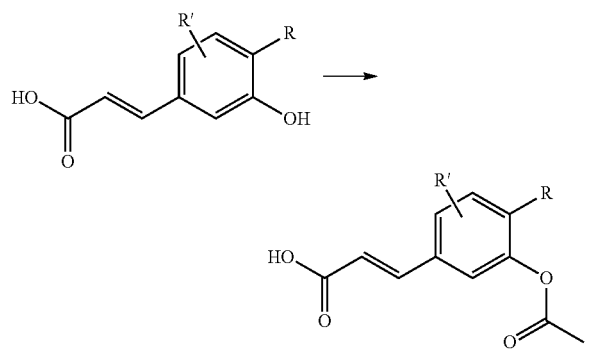

According to the procedure described in Example 8, the following compounds were prepared by coupling the suitable acrylic acid with acetic anhydride:

(241) (E)-3-(3-Acetoxy-4-chloro-phenyl)-acrylic acid

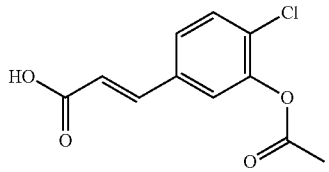

¹H NMR (DMSO-d6) δ (ppm): 12.48 (bs, 1H), 7.71 (d, J=1.17 Hz, H), 7.64 (dd, J=8.51 Hz, J=1.76 Hz, 1H), 7.61 (d, J=7.63 Hz, 1H), 7.56 (d, J=16.14 Hz, 1H), 6.58 (d, J=15.85 Hz, 1H), 2.35 (s, 3H).

(ES+) [M+H]+: 241.

(242) (E)-3-(3-Acetoxy-2-chloro-4-methoxy-phenyl)-acrylic acid

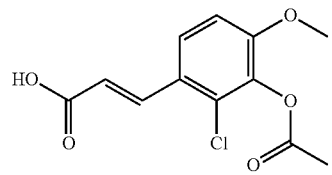

¹H NMR (DMSO-d6) δ (ppm): 12.51 (bs, 1H), 7.87 (d, J=8.80 Hz, 1H), 7.79 (d, J=15.85 Hz, 1H), 7.21 (d, J=9.10 Hz, 1H), 6.55 (d, J=15.85 Hz, 1H), 3.87 (s, 3H), 2.35 (s, 3H).

(ES+) [M+H]+: 271.

(243) (E)-3-(3-Acetoxy-2,4-difluoro-phenyl)-acrylic acid

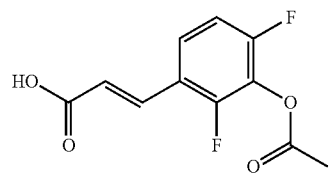 [SMILES: CC(=O)Oc1c(F)ccc(/C=C/C(=O)O)c1F]

¹H NMR (DMSO-d₆) δ (ppm): 12.61 (bs, 1H), 7.85 (td, J=8.62, 6.24 Hz, 1H), 7.59 (d, J=16.14 Hz, 1H), 7.36 (td, J=9.17, 1.83 Hz, 1H), 6.61 (d, J=16.14 Hz, 1H), 2.43 (s, 3H).

Biological Testing

Example 1

The following compounds:

1, 2, 6, 7, 8, 17, 19, 21, 25, 28, 32, 39, 40, 41, 42, 44, 45, 46, 47, 48, 49, 50, 51, 52, 55, 58, 59, 62, 64, 65, 71, 72, 78, 79, 81, 141, 143, 144, 145, 146, 147, 148, 149, 150, 153, 154, 157, 158, 159, 162, 163, 166, 169, 170, 171, 172, 173, 183.

screened at 1 μM concentration in the Calcium Retention Capacity (CRC) assay according to the methods described in the pharmacology section above, showed potent inhibitory effect on the MPTP, with CRC efficacy values above 2.

The invention claimed is:

1. A method for the treatment of a disease or condition associated with the activity of the mitochondrial permeability transition pore (MPTP) in a subject afflicted therewith comprising administering to the subject a compound of the general formula (I)

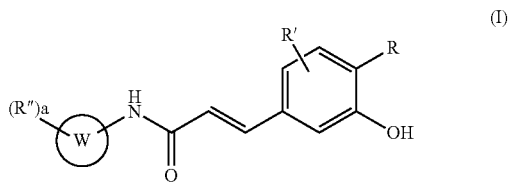

wherein:

W is aryl or heteroaryl;

a is 0, 1, 2, or 3;

R and R' are the same or different and, independently from each other, is: hydrogen; halogen; (C1-C3)alkoxy; (C1-C2)haloalkoxy; (C1-C2)haloalkyl; $NR_1R_2$; CN; $SO_2NH_2$; or optionally substituted (C1-C6)alkyl, aryl or heteroaryl;

R" is:

halogen; (C1-C3)alkyl; (C1-C3)alkoxy; (C1-C3)alkoxyalkyl; (C1-C2)haloalkoxy; (C1-C2)haloalkyl; $NR_3R_4$; or $(CH_2)_n$—X—$(CH_2)_m$-Q, wherein:

n, m independently, are 0, 1, or 2;

X is a direct bond; O; S; NH; or N(C1-C3)alkyl;

Q is an optionally substituted aryl, heteroaryl, heterocycloalkyl or cycloalkyl;

$R_1$, $R_2$, $R_3$, and $R_4$ are the same or different and, independently from each other, is a hydrogen atom; a (C1-C3)alkyl or, taken together with the nitrogen atom to which they are attached, $R_1$—N—$R_2$ and $R_3$—N—$R_4$ may form a heterocyclic ring of formula:

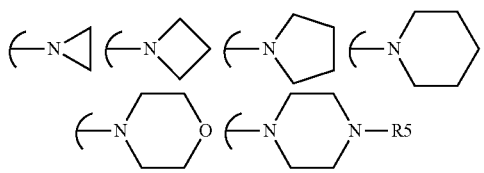

wherein:

$R_5$ is a hydrogen atom or a (C1-C3)alkyl group;

with the proviso that:

when W is phenyl, a is 1, 2 or 3;

when W is phenyl and R is hydrogen, R" is other than chlorine, methyl, isopropyl, $CF_3$ or $NH_2$;

when W is indazol-5-yl or pyrid-2-yl, R is other than hydrogen, (C1-C3)alkoxy;

or a tautomer, a racemate, an enantiomer, a diastereomer, an epimer, a mixture thereof, a prodrug thereof or a pharmaceutically acceptable salt thereof, and wherein the disease or condition associated with the activity of the mitochondrial permeability transition pore (MPTP) is myocardial infarction, heart failure, organ ischemia, ischemic and traumatic brain damage, Duchenne muscular dystrophy, Ullrich congenital muscular dystrophy, Bentham myopathy, amyotrophic lateral sclerosis, Huntington's disease, Alzheimer's disease, Parkinson's disease, diabetes type I and type II, diabetic complications, hyperglycemic tissue damage, hypoglycemic tissue damage, cholestasis, or alcohol-induced damage.

2. The method according to claim 1, wherein the disease or condition associated with the activity of the mitochondrial permeability transition pore (MPTP) is a disease resulting from ischemia/reperfusion damage or oxidative damage, an age-related disease, a degenerative disease or a neurodegenerative disease.

3. A method for the treatment of a disease or condition associated with the activity of the mitochondrial permeability transition pore (MPTP) in a subject afflicted therewith comprising administering to the subject a compound of the general formula (I)

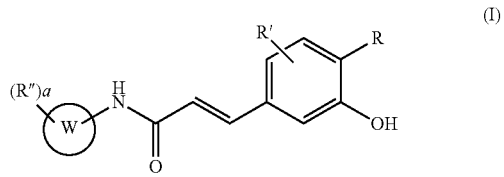

wherein:

W is aryl or heteroaryl;

a is 0, 1, 2, or 3;

R and R' are the same or different and, independently from each other, is: hydrogen; halogen; (C1-C3)alkoxy; (C1-C2)haloalkoxy; (C1-C2)haloalkyl; $NR_1R_2$; CN; $SO_2NH_2$; or optionally substituted (C1-C6)alkyl, aryl or heteroaryl;

R" is:

halogen; (C1-C3)alkyl; (C1-C3)alkoxy; (C1-C3)alkoxyalkyl; (C1-C2)haloalkoxy; (C1-C2)haloalkyl; $NR_3R_4$; or $(CH_2)_n$—X—$(CH_2)_m$-Q, wherein:

n, m independently, are 0, 1, or 2;

X is a direct bond; O; S; NH; or N(C1-C3)alkyl;

Q is an optionally substituted aryl, heteroaryl, heterocycloalkyl or cycloalkyl;

$R_1$, $R_2$, $R_3$, and $R_4$ are the same or different and, independently from each other, is a hydrogen atom; a (C1-C3)alkyl or, taken together with the nitrogen atom to which they are attached, $R_1$—N—$R_2$ and $R_3$—N—$R_4$ may form a heterocyclic ring of formula:

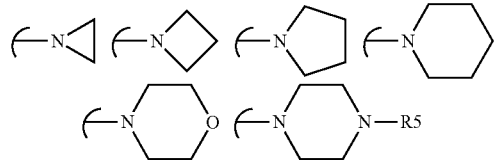

wherein:

$R_5$ is a hydrogen atom or a (C1-C3)alkyl group;

with the proviso that:

when W is phenyl, a is 1, 2 or 3;

when W is phenyl and R is hydrogen, R" is other than chlorine, methyl, isopropyl, $CF_3$ or $NH_2$;

when W is indazol-5-yl or pyrid-2-yl, R is other than hydrogen, (C1-C3)alkoxy;

or a pharmaceutically acceptable salt thereof, and wherein the disease or condition associated with the activity of the mitochondrial permeability transition pore (MPTP) is myocardial infarction, heart failure, organ ischemia, ischemic and traumatic brain damage, Duchenne muscular dystrophy, Ullrich congenital muscular dystrophy, Bentham myopathy, amyotrophic lateral sclerosis, Huntington's disease, Alzheimer's disease, Parkinson's disease, diabetes type I and type II, diabetic complications, hyperglycemic tissue damage, hyopglycemic tissue damage, cholestasis, or alcohol-induced damage.

4. The method according to claim 3, wherein the disease or condition associated with the activity of the mitochondrial permeability transition pore (MPTP) is a disease resulting from ischemia/reperfusion damage or oxidative damage, an age-related disease, a degenerative disease or a neurodegenerative disease.

* * * * *